US008703915B2

(12) United States Patent
Jazayeri-Dezfuly et al.

(10) Patent No.: US 8,703,915 B2
(45) Date of Patent: Apr. 22, 2014

(54) MUTANT PROTEINS AND METHODS FOR PRODUCING THEM

(75) Inventors: Seyed Ali Jazayeri-Dezfuly, Hertfordshire (GB); Guillaume Pierre Lebon, Cambridge (GB); Fiona Hamilton Marshall, Hertfordshire (GB); Christopher Gordon Tate, Cambridge (GB); Nathan Robertson, Hertfordshire (GB)

(73) Assignee: Heptares Therapeutics Limited, Hertfordshire (GB)

( * ) Notice: Subject to any disclaimer, the term of this patent is extended or adjusted under 35 U.S.C. 154(b) by 0 days.

(21) Appl. No.: 13/379,872

(22) PCT Filed: Jun. 22, 2010

(86) PCT No.: PCT/GB2010/001227
§ 371 (c)(1),
(2), (4) Date: Mar. 9, 2012

(87) PCT Pub. No.: WO2010/149964
PCT Pub. Date: Dec. 29, 2010

(65) Prior Publication Data
US 2012/0165507 A1    Jun. 28, 2012

Related U.S. Application Data

(60) Provisional application No. 61/271,509, filed on Jul. 22, 2009.

(30) Foreign Application Priority Data

Jun. 22, 2009  (GB) .................................. 0910725.1

(51) Int. Cl.
*C07K 14/705*     (2006.01)
*C12P 21/00*      (2006.01)

(52) U.S. Cl.
USPC .......................................... 530/350; 435/69.1

(58) Field of Classification Search
None
See application file for complete search history.

(56) References Cited

U.S. PATENT DOCUMENTS

| 4,816,567 | A  | 3/1989  | Cabilly et al.  |
|-----------|----|---------|-----------------|
| 4,946,778 | A  | 8/1990  | Ladner et al.   |
| 5,223,409 | A  | 6/1993  | Ladner et al.   |
| 5,290,681 | A  | 3/1994  | Kuroda et al.   |
| 5,585,277 | A  | 12/1996 | Bowie et al.    |
| 5,834,250 | A  | 11/1998 | Wells et al.    |
| 5,925,549 | A  | 7/1999  | Hsueh et al.    |
| 6,153,410 | A  | 11/2000 | Arnold et al.   |
| 6,448,377 | B1 | 9/2002  | Kobilka et al.  |
| 6,537,749 | B2 | 3/2003  | Kuimelis et al. |
| 7,094,593 | B1 | 8/2006  | Pausch et al.   |
| 7,115,377 | B2 | 10/2006 | Yao et al.      |
| 7,462,457 | B2 | 12/2008 | Beachy et al.   |
| 2002/0028443 | A1 | 3/2002 | Short          |
| 2002/0147170 | A1 | 10/2002 | Kopin et al.   |
| 2003/0036092 | A1 | 2/2003 | Iverson et al. |
| 2003/0096297 | A1 | 5/2003 | Gilchrist et al. |
| 2003/0129649 | A1 | 7/2003 | Kobilka et al. |
| 2004/0157268 | A1 | 8/2004 | Kobilka et al. |
| 2005/0136392 | A1 | 6/2005 | Torres et al.  |
| 2005/0143402 | A1 | 6/2005 | Cheetham et al. |
| 2005/0287565 | A1 | 12/2005 | Merchiers et al. |
| 2007/0154947 | A1 | 7/2007 | Broach et al.  |
| 2007/0196389 | A1 | 8/2007 | Caligiuri et al. |
| 2010/0190188 | A1 | 7/2010 | Henderson et al. |
| 2011/0027910 | A1 | 2/2011 | Weir et al.    |
| 2011/0028700 | A1 | 2/2011 | Heal           |
| 2011/0046351 | A1 | 2/2011 | Weir et al.    |
| 2011/0112037 | A1 | 5/2011 | Warne et al.   |
| 2012/0270230 | A1 | 10/2012 | Henderson et al. |
| 2013/0224238 | A1 | 8/2013 | Hutchings et al. |

FOREIGN PATENT DOCUMENTS

| EP | 0 184 187 A2 | 6/1986 |
| EP | 0 239 400 A2 | 9/1987 |
| EP | 0 397 834 B1 | 2/2000 |
| EP | 1 376 132 A1 | 1/2004 |
| EP | 1 505 074 A1 | 2/2005 |

(Continued)

OTHER PUBLICATIONS

Hulme et al., Phenotypic classification of mutants: a tool for understanding ligand binding and activation of muscarinic acetylcholine receptors, 2007, Biochemical Society Transactions 35(4):742-745.*
U.S. Appl. No. 60/080,686, filed Apr. 3, 1998, Kuimelis et al.
International Search Report and Written Opinion for PCT/GB2008/000986 mailed Jan. 19, 2009.
International Preliminary Report on Patentability for PCT/GB2008/000986 mailed Jul. 6, 2009.
International Search Report and Written Opinion for PCT/GB2008/004032 mailed Aug. 19, 2009.
International Preliminary Report on Patentability for PCT/GB2008/004032 issued Jun. 8, 2010.
International Search Report and Written Opinion for PCT/GB2008/004223 mailed Aug. 19, 2009.
International Preliminary Report on Patentability for PCT/GB2008/004223 issued Jun. 22, 2010.

(Continued)

*Primary Examiner* — John Ulm
(74) *Attorney, Agent, or Firm* — Wolf, Greenfield & Sacks, P.C.

(57) ABSTRACT

A method for producing a mutant G-protein coupled receptor (GPCR) with increased stability relative to a parent GPCR, the method comprising making one or more mutations in the amino acid sequence that defines a parent GPCR, wherein (i) the one or more mutations are located within a window of/plus or minus 5 residues, where/is the position of amino acid residue 2.46 in the parent GPCR when the parent GPCR is a Class 1 GPCR, or where/is the position of an equivalent amino acid residue in the parent GPCR when the parent GPCR is a Class 2 or 3 GPCR, and/or (ii) the one or more mutations are located within an amino acid sequence of transmembrane helix 7 in the parent GPCR which amino acid sequence interacts with the window of/plus or minus 5 residues, to provide one or more mutants of the parent GPCR with increased stability.

23 Claims, 22 Drawing Sheets

(56) References Cited

FOREIGN PATENT DOCUMENTS

| | | |
|---|---|---|
| GB | 2 188 638 A | 10/1987 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 95/32425 A1 | 11/1995 |
| WO | WO 97/35881 A2 | 10/1997 |
| WO | WO 00/22129 A1 | 4/2000 |
| WO | WO 01/36471 A2 | 5/2001 |
| WO | WO 02/059346 A2 | 8/2002 |
| WO | WO 02/068600 A2 | 9/2002 |
| WO | WO 03/035693 A2 | 5/2003 |
| WO | WO 2005/121755 A1 | 12/2005 |
| WO | WO 2006/023248 A2 | 3/2006 |
| WO | WO 2008/068534 A2 | 6/2008 |
| WO | WO 2008/114020 A2 | 9/2008 |
| WO | WO 2009/071914 A2 | 6/2009 |
| WO | WO 2009/081136 A2 | 7/2009 |

OTHER PUBLICATIONS

International Search Report and Written Opinion for PCT/GB2009/000310 mailed Jun. 23, 2009.
International Preliminary Report on Patentability for PCT/GB2009/000310 mailed Aug. 26, 2010.
International Search Report and Written Opinion for PCT/GB2008/000740 mailed Jul. 28, 2008.
International Preliminary Report on Patentability for PCT/GB2008/000740 issued Sep. 7, 2010.
International Search Report and Written Opinion for PCT/GB2010/001227 mailed Jun. 20, 2011.
International Preliminary Report on Patentability for PCT/GB2010/001227 mailed Jan. 12, 2012.
Office Action mailed Feb. 14, 2012 for U.S. Appl. No. 12/450,358.
[No author listed] Uniprot Database Accession No. P08482. 1988. Muscarinic acetylcholine receptor M1.
[No author listed] The CCP4 suite: programs for protein crystallography. Collaborative Computational Project, No. 4. Acta Crystallogr. 1994. D50:760-763.
Abagyan & Totrov. High-throughput docking for lead generation. Curr. Opin. Chem. Biol. 2001. 5:375-382.
Abagyan et al., ICM—a new method for protein modelling and design. Applications to docking and structure prediction from the distorted native conformation. J. Comput. Chem. 1994. 15:488-506.
Adams et al., Phenix: building new software for automated crystallographic structure determination. Acta Crystallogr. 2002. D58:1948-1954.
Afonine et al., The Phenix refinement framework. CCP Newsletter. 2005. Contribution 8.
Alexandrov et al., Microscale Fluorescent Thermal Stability Assay for Membrane Proteins; Structure; 2008;16:351-359.
Ali & Caffrey. Membrane Protein Crystallization in Lipidic Mesophases: Detergent Effects. Biophys. J. 2000.79:394-405.
Alkhatib et al., HIV coreceptors: from discovery and designation to new paradigms and promise. Eur. J. Med. Res. 2007 12(9):375-384.
Altschul & Gish. Local alignment statistics. Methods in Enzymology. 1996. 266:460-480.
Altschul et al., Basic local alignment search tool. J. Mol. Biol. 1990. 215:403-410.
Altschul et al., Gapped BLAST and PSI-BLAST: a new generation of protein database search programs. Nucl Acids Res. 1997 25:3389-3402.
Alves et al., Plasmon Resonance Methods in GPCR Signaling and Other Membrane Events. Curr. Prot. & Peptide Sci. 2005 6:293-312.
Artymiuk et al., Graph theoretic methods for the analysis of structural relationships in biological macromolecules. J Amer. Soc. Info. Sci Tech. 2005 56(5):518-528.
Avlani et al., Critical role for the second extracellular loop in the binding of both orthosteric and allosteric G protein-coupled receptor ligands. J Biol Chem. 2007. 282:25677-25686.
Babcook et al., A novel strategy for generating monoclonal antibodies from single, isolated lymphocytes producing antibodies of defined specificities. PNAS. 1996 93:7843-7848.
Baker. The selectivity of β-adrenoceptor antagonists at the human β1, β2 and β3 adrenoceptors. British J. Pharmacol. 2005. 144:317-322.
Bakker et al., Constitutively Active Mutants of the Histamine H1 Receptor Suggest a Conserved Hydrophobic Asparagine-Cage That Constrains the Activation of Class A G Protein-Coupled Receptors. Mol. Pharmacol. 2008. 73:94-103.
Balbes et al., A Perspective of Modern Methods in Computer-Aided Drug Design. Reviews in Computational Chemistry. 1994. 5:337-380.
Baldwin et al., An alpha-carbon template for the transmembrane helices in the rhodopsin family of G-proteincoupled receptors. J. Mol. Biol. 1997. 272:144-164.
Ballesteros & Weinstein. Integrated methods for the construction of three-dimensional models and computational probing of structure-function relations in G-protein coupled receptors. Methods in Neurosciences. 1995 Sealfon, S.C.and Conn, P.M. (eds.). Academic Press San Diego, CA 366-428.
Ballesteros et al., Activation of the beta 2-adrenergic receptor involves disruption of an ionic lock between the cytoplasmic ends of transmembrane segments 3 and 6. J. Biol. Chem. 2001. 276:29171-29177.
Ballesteros et al., Structural mimicry in GPCR: Implications of the high-resolution structure of rhodopsin for structure-function analysis of rhodopsin-like receptors. Mol. Pharmacology 60, 1-19, 2001.
Bamber et al., Yeast mitochondrial ADP ATP carriers are monomeric in detergents. PNAS. 2006 103:16224-16229.
Baneres et al., Molecular Characterization of a Purified 5-HT4 Receptor. J. Biol. Chem. 2005. 208:20253-20260.
Baranski et al., C5a Receptor Activation. J. Biol. Chem. 1999. 274(22):15757-15765.
Barbas et al., Assembly of combinatorial antibody libraries on phage surfaces: The gene III site. PNAS. 1991 88:7978-7982.
Baroni et al., A Common Reference Framework for Analyzing/Comparing Proteins and Ligands. Fingerprints for Ligands and Proteins (FLAP): Theory and Application. J. Chem Inf. Mod. 2007. 47:279-294.
Barroso S. et al., 2000, Identification of Residues Involved in Neurotensin Binding and Modeling of the Agonist Binding Site in Neurotensin Receptor 1, Journal of Biological Chemistry, 275(1):328-336.
Barroso S. et al., 2002, Constitutive activation of the neurotensin receptor 1 by mutation of Phe358 in Helix seven, British Journal of Pharmacology, 135:997-1002.
Barry et al., Quantitative protein profiling using antibody arrays. Proteomics. 2004 4:3717-3726.
Bartlett et al., CAVEAT: A Program to Facilitate the Structure-Derived Design of Biologically Active Molecules. Molecular Recognition: Chemical and Biological Problems, 1989. S. M. Roberts, Editor, Royal Society of Chemistry. 78:182-196.
Bee et al., 2007, Functional analysis of transmembrane domain 2 of the M1 muscarinic acetylocholine receptor, J. Biol. Chem. 282(44):32471-32479.
Behr et al., Novel mutants of the human β1-adrenergic receptor reveal amino acids relevant for receptor activation. J. Biol. Chem. 2006. 281(26):18120-18125.
Berchiche et al., Direct Assessment of CXCR4 Mutant Conformations Reveals Complex Link between Receptor Structure and G(alpha)(i) Activation. J. Biol. Chem. 2007. 282(8):5111-5115.
Besenicar et al., Surface plasmon resonance in protein—membrane interactions. Chem. Phys. Lipids. 2006 141:169-178.
Black. Drugs from Emasculated Hormones: The Principle of Syntopic Antagonism (Nobel Lecture). Angew Chem. Int. Edit. 1989. 28:886-894.
Blundell et al., Knowledge-based prediction of protein structures and the design of novel molecules. Nature. 1987. 326:347-352.
Blundell et al., Knowledge-based protein modelling and design; 18th Sir Hans Krebs Lecture Eur. J. Biochem. 1988. 173:513-520.

(56) References Cited

OTHER PUBLICATIONS

Bockaert and Pin. Molecular tinkering of G protein-coupled receptors: an evolutionary success. EMBO J. 1999. 18:1723-1729.
Bockaert et al., GPCR-GIP networks: a first step in the discovery of new therapeutic drugs? Curr Opin Drug Discov and Dev. 2004. 7:649-657.
Bohm. The computer program LUDI: a new method for the de novo design of enzyme inhibitors. J. Comput. Aided Mol. Des. 1992. 6:61-78.
Bommarius et al., High-throughput screening for enhanced protein stability. Curr Opin Biotechnol. 2006. 17(6):606-610. Epub Oct. 17, 2006.
Bonner et al., Identification of a family of muscarinic acetylcholine receptor genes. Science. 1987. 237:527-532.
Boucard et al., Constitutive Activation of the Angiotensin II Type 1 Receptor Alters the Spatial Proximity of Transmembrane 7 to the Ligand-binding Pocket. J. Biol. Chem. 2003. 278(38):36628-36636. Epub Jul. 3, 2003.
Bowie. Stabilizing membrane proteins. Curr. Opin. Struct. Biol. 2001. 11(4):397-402.
Brenner & Lerner. Encoded combinatorial chemistry. PNAS. 1992. 89:5381-5383.
Brodeur et al., Mouse-Human Myeloma Partners for the Production of Heterohybridomas. Mono. Antib. Prod. Tech. Apps. 1987. 51-63.
Brunger et al., Recent developments for the efficient crystallographic refinement of macromolecular structures. Curr. Opin. Struct. Biol. 1998. 8(5):606-611.
Bruns et al., Human glutathione transferase A4-4 crystal structures and mutagenesis reveal the basis of high catalytic efficiency with toxic lipid peroxidation products. J Mol Biol. 1999. 288:427-439.
Burstein et al., The second intracellular loop of the m5 muscarinic receptor is the switch which enables G-protein coupling. J Biol Chem. 1998. 273:24322-24327.
Caron et al., Affinity chromatography of the beta-adrenergic receptor. J. Biol. Chem.1979. 254:2923-2927.
Carrillo H. & Lipman D.J. The multiple sequence alignment problem in biology. SIAM J. Appl. Math. 1988; 48:1073-1082.
Carson. Ribbons 2.0. Appl. Crystallogr. 1991. 24:958-961.
Chan et al., Allosteric modulation of the muscarinic M4 receptor as an approach to treating schizophrenia. PNAS. 2008. 105:10978-10983.
Chapple et al., Multiplexed expression and screening for recombinant protein production in mammalian cells. BMC Biotechnol. 2006. 22:6-49.
Cherezov et al., A robotic system for crystallizing membrane and soluble proteins in lipidic mesophases. Acta. Crystallogr. D. Biol. Crystallogr. 2004. 60(Pt 10):1795-1807. Epub Sep. 23, 2004.
Cherezov et al., Crystallization Screens: Compatibility with the Lipidic Cubic Phase for in Meso Crystallization of Membrane Proteins. Biophys. J. 2001. 81:225-242.
Cherezov et al., High Resolution Crystal Structure of an Engineered Human β-Adrenergic G protein-Coupled Receptor. Science. 2007. 318(5854):1258-1265. Epub Oct. 25, 2007.
Cherezov et al., Room to Move: Crystallizing Membrane Proteins in Swollen Lipidic Mesophases. J. Mol.-Biol. 2006. 357:1605-1618.
Christopoulos. Allosteric binding sites on cell-surface receptors: Novel targets for drug discovery. Nat. Rev. Drug Discov. 2002. 1:198-210.
Clackson et al., Making antibody fragments using phage display libraries. Nature. 1991. 352:624-628.
Claeysen et al., A single mutation in the 5-HT4 receptor (5-HT4-R D100(3.32)A) generates a Gs-coupled receptor activated exclusively by synthetic ligands (RASSL).J Biol Chem. Jan. 10, 2003;278(2):699-702. Epub Nov. 18, 2002.
Cohen et al., Molecular modeling software and methods for medicinal chemistry. J. Med. Chem. 1990. 33:883-894.
Conklin et al., Engineering GPCR signaling pathways with RASSLs. Nat Methods. Aug. 2008;5(8):673-8.
Cooper. Advances in membrane receptor screening and analysis. J. Mol. Recognit. 2004. 17(4):286-315.
Cooper. Non-optical screening platforms: the next wave in label-free screening? Drug Discov. Today. 2006. 11(23-24):1068-1074. Epub Oct. 20, 2006.
Cornell et al., A Second Generation Force Field for the Simulation of Proteins, Nucleic Acids, and Organic Molecules. JACS. 1995. 117(19):5179-5197.
D'Antona et al., A cannabinoid receptor 1 mutation proximal to the DRY motif results in constitutive activty and reveals intramolecular interactions involved in receptor activation. Brain Research. 2006 1108(1):1-11.
D'Antona et al., Mutations of CB1 T210 Produce Active and Inactive Receptor Forms: Correlations with Ligand Affinity, Receptor Stability, and Cellular Localization. Biochemistry. 2006. 45:5606-5617.
Day et al., A monoclonal antibody for G protein—coupled receptor crystallography. Nat Methods. 2007. 4(11):927-929.
Degrip. Thermal Stability of Rhodopsin and Opsin in Some Novel Detergents. Methods in Enzymology. 1982. 81:256-265.
Devereux et al., A comprehensive set of sequence analysis programs for the VAX; Nucl. Acids Rec. 12:387-395, 1984.
Dignam. Preparation of extracts from higher eukaryotes. Methods in Enzymology. 1990. 182:194-203.
Domazet et al., The second transmembrane domain of the human type 1 angiotensin II receptor participates in the formation of the ligand binding pocket and undergoes integral pivoting movement during the process of receptor activation. J Biol Chem. May 1, 2009;284(18):11922-9. Epub Mar. 9, 2009.
Dupriez et al. Aequorin-based functional assays for G-protein-coupled receptors, ion channels and tyrosine kinase receptors. Receptors Channels. 2002. 8(5-6):319-330.
Dyson et al., Identification of soluble protein fragments by gene fragmentation and genetic selection. Nucl. Acid Research. 2008. 36:e51.
Dyson et al., Production of soluble mammalian proteins in *Escherichia coli*: identification of protein features that correlate with successful expression. BMC Biotechnology. 2004. 4:32.
Eddy et al., Maximum Discrimination Hidden Markov Models of Sequence Consensus. J. Comput Biol. 1995. 2(1):9-23.
Eglen. Functional G protein-coupled receptor assays for primary and secondary screening. Comb. Chem. High Throughput Screen. 2005. 8(4):311-318.
Eisen et al., HOOK: a program for finding novel molecular architectures that satisfy the chemical and steric requirements of a macromolecule binding site. Proteins:Structure, Function and Genetics. 1994.19(3):199-221.
Eldridge et al., Empirical scoring functions: I. the development of a fast empirical scoring function to estimate the binding affinity of ligands in receptor complexes. J. Comp. Aided Mol. Des. 1997. 11(5):425-445.
Ernst et al., Intrinsic biophysical monitors of transducin activation: fluorescence, UV-visible spectroscopy, light scattering, and evanescent field techniques. Meth. Enzymol. 2000. 315:471-489.
Evans & McCoy. An introduction to molecular replacement. Acta Crystallogr. 2008. D64:1-10.
Faham et al., Side-chain contributions to membrane protein structure and stability. J. Mol. Biol. 2004. 335:297-305.
Fanelli. Theoretical study on mutation-induced activation of the luteinizing hormone receptor. J. Mol. Biol. 2000. 296(5):1333-1351.
Fang et al., G protein-coupled receptor microarrays for drug discovery. Drug Discovery Today. 2003. 8:755-761.
Felix et al., Immunoadsorption as a new therapeutic principle for treatment of dilated cardiomyopathy. Eur. Heart J. Supplements. 2002. 4:163-168.
Ferracci et al., Real time analysis of intact organelles using surface plasmon resonance. Anal. Biochem. 2004. 334:367-375.
Ferro & Hermans. A different best rigid body molecular fit routine. Acta Cryst. 1977. A33:345-347.
Fetrow & Bryant. New programs for protein tertiary structure prediction. Biotechnology. 1993. 11(4):479-484.
Folkertsma et al., A family-based approach reveals the function of residues in the nuclear receptor ligand-binding domain. J. Mol. Biol. 2004. 341(2):321-335.
Foord et al., International Union of Pharmacology. XLVI. G Protein-Coupled Receptor List. Pharmacol. Rev. 2005. 57:279-288.

(56) References Cited

OTHER PUBLICATIONS

Foord S.M. & Marshall F.H. RAMPs: accessory proteins for seven transmembrane domain receptors, Trends Pharmacol Sci. 20(5):184-187 1999.
Frändberg et al., Cysteine Residues Are Involved in Structure and Function of Melanocortin 1 Receptor: Substitution of a Cysteine Residue in Transmembrane Segment Two Converts an Agonist to Antagonist. Biochem. Biophys. Res. Commun. 2001. 281(4):851-857.
Frielle et al., Cloning of the cDNA for the human-β-adrenergic receptor. PNAS. 1987. 84:7920-7924.
Fuchs et al., Targeting recombinant antibodies to the surface of *Escherichia coli*: fusion to a peptidglycan associated lipoprotein. Biotechnology. 1991. 9:1369-1372.
Gales et al., Real-time monitoring of receptor and G-protein interactions in living cells, Nat. Methods. 2(3):177-184 (2005).
Garcia-Lopez et al., Strategies for design of non peptide CCK1R agonist/antagonist ligands. Curr. Top. Med. Chem. 2007. 7(12):1180-1194.
Gardella et al., Transmembrane residues of the parathyroid hormone (PTH)/PTH-related peptide receptor that specifically affect binding and signaling by agonist ligands. J Biol Chem. May 31, 1996;271(22):12820-5.
Garrard et al., $F_{ab}$ assembly and enrichment in a monovalent phage display system. Biotechnology. 1991. 9:1373-1377.
Gerber et al., An Activation Switch in the Ligand Binding Pocket of the C5a Receptor. J. Biol. Chem. 2001. 276(5):3394-3400.
Gether et al., Structural Instability of a Constitutively Active G Protein-coupled Receptor Agonist-Independent Activation Due to Conformational Flexibility. J. Biol. Chem. 1997. 272:2587-2590.
Gether. Uncovering Molecular Mechanisms Involved in Activation of G Protein-Coupled Receptors. Endocr. Rev. 2000. 21:90-113.
Gillet et al., SPROUT—a program for structure generation. J. Comput. Aided Mol. Des.1993. 7:127-153.
Ginalski, Comparative modeling for protein structure prediction. Curr. Op. Struct. Biol. 2006. 16(2):172-177.
Gish & States. Identification of protein coding regions by database similarity search. Nature Genetics. 1993. 3:266-272.
Goding. Production of Monoclonal Antibodies: Principles and Practice. Academic Press. 1986. 59-103.
Goodford. A Computational Procedure for Determining Energetically Favorable Binding Sites on Biologically Important Macromolecules. J. Med. Chem. 1985. 28:849-857.
Goodsell et al., Automated docking of substrates to proteins by simulated annealing. Proteins: Structure, Function and Genetics. 1990. 8:195-202.
Gram et al., In vitro selection and affinity maturation of antibodies from a naïve combinatorial immunoglobulin library. PNAS. 1992. 89:3576-3580.
Graneli et al., Characterization of a proton pumping transmembrane protein incorporated into a supported three-dimensional matrix of proteoliposomes. Anal. Biochem. 2007. 367:87-94.
Graneli et al., Utilizing adsorbed proteoliposomes trapped in a non-ruptured state on SiO2 for amplified detection of membrane proteins. Biosens. Bioelectron. 2004. 20:498-504.
Gray et al., Identification of Two Serine Residues Essential for Agonist-Induced 5-HT2a Receptor Desensitization. Biochemistry. 2003. 42(36):10853-10862.
Gray. High-resolution protein-protein docking. Curr. Opin. Struct. Biol. 2006. 16:183-193.
Greer et al., Application of the Three-Dimensional Structures of Protein Target Molecules in Structure-Based Drug Design. J. Med. Chem. 1994. 37:1035-1054.
Greer. Comparative modeling of homologous proteins. Methods in Enzymology. 1991. 202:239-252.
Greer. Model structure for the inflammatory protein C5a. Science. 1985. 228:1055-1060.
Griffiths et al. Human anti-self antibodies with high specificity from phage display libraries. EMBO J. 1993. 12:725-734.
Grindley et al., Identification of Tertiary Structure Resemblance in Proteins Using a Maximal Common Subgraph Isomorphism Algorithm. J. Mol. Biol. 1993. 229:707-721.
Grisshamer et al. Expression of a rat neurotensin receptor in *Escherichia coli*. Biochem J. 1993. 295(2):571-576.
Grisshammer & Tate. Overexpression of integral membrane proteins for structural studies. Q. Rev. Biophys. 1995. 28:315-422.
Groves & Dustin. Supported planar bilayers in studies on immune cell adhesion and communication. Immunol. Meth. 2003. 278:19-32.
Groves. Membrane array technology for drug discovery. Curr. Op. Drug Discov. Develop. 2002. 5:606-612.
Gschwend & Kuntz. Orientational sampling and rigid-body minimization in molecular docking revisited: on-the-fly optimization and degeneracy removal. J. Comput. Aided Mol. Des. 1996. 10:123-132.
Guida. Software for structure-based drug design. Curr. Opin. Struct. Biol. 1994. 4:777-781.
Gupta & Devi. The use of receptor-specific antibodies to study G-protein-coupled receptors. Mt. Sinai J. Med. 2006. 73(4):673-681.
Gupta et al., Conformation State-sensitive Antibodies to G-protein-coupled Receptors. J. Biol. Chem. 2007. 282(8): 5116-5124.
Halperin et al., Principles of docking: An overview of search algorithms and a guide to scoring functions. Proteins. 2002. 47:409-443.
Hamuro et al., Hydrogen/deuterium-exchange (H/D-Ex) of PPARγ LBD in the presence of various modulators. Protein Science. 2006. 15(8):1883-1892.
Han et al., Constitutive activation of opsin by mutation of methionine 257 on transmembrane helix 6. Biochemistry. Jun. 2, 1998;37(22):8253-61.
Harding et al., Direct analysis of a GPCR-agonist interaction by surface plasmon resonance. Eur. Biophys. J. Biophys. Let. 2006. 35:709-712.
Harding. Metal-ligand geometry relevant to proteins and in proteins: sodium and potassium. Acta Crystallogr. 2002. D58:872-874.
Hawkins et al., Selection of phage antibodies by binding affinity: mimicking affinity maturation. J. Mol. Biol. 1992. 226:889-896.
Hay et al., Bacteriophage Cloning and *Escherichia coli* Expression of a Human IgM Fab. Hum. Antibod. Hybridomas. 1992. 3:81-85.
Hendrickson. Transformations to optimize the superposition of similar structures. Acta Crystallogr. 1979. A35:158-163.
Henikoff & Henikoff. Amino acid substitution matrices from protein blocks. Proc Natl Acad Sci U.S.A. Nov. 15, 1992; 89(22):10915-10919.
Hoffmann et al., A FlAsH-based FRET approach to determine G protein-coupled receptor activation in living cells. Nat Methods. Mar. 2005;2(3):171-6. Epub Feb. 17, 2005.
Holm & Sander. Dali/FSSP classification of three-dimensional protein folds. Nucl. Acids Res. 1997. 25:231-234.
Holm & Sander. Mapping the Protein Universe. Science. 1996. 273:595-602.
Hoogenboom et al., Multi-subunit proteins on the surface of filamentous phage: methodologies for displaying antibody (Fab) heavy and light chains. Nuc. Acid Res. 1991. 19:4133-4137.
Hopkins & Groom. The druggable genome. Nature Rev. Drug Discovery. 2002. 1:727-730.
Hoppe & Schomburg. Prediction of protein thermostability with a direction- and distance-dependent knowledge-based potential. Protein Science. 2005. 14:2682-2692.
Huang et al., A probabilistic method to correlate ion pairs with protein thermostability. Applied Bioinformics. 2004. 3(1):21-29.
Hubbell et al., Rhodopsin structure, dynamics, and activation: a perspective from crystallography, site-directed spin labeling, sulfhydryl reactivity, and disulfide cross-linking. Adv. Protein Chem. 2003. 63:243-290.
Hulme & Curtis. Purification of recombinant M1 muscarinic acetylcholine receptor. Biochemical Society Transactions. 1998. 26:S361.
Hunte et al., Structure at 2.3 Å resolution of the cytochrome bc 1 complex from the yeast *Saccharomyces cerevisiae* co-crystallized with an antibody Fv fragment. Structure. 2000. 8:669-684.
Hus et al. Assignment strategy of proteins with known structure. J. Magn. Reson. 2002. 157(1):119-123.
Huse et al., Generation of a large combinatorial library of the immunoglobulin repertoire in phage lambda. Science. 1989. 246:1275-1281.

(56) References Cited

OTHER PUBLICATIONS

Ikuta et al., Crystallographic Approach to Identification of Cyclin-dependent Kinase 4 (CDK4)-specific Inhibitors by Using CDK4 Mimic CDK2 Protein. J. Biol. Chem. 2001. 276:27548-27554.
Isogaya et al., Binding pockets of the β1 and β2 adrenergic receptors for subtype-selective agonists. Mol. Pharmacol. 1999. 56(5):875-885.
Isogaya et al., Identification of a Key Amino Acid of the β2-Adrenergic Receptor for High Affinity Binding of Salmeterol. Mol. Pharmacol. 1998. 54:616-622.
Jaakola et al., The 2.6 Å Crystal Structure of a Human A2A Adenosine Receptor Bound to an Antagonist. Science. 2008. 322:1211-1217.
Jaenicke & Bohm. The stability of proteins in extreme environments. Current Opinion in Structural Biology. 1998. 8:738-748.
Jahns et al., Direct evidence for a β1-adrenergic receptor—directed autoimmune attack as a cause of idiopathic dilated cardiomyopathy. J. Clinical Investigation. 2004. 113(10):1419-1429.
Jahns et al., Modulation of Beta1-Adrenoceptor Activity by Domain-Specific Antibodies and Heart Failure—Associated Autoantibodies. J. Am. Coll. Cardiol. 2000. 36(4):1280-1287.
Jameson et al., Real-time Detection of Basal and Stimulated G Protein GTPase Activity Using Fluorescent GTP Analogues. J. Biol. Chem. 2005. 280(9):7712-7719.
Jane-wit D. et al., β1-Adrenergic Receptor Autoantibodies Mediate Dilated Cardiomyopathy by Agonistically Inducing Cardiomyocyte Apoptosis. Circulation. 2007. 116(4):399-410. Epub Jul. 9, 2007.
Jap et al., 2D crystallization: from art to science; Ultramicroscopy. 1992. 46(1-4):45-84.
Jerne & Nordin. Plaque formation in agar in single antibody-producing cells. Science. 1963. 140:405.
Johnson & Chriswell. Human antibody engineering. Curr. Op. Structural Biol. 1993. 3:564-571.
Johnson et al., A 1,536-well 35S GTPgammaS scintillation proximity binging assay for ultra-high-throughput screening of an orphan galphai-coupled GPCR. Assay Drug Dev Technol 6, 327-337 (2008).
Johnson et al., Knowledge-based protein modeling. Crit Rev Biochem Mol Biol. 1994. 29:1-68.
Jones et al., Development and validation of a genetic algorithm for flexible docking. J Mol. Biol. 1997. 267:727-748.
Jones et al., Docking small-molecule ligands into active sites. Curr. Opin. Biotech. 1995. 6:652-656.
Jones et al., Improved methods for building protein models in electron density maps and the location of errors in these models. Acta Crystallogr. 1991. A47:110-119.
Jones et al., Molecular Recognition of Receptor Sites Using a Genetic Algorithm with a Description of Desolvation. J Mol Biol. 1995. 245:43-53.
Kabsch, A discussion of the solution for the best rotation to relate two sets of vectors. Acta Crystallogr. 1978. A34:827-828.
Kabsch., A solution of the best rotation to relate two sets of vectors. Acta Crystallogr. 1976. A32:922-23.
Karlin & Altschul. Applications and statistics for multiple high-scoring segments in molecular sequences. PNAS. 1993. 90:5873-5877.
Karlsson & Lofas. Flow-Mediated On-Surface Reconstitution of G-Protein Coupled Receptors for Applications in Surface Plasmon Resonance Biosensors. Anal. Biochem. 2002. 300(2):132-138.
Kearsley. On the orthogonal transformation used for structural comparisons. Acta Crystallogr. 1989. A45:208-210.
Kenakin et al., Protean agonists. Keys to active receptor states? Ann. N.Y. Acad. Sci. 1997. 812:116-125.
Kenakin. Inverse, protean, and ligand-selective agonism: matters of receptor conformation. FASEB J. 2001. 15(3):598-611.
Kent et al., Development of a Generic Dual-Reporter Gene Assay for Screening G-Protein-Coupled Receptors. J. Biomol. Screen. 2005. 10(5):437-446.
Kent et al., G-protein-coupled receptor heterodimerization: assay technologies to clinical significance. Curr. Opin. Drug Discov. Devel. 2007. 10(5):580-589.
Kerr et al., Encoded combinational peptide libraries containing non-natural amino acids. JACS. 1993. 115:2529-2531.
Kikkawa et al., The Role of the Seventh Transmembrane Region in High Affinity Binding of a b2-Selective Agonist TA-2005. Mol. Pharmacol. 1998. 53:128-134.
Klco et al., Essential role for the second extracellular loop in C5a receptor activation. Nat Struct Mol Biol. 2005. 12:320-326.
Kleywegt & Jones. A super position. CCP4/ESF-EACBM Newsletter on Protein Crystallography. 1994.31:9-14.
Kobilka & Deupi. Conformation complexity of G-protein coupled receptors. Trends in Pharmacological Sciences. 2007. 28(8):397-406.
Kobilka & Schertler. New G-protein-coupled receptor crystal structures: insights and limitations. Trends Pharm. Sci. 2008. 29(2):79-83.
Köhler & Milstein. Continuous cultures of fused cells secreting antibody of predefined specificity. Nature. 1975. 256:495-497.
Komolov et al., Surface Plasmon Resonance Study of G Protein/Receptor Coupling in a Lipid Bilayer-Free System. Anal. Chem. 2006. 78:1228-1234.
Kozbor et al., A human hybrid myeloma for production of human monoclonal antibodies. J. Immunol. 1984. 133:3001-3005.
Kristiansen. Molecular mechanisms of ligand binding, signalling, and regulation within the superfamily of G-protein-coupled receptors: molecular modelling and mutagenesis approaches to receptor structure and function. Pharmacology and therapeutics. 2004. 103:21-80.
Kuhlbrandt. Three-dimensional crystallization of membrane proteins. Q. Rev. Biophys. 1988. 21:429-477.
Kuhlbrandt. Two-dimensional crystallization of membrane proteins. Q. Rev. Biophys. 1992. 25(1):1-49.
Kukkonen et al., Muscarinic Toxin 7 Selectivity Is Dictated by Extracellular Receptor Loops. J. Biol. Chem. 2004. 279:50923-50929.
Kuntz et al., A Geometric Approach to Macromolecule-Ligand Interactions. J. Mol. Biol. 1982. 161:269-288.
Kuroda et al., Systems for the detection and analysis of protein-protein interactions. Appl. Microbiol. Biotechnol. 2006. 71(2):127-136.
Kyte & Doolittle. A Simple Method for Displaying the Hydropathic Character of a Protein. J. Mol. Biol. 1982. 157:105-132.
Labbé-Jullié C. et al., 1998, Mutagenesis and Modeling of the Neurotensin Receptor NTR1, Journal of Biological Chemistry, 273(26):16351-16357.
Lamb et al., Modulation of the ligand binding properties of the transcription repressor NmrA by GATA-containing DNA and site-directed mutagenesis. Prot. Sci. 2004. 13(12):3127-3138.
Landau & Rosenbusch. Lipidic cubic phases: A novel concept for the crystallization of membrane proteins. PNAS USA. 1996. 93:14532-14535.
Lane et al., Protean agonism at the dopamine D2 receptor: (S)-3-(3-hydroxyphenyl)-N-propylpiperidine is an agonist for activation of Goα1 but an antigonist/inverse agonist for Giα1, Giα2, and Giα3. Mil Pharmacol. 2007 71(5):1349-1359. Epub Feb. 7, 2007.
Lang et al., Structure-activity relationship studies: Methods and ligand design for g-protein coupled peptide receptors. Curr. Prot. Peptide Sci. 2006. 7:335-353.
Latronico et al., Gonadotropin-Independent Precocious Puberty Due to Luteinizing Hormone Receptor Mutations in Brazilian Boys: A Novel Constitutively Activating Mutation in the First Transmembrane Helix. J. Clin. Endocrinol. Metabl. 2000. 85(12):4799-4805.
Lattion et al., Constitutively active mutants of the β-adrenergic receptor. FEBS Letters 1999 457(3):302-306.
Lattman. Use of Rotation and Translation Functions. Meth. Enzymol. 1985. 115:55-77.
Lau et al., Changing single side chains can greatly enhance the resistance of a membrane protein to irreversible inactivation. J. Mol. Biol. 1999. 290:559-564.
Lauri & Bartlett. CAVEAT: A Program to Facilitate the Design of Organic Molecules. J. Comp. Aided Mol. Design. 1994. 8:51-66.

(56) References Cited

OTHER PUBLICATIONS

Lee et al., Alanine scanning mutagenesis of conserved arginine/lysine-arginine/lysine-x-x-arginie/lysine G protein/activating motifs on M 1 muscarinic acetylcholine receptors. Molecular Pharmacology. 1996 50(1):140-148.

Lee et al., D2 Dopamine receptor homodimerization is mediated by multiple sites of interaction, including an intermolecular interaction involving transmembrane domain 4. Biochemistry. 2003. 42(37):11023-31.

Lee et al., State of the art in studying protein folding and protein structure predictio using molecular dynamics methods. J. Mol. Graph & Modelling. 2001. 19(1):146-149.

Lefevre et al., Alanine-stretch scanning mutagenesis: a simple and efficient method to probe protein structure and function. Nucl. Acids Res. 1997. 25(2):447-448.

Lehmann et al., The consensus concept for thermostability engineering of proteins: further proof of concept. Protein Engineering. 2002. 15(5):403-411.

Leifert et al., G-Protein-Coupled Receptors in Drug Discovery: Nanosizing Using Cell-Free Technologies and Molecular Biology Approaches. J. Biomol. Screening. 2005. 10:765-779.

Leroy et al., G Protein-coupled receptor-mediated ERK1/2 phosphorylation: towards a generic sensor of GPCR activation. J. Recept. Signal. Transduct. Res. 2007. 27(1):83-97.

Lewis & Lofthouse. Adverse reactions with beta-adrenoceptor blocking drugs: an update. Drug Safety. 1993. 9:272-279.

Li et al., Distinct Structural Changes in a G Protein-coupled Receptor Caused by Different Classes of Agonist Ligands. J. Biol. Chem. 2007. 282(36):26284-26293.

Li et al., Random Mutagenesis of the M3 Muscarinic Acetylcholine Receptor Expressed in Yeast. J. Biol. Chem. 2005. 280:5664-5675.

Li et al., Structure of Bovine Rhodopsin in a Trigonal Crystal Form. J. Mol. Biol. 2004. 343:1409-1438.

Liu & Wu. Analysis of the coupling of G12/13 to G protein-coupled receptors using a luciferase reporter assay. Methods Mol. Biol. 2004. 237:145-149.

Lohse et al. Kinetic analysis of G protein-coupled receptor signaling using fluorescence resonance energy transfer in living cells. Adv Protein Chem 2007 74:167-188.

Luecke et al., Structure of bacteriorhodopsin at 1.55 A resolution. J. Mol. Biol. 1999. 291(4):899-911.

Maclean et al., Encoded combinatorial chemistry: Synthesis and screening of a library of highly functionalized pyrrolidines. PNAS. 1997. 94:2805-2810.

Madabushi et al., Evolutionary Trace of G Protein-coupled Receptors Reveals Clusters of Residues That Determine Global and Class-specific Functions; J Biol Chem 2004 279(9):8126-8132.

Magnani et al., Co-evolving stability and conformational homogeneity of the human adenosine A2a receptor. PNAS. 2008. 105(31):10744-10749.

Makino et al., Automated flexible ligand docking method and its application for database search. J Comput. Chem. 1997. 18:1812-1825.

Marshall. Heterodimerization of G-protein-coupled receptors in the CNS. Curr. Opin. Pharmacol. 2001. 1(1):40-44.

Martin et al., A simple vector system to improve performance and utilisation of recombinant antibodies. BMC Biotechnology. 2006. 6:46.

Martin et al., Apolipoprotein A-I Assumes a "Looped Belt" Conformation on Reconstituted High Density Lipoprotein. J. Biol. Chem. 2006. 281(29):20418-20426.

Martin. 3D Database searching in drug design. J. Med. Chem. 1992. 35:2145-2154.

Martin-Garcia et al., Interaction with CD4 and Antibodies to CD4-Induced Epitopes of the Envelope gp120 from a Microglial Cell-Adapted Human Immunodeficiency Virus Type 1 Isolate. J. Virology. 2005. 79:6703-6713.

Mathews & Rossmann. Comparison of Protein Structures. Methods of Enzymology. 1985. 115:397-420.

Matsui et al., Specific removal of β1-adrenoceptor autoantibodies by immunoabsorption in rabbits with autoimmune cardiomyopathy improved cardiac structure and function. J. Mol. Cell Cardiol. 2006. 41(1):78-85. epub Jun. 14, 2006.

McCafferty et al., Phage antibodies: filamentous phage displaying antibody variable domains. Nature. 1990. 348:552-554.

McCoy. Phaser crystallographic software. Acta Crystallogr. 2007. 40:658-674.

McCoy. Solving Structures of protein complexes by molecular replacement with Phaser. Acta Crystallogr. 2007. D63:32-41.

McLachlan. Gene duplications in the structural evolution of chymotrypsin. J. Mol. Biol. 1979. 128, 49-79.

Mehler et al., Ab initio computational modelling of loops in G-protein-coupled receptors: Lessons from the crystal structure of rhodopsin. Proteins Structures Function and Bioinformatics. 2006. 64(3):673-690.

Meng et al., Automated docking with grid-based energy evaluation. J. Comp. Chem. 1992. 13:505-524.

Mezzasalma et al., Enhancing recombinant protein quality and yield by protein stability profiling. J. Biolmol. Screening. 2007. 12(3):418-428.

Michaelson et al., Antibodies to muscarinic acetylcholine receptors in myasthenia gravis. Biochem. Biophys. Res. Commun. 1982. 104(1):52-57.

Milligan & White. Protein—protein interactions at G-protein-coupled receptors. Trends Pharmacol. Sci. 2001. 22:513-518.

Milligan. G protein-coupled receptor dimerisation: Molecular basis and relevance to function. Biochim. Biophys Acta. 2007. 1768(4):825-835.

Milstein & Cuello. Hybrid hybridomas and their use in immunohistochemistry. Nature. 1983. 305:537-540.

Minic et al., Immobilization of native membrane-bound rhodopsin on biosensor surfaces. Biochim. Biophys. Acta-General Subjects. 2005. 1924:324-332.

Minneman et al., A Comparison of the Beta-Adrenergic Receptor of the Turkey Erythrocyte with Mammalian Beta1 and Beta2 Receptors. Mol. Pharmacol. 1980. 17:1-7.

Miranker et al., Functionality Maps of Binding Sites: A Multiple Copy Simultaneous Search Method Proteins: Structure, Function and Genetics. 1991. 11:29-34.

Misquitta et al. Membrane Protein Crystallization in Lipidic Mesophases with Tailored Bilayers. Structure. 2004. 12:2113-2124.

Moran et al., Radio frequency tag encoded combinatorial library method for the discovery of tripeptide-substituted cinnamic acid inhibitors of the protein tyrosine phosphatase PTB1B. JACS. 1995. 117:10787-10788.

Morris et al., Automated docking using a Lamarckian genetic algorithm and an empirical binding free energy function. J. Comput. Chem. 1998. 19:1639-1662.

Morrison. Success in specification. Nature. 1994. 368:812-813.

Mozsolits et al., Surface plasmon resonance spectroscopy in the study of membrane-mediated cell signalling. J. Peptide Sci. 2003. 9:77-89.

Munson & Rodbard. Ligand: a versatile computerized approach for characterization of ligand-binding systems. Anal. Biochem. 1980. 107:220-239.

Murakami et al., Crystal structure of squid rhodopsin. Nature. May 15, 2008;453(7193):363-7.

Myburgh et al., A single amino acid substitution in transmembrane helix VI results in overexpression of the human GnRH receptor. Eur. J. Endocrinol. 1998. 139(4):438-447.

Navarro et al., Receptor-Dependent G-Protein activation in Lipidic Cubic phase. Biopolymers. 2002. 67:167-177.

Navaza. AMoRe: an Automated Package for Molecular Replacement. Acta Cryst. 1994. D50:157-163.

Navia & Murko. Use of structural information in drug design. Curr Opin Struc Biol. 1992. 2:202-210.

Navratilova et al., Analyzing ligand and small molecule binding activity of solubilized GPCRs using biosensor technology. Anal. Biochem. 2006. 355:132-139.

Nawaratne et al., New insights into the function of M4 muscarinic acetylcholine receptors gained using a novel allosteric modulator and

(56) References Cited

OTHER PUBLICATIONS a DREADD (designer receptor exclusively activated by a designer drug). Mol Pharmacol. Oct. 2008;74(4):1119-31. Epub Jul. 15. 2008.
Needleman SB & Wunsch C.D. A general method applicable to the search for similarities in the amino acid sequence of two proteins. J Mol Biol Mar. 1970; 48(3):443-453.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Newman-Tancredi et al., Agonist and inverse agonist efficacy at human recombinant serotonin 5-HT1A receptors as a function of receptor:G-protein stoichiometry. Neurophamacology. 1997. 36:451-459.
Nicolaou et al., Radiofrequency encoded combinatorial chemistry. Angew. Chem. Int. Ed. Engl. 1995. 34:2289-2291.
Nishibata et al., Automatic creation of drug candidate structures based on receptor structure. Starting point for artificial lead generation. Tetrahedron. 1991. 47:8985-8990.
Nunomura et al., Regulation of Protein 4.1R, p55, and Glycophorin C Ternary Complex in Human Erythrocyte Membrane. J. Biol. Chem. 2000. 275:24540-24546.
Ohlmeyer et al., Complex synthetic chemical libraries indexed with molecular tags. PNAS. 1993. 90:10922-10926.
Oldham et al., Mapping allosteric connections from the receptor to the nucleotide-binding pocket of heterotrimeric G proteins. PNAS. 2007. 104(19):7927-7932.
Omerovic et al., Induction of Cardiomyopathy in Immunodeficiency Mice by Transfer Patients with Idiopathic Dilated Cardiomyopathy. Autoimmunity. 2000. 32(4):271-280.
Osbourn et al., Directed selection of MIP-1 alpha neutralizing CCR5 antibodies from a phage display human antibody library. Nature Biotechnology. 1998. 16:778-781.
Ostermeier & Michel. Crystalization of Membrane Proteins. Curr. Opin. Struct. Biol. 1997. 7:697-701.
Ott et al., Engineering and functional immobilization of opioid receptors. Prot. Eng. Design & Selection. 2005. 18:153-160.
Overington et al., How many drug targets are there? Natur Rev. Drug Discovery. 2006. 5:993-996.
Palczewski et al., Crystal Structure of Rhodopsin: A G Protein-Coupled Receptor. Science. 2000. 289:739-745.
Palmer et al., Treatment of systemic lupus erythematosus by extracorporeal immunoadsorption. Lancet. 1988. 2(8605):272.
Pardo et al., The role of internal water molecules in the structure and function of the rhodopsin family of G protein-coupled receptors. Chembiochem. Jan. 2, 2007;8(1):19-24.
Park et al., Characterization of radioligand binding to a transmembrane receptor reconstituted into Lipobeads. FEBS Lett. 2004. 567:344-348.
Parker & Ross. Truncation of the Extended Carboxyl-terminal Domain Increases the Expression and Regulatory Activity of the Avian,& Adrenergic Receptor. J. Biol. Chem. 1991. 266:9987-9996.
Parker et al., Carboxyl terminal domains in the avian β1-adrenergic receptor that regulate agonist-promoted endocytosis. J. Biol. Chem. 1995. 270:6482-6487. Erratum in: J Biol Chem 1995. 270(17):10358.
Parker et al., Reconstitutively Active G Protein-coupled Receptors Purified from Baculovirus-infected Insect Cells. J. Biol. Chem. 1991. 266:519-527.
Parsons et al., Directing phage selections towards specific epitopes. Protein Engineering. 1996. 9:1043-1049.
Perez. From Plants to Man: The GPCR "Tree of Life". Mol. Pharmacol. 2005. 67:1383-1384.
Pin et al., Evolution, structure, and activation mechanism of family 3/C G-protein-coupled receptor, Pharm. & Ther. 2003 98 325-354.
Plant et al., Phospholipid/alkanethiol bilayers for cell-surface receptor studies by surface plasmon resonance. Analyt. Biochem. 1995. 226(2):342-348.

Ponsioen et al. Detecting cAMP-induced Epac activation by fluorescence resonance energy transfer: epac as a novel cAMP indicator, 2004 EMBO Rep.;5(12):1176-1180.
Qian et al., High-resolution structure prediction and the crystallographic phase problem. Nature. 2007. 450:259-264.
Quick & Javitch. Monitoring the function of membrane transport proteins in detergent-solubilized form. PNAS. 2007. 104(9):3603-3608.
Rarey et al., A fast flexible docking method using an incremental construction algorithm. J. Mol. Biol. 1996. 261:470-489.
Rasmussen et al., Crystal structure of the human β2 adrenergic g-protein-coupled receptor. Nature. 2007. 450:383-387.
Rasmussen et al., Mutation of a Highly Conserved Aspartic Acid in the β2 Adrenergic Receptor: Constitutive Activation, Structural Instability, and Conformational Rearrangement of Transmembrane Segment 6. Molecular Pharmacol. 1999. 56:175-84.
Riekel et al., Protein crystallography microdiffraction. Curr. Opin. Struct. Biol. 2005. 15(5):556-562.
Rigaut et al., A generic protein purification method for protein complex characterization and proteome exploration. Nature Biotechnol. 1999. 17(10):1030-1032.
Roberts & Strange. Mechanisms of inverse agonist action at D2 dopamine receptors. Br. J. Pharmacol. 2005. 145:34-42.
Robinson-Rechavi et al., Contribution of Electrostatic Interactions, Compactness and Quaternary Structure to Protein Thermostability: Lessons from Structural Genomics of Thermotoga maritima. J. Mol. Biol. 2006. 356:547-557.
Rodgers et al., Development of displacement binding and GTPγS scintillation proximity assays for the identification of antagonists of the μ-opiod receptor. Assay Drug Dev. Technol. 2003. 1(5):627-636.
Rosenbaum et al., GPCR Engineering Yields High-Resolution Structural Insights into b2-Adrenergic Receptor Function. Science. 2007. 318:1266-1273.
Rossmann & Argos. A Comparison of the Heme Binding Pocket in Globins and Cytochrome b. J. Biol. Chem. 1975. 250:7525-7532.
Roth et al., Stabilization of the β2-adrenergic Receptor 4-3-5 Helix Interface by Mutagenesis of Glu-122 3.41, A Critical Residue in GPCR Structure. J. Mol. Biol. 2008. 376:1305-1319.
Rovati et al., The Highly Conserved DRY Motif of Class A G Protein-Coupled Receptors: Beyond the Ground State. Mol. Pharmacol. 2007. 71(4):959-964.
Rummel et al., Lipidic Cubic Phases: New Matrices for the Three-Dimensional Crystallization of Membrane Proteins. J. Struct. Biol. 1998. 121:82-91.
Sali & Blundell. Comparative protein modelling of satisfaction by spatial restraints. J. Mol. Biol. 1993. 234(3):779-815.
Samama et al., A mutation-induced activated state of the β2-adrenergic receptor. J Biol Chem. 1993 268(7):4625-4636.
Sarkar et al., Directed evolution of a G protein-coupled receptor for expression, stability, and binding selectivity. PNAS. 2008. 105(39):14808-14813.
Savinainen et al., Identification of WIN55212-3 as a competitive neutral antagonist of the human cannabinoid CB2 receptor. Br. J. Pharmacol. 2005. 145:636-645.
Sayle et al., RASMOL: biomolecular graphics for all. Trends in Biochemical Sciences. 1995. 20:374-376.
Scarselli et al., Multiple Residues in the Second Extracellular Loop Are Critical forM3 Muscarinic Acetylcholine Receptor Activation. J. Biol. Chem. 2007. 282:7385-7396.
Schaffner & Weissmann. A Rapid, Sensitive, and Specific Method for the Determination of Protein in Dilute Solution. Anal. Biochem. 1973. 56:502-514.
Schena et al., Quantitative monitoring of gene expression patterns with a complementary DNA microarray. Science. 1995. 270:467-470.
Schnare et al. Comprehensive comparison of structural characteristics in eukaryotic cytoplasmic large subunit (23S-like) ribosomal RNA. J. Mol. Biol. 1996. 256:701-719.
Schofield et al., Application of phage display to high throughput antibody generation and characterization. Genome Biology. 2007. 8(11):R254.

(56) References Cited

OTHER PUBLICATIONS

Schultz et al., Requirement of Specific Intrahelical Interactions for Stabilizing the Inactive Conformation of Glycoprotein Hormone Receptors. J. Biol. Chem. 2000. 275(48):37860-37869.

Screpanti et al., Crucial Steps in the Structure Determination of the Na+/H+ Antiporter NhaA in its Native Conformation. J. Mol. Biol. 2006. 362:192-202.

Sebestyen et al., Efficiency and limitations of the 'portioning-mixing' peptide synthesis. Pept. Proc. Eur. Pept. Symp. 22nd 1992. 1993. 63-64.

Sen et al., Functional studies with membrane-bound and detergent-solubilized alpha2-adrenergic receptors expressed in Sf9 cells. Biochim Biophys Acta. 2005 1712(1):62-70. Epub Apr. 26, 2005.

Serrano-Vega et al., Conformational thermostabilisation of the β1-adrenergic receptor in a detergent-resistant form. PNAS. 2008 105(3):877-882.

Shi & Javitch. The second extracellular loop of the dopamine D2 receptor lines the binding-site crevice. PNAS 2004. 101:440-445.

Shi et al., Beta2 adrenergic receptor activation. Modulation of the proline kink in transmembrane 6 by a rotamer toggle switch. J Biol Chem. Oct. 25, 2002;277(43):40989-96. Epub Aug. 6, 2002.

Shibata et al. Thermostabilization of the Neurotensin Receptor NTS1, J. Mol. Biol. 2009 390(2):262-277.

Skerra. 'Anticalins': a new class of engineered ligand-binding proteins with antibody-like properties. J. Biotechnol. 2001. 74(4):257-275.

Sobek et al., Microarray technology as a universal tool for high-throughput analysis of biological systems. Combinat. Chem. & High Throughput Screening. 2006. 9:365-380.

Spalding et al., Structural Requirements of Transmembrane Domain 3 for Activation by the M1 Muscarinic Receptor Agonists AC-42, AC-260584, Clozapine, and N-Desmethylclozapine: Evidence for Three Distinct Modes of Receptor Activation. Mol. Pharmacol. 2006. 70:1974-1983.

Standfuss et al., Crystal Structure of a thermally stable rhodopsin mutant. J Mol Biol. 2007 372(5):1179-1188.

Steipe et al., Sequence statistics reliably predict stabilizing mutations in a protein domain. J. Mol. Biol. 1994. 240:188-192.

Stenlund et al., Capture and reconstitution of G protein-coupled receptors on a biosensor surface. Analytical Biochemistry. 2003. 316:243-250.

Stock et al., Robotic nanolitre protein crystallisation at the MRC Laboratory of Molecular Biology. Prog. Biophys. Mil. Biol. 2005. 88:311-327.

Sugimoto et al., Beta(1)-selective agonist (−)-(3,4-dimethoxyphenetylamino)-3-(3,4-dihydroxy)-2-propanol [(-31)-RO363] differentially interacts with key amino acids responsible for beta(1)-selective binding in resting and active states. J Pharmacol Exp Ther. Apr. 2002;301(1):51-8.

Sung et al., Rhodopsin Mutations Responsible for Autosomal Dominant Retinitis Pigmentosa. J. Biol. Chem. 1993. 268(35):26645-26649.

Sutcliffe et al., Knowledge based modelling of homologous proteins, part I: three-dimensional frameworks derived from the simultaneous superposition of multiple structures. Protein Eng. 1987. 1:377-384.

Swaminath et al., Sequential Binding of Agonists to the 2 Adrenoceptor. J. Biol. Chem. 2004. 279(1):686-691.

Szklarz & Halpert. Use of homology modeling in conjunction with site-directed mutagenesis for analysis of structure-function relationships of mammalian cytochromes P450. Life Sci. 1997. 61:2507-2520.

Tan et al., FGF and stress regulate CREB and ATF-1 via a pathway involving p38 MAP kinase and MAPKAP kinase-2. EMBO J. 1996. 15(17):4629-4642.

Tao et al., Chimeras of the Rat and Human FSH Receptors (FSHRs) Identify Residues that Permit or Suppress Transmembrane 6 Mutation-Induced Constitutive Activation of the FSHR via Rearrangements of Hydrophobic Interactions Between Helices 6 and 7. Mol. Endocrinol. 2002. 16(8):1881-1892.

Tate. Overexpression of mammalian integral membrane proteins for structural studies. FEBS Lett. 2001. 504:94-98.

Tate. Baculovirus-Mediated Expression of Neurotransmitter Transporters. Methods Enzymol. 1998. 296:443-455.

Teng et al., Control of feeding behavior in *C. elegans* by human G protein-coupled receptors permits screening for agonist-expressing bacteria. PNAS. 2008. 105(39):14826-14831.

Teng et al., Expression of mammalian GPCRs in *C. elegans* generates novel behavioural responses to human ligands. BMC Biology. 2006. 4:22.

Themmen & Huhtaniemi. Mutations of Gonadotropins and Gonadotropin Receptors: Elucidating the Physiology and Pathophysiology of Pituitary-Gonadal Function. Endocr. Rev. 2000. 21(5):551-583.

Thompson et al., Clustal W: improving the sensitivity of progressive multiple sequence alignment through sequence weighting, position-specific gap penalties and weight matrix choice Nucl. Acids Res. 1994. 22:4673-4680.

Yano et al., Phe576 Plays an Important Role in the Secondary Structure and Intracellular Signaling of the Human Luteinizing Hormone/Chorionic Gonadotropin Receptor. J. Clin. Endocrinol. Metabl. 1997. 82(8):2586-2591.

Yao et al., Coupling ligand structure to specific conformational switches in the β2-adrenoceptor. Nat. Chem. Biol. 2006. 2(8):417-422.

Yarden et al., The avian beta-adrenergic receptor: Primary structure and membrane topology. Proc. Natl. Acad. Sci. USA. 1986. 83:6795-6799.

Yohannan et al., The evolution of transmembrane helix kinks and the structural diversity of G protein-coupled receptors. PNAS. 2004. 101(4):959-963.

Yokogawa et al., Bead-linked Proteoliposomes: A Reconstitution Method for NMR Analyses of Membrane Protein-Ligand Interactions. J. Am. Chem. So. 2005. 127:12021-12027.

Zeitoun, O. et al., 2006, Mutagenesis within Helix 6 of the Human β1-Adrenergic Receptor Identifies Lysine324 as a Residue Involved in Imparting the High-Affinity Binding State of Agonists, Molecular Pharmacology, 70(3):838-850.

Zhang et al., Structure modelling of all identified G-protein coupled receptors in the human genome. PloS Computational Biology. 2006. 2(2):88-99.

Zhao et al. A homogeneous enzyme fragement complementation-based {beta}-Arrestin translocation assay for high-throughput screening of G-Protein-Coupled receptors: J. Biomol Screen 2008;13(8):737-747; Epub 2008.

Zheng et al., An efficient one-step site-directed and site-saturation mutagenesis protocol. Nucl. Acids Res. 2004. 32:e115.

Zhou & Bowie. Building a Thermostable Membrane Protein. J. Biol. Chem. 2000. 275:6975-6979.

Zurawski et al., A novel biosensor assay for screening peptide antagonism of the interaction between HIV-1 envelope, CD4 and membrane-embedded CCR5. Biopolymers. 2003. 71:388-389. Abstract P395.

Lehmann et al., The consensus concept for thermostability engineering of proteins. Biochim Biophys Acta. Dec. 29, 2000;1543(2):408-415.

Lu et al., Transmembrane domains 4 and 7 of the M(1) muscarinic acetylcholine receptor are critical for ligand binding and the receptor activation switch. J Biol Chem. Sep. 7, 2001;276(36):34098-104. Epub Jul. 5, 2001.

Pogozheva et al., Interactions of human melanocortin 4 receptor with nonpeptide and peptide agonists. Biochemistry. Aug. 30, 2005;44(34):11329-41.

Robertson et al., The properties of thermostabilised G protein-coupled receptors (StaRs) and their use in drug discovery. Neuropharmacology 60: 36-44, 2011.

Shoichet et al., Structure-based drug screening for G-protein-coupled receptors. Trends in Pharma Science 33(5): 268-272, 2012.

Voet et al., Protein Stability. Chapter 7: Three-Dimensional Structures of Proteins; Section 7-4. Protein Stability. Biochemistry $2^{nd}$ Edition. 1995. 179-180.

Zhang et al., Adopting selected hydrogen bonding and ionic interactions from *Aspergillus fumigatus* phytase structure improves the

(56) References Cited

OTHER PUBLICATIONS thermostability of *Aspergillus niger* PhyA phytase. Appl Environ Microbiol. May 2007;73(9):3069-76. Epub Mar. 9, 2007.
Alberts et al., Solubilizing membrane proteins with a mild detergent. Molecular Biology of the Cell 2002;4th Edition. New York: Garland Science. Figure 10-24.
Schimerlik, Overview of membrane protein solubilization. Current Protocols in Neuroscience 2001;5.9.1-5.9.5. Abstract.
Topiol & Sabio. Use of the X-ray structure of the β-adrenergic receptor for drug discovery. Bioorganic & Medicinal Chemistry. 2008. 18(5):1598-1602.
Traunecker et al., Bispecific single chain molecules (Janusins) target cytotoxic lymphocytes on HIV infected cells. EMBO J. 1991. 10:3655-3659.
Tucker & Grisshammer. Purification of a rat neurotensin receptor expressed in *Escherichia coli*. Biochem. J. 1996. 317(Pt. 3):891-899.
Urizar et al. An activation switch in the rhodopsin family of G protein-coupled receptors: The Thyrotropin receptor J. Biol Chem 2005 280(17):17135-17141.
Vagin & Teplyakov. MOLREP: an automated program for molecular replacement. J. Appl. Cryst. 1997. 30:1022-1025.
Vakser. Evaluation of GRAMM low-resolution docking methodology on hemagglutinin-antibody complex. Proteins, Suppl. 1997. 1:226-230.
Venturi & Hunte. Monoclonal antibodies for the structural analysis of the Na+/H+ antiporter NhaA from *Escherichia coli*. Biochimica et aBiophysica Acta. 2003. 1610:46-50.
Walters et al., Virtual screening—an overview. Drug Discovery Today. 1998. 3(4):160-178.
Wang. Basic Amino Acids at the C-Terminus of the Third Intracellular Loop Are Required for the Activation of Phospholipase C by Cholecystokinin-B Receptors. J. Neurochem. 1997. 68(4):1728-1735.
Warne et al., Structure of a β1-adrenergic G protein-coupled receptor. Nature. 2008. 454:486-491.
Warne et al., Expression and purification of truncated, non-glycosylated turkey beta-adrenergic receptors for crystallization. Biochim. Biophys. Acta. 2003. 1610:133-140.
Warne et al., The purification of G-protein coupled receptors for crystallization, Structural Biology of Membrane Proteins, Royal Society of Chemistry. 2006. 51-71.
Weber et al., A 1,536-Well cAMP Assay for Gs- and Gi-Coupled Receptors Using Enzyme Fragmentation Complementation. Assay Drug Dev. Technol. 2004.2(1):39-49.
Weiβ & Grisshammer. Purification and characterization of the human adenosine A2a receptor functionally expressed in *Escherichia coli*. Eur. J. Biochem. 2002. 269:82-92.
Wess. Molecular Basis of Receptor/G-Protein-Coupling Selectivity. Pharmacol. Ther. 1998. 80:231-264.
White. The progress of membrane protein structure determination. Protein Science. 2004. 13:1948-1949.
Williams & Addona. The integration of SPR biosensors with mass spectrometry: possible applications for proteome analysis. Trends Biotechnol. 2000. 18(2):45-48.
Williams. Biotechnology match making: screening orphan ligands and receptors. Curr. Opin. Biotechnol. 2000. 11(1):42-46.
Winter & Milstein. Man-made antibodies. Nature. 1991. 349:293-299.
Winter et al., Surface binding affinity measurements from order transitions of lipid-membrane-coated colloidal particles. Anal. Chem. 2006. 78:174-180.
Wurch et al., Chimeric Receptor Analysis of the Ketanserin Binding Site in the Human 5-Hydroxytryptamine 1D Receptor: Importance of the Second Extracellular Loop and Fifth Transmembrane Domain in Antagonist Binding. Mol. Pharmacol. 1998. 54(6):1088-1096.
Wyckoff. Diffractometry. Methods in Enzymology. 1985. 114:330-386.

* cited by examiner

Figure 1A

Class 1
Clustal W alignment of transmembrane 2 Human sequences
Including Ballesteros residues 1.50 (N) and 2.50 (D)

```
                         N                                D
GPR162      ---ANAWIILSIS-AKQQKH------KPLE----LLLCFLAGTHILMAAVPLTTFAVVQL
GPR153      ---ANAWGILSVG-AKQKKW------KPLE----FLLCTLAATHMLNVAVPIATYSVVQL
MrgX3       ---GNAVVLWLLG-CRMRR-------NAVS----IYILNLVAADFLFLSGHIICSPLRLI
MrgX4       ---GNAVVLWLLG-YRMRR-------SAVS----IYILNLAAADFLFLSFQIIRSPLRLI
MrgX1       ---GNAVVLWLLG-CRMRR-------NAFS----IYILNLAAADFLFLSGRLIYSLLSFI
MrgX2       ---GNGFVLWLLG-FRMRR-------NAFS----VYVLSLAGADFLFLCFQIINCLVYLS
MRGD        ---GNSMVIWLLG-FRMHR-------NPFC----IYILNLAAADLLFLFSMASTLSLETQ
MrgE        ---GNGAVLWLLS-SNVYR-------NPFA----IYLLDVACADLIFLGCHMVAIVPDLL
MrgG        ---GNGLVLWNLG-FRIKK-------GPFS----IYLLHLAAADFLFLSCRVGFSVAQAA
MrgF        ---GNGLVLWFFG-FSIKR-------NPFS----IYFLHLASADVGYLFSKAVFSILNTG
MRG         ---LNGTVFWLLC-CGAT--------NPYM----VYILHLVAADVIYLCCSAVGFLQVTL
MAS1        ---ENGILLWFLC-FRMRR-------NPFT----VYITHLSIADISLLFCIFILSIDYAL
GPR139      GLPANILTVIILSQLVARRQ------KSSY----NYLLALAAADILVLFFIVFVDFLLED
GPR142      GLPVSLLTAVALARLATRTR------RPSY----YYLLALTASDIIIQVVIVFAGFLLQG
GPR26       ---SNALVLLCLLH---------SADIRRQAPALFTLNLTCGNLLCTVVNMPLTLAGVV
GPR62       ---SNALVLLCLLH---------SADIRRQAPALFTLNLTCGNLLCTVVNMPLTLAGVV
GPR78       ---SNALVLLCCAY---------SAELRTRASGVLLVNLSLGHLLLAALDMPFTLLGVM
PTGER1      ---SNLLALALLAQ-----AAGRLRRRSATTFLLFVASLLATDLAGHVIPGALVLRLYT
PTGFR       ---SNSLAIAILMK-----AYQRFRQK-SKASFLLLASGLVITDFFGHLINGAIAVFVYA
TBXA2R      ---SNLLALSVLAG-----ARQ--GGSHTRSSFLTFLCGLVLTDFLGLLVTGTIVVSQHA
PTGER3      ---GNALAMLLVSR-----SYRR-RESKRKKSFLLCIGWLALTDLVGQLLTTPVVIVVYL
PTGIR       ---GNGLALGILS--------ARRPAR--PSAFAVLVTGLAATDLLGTSFLSPAVFVAYA
PTGDR       ---GNLLALGLLARSGLGWC-SRRPLRPLPSVFYMLVCGLTVTDLLGKCLLSPVVLAAYA
PTGER2      ---GNLIALALLARRWRGDVGCSAGRRSSLSLFHVLVTELVFTDLLGTCLISPVVLASYA
PTGER4      ---GNLVAIVVLCK---------SRKEQKETTFYTLVCGLAVTDLLGTLLVSPVTIATYM
GPR173      ---GNAILPLLVLKERAL-H------KAPY----YFLLDLCLADGIRSAVCFPFVLASVR
GPR85       ---GNLLISILLVKDKTL-H------RAPY----YFLLDLCCSDILRSAICFPFVFNSVK
GPR27       ---GNVLFALLIVRERSL-H------RAPY----YLLLDLCLADGLRALACLPAVMLAAR
ADORA2      ---GNVLVCWAVWLNSNL-Q------NVTN----YFVVSLAAADIAVGV-LAIP--FAIT
ADORA2B     ---GNVLVCAAVGTANTL-Q------TPTN----YFVLSLAAADVAVGL-FAIP--FAIT
ADORA1      ---GNVLVIWAVKVNQAL-R------DATF----CFIVSLAVADVAVGA-LVIP--LAIL
ADORA3      ---GNVLVICVVKLNPSL-Q------TTTF----YFIVSLALADIAVGV-LVMP--LAIV
MC4R        ---ENILVIVAIAKNKNL-H------SPMY----FFICSLAVADMLVSVSNGSETIIITL
MC5R        ---ENILVIGAIVKNKNL-H------SPMY----FFVCSLAVADMLVSMSSAWETITIYL
MC3R        ---ENILVILAVVRNGNL-H------SPMY----FFLCSLAVADMLVSVSNALETIMIAI
MC1R        ---ENALVVATIAKNRNL-H------SPMY----CFICCLALSDLLVSGTNVLETAVILL
MC2R        ---ENLIVLLAVFKNKNL-Q------APMY----FFICSLAISDMLGSLYKILENILIIL
EDG1        ---ENIFVLLTIWKTKKF-H------RPMY----YFIGNLALSDLLAGVAYTAN--LLLS
EDG3        ---ENLMVLIAIWKNNKF-H------NRMY----FFIGNLALCDLLAGIAYKVN--ILMS
EDG5        ---ENLLVLIAVARNSKF-H------SAMY----LFLGNLAASDLLAGVAFVAN--TLLS
EDG8        ---ENLAVLVLGRHPRF-H------APMF----LLLGSITLSDLLAGAAYAAN--ILLS
EDG6        ---ENLVLVLAAITSHMRS-R------RWVY----YCLVNITLSDLLTGAAYLAN--VLLS
EDG2        ---ANLLVMVAIYVNRRF-H------FPIY----YLMANLAAADFFAGLAYFYL--MFNT
EDG4        ---TNLLVIAAIASNRRF-H------QPIY----YLLGNLAAADLFAGVAYLFL--MFHT
EDG7        ---SNSLVIAAVIKNRKF-H------FPFY----YLLANLAAADFFAGIAYVFL--MFNT
CNR1        ---ENLLVLCVILHSRSL-RC-----RPSY----HFIGSLAVADLLGSVIFVYS--FIDF
CNR2        ---ENVAVLYLILSSHQL-RR-----KPSY----LFIGSLAGADFLASVVFACS--FVNF
GPR6        ---ENALVVALIASTPAL-R------TPMF----VLVGSLATADLLAGCGLILH--FVFQ
GPR12       ---ENAIVVLIIFHNPSL-R------APMF----LLIGSLALADLLAGIGLITN--FVFA
GPR3        ---ENALVVAIIVGTPAF-R------APMF----LLVGSLAVADLLAGLGLVLH--FAAV
MTNR1A      ---GNLLVILSVYRNKKL-R------NAGN----IFVVSLAVADLVVAI-YPYPLVLMSI
MTNR1B      ---GNLLVILSVLRNRKL-R------NAGN----LFLVSLALADLVVAF-YPYPLILVAI
GPR50       ---GNSMVILAVTKNKKL-R------NSGN----IFVVSLSVADMLVAI-YPYPLMLHAM
HTR1B       S---NAFVIATVYRTRKL-HT-----PAN----YLIASLAVTDLLVSILVMPISTMYTV
```

Figure 1B

```
HTR1D    S---NAFVLTTILLTRKL-HT------PAN----YLIGSLATTDLLVSILVMPISIAYTI
HTR1E    ----NLAVIMAIGTTKKL-HQ------PAN----YLICSLAVTDLLVAVLVMPLSIIYIV
HTR1F    I---NSLVIAAIIVTRKL-HH------PAN----YLICSLAVTDFLVAVLVMPFSIVYIV
HTR1A    G---NACVVAAIALERSL-QN------VAN----YLIGSLAVTDLMVSVLVLPMAALYQV
HTR5A    W---NLLVLATILRVRTF-HR------VPH----NLVASMAVSDVLVAALVMPLSLVHEL
HTR5B    W---NLLVPVTIPRVRAF-HR------VPH----NLVASTAVSDELVAALAMPPSLASEL
HTR2C    G---NILVIMAVSMEKKL-HN------ATN----YFLMSLAIADMLVGLLVMPLSLLAIL
HTR2A    G---NILVIMAVSLEKKL-QN------ATN----YFLMSLAIADMLLGFLVMPVSMLTIL
HTR2B    G---NTLVILAVSLEKKL-QY------ATN----YFLMSLAVADLLVGLFVMPIALLTIM
ADRA2A   G---NVLVIIAVFTSRAL-KA------PQN----LFLVSLASADILVATLVIPFSLANEV
ADRA2C   G---NVLVVIAVLTSRAL-RA------PQN----LFLVSLASADILVATLVMPFSLANEL
ADRA2B   G---NALVILAVLTSRSL-RA------PQN----LFLVSLAAADILVATLIIPFSLANEL
ADRA1D   G---NLLVILSVACNRHL-QT------VTN----YFIVNLAVADLLLSATVLPFSATMEV
ADRA1B   G---NILVILSVACNRHL-RT------PTN----YFIVNLAMADLLLSFTVLPFSAALEV
ADRA1A   G---NILVILSVACHRHL-HS------VTH----YYIVNLAVADLLLTSTVLPFSAIFEV
DRD1     G---NTLVCAAVIRFRHL-RS------KVTN---FFVISLAVSDLLVAVLVMPWKAVAEI
DRD5     G---NVLVCAAIVRSRHL-RA------NMTN---VFIVSLAVSDLFVALLVMPWKAVAEV
DRD2     G---NVLVCMAVSREKAL-QT------TTN----YLIVSLAVADLLVATLVMPWVVYLEV
DRD3     G---NGLVCMAVLKERAL-QT------TTN----YLVVSLAVADLLVATLVMPWVVYLEV
DRD4     G---NSLVCVSVATERAL-QT------PTN----SFIVSLAAADLLLALLVLPLFVYSEV
HTR4     G---NLLVMVAVCWDRQL-RK------IKTN---YFIVSLAFADLLVSVLVMPFGAIELV
HRH2     G---NVVVCLAVGLNRRL-RN------L-TN---CFIVSLAITDLLLGLLVLPFSAIYQL
HTR7     G---NCLVVISVCFVKKL-RQ------PSN----YLIVSLALADLSVAVAVMPFVSVTDL
ADRB1    G---NVLVIVAIAKTPRL-QT------LTN----LFIMSLASADLVMGLLVVPFGATIVV
ADRB2    G---NVLVITAIAKFERL-QT------VTN----YFITSLACADLVMGLAVVPFGAAHIL
ADRB3    G---NLLVIVAIAWTPRL-QT------MTN----VFVTSLAAADLVMGLLVVPPAATLAL
HTR6     A---NSLLIALICTQPAL-RN------TSN----FFLVSLFTSDLMVGLVVMPPAMLNAL
GPR88    A---NGMVIYLVSSFRKL-QT------TSN----AFIVNGCAADLSVCALWMPQEAVLGL
HRH1     ---LNLLVLYAVRSERKL-HT------VGN----LYIVSLSVADLIVGAVVMPNILYLL
GPR22    GSNLTVLVLYCMKSN-LI-NS------VSN----IITMNLHVLDVIICVGCIPLTIVILL
CHRM1    G---NLLVLISFKVNTEL-KT------VNN----YFLLSLACADLIIGTFSMNLYTTYLL
CHRM5    G---NVLVMISFKVNSQL-KT------VNN----YYLLSLACADLIIGIFSMNLYTTYIL
CHRM3    G---NILVIVSFKVNKQL-KT------VNN----YFLLSLACADLIIGVISMNLFTTYII
CHRM2    G---NILVMVSIKVNRHL-QT------VNN----YFLFSLACADLIIGVFSMNLYTLYTV
CHRM4    G---NILVMLSIKVNRQL-QT------VNN----YFLFSLACADLIIGAFSMNLYTVYII
HRH3     G---NALVMLAFVADSSL-RT------QNN----FFLLNLAISDFLVGAFCIPLYVPYVL
HRH4     G---NALVILAFVVDKNL-RH------RSS----YFFLNLAFGDLLVGVISIPLYIPHTL
GPR58    ---GNLAMIISISYFKQL-HT------PTN----FLILSMAITDFLLGFTIMPYSMIRSV
GPR57    ---GNLVIMVSISHFKQL-HS------PTN----FLILSMATTDFLLGFVIMPYSIMRSV
TA1      ---GNLIIVISISHFKQL-HT------PTN----WLIHSMATVDFLLGCLVMPYSMVRSA
TA4      ---GNLLVMISILHFKQL-HS------PTN----FLVASLACADFLVGVTVMPFSMVRTV
TA5      ---GNLLVMTSVLHFKQL-HS------PTN----FLIASLACADFLVGVTVMLFSMVRTV
TA3      ---GNLLVMIAILHFKQL-HT------PTN----FLIASLACADFLVGVTVMPFSTVRSV
PNR      ---GNVFVAFAVSYFKAL-HT------PTN----FLLLSLALADMFLGLLVLPLSTIRSV
PROKR2   ---GNFVFIAALTR-YKK-LR------NLTN---LLIANLAISDFLVAIICCPFEMDYYV
PROKR1   ---GNFIFIAALVR-YKK-LR------NLTN---LLIANLAISDFLVAIVCCPFEMDYYV
GPR84    ---GNVLTLLALAI-QPK-LR------TRFN---LLIANLTLADLLYCTLLQPFSVDTYL
OX1R     ---GNTLVCLAVWR-NHH-MR------TVTN---YFIVNLSLADVLVTAICLPASLLVDI
OX2R     ---GNLVCVAVWK-NHH-MR-------TVTN---YFIVNLSLADVLVTITCLPATLVVDI
NPFF2    ---GNTVVCFIVMR-NKH-MH------TVTN---LFILNLAISDLLVGIFCMPITLLDNI
NPFF1    ---GNTLVCFIVLK-NRH-MH------TVTN---MFILNLAVSDLLVGIFCMPTTLVDNL
GPR103   ---GNALVFYVVTR-SKA-MR------TVTN---IFICSLALSDLLITFFCIPVTMLQNI
NPY2R    ---GNSLVIHVVIK-FKS-MR------TVTN---FFIANLAVADLLVNTLCLPFTLTYTL
CCKAR    ---GNTLVITVLIR-NKR-MR------TVTN---IFLLSLAVSDLMLCLFCMPFNLIPNL
CCKBR    ---GNMLIIVVLGL-SRR-LR------TVTN---AFLLSLAVSDLLLAVACMPFTLLPNL
NPY1R    ---GNLALIIIILK-QKE-MR------NVTN---ILIVNLSFSDLLVAIMCLPFTFVYTL
NPY6R    ---GNLSLIIIIFKKQRK-AQ------NFTS---ILIANLSLSDTLVCVMCIHFTIIYTL
NPY4R    ---GNLCLMCVTVR-QKE-KA------NVTN---LLIANLAFSDFLMCLLCQPLTAVYTI
NPY5R    ---GNLLILMALMK-KRN-QK------TTVN---FLIGNLAFSDILVVLFCSPFTLTSVL
GPR10    ---GNCLVLVIAR-VRR-LH-------NVTN---FLIGNLALSDVLMCTACVPLTLAYAF
GRPR     ---GNITLIKIFCT-VKS-MR------NVPN---LFISSLALGDLLLITCAPVDASRYL
NMBR     ---GNIMLVKIFIT-NSA-MR------SVPN---IFISNLAAGDLLLLTCVPVDASRYF
BRS3     ---GNAILIKVFFK-TKS-MQ------TVPN---IFITSLAFGDLLLLLTCVPVDATHYL
EDNRA    ---GNATLLRIIYQ-NKC-MR------NGPN---ALIASLALGDLIYVVIDLPINVFKLL
EDNRB    ---GNSTLLRIIYK-NKC-MR------NGPN---ILIASLALGDLLHIVIDIPINVYKLL
```

Figure 1C

```
GPR37L1    ---GNLSVMCIVWH-SYY-LK-----SAWN----SILAS ALWDFLVLFFCLPIVIFNEI
GPR72      ---GNVVVCHVIFK-NQR-MH-----SATS----LFIVN TVADIMITLLNTPFTLVRFV
GPR19      ---GNSLVCLVIHR-SRR-TQ-----STTN----YFVVSMACADLLISVASTPFVLLQFT
GPR45      ---GNTVVCIIVYQ-RPA-MR-----SAIN----LLLAT AFSDIMLSLCCMPFTAVTLI
GPR63      ---GNLVVCLMVYQ-KAA-MR-----SAIN----ILLAS AFADMLLAVLNMPFALVTIL
GPR161     ---GNLVIVVTLYKKSYL-LT------LSN----KFVFS TLSNFLLSVLVLPFVVTSSI
GPR101     ----GNIVLALVLQRKPQL-LQ------VTN----RFIFN LVTDLLQISLVAPWVVATSV
GPR136     ---GNGYVLYMSSRRKKK-L------RPAE----IMTIN AVCDLGISVVGKPFTIISCF
OPN4       ---GNLTVIYTFCRSRSL-R------TPAN----MFIIN AVSDFLMSFTQAPVFFTSSL
OPN3       ---NNLLVLVLYYKFQRL-R------TPTH----LLLVN SLSDLLVSLFGVTFTFVSCL
RGR        ---LNTLTIFSFCKTPEL-R------TPCH----LLVLS ALADSGISLNALVAATSSLL
OPN1LW     ---TNGLVLAATMKFKKL-R------HPLN----WILVN AVADLAETVIASTISIVNQV
OPN1MW     ---TNGLVLAATMKFKKL-R------HPLN----WILVN AVADLAETVIASTISVVNQV
OPN1SW     ---LNAMVLVATLRYKKL-R------QPLN----YILVNVSFGGFLLCIFSVFPVFVASC
OPN2       ---INFLTLYVTVQHKKL-R------TPLN----YILLN AVADLFMVLGGFTSTLYTSL
TRHR       ---GNIMVLVVMRTKHM-R-------TPTN----CYLVS AVADLMVLVAAGLPNITDSI
GHSR       ---GNLLTMLVVSRFREL-R------TTTN----LYLSSMAFSDLLIFLC-MPLDLV-RL
MTLR1      ---GNVVTVMLIGRYRDM-R------TTTN----LYLGSMAVSDLLILLG-LPFDLY-RL
NMU1R      ---GNGLTCLVILRHKAM-R------TPTN----YYLFS AVSDLLVLLVGLPLELY-EM
NMU2R      ---GNVLVCLVILQHCAM-K------TPTN----YYLFS AVSDLLVLLLGMPLEVY-EM
NTSR1      ---GNTVTAFTLARKKSL-QSL---QSTVH----YHLGS ALSDLLTLLLAMPVELYNFI
NTSR2      ---GNALSVHVVLKARAG-R-----AGRLR----HHVLS ALAGLLLLVGVPVELYSFV
GPR39      ---GNSATIRVTQVLQKK-GYL---QKEVT----DHMVS ACSDILVFLIGMPMEFYSII
GPR52      ---GNLTVIFVFHCAP------LLHHYTTS----YFIQTMAYADLFVGVSCLVPTLSLLH
GPR21      ---GNIIVIFVFHCAP------LLNHHTTS----YFIQTMAYADLFVGVSCVVPSLSLLH
GPR135     ---GNCAVMGVIVK--------HRQLRTVN---AFILS SLSDLLTALLCLPAAFLDLF
GPR75      ---GNFIVFLSFFDPA------FRKFRTNFD---FMILN SFCDLFICGVTAPMFTVFL
TACR1      ---GNVVVMWIIAHKR-------MRTVTN----YFLVN AFAEASMAAFNTVVNFTYAV
TACR3      ---GNLIVIWIILAHKR-------MRTVTN----YFLVN AFSDASMAAFNTLVNFIYAL
TACR2      ---GNAIVIWIILAHRG-------MRTVTN----YFIVN ALADLCMAALNAAFNFVYAS
GALR2      ---GNTLVLAVLLRGG-------QAVSTTN----LFILN GVADLCFILCCVPFQATIYT
GALR3      ---GNGLVLAVLLQPGPS-AW-QEPGSTTD----LFILN AVADLCFILCCVPFQATIYT
GALR1      ---GNSLVITVLARSKPG-----KPRSTTN----LFILN SIADLAYLLFCIPFQATVYA
KISS1R     ---GNSLVIYVICRHKP-------MRTVTN----FYIAN AATDVTFLLCCVPFTALLYP
APLNR      ---GNGLVLWTVFRSSR-----EKR-RSAD----IFIAS AVADLTF-VVTLPLWATYTY
GPR15      ---GN-LVLMGALHFKP-----GSR-RLID----IFLVTLPLWVDKEA
RXFPR3     ---GNLLVLYLMKSMQG-----WRK-SSIN----LFVTN ALTDFQF-VLTLPFWAVENA
GPR100     ---GNLAVLWVLSNCAR-----RAPGPPSD----TFVFN ALADLGL-ALTLPFWAAESA
BDKRB1     ---GNLFVLLVFLLPRR-----QLN--VAE----IYLAN AASDLVF-VLGLPFWAENIW
BDKRB2     ---ENIFVLSVFCLHKS-----SCT--VAE----IYLGN AAADLIL-ACGLPFWAITIS
AGTR2      ---VNIVVVTLFCCQKG-----PKK--VSS----IYIFN AVADLLL-LATLPLWATYYS
CXCR1      ---GNSLVMLVILYSRV-----GRS--VTD----VYLLN ALADLLF-ALTLPIWAA-SK
CXCR2      ---GNSLVMLVILYSRV-----GRS--VTD----VYLLN ALADLLF-ALTLPIWAA-SK
CCR9       ---GNSLVILVYWYCTR-----VKT--MTD----MFLLN AIADLLF-LVTLPFWAI-AA
CXCR4      ---GNGLVILVMGYQKK-----LRS--MTD----KYRLH SVADLLF-VITLPFWAV-DA
CCR6       ---GNILVVITFAFYKK-----ARS--MTD----VYLLNMAIADILF-VLTLPFWAV-SH
CCR7       ---GNGLVVLTYIYFKR-----LKT--MTD----TYLLN AVADILF-LLTLPFWAY-SA
CCR11      ---GNSMVVAIYAYYKK-----QRT--KTD----VYILN AVADLLL-LFTLPFWAV-NA
CXCR6      ---GNSLVLVISIFYHK-----LQS--LTD----VFLVN LPLADLVF-VCTLPFWAY-AG
AGTR1      ---GNSLVVIVIYFYMK-----LKT--VAS----VFLLN ALADLCF-LLTLPLWAVYTA
CCR4       ---GNSVVVLVLFKYKR-----LRS--MTD----VYLLN VFSDLLF-VFSLPFWGYYAA
CCR8       ---GNSLVILVLEVCKK-----LRS--ITD----VYLLN ALSDLLF-VFSFPFQTYYLL
CCR10      ---GNLLLLMVLLRYVP-----RRR--MVE----IYLLN AISNLLF-LVTLPFWGISVA
CCR3       ---GNVVVVMILIKYRR-----LRI--MTN----IYLLN AISDLLF-LVTLPFWIHYAR
CCR1       ---GNILVVLVLVQYKR-----LKN--MTS----IYLLN AISDLLF-LFTLPFWIDYKL
CCRL2      ---DNLLVVLILVKYKG-----LKR--VEN----IYLLN AVSNLCF-LLTLPFWAHAG-
CCR2       ---GNMLVVLILINCKK-----LKC--LTD----IYLLN AISDLLF-LITLPLWAHSAA
CCR5       ---GNMLVILILINCKK-----LRS--MTD----IYLLN AISDLLF-LLTVPFWAHYAA
CX3CR1     ---GNLLVVFALTNSKK-----PKS--VTD----IYLLN ALSDLLF-VATLPFWTHYLI
GPR182     ---ENLLVICVNWRGSG-----RAG--LMN----LYILNMAIADLGI-VLSLPWMLEVT
CXCR7      ---ANSVVVWVNIQAKT-----TGY--DTH----CYILN AIADLWV-VLTIPVWVVSLV
GPR30      ---GNILILVVNISFRE-----KMT--IPD----LYFIN AVADLIL-VADSLIEVFN--
OPRD1      ---GNVLVMFGIVRYTK-------MKTATN----IYIFN ALADALA-TSTLPFQSAKYL
OPRM1      ---GNFLVMYVIVRYTK-------MKTATN----IYIFN ALADALA-TSTLPFQSVNYL
```

Figure 1D

```
OPRK1      ---GNSLVMFVIIRYTK-------MKTATN----IYIFNLALADALV-TTTMPFQSTVYL
OPRL1      ---GNCLVMYVILRHTK-------MKTATN----IYIFNLALADTLV-LLTLPFQGTDIL
SSTR1      ---GNSMVIYVILRYAK-------MKTATN----IYILNLAIADELL-MLSVPFLVTSTL
SSTR4      ---GNALVIFVILRYAK-------MKTATN----IYLLNLAVADELF-MLSVPFVASSAA
SSTR2      ---GNTLVIYVILRYAK-------MKTITN----IYILNLAIADELF-MLGLPFLAMQVA
SSTR5      ---GNTLVIYVVLRFAK-------MKTVTN----IYILNLAVADVLY-MLGLPFLATQNA
SSTR3      ---GNSLVIYVVLRHTA-------SPSVTN----VYILNLALADELF-MLGLPFLAAQNA
NPBWR1     ---GNSAVLYVLLRAPR-------MKTVTN----LFILNLAIADELF-TLVLPINIADFL
NPBWR2     ---GNTAVILVILRAPK-------MKTVTN----VFILNLAVADGLF-TLVLPVNIAEHL
MCHR1      ---GNSTVIFAVVKKSKL----HWCNNVPD----IFIINLSVVDLLF-LLCMPFMIHQLM
GPR145     ---GNILIVFTIIRSRK-------KTVPD----IYICNLAVADLVH-IVGMPFLIHQWA
GPR120     ---GNVCAL-VLVARR-------RRRGATA----CLVLNLFCADLLF-ISAIPLVLAVRW
GPR31      ---GNAVALWTFLFRV-------RVWKPYA----VYLLNLALADLLL-AACLPFLAAFYL
GPR14      ---GNAYTLVVTCRSL-------RAVASMY----VYVVNLALADLLY-LLSIPFIVATYV
GPR25      ---GNAFVVWL-LAGR------RGPRRLVD----TFVLHLAAADLGF-VLTLPLWAAAAA
CXCR3      ---GNGAVAAV-LLSR------RTALSSTD----TFLLHLAVADTLL-VLTLPLWAVDAA
CXCR5      ---GNVLVLVI-LERH------RQTRSSTE----TFLFHLAVADLLL-VFILPFAVAEGS
GPR2       ---GNGLVLATHLAAR------RAARSPTS----AHLLQLALADLLL-ALTLPFAAAGAL
GPR1       ---GNAIVIWFTG--------LKWKKTVT---TLWFLNLAIADFIF-LLFLPLYISYVA
CMKLR1     ---GNGLVIIIAT---------FKMKKTVN---MVWFLNLAVADFLF-NVFLPIHITYAA
FPRL1      ---GNGLVIWVAG---------FRMTRTVT---TICYLNLALADFSF-TATLPFLIVSMA
FPRL2      ---GNGLVIWVAG---------FRMTRTVN---TICYLNLALADFSF-SAILPFRMVSVA
FPR1       ---GNGLVIWVAG---------FRMTHTVT---TISYLNLAVADFCF-TSTLPFFMVRKA
GPR33      ---TNGLYLWVLR---------FKMKQTVN---TLLFFHLILSYFIS-TMILPFMATSQL
GPR44      ----NGVILFVVG---------CRMRQTVV---TTWVLHLALSDLLA-SASLPFFTYFLA
C3AR1      ---GNGLVLWVAG---------LKMQRTVN---TIWFLHLTLADLLC-CLSLPFSLAHLA
GPR32      ---GNGLVLWMTV---------FRMARTVS---TVCFFHLALADFML-SLSLPIAMYYIV
GPR77      ---GNAMVAWVAG---------KVARRRVG---ATWLLHLAVADLLC-CLSLPILAVPIA
C5AR1      ---GNALVVWVTA---------FEAKRTIN---AIWFLNLAVADFLS-CLALPILFTSIV
GPR152     ---ANGLMAWLAG---------SQARHGAGTRLALLLLSLALSDFLF-LAAAAFQILEIR
LTB4R      ---GNSFVVWSIL--K------RMQKRSVT---ALMVLNLALADLAV-LLTAPFFLHFLA
LTB4R2     ---GNGFVVWSLAGWR------PARGRPLA---ATLVLHLALADGAV-LLLTPLFVAFLT
GPR40      ----LNVLAIRGATAH------ARLR---LTPSLVYALNLGCSDLLL-TVSLPLKAVEAL
GPR55      ----LNLLAIHGFSTF------LKNRWPDYAATSIYMINLAVFDLLL-VLSLPFKMVLSQ
GPR41      ----LNLLALVVFVGK------LQR---RPVAVDVLLLNLTASDLLL-LLFLPFRMVEAA
GPR43      ---PANLLALRAFVGR------IRQP--QPAPVHILLLSLTLADLLL-LLLLPFKIIEAA
F2R        ---LNIMAIVVFILKM-------KVKKPAV----VYMLHLATADVLF-VSVLPFKISYYF
GPR17      ---GNTLALWLFIRDH-------KSGTPAN----VFLMHLVLSDLSC-CLVLPTRLVYHF
P2Y5       ---SNCVAIYIFICVL-------KVRNETT----TYMINLAMSDLLF-VFTLPFRIFYFT
P2Y9       ---TNSVSLFVVFCFRM------KMRSETA----IFITNLAVSDLLF-VCTLPFKIFYNF
P2RY8      ---GNLFSLWVLCRRM-------GPRSPSV----IFMINLSVTDLML-ASVLPFQIYYHC
P2RY10     ---ANSAALWVLCRFI-------SKKNKAI----IFMINLSVADLAH-VLSLPLRIYYYI
GPR174     ---GNILALWVFYGYM-------KETKRAV----IFMINLAIADLLQ-VLSLPLRIFYYL
F2RL1      ---SNGMALWVFLFRT-------KKKHPAV----IYMANLALADLLS-VIWFPLKIAYHI
F2RL2      ---ANAVTLWMLFFRT-------RSICTTV----FYT-NLAIADFLF-CVTLPFKIAYHL
F2RL3      ---ANGLALWVLATQA-------PRLPSTM----LLM-NLDATADLLL-ALALPPRIAYHL
CYSLTR2    ---GNGLSIYVFLQPY-------KKSTSVN----VFMLNLAISDLLF-ISTLPFRADYYL
CYSLT1     ---GNGFVLYVLIKTY-------HKKSAFQ----VYMINLAVADLLC-VCTLPLRVVYYV
PTAFR      ---ANGYVLWVFARLYP-----CKKFNEIK----IFMVNLTMADMLF-LITLPLWIVYYQ
EBI2       ---GNLLALVVIVQNR-------KKINSTT----LYSTNLVISDILF-TTALPTRIAYYA
GPR68      ---ANCLSLYFGYLQI-------KARNELG----VYLCNLTVADLFY-ICSLPFWLQYVL
GPR4       ---TNCLALWAAYRQV-------QQRNELG----VYLMNLSIADLLY-ICTLPLWVDYFL
GPR132     ---ANCLTAWLALLQV-------LQGNVLA----VYLLCLALCELLY-TGTLPLWVIYIR
GPR65      ---ANIGSLCVSFLQA-------KKESELG----IYLFSLSLSDLLY-ALTLPLWIDYTW
P2RY2      ---LNAVALYIFLCRL-------KTWNAST----TYMFHLAVSDALY-AASLPLLVYYA
P2RY4      ---LNAPTLWLFIFRL-------RPWDATA----TYMFHLALSDTLY-VLSLPTLIYYA
GPR79      ---LNGTVLWHSWGQT-------KRWSCAT----TYLVNLMVADLLY-VL-LPFLIITYS
P2RY6      ---LNICVITQICTSR-------RALTRTA----VYTLNLALADLLY-ACSLPLLIYNYA
P2RY1      ---GNSVAIWMFVFHM-------KPWSGIS----VYMFNLALADFLY-VLTLPALIFYYF
GPR80      ---GNAVVISTYIFKM-------RPWKSST----IIMLNLACTDLLY-LTSLPFLIHYYA
GPR91      ---GNTIVVYGYIFSL-------KNWNSSN----IYLFNLSVSDLAF-LCTLPMLIRSYA
GPR34      ---GNIIALYVFLGIH-------RKRNSIQ----IYLLNVAIADLLL-IFCLPFRIMYHI
GPR18      ---VNITALWVFSCTT-------KKRTTVT----IYMMNVALVDLIF-IMTLPFRMFYYA
GPR35      ---LNSLALWVFCCRM-------QQWTETR----IYMTNLAVADCLL-LCTLPFVLHS-L
GPR20      ---LNGLALYVFCCRT-------RAKTPSV----IYTINLVVTDLLV-GLSLPTRFAV-Y
```

Figure 1E

```
GPR92        ---LNALALWVFLRAL-------RVHSVVS----VYMCN AASDLLF-TLSLPVRLSY-Y
GPR105       ---LNGVSGWIFFYVP-------SSKSFI-----IYLKN VIADFVM-SLTFPFKILGDS
GPR86        ---LNTLALWVFVHIP-------SSSTFI-----IYLKNTLVADLIM-TLMLPFKILSDS
P2RY12       ---TNGLAMRIFFQIR-------SKSNFI-----IFLKNTVISDLLM-ILTFPFKILSDA
GPR87        ---LNGLAVWIFFHIR-------NKTSFI-----FYLKN VVADLIM-TLTFPFRIVHDA
GPR171       ---GSCFATWAFIQKN-------TNHRCVS----IYLIN LTADFLL-TLALPVKIVVDL
XCR1         ---GSCFATWAFIQKN-------TNHRCVS----IYLIN LTADFLL-TLALPVKIVVDL
GPR109A      ---GNGLALWIFCFH--------LKSWKSSR---IFLFN AVADFLL-IICLPFLMDNYV
GPR109       ---GNGLALWIFCFH--------LKSWKSSR---IFLFN AVADFLL-IICLPFVMDYYV
GPR81        ---GNGVALCGFCFH--------MKTWKPST---VYLFN AVADFLL-MICLPFRTDYYL
OXER1        ---GNSLALFIFCIH--------TRPWTSNT---VFLVS VAADFLL-ISNLPLRVDYYL
P2RY11       ---SNGLALYRFSIRK-------QRPWHPAV---VFSVQ AVSDLLC-ALTLPPLAAYLY
AVPR1A       ---GNSSVLLALHRTPRK-----TSRMH------LFIRH SLADLAVAFFQVLPQMCWDI
AVPR1B       ---GNLAVLLTLGQLGRK-----RSRMH------LFVLH ALTDLAVALFQVLPQLLWDI
OXTR         ---GNACVLLALRTTRQK-----HSRLF------FFMKH SIADLVVAVFQVLPQLLWDI
AVPR2        ---SNGLVLAALARRGRR-G---HWAPIH-----VFIGH LCLADLAVALFQVLPQLAWKA
NPSR1        ---GNSVVLFSTWRRKKK-----SRMT-------FFVTQ AITDSFTGLVNILTDIIWRF
LHCGR        ----GNMTVLFVLLTSRYKLT------VPR----FLMCN SFADFCMGLYLLLIASVDSQ
TSHR         ----GNVFVLLILLTSHYKLN------VPR----FLMCN AFADFCMGMYLLLIASVDLY
FSHR         ----GNIIVLVILTTSQYKLT------VPR----FLMCN AFADLCIGIYLLLIASVDIH
LGR5         ---CNALVTSTVFR-SPLYIS------PIK----LLIGV AAVNMLTGVSSAVLAGVDAF
LGR6         ---CNGLVLLTVFAGGPVPLP------PVK----FVVGA AGANTLGISCGLLASVDAL
LGR4         ---FNLLVILTTFA-SCTSLP------SSK----LFIGL SVSNLFMGIYTGILTFLDAV
HB954        ---GNFMVLWSTCRTTVF-------KSVTN----RFIKN ACSGICASLVCVPFDIILST
GNRHR        ---FNASFLLKLQKWTQKKEK-GKKLSRMK----LLLKH TLANLLETLIVMPLDGMWNI
GPRT151      ---GNLCVIGILLHNAWK-----GKFSMIH----SLILN SLADLSLLLFSAPIRATAYS
RXFP1        ---GNIFVICMRPYIRSE--------NKLY---AMSIIS CCADCLMGIYLFVIGGFDLK
GPR82        ---GNTLSQWIFLTKIGK-------KTSTH----IYLSH VTANLLV-CSAMPFMSIYFL
GPR119       ---TNTLVAVAVLLLIHK-------NDGVS---LCFTLN AVADTLIGVAISGLLTDQLS
GPR148       ---VSPLLLVTILRNQRLRQ------EPHY----LLPAN LLSDLAY--ILLHMLISSSS
GPBAR1       ---ANLLLALGIAWDRRLRS------PPAG----CFFLS LLAGLLTGLALPTLPGLWNQ
FY           ---ASSTVLFMLFRPLFR-------WQLCPG--WPVLAQ AVGSALF-SIVVPVLAPGLG xxxxxxxxxxxxxxxxxxxxxxxxxxx
                                                 TM 2
```

Figure 1F

Class 2
Clustal W alignment Transmembrane 2 Human sequences

```
CALCR      SLGCQRVTLHKNMFLTYI NSMIIIIHLVEVVPNGELVRRD------------PVS---
CALCRL     SLSCQRITLHKNLFFSFVCNSVVTIIHLTAVANNQALVATN------------PVS---
GLP1R      HLHCTRNYIHLNLFASFI RALSVFIKDAALKWMYSTAAQQ---------HQWDGLLSY
GLP2R      KLHCTRNYIHMNLFASFI RTLAVLVKDVVFYNSYSKRPDN---------E--NGWMSY
VIPR2      KLHCTRNYIHLNLFLSFI RAISVLVKDDVLYSSSGTLHCP---------DQPSSWVG-
VIPR1      KLHCTRNYIHMHLFISFI RAAVFIKDLALFDSGESDQCS---------E---GSVG-
SCTR       RLHCTRNYIHMHLFVSFI RALSNFIKDAVLFSSDDVTYCD---------P---HRAG-
PACAPR     KLHCTRNFIHMNLFVSFM RAISVFIKDWILYAEQDSNHCF---------I---STVE-
GHRHR      RLHCPRNYVHTQLFTTFI KAGRVFLKDAALFHSDDTDHCS---------F---STVL-
GIPR       RLHCTRNYIHINLFTSFM RAAAILSRDRLLP-RPGPYLG---------DQALALWN-
GCGR       KLHCTRNAIHANLFASFV KASSVLVIDGLLRTRYSQKIGD---------DLSVSTWLS
PTHR1      RLHCTRNYIHMHLFLSFM RAVSIFVKDAVLYSGATLDEAERLTEEELRAIAQAPPPAT
PTHR2      RLHCTRNYIHMHLFVSFM RATSIFVKDRVVHAHIGVKELESLIMQD--DPQNSIEATSV
CRHR1      SIRCLRNIIHWNLISAFI RNATWFVVQLTMSPEVHQSNVG------------------
CRHR2      SIRCLRNVIHWNLITTFI RNVMWFLLQL-VDHEVHESNEV------------------
           : * *  :* ::: ::: .      :      .
              xxxxxxxxxxxxxxxxxxxx
                       TM2
```

Figure 1G

Class 3
Clustal W alignment transmembrane 2 Human sequences.

```
MGLUR1      LGILVTLFVTLIFVLYRDTPVVKSSSRELCYII AGIFLGYVCPFTLIAKPTTTSC
MGLUR5      LGLLATLFVTVVFIIYRDTPVVKSSSRELCYII AGICLGYLCTFCLIAKPKQIYC
MGLUR2      LGALATLFVLGVFVRHNATPVVKASGRELCYIL GGVFLCYCMTFFIFIAKPSTAVC
MGLUR3      LGFMCTCMVVTVFIKHNNTPLVKASGRELCYILL FGVGLSYCMTFFFIAKPSPVIC
MGLUR8      LGIIATTFVIVTFVRYNDTPIVRASGRELSYVL TGIFLCYSITFLMIAAPDTIIC
MGLUR7      LGIIATIFVMATFIRYNDTPIVRASGRELSYVL TGIFLCYIITFLMIAKPDVAVC
MGLUR4      VGIAATLFVVITFVRYNDTPIVKASGRELSYVL AGIFLCYATTFLMIAEPDLGTC
MGLUR6      LGIVATTTVVATFVRYNNTPIVRASGRELSYVL TGIFLIYAITFLMVAEPGAAVC
CASR        LGIFLTAFVLGVFIKFRNTPIVKATNRELSYLL FSLLCCFSSSLFFIGEPQDWTC
GABABR1     LGIVLAVVCLSFNIYNSHVRYIQNSQPNLNNLTAVGCSLALAAVFPLGLDGYHIGR
GABABR2     LGMIMASAFLFFNIKNRNQKLIKMSSPYMNNLI LGGMLSYASIFLFGLDGSFVSE
GPRC5C      IVTTFVLTIILVASLPFVQDTKKRSLLGTQVFF LGTLGLFCLVFACVVKPDFSTC
RAI3        VVTSVAFMLTLPILVCKVQDSNRRKMLPTQFLF LGVLGIFGLTFAFIIGLDGSTG
GPRC5D      IVVTILLLLAFLFLMRKIQDCSQWNVLPTQLLF LSVLGLFGLAFAFIIELNQQTA
GPRC5B      ALITLLLMLILLVRLPFIKEKEKKSPVGLHFLF LGTLGLFGLTFAFIIQEDETIC
                                          xxxxxxxxxxxxxxxxxxxxx
                                               TM 2
```

Figure 2

```
  1 MPIMGSSVYI TVELAIAVLA ILGNVLVCWA VWLNSNLQNV TNYFVVSLAA ADIAVGVLAI
 61 PFAITISTGF CAACHGCLFI ACFVLVLTQS SIFSLLAIAI DRYIAIRIPL RYNGLVTGTR
121 AKGIIAICWV LSFAIGLTPM LGWNNCGQPK EGKNHSQGCG EGQVACLFED VVPMNYMVYF
181 NFFACVLVPL LLMLGVYLRI FLAARRQLKQ MESQPLPGER ARSTLQKEVH AAKSLAIIVG
241 LFALCWLPLH IINCFTFFCP DCSHAPLWLM YLAIVLSHTN SVVNPFIYAY RIREFRQTFR
301 KIIRSHVLRQ QEPFKAAGTS ARVLAAHGSD GEQVSLRLNG HPPGVWANGS APHPERRPNG
361 YALGLVSGGS AQESQGNTGL PDVELLSHEL KGVCPEPPGL DDPLAQDGAG VS
```

Figure 3

```
  1 MVNLRNAVHS FLVHLIGLLV WQCDISVSPV AAIVTDIFNT SDGGRFKFPD GVQNWPALSI
 61 VIIIIMTIGG NILVIMAVSM EKKLHNATNY FLMSLAIADM LVGLLVMPLS LLAILYDYVW
121 PLPRYLCPVW ISLDVLFSTA SIMHLCAISL DRYVAIRNPI EHSRFNSRTK AIMKIAIVWA
181 ISIGVSVPIP VIGLRDEEKV FVNNTTCVLN DPNFVLIGSF VAFFIPLTIM VITYCLTIYV
241 LRRQALMLLH GHTEEPPGLS LDFLKCCKRN TAEEENSANP NQDQNARRRK KKERRPRGTM
301 QAINNERKAS KVLGIVFFVF LIMWCPFFIT NILSVLCEKS CNQKLMEKLL NVFVWIGYVC
361 SGINPLVYTL FNKIYRRAFS NYLRCNYKVE KKPPVRQIPR VAATALSGRE LNVNIYRHTN
421 EPVIEKASDN EPGIEMQVEN LELPVNPSSV VSERISSV
```

Figure 4

```
  1 MANFTPVNGS SGNQSVRLVT SSSHNRYETV EMVFIATVTG SLSLVTVVGN ILVMLSIKVN
 61 RQLQTVNNYF LFSLACADLI IGAFSMNLYT VYIIKGYWPL GAVVCDLWLA LDYVVSNASV
121 MNLLIISFDR YFCVTKPLTY PARRTTKMAG LMIAAAWVLS FVLWAPAILF WQFVVGKRTV
181 PDNQCFIQFL SNPAVTFGTA IAAFYLPVVI MTVLYIHISL ASRSRVHKHR PEGPKEKKAK
241 TLAFLKSPLM KQSVKKPPPG EAAREELRNG KLEEAPPPAL PPPPRPVADK DTSNESSSGS
301 ATQNTKERPA TELSTTEATT PAMPAPPLQP RALNPASRWS KIQIVTKQTG NECVTAIEIV
361 PATPAGMRPA ANVARKFASI ARNQVRKKRQ MAARERKVTR TIFAILLAFI LTWTPYNVMV
421 LVNTFCQSCI PDTVWSIGYW LCYVNSTINP ACYALCNATF KKTFRHLLLC QYRNIGTAR
```

Figure 5
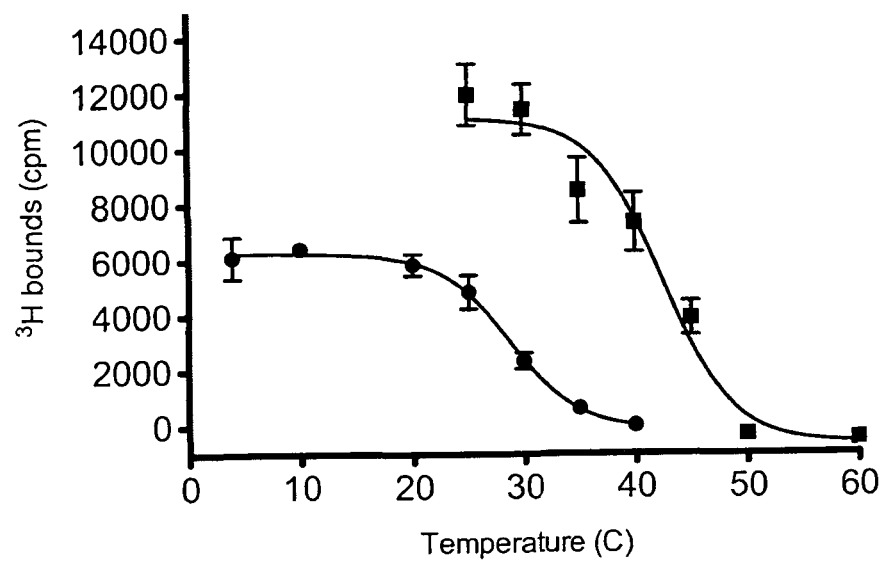
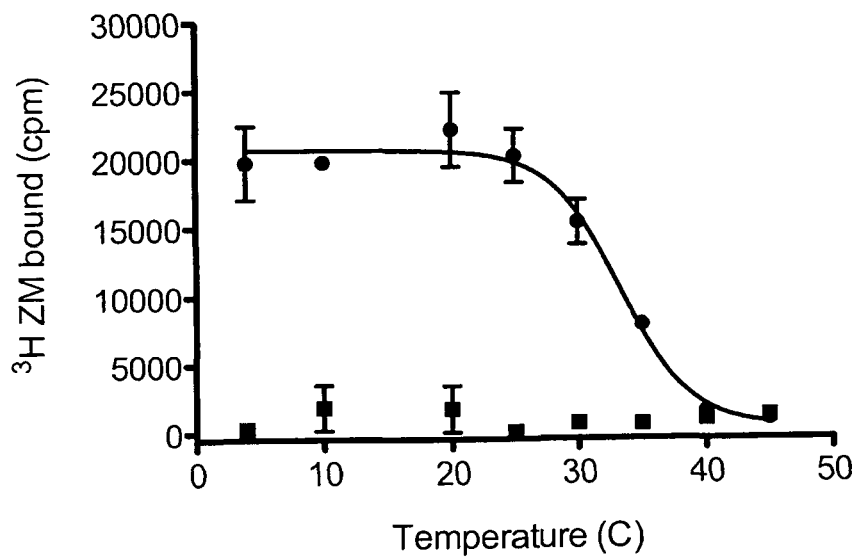

Figure 8
A
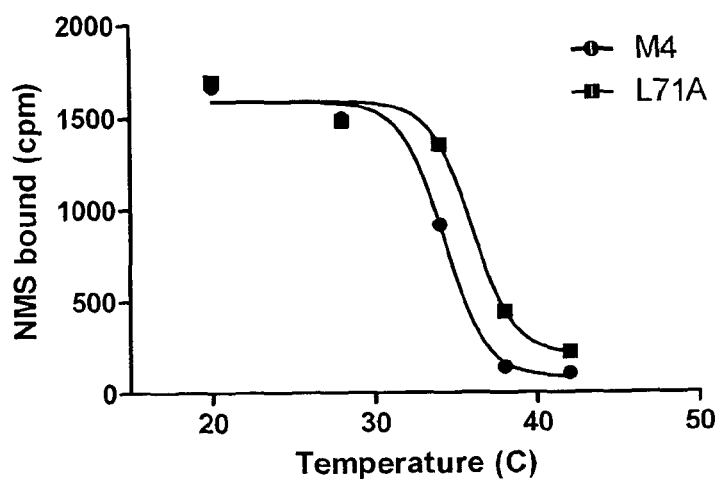
B
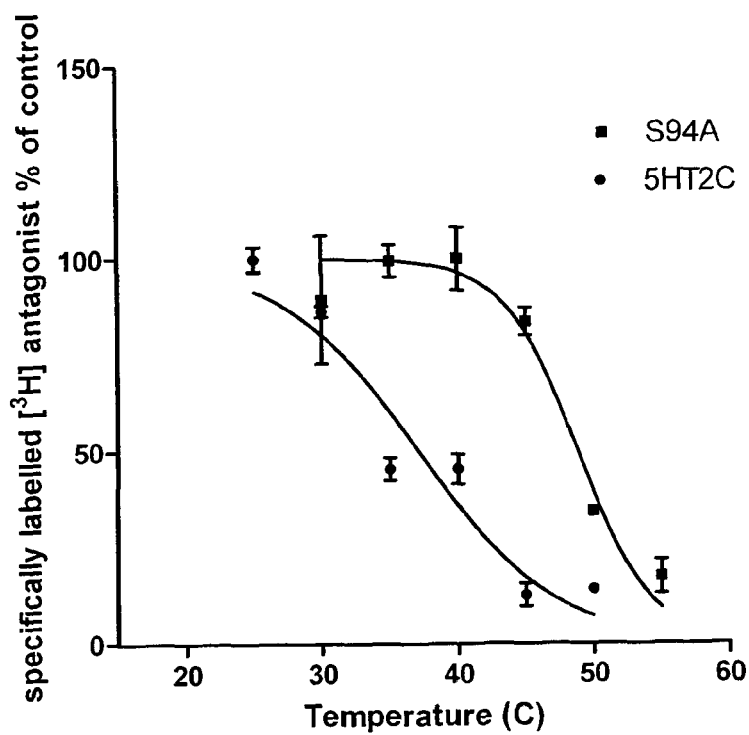

Adenosine A2a – L2.46 and NPxxY C alpha distances

Figure 11

```
  1 mhlnssvpqg tpgepdaqpf sgpqsemeat flalslsngs gntsesdtag pnsdldvntd
 61 iyskvlvtai ylalfvvgtv gnsvtaftla rkkslqslqs tvhyhlgsla lsdllillla
121 mpvelynfiw vhhpwafgda gcrgyyflrd actyatalnv aslsveryla ichpfkaktl
181 msrsrtkkfi saiwlasall aipmlftmgl qnrsgdgthp gglvctpivd tatvkvviqv
241 ntfmsflfpm lvisilntvi ankltvmvhq aaeqgrvctv gthnglehst fnmtiepgrv
301 qalrhgvlvl ravviafvvc wlpyhvrrlm fcyisdeqwt tflfdfyhyf ymltnalfyv
361 ssainpilyn lvsanfrqvf lstlaclcpg wrhrrkkrpt fsrkpnsmss nhafststr
421 etly
```

Figure 12

```
  1 MGGHPQLRLV KALLLLGLNP VSASLQDQHC ESLSLASNIS GLQCNASVDL IGTCWPRSP
 61 GQLVVRPCPA FFYGVRYNTT NNGYRECLAN GSWAARVNYS ECQEILNEEK KSKVHYHVAV
121 IINYLGHCIS LVALLVAFVL FLRLRSIRCL RNIIHWNLIS AFILRNATWF VVQLTMSPEV
181 HQSNVGWCRL VTAAYNYFHV TNFFWMFGEG CYLHTAIVLT YSTDRLRKWM FICIGWGVPF
241 PIIVAWAIGK LYYDNEKCWF GKRPGVYTDY IYQGPMILVL LINFIFLFNI VRILMTKLRA
301 STTSETIQYR KAVKATLVLL PLLGITYMLF FVNPGEDEVS RVVFIYFNSF LESFQGFFVS
361 VFYCFLNSEV RSAIRKRWHR WQDKHSIRAR VARAMSIPTS PTRVSFHSIK QSTAV
```

Figure 13

```
  1 MSGTKLEDSP PCRNWSSASE LNETQEPLLN PTDYDDEEFL RYLWREYLHP KEYEWVLIAG
 61 YIIVFVVALI GNVLVCVAVW KNHHMRTVTN YFIVNLSLAD VLVTITCLPA TLVVDITETW
121 FFGQSLCKVI PYLQTVSVSV SVLTLSCIAL DRWYAICHPL MFKSTAKRAR NSIVIIWIVS
181 CIIMIPQAIV MECSTVFPGL ANKTTLFTVC DERWGGEIYP KMYHICFFLV TYMAPLCLMV
241 LAYLQIFRKL WCRQIPGTSS VVQRKWKPLQ PVSQPRGPGQ PTKSRMSAVA AEIKQIRARR
301 KTARMLMVVL LVFAICYLPI SILNVLKRVF GMFAHTEDRE TVYAWFTFSH WLVYANSAAN
361 PIIYNFLSGK FREEFKAAFS CCCLGVHHRQ EDRLTRGRTS TESRKSLTTQ ISNFDNISKL
421 SEQVVLTSIS TLPAANGAGP LQNW
```

Figure 14

```
                    50              55           60              65           70           75
CRFR1_RAT     R N I I H W N L I S A F I L R N A T W F V V Q L T V S P E V H
CRFR1_MOUSE   R N I I H W N L I S A F I L R N A T W F V V Q L T V S P E V H
CRFR1_HUMAN   R N I I H W N L I S A F I L R N A T W F V V Q L T M S P E V H
CRFR2_MOUSE   R N V I H W N L I T T F I L R N I A W F L L Q L I D H E V H E
CRFR2_RAT     R N V I H W N L I T T F I L R N I T W F L L Q L I D H E V H E
CRFR2_HUMAN   R N V I H W N L I T T F I L R N V M W F L L Q L V D H E V H E
PTHR1_RAT     R N Y I H M H M F L S F M L R A A S I F V K D A V L Y S G F T
PTHR1_MOUSE   R N Y I H M H M F L S F M L R A A S I F V K D A V L Y S G F T
PTHR1_HUMAN   R N Y I H M H L F L S F M L R A V S I F V K D A V L Y S G A T
PTHR2_MOUSE   R N Y I H L H L F V S F M L R A M S I F V K D R V A Q A H L G
PTHR2_RAT     R N Y I H L H L F V S F M L R A   S I F V K D R V A Q A H L G
PTHR2_HUMAN   R N Y I H M H L F V S F M L R A T S I F V K D R V V H A H I G
VIPR1_MOUSE   R N Y I H M H L F M S F I L R A T A V F I K D M A L F N N G E
VIPR1_RAT     R N Y I H M H L F M S F I L R A T A V F I K D M A L F N S G E
VIPR1_HUMAN   R N Y I H M H L F I S F I L R A A A V F I K D L A L F D S G E
VIPR2_MOUSE   R N Y I H L N L F L S F M L R A I S V L V K D S V L Y S S S G
VIPR2_RAT     R N Y I H L N L F L S F M L R A I S V L V K D S V L Y S S S G
VIPR2_HUMAN   R N Y I H L N L F L S F I L R A I S V L V K D D V L Y S S S G
PACR_MOUSE    R N F I H M N L F V S F M L R A I S V F I K D W I L Y A E Q D
PACR_RAT      R N F I H M N L F V S F M L R A I S V F I K D W I L Y A E Q D
PACR_HUMAN    R N F I H M N L F V S F M L R A I S V F I K D W I L Y A E Q D
SCTR_HUMAN    R N Y I H M H L F V S F I L R A L S N F I K D A V L F S S D D
SCTR_RAT      R N Y I H M H L F V S F I L R A L S N F I K D A V L F S S D D
GHRHR_MOUSE   R N Y I H T Q L F A T F I L K A S A V F L K D A A I F Q G D S
GHRHR_RAT     R N Y I H T Q L F A T F I L K A S A V F L K D A A V F Q G D S
GHRHR_HUMAN   R N Y V H T Q L F T T F I L K A G A V F L K D A A L F H S D D
GIPR_HUMAN    R N Y I H I N L F T S F M L R A A A I L S R D R L L P R P G P
GIPR_RAT      R N Y I H M N L F T S F M L R A G A I L T R D Q L L P P L G P
GLP1R_MOUSE   R N Y I H L N L F A S F I L R A L S V F I K D A A L K W M Y S
GLP1R_RAT     R N Y I H L N L F A S F I L R A L S V F I K D A A L K W M Y S
GLP1R_HUMAN   R N Y I H L N L F A S F I L R A L S V F I K D A A L K W M Y S
GLP2R_HUMAN   R N Y I H M N L F A S F I L R T L A V L V K D V V F Y N S Y S
GLP2R_RAT     R N Y I H M N L F A S F I L K V L A V L V K D M V S H N S Y S
GLR_MOUSE     R N Y I H G N L F A S F V L K A G S V L V I D W L L K T R Y S
GLR_RAT       R N Y I H G N L F A S F V L K A G S V L V I D W L L K T R Y S
GLR_HUMAN     R N A I H A N L F A S F V L K A S S V L V I D G L L R T R Y S
CALCR_MOUSE   R V T L H K H M F L T Y I L N S I I I I H L V E V V P N G D
CALCR_RAT     R V T L H K N M F L T Y I L N S I I I I H L V E V V P N G D
CALCR_HUMAN   R V T L H K N M F L T Y I L N S M I I I H L V E V V P N G E
CALRL_RAT     R I T L H K N L F F S F V C N S I V T I I H L T A V A N N Q A
CALRL_HUMAN   R I T L H K N L F F S F V C N S V V T I I H L T A V A N N Q A
CALRL_MOUSE   R I T L H K N L F F S F I C N S I V T I I H L T A V A N N Q A
              *       : *       :   :   :   :   : .                 :
```

MUTANT PROTEINS AND METHODS FOR PRODUCING THEM

RELATED APPLICATIONS

This application is a national stage filing under 35 U.S.C. §371 of International Application No. PCT/GB2010/001227, filed Jun. 22, 2010, which was published under PCT Article 21(2) in English, the disclosure of which is incorporated in its entirety herein by reference. International Application No. PCT/GB2010/001227 claims priority under 35 U.S.C. §119 (a) to UK Application No. GB0910725.1, filed Jun. 22, 2009, the disclosure of which is incorporated in its entirety herein by reference. International Application No. PCT/GB2010/001227 claims priority under 35 U.S.C. §119(e) to U.S. Provisional Application Ser. No. 61/271,509, filed on Jul. 22, 2009, the disclosure of which is incorporated in its entirety herein by reference.

BACKGROUND OF THE INVENTION

Over the past 20 years the rate of determination of membrane protein structures has gradually increased, but most success has been in crystallising membrane proteins from bacteria rather than from eukaryotes [1].

The listing or discussion of an apparently prior-published document in this specification should not necessarily be taken as an acknowledgement that the document is part of the state of the art or is common general knowledge.

SUMMARY OF THE INVENTION

The present invention relates to mutant 7-transmembrane spanning receptors (7-TMRs) or G protein coupled receptors (GPCRs) and methods for selecting those with increased stability. In particular, it relates to the selection and preparation of mutant GPCRs which have increased stability under a particular condition compared to their respective parent proteins. Such proteins are more likely to be crystallisable, and hence amenable to structure determination, than the parent proteins. They are also useful for drug discovery and development studies.

Aspects of the invention relate to methods for producing a mutant G-protein coupled receptor (GPCR) with increased stability relative to a parent GPCR, the method comprising making one or more mutations in the amino acid sequence that defines a parent GPCR, wherein (i) the one or more mutations are located within a window of i plus or minus 5 residues, where i is the position of amino acid residue 2.46 in the parent GPCR when the parent GPCR is a Class 1 GPCR, or where i is the position of an equivalent amino acid residue in the parent GPCR when the parent GPCR is a Class 2 or 3 GPCR, and/or (ii) the one or more mutations are located within an amino acid sequence of transmembrane helix 7 in the parent GPCR which amino acid sequence interacts with the window of i plus or minus 5 residues, to provide one or more mutants of the parent GPCR with increased stability.

In some embodiments, the one or more mutations in step (i) are located within a window of i plus or minus 4 residues, and the one or more mutations in step (ii) are located within an amino acid sequence of transmembrane helix 7 in the parent GPCR which amino acid sequence interacts with the window of i plus or minus 4 residues. In some embodiments, the one or more mutants of the parent GPCR have increased stability of a particular conformation. In some embodiments, the one or more mutants have increased stability in an agonist or antagonist conformation.

In some embodiments, the one or more mutants of the parent GPCR have increased stability to any one or more of heat, a detergent, a chaotropic agent and an extreme of pH. In some embodiments, the one or more mutants have increased thermostability. In some embodiments, it is determined whether the one or mutants of the parent GPCR are able to couple to a G protein.

In some embodiments, the parent GPCR is a Class 1 GPCR or a Class 2 GPCR. In some embodiments, the parent GPCR is any of an adenosine receptor, a serotonin receptor, a 13-adrenergic receptor, a neurotensin receptor, a muscarinic receptor, a corticotropin releasing hormone receptor or an orexin receptor.

In some embodiments, the amino acid sequence of transmembrane helix 7 in the parent GPCR, which amino acid sequence interacts with the window of i plus or minus 5 residues, is the NPxxY (SEQ ID NO: 1) motif plus or minus 3 residues when the parent GPCR is a Class 1 GPCR or is the SFQ motif plus or minus 3 residues when the parent GPCR is a Class 2 GPCR or is the xPKxY (SEQ ID NO: 4) motif plus or minus 3 residues when the parent GPCR is a Class 3 GPCR.

In some embodiments, the mutant GPCR with increased stability relative to its parent GPCR, is a mutant adenosine receptor which, when compared to the corresponding parent receptor, has a different amino acid at a position which corresponds to any one or more of Leu 48 and Asn 284 according to the numbering of the human adenosine $A_{2A}$ receptor as set out in FIG. 2.

In some embodiment, the mutant adenosine receptor has an amino acid sequence which is at least 20% identical to that of the human adenosine $A_{2A}$ receptor whose sequence is set out in FIG. 2.

In some embodiments, the mutant GPCR with increased stability relative to its parent GPCR, is a mutant serotonin receptor which, when compared to the corresponding parent receptor, has a different amino acid at a position which corresponds to any one or more of Met 93, Ser 94, Leu 95, Ile 363 and Leu 366 according to the numbering of the human $5HT_{2C}$ receptor as set out in FIG. 3. In some embodiments, the mutant serotonin receptor has an amino acid sequence which is at least 20% identical to that of the human $5HT_{2C}$ receptor whose sequence is set out in FIG. 3.

In some embodiments, the mutant GPCR with increased stability relative to its parent GPCR, is a mutant muscarinic receptor which, when compared to the corresponding parent receptor, has a different amino acid at a position which corresponds to Leu 71, according to the numbering of the human M4 muscarinic receptor as set out in FIG. 4. In some embodiments, the mutant muscarinic receptor has an amino acid sequence which is at least 20% identical to that of the human M4 muscarinic receptor whose sequence is set out in FIG. 4.

In some embodiments, the mutant GPCR with increased stability relative to its parent GPCR, is a mutant neurotensin receptor which, when compared to the corresponding parent receptor, has a different amino acid at a position which corresponds to Tyr 369, according to the numbering of the rat neurotensin receptor as set out in FIG. 11. In some embodiments, the mutant neurotensin receptor has an amino acid sequence which is at least 20% identical to that of the rat neurotensin receptor whose sequence is set out in FIG. 11.

In some embodiments, the mutant GPCR with increased stability relative to its parent GPCR, is a mutant corticotropin releasing hormone receptor which, when compared to the corresponding parent receptor, has a different amino acid at a position which corresponds to Ile 163 according to the numbering of human $CRF_1$ as set out in FIG. 12. In some embodiments, the mutant corticotropin releasing hormone receptor has an amino acid sequence which is at least 20% identical to that of human CRF$_1$ whose sequence is set out in FIG. 12.

In some embodiment, the mutant GPCR with increased stability relative to its parent GPCR, is a mutant orexin receptor which, when compared to the corresponding parent receptor, has a different amino acid at a position which corresponds to Tyr 91 according to the numbering of human OX$_2$ as set out in FIG. 13. In some embodiments, the mutant orexin receptor has an amino acid sequence which is at least 20% identical to that of human OX$_2$ whose sequence is set out in FIG. 13.

Further aspects of the invention relate to mutant GPCRs with increased stability relative to its parent GPCR produced by methods described herein.

Further aspects of the invention relate to a mutant GPCR which, when compared to a parent GPCR, has one or more mutations in the amino acid sequence defining the parent GPCR, wherein (i) the one or more mutations are located within a window of i plus or minus 5 residues, where i is the position of amino acid residue 2.46 in the parent GPCR when the parent GPCR is a Class 1 GPCR, or where i is the position of an equivalent amino acid in the parent GPCR when the parent GPCR is a Class 2 or 3 GPCR and/or (ii) the one or more mutations are located within an amino acid sequence of transmembrane helix 7 in the parent GPCR which amino acid sequence interacts with the window of i plus or minus 5 residues, which mutant GPCR has increased stability compared to a parent GPCR when exposed to a destabilising condition.

Further aspects of the invention relate to a composition comprising a mutant GPCR which, when compared to a parent GPCR, has one or more mutations in the amino acid sequence defining the parent GPCR, wherein (i) the one or more mutations are located within a window of i plus or minus 5 residues, where i is the position of amino acid residue 2.46 in the parent GPCR when the parent GPCR is a Class 1 GPCR, or where i is the position of the equivalent amino acid residue in the parent GPCR when the parent GPCR is a Class 2 or 3 GPCR and/or (ii) the one or more mutations are located within an amino acid sequence of transmembrane helix 7 in the parent GPCR which amino acid sequence interacts with the window of i plus or minus 5 residues, characterised in that the mutant GPCR is exposed to a destabilising condition effective to destabilise a parent GPCR to a greater extent than the mutant GPCR.

In some embodiments of mutant GPCRs or compositions described herein, the mutant GPCR is a mutant adenosine receptor which, when compared to the corresponding parent receptor, has a different amino acid at a position which corresponds to any one or more of Leu 48 and Asn 284 according to the numbering of the human adenosine A$_{2A}$ receptor as set out in FIG. 2. In some embodiments, the adenosine receptor has an amino acid sequence which is at least 20% identical to that of the human adenosine A$_{2A}$ receptor whose sequence is set out in FIG. 2.

In some embodiments of mutant GPCRs or compositions described herein, the mutant GPCR is a mutant serotonin receptor which, when compared to the corresponding parent receptor, has a different amino acid at a position which corresponds to any one or more of Met 93, Ser 94, Leu 95, Ile 363 and Leu 366 according to the numbering of the human 5HT$_{2C}$ receptor as set out in FIG. 3. In some embodiments, the mutant serotonin receptor has an amino acid sequence which is at least 20% identical to that of the human 5HT$_{2C}$ receptor whose sequence is set out in FIG. 3.

In some embodiments of mutant GPCRs or compositions described herein, the mutant GPCR is a muscarinic receptor which, when compared to the corresponding parent receptor, has a different amino acid at a position which corresponds to Leu 71 according to the numbering of the human M4 muscarinic receptor as set out in FIG. 4. In some embodiments, the mutant muscarinic receptor has an amino acid sequence which is at least 20% identical to that of the human M4 muscarinic receptor whose sequence is set out in FIG. 4.

In some embodiments of mutant GPCRs or compositions described herein, the mutant GPCR is a neurotensin receptor which, when compared to the corresponding parent receptor, has a different amino acid at a position which corresponds to Tyr 369 according to the numbering of the rat neurotensin receptor as set out in FIG. 11. In some embodiments, the mutant neurotensin receptor has an amino acid sequence which is at least 20% identical to that of the rat neurotensin receptor whose sequence is set out in FIG. 11.

In some embodiments of mutant GPCRs or compositions described herein, the mutant GPCR is a corticotropin releasing hormone receptor which, when compared to the corresponding parent receptor, has a different amino acid at a position which corresponds to Ile 163 according to the numbering of human CRF$_1$ as set out in FIG. 12. In some embodiments, the mutant corticotropin releasing hormone receptor has an amino acid sequence which is at least 20% identical to that of the human CRF$_1$ whose sequence is set out in FIG. 12.

In some embodiments of mutant GPCRs or compositions described herein, the mutant GPCR is an orexin receptor which, when compared to the corresponding parent receptor, has a different amino acid at a position which corresponds to Tyr 91 according to the numbering of human OX$_2$ as set out in FIG. 13. In some embodiments, the mutant orexin receptor has an amino acid sequence which is at least 20% identical to that of human OX$_2$ whose sequence is set out in FIG. 13.

In some embodiments of mutant GPCRs or compositions described herein, the mutant GPCR is membrane free.

In some embodiments of mutant GPCRs or compositions described herein, the mutant GPCR has increased stability compared to a parent GPCR in the absence of a ligand.

In some embodiments of mutant GPCRs or compositions described herein, the mutant GPCR has increased stability compared to its parent GPCR when in the presence of a ligand.

In some embodiments of mutant GPCRs or compositions described herein, the destabilising condition is any of heat, a detergent, a chaotropic agent, an extreme of pH, an organic solvent, an aqueous solution or a membrane free environment.

In some embodiments of mutant GPCRs or compositions described herein, the mutant GPCR has increased stability to any one of heat, a detergent, a chaotropic agent and an extreme of pH.

In some embodiments of mutant GPCRs or compositions described herein, the mutant GPCR has increased thermostability.

In some embodiments of mutant GPCRs or compositions described herein, the mutant GPCR is at least 1° C. more stable than its parent.

In some embodiments of mutant GPCRs or compositions described herein, the mutant GPCR is in a solubilised form.

In some embodiments of mutant GPCRs or compositions described herein, the mutant GPCR is substantially free of other proteins.

In some embodiments of mutant GPCRs or compositions described herein, the mutant GPCR is immobilized to a solid support.

Further aspects of the invention relate to a solid support to which is immobilized a mutant GPCR or a composition described herein.

Further aspects of the invention relate to use of a mutant GPCR or a composition described herein for crystallisation.

Further aspects of the invention relate to use of a mutant GPCR or a composition described herein for drug discovery. In some embodiments, the mutant GPCR or composition is used in a ligand binding screen or in assay development.

Further aspects of the invention relate to use of a mutant GPCR or a composition described herein as a biosensor.

BRIEF DESCRIPTION OF THE DRAWINGS

The invention will now be described in more detail with respect to the following Figures and Examples wherein:

FIG. 1A-G: Clustal W analysis of GPCRs. FIG. 1A-E shows an alignment of Class 1 GPCRs (SEQ ID NOS: 5-284); FIG. 1F shows Class 2 GPCRs (SEQ ID NOS: 285-299); and FIG. 1G shows Class 3 GPCRs (SEQ ID NOS: 300-314), where highlighted region indicates conserved 2.46 residue or its equivalent as the case may be, in each class.

FIG. 2: Amino acid sequence of human adenosine $A_{2A}$ receptor (SEQ ID NO: 315).

FIG. 3: Amino acid sequence of human 5HT2C receptor (SEQ ID NO: 316).

FIG. 4: Amino acid sequence of human M4 muscarinic receptor (SEQ ID NO: 317).

FIG. 5: Thermostability of $A_{2A}$-WT receptor (black circle) and $A_{2A}$-L48A mutant (black square) in ligand-bound state solubilised in DDM. (A) NECA agonist-bound state, $Tm_{WT}=28.7\pm0.5°$ C., $Tm_{L48A}=42.5\pm1.0°$ C.; (B) ZM antagonist bound state, $Tm_{WT}=33.0\pm0.7°$ C., $Tm_{L48A}=$n.a; no binding detected. ZM and NECA are used at a concentration of 10× the $K_d$, respectively 100 nM and 400 nM.

FIG. 8: (A) Thermostability of M4 receptor bound to antagonist. $Tm_{M4}=34.0°$ C. and $Tm_{L71A}=36.0°$ C.; (B) Thermostability of 5HT2C receptor bound to antagonist. $Tm_{5HT2C}=37.1°$ C. and $Tm_{S94A}=48.9°$ C.

FIG. 11: Amino acid sequence of rat neurotensin receptor (SEQ ID NO: 318).

FIG. 12: Amino acid sequence of human $CRF_1$ (SEQ ID NO: 319).

FIG. 13: Amino acid sequence of human $OX_2$ (SEQ ID NO: 320).

FIG. 14: Alignment of TM2 region of Class 2 GPCRs (SEQ ID NOS: 321-362). The conserved residue 2.59 is highlighted. Residue 2.50 is also highlighted for reference.

DETAILED DESCRIPTION OF THE INVENTION

Figure 6:
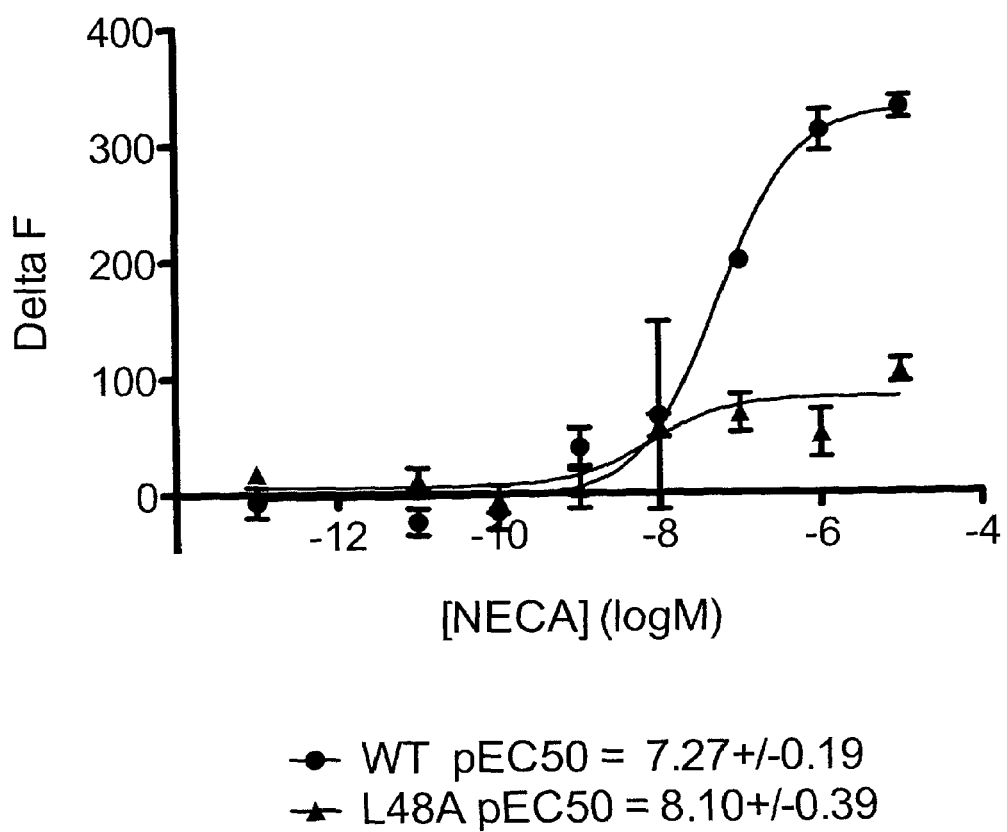
FIG. 6: Representative cAMP dose response curve showing the effect of NECA stimulation. (black circle) $A_{2A}$-WT; $pEC_{50}=7.3\pm0.2°$ C. (black triangle) $A_{2A}$-L48A; $pEC_{50}=8.1\pm0.4°$ C.

Bacterial membrane proteins have been easier to overexpress using standard techniques in *Escherichia coli* than eukaryotic membrane proteins [2,3] and the bacterial proteins are sometimes far more stable in detergent, detergent-stability being an essential prerequisite to purification and crystallisation. Genome sequencing projects have also allowed the cloning and expression of many homologues of a specific transporter or ion channel, which also greatly improves the chances of success during crystallisation. Although the structures of over 100 unique polytopic integral membrane proteins have been determined (see blanco.biomol.uci.edu/), less than 10% of these membrane proteins are of mammalian origin and over half were purified from natural sources and are stable in detergent solutions. Apart from the difficulties in overexpressing eukaryotic membrane proteins, they often have poor stability in detergent solutions, which severely restricts the range of crystallisation conditions that can be explored without their immediate denaturation or precipitation. Ideally, membrane proteins should be stable for many days in any given detergent solution, but the detergents that are best suited to growing diffraction-quality crystals tend to be the most destabilising detergents ie those with short aliphatic chains and small or charged head groups. It is also the structures of human membrane proteins that we would like to solve, because these are required to help the development of therapeutic agents by the pharmaceutical industry; often there are substantial differences in the pharmacology of receptors, channels and transporters from different mammals, whilst yeast and bacterial genomes may not include any homologous proteins. There is thus an overwhelming need to develop a generic strategy that will allow the production of detergent-stable eukaryotic integral membrane proteins for crystallisation and structure determination and potentially for other purposes such as drug screening, bioassay and biosensor applications.

Membrane proteins have evolved to be sufficiently stable in the membrane to ensure cell viability, but they have not evolved to be stable in detergent solution, suggesting that membrane proteins could be artificially evolved and detergent-stable mutants isolated [4]. This was subsequently demonstrated for two bacterial proteins, diacylglycerol kinase (DGK) [5,6] and bacteriorhodopsin [7]. Random mutagenesis of DGK identified specific point mutations that increased thermostability and, when combined, the effect was additive so that the optimally stable mutant had a half-life of 35 minutes at 80° C. compared with a half-life of 6 minutes at 55° C. for the native protein [6]. It was shown that the trimer of the detergent-resistant DGK mutant had become stable in SDS and it is thus likely that stabilisation of the oligomeric state played a significant role in thermostabilisation. Although the aim of the mutagenesis was to produce a membrane protein suitable for crystallisation, the structure of DGK has yet to be determined and there have been no reports of successful crystallization. A further study on bacteriorhodopsin by cysteine-scanning mutagenesis along helix B demonstrated that it was not possible to predict which amino acid residues would lead to thermostability upon mutation nor, when studied in the context of the structure, was it clear why thermostabilisation had occurred [7].

GPCRs constitute a very large family of proteins that control many physiological processes and are the targets of many effective drugs. Thus, they are of considerable pharmacological importance. A list of GPCRs is given in Foord et al (2005) *Pharmacol Rev.* 57, 279-288, which is incorporated herein by reference. GPCRs are generally unstable when isolated, and until recently, it has not been possible to crystallise any except bovine rhodopsin, which is exceptionally stable in its native unilluminated state.

By GPCRs we include all 7-TMRs within the GPCR superfamily, including receptors that signal to G proteins as well as those receptors which do not signal to G proteins.

GPCRs are druggable targets and reference is made to Overington et al (2006) *Nature Rev. Drug Discovery* 5, 993-996 which indicates that more than a quarter of current drugs target GPCRs. There are 52 GPCR targets for orally available drugs out of a total of 186 total targets in this category. GPCRs are thought to exist in multiple distinct conformations which are associated with different pharmacological classes of ligand such as agonists and antagonists, and to cycle between these conformations in order to function (Kenakin T. (1997) *Ann N Y Acad Sci*812, 116-125).

GPCRs have evolved to recognise a wide range of different ligands; however, the basic mechanisms for receptor activation are conserved across receptors and as a result there are well known structural motifs which are present in the vast majority of GPCRs within the different subfamilies. These motifs include the NPxxY (SEQ ID NO: 1) sequence in transmembrane helix 7 (TM7) of Class 1 GPCRs (Ballesteros, Shi and Javitch 2001 Mol Pharmacology 60, 1-19), a region which is thought to be involved in coupling to effectors such as G proteins. Transmembrane helix 2 (TM2) is part of the core structure of GPCRs and in Class 1 contains the highly conserved sequence motif (N/S)LAX(A/S)D (SEQ ID NO: 2) also known as the SLACAD (SEQ ID NO: 3) (Baldwin, J. M., Schertler, G. F. X., and Unger, V. M. (1997) J. Mol. Biol. 272, 144-164) motif which is present in biogenic amine receptors. The leucine within this motif is L2.46 as defined using the Ballesteros numbering system described below. Reciprocal mutagenesis studies have suggested a link between TM2 and TM7 involving the NPxxY (SEQ ID NO: 1) motif and the (N/S)LAX(A/S)D (SEQ ID NO: 2) motif (Bee and Hulme J Biol. Chem. 2007 Nov. 2; 282(44):32471-9 and references therein). These regions are involved in receptor activation and the switch between active and inactive states which have altered affinities for agonists and antagonist ligands relative to each other. Mutagenesis of residues within these two motifs can alter the conformation of the receptor.

In Class 2 GPCRs there is also evidence for a functionally important link between TM2 and TM7. TM7 contains the motif SFQ which is conserved among Class 2 GPCRs and this has been shown to be linked to the ARL motif in TM2. For example, in the parathyroid receptor (PTHR1) Arg233 (adjacent to Leu232) in TM2 and Gln451 in TM7 have effects on agonist binding and signalling (Gardella T J, Luck M D, Fan M H, Lee C Biol. Chem. 1996 May 31; 271(22):12820-5). Thus, the leucine in the ARL motif which is Leu232 in the PTHR1 receptor has an equivalent role to L2.46 described above. It is of note that the only Class 2 secretin family member which does not have a leucine in this position is the calcitonin receptor like receptor (CRLR). This is the only receptor in this group which does not function alone as a signalling GPCR but requires interaction with a RAMP protein (Foord and Marshall, Trends Pharmacol Sci. 1999 May; 20(5):184-7).

The NPxxY (SEQ ID NO: 1) motif is also present in Class 3 GPCRs (xPKxY; SEQ ID NO: 4) (Pin, Galvez and Prezeau, Pharmacology and Therapeutics 98, 325-354) and may be linked to a highly conserved leucine residue in TM2 (Leu635 in metabotropic glutamate receptor1) in an equivalent way to L2.46 in Class 1 receptors. It is of note that the only Class 3 GPCR which does not have a leucine or related amino acid in this position is the R1 subunit of the $GABA_B$ receptor. This receptor does not signal directly to G proteins but instead signals via its binding partner $GABA_B$ R2 (Duthey et al, J Biol. Chem. 2002 Feb. 1; 277(5):3236-41), which does contain the closely related isoleucine at this position.

The inventors have previously developed various methodologies for selecting mutations that improve the stability of GPCRs, and, in addition, that preferentially lock the receptor in a specific biologically relevant conformation. Such methods are described in WO 2008/114020 and in WO 2009/071914, incorporated herein by reference.

The inventors have now developed a further method for producing mutant GPCRs with increased stability relative to a parent GPCR. Specifically, they have identified that mutating amino acid residue 2.46 and nearby residues can be used to provide mutant GPCRs with increased stability in a particular conformation.

Accordingly, a first aspect of the invention provides a method for producing a mutant G-protein coupled receptor (GPCR) with increased stability relative to a parent GPCR, the method comprising making one or more mutations in the amino acid sequence that defines a parent GPCR, wherein (i) the one or more mutations are located within a window of i plus or minus 5 residues, where i is the position of amino acid residue 2.46 in the parent GPCR when the parent GPCR is a Class 1 GPCR, or where i is the position of an equivalent amino acid residue in the parent GPCR when the parent GPCR is a Class 2 or 3 GPCR, and/or (ii) the one or more mutations are located within an amino acid sequence of transmembrane helix 7 of the parent GPCR which amino acid sequence interacts with the window of i plus or minus 5 residues, to provide one or more mutants of the parent GPCR with increased stability.

Thus, the invention provides a method for producing a mutant G-protein coupled receptor (GPCR) with increased stability relative to a parent GPCR, the method comprising making one or more mutations in the amino acid sequence that defines a parent GPCR, wherein (i) the one or more mutations are located within a window of i plus or minus 4 residues, where i is the position of amino acid residue 2.46 in the parent GPCR when the parent GPCR is a Class 1 GPCR, or where i is the position of an equivalent amino acid residue in the parent GPCR when the parent GPCR is a Class 2 or 3 GPCR, and/or (ii) the one or more mutations are located within an amino acid sequence of transmembrane helix 7 of the parent GPCR which amino acid sequence interacts with the window of i plus or minus 4 residues, to provide one or more mutants of the parent GPCR with increased stability.

Suitable GPCRs for use in the practice of the invention include, but are not limited to adenosine receptor, in particular adenosine $A_{2A}$ receptor (gene name: ADORA2A), muscarinic receptor, serotonin receptor (eg $5HT_2$; gene name HTR2C), β-adrenergic receptor (e.g. βAR-1; gene name: ADRB1), neurotensin receptor ($NTS_1$; gene name: NTSR1), corticotropin releasing hormone receptor (e.g. CRF1; gene name: CRHR1), and orexin receptor (e.g. $OX_2$; gene name: HTR2C). In addition, the International Union of Pharmacology produces a list of GPCRs (Foord et al (2005) *Pharmacol. Rev.* 57, 279-288, incorporated herein by reference and this list is periodically updated at iuphar-db.org/GPCR/Receptor-FamiliesForward). It will be noted that GPCRs are divided into different classes, principally based on their amino acid sequence similarities, for example Classes 1, 2 and 3 whose archetypes are rhodopsin, the secretin receptor and the metabotropic glutamate receptor 1. A list of Class 1, 2 and 3 GPCRs is provided in FIGS. 1a, 1b and 1c respectively. Class 2 GPCRs are also listed in FIG. 14. GPCRs are also divided into families by reference to the natural ligands to which they bind. All GPCRs, including 7-TMRs in the superfamily of GPCRs, are included in the scope of the invention.

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene (ncbi.nlm.nih.gov/entrez). It should be noted, also, that because the sequence of the human genome is substantially complete, the amino acid sequences of human GPCRs can be deduced therefrom.

Although the parent GPCR may be any GPCR, it is particularly preferred if it is a eukaryotic GPCR, that is the cDNA or gene encoding the GPCR is a eukaryotic cDNA or gene. For example, it is particularly preferred if the parent GPCR is a vertebrate GPCR such as a GPCR from a mammal. It is particularly preferred if the parent GPCR is from rat, mouse, rabbit or dog or non-human primate or human, or from chicken or turkey.

It is appreciated that the amino acid sequence defining the parent GPCR need not be an amino acid sequence defining the naturally occurring protein. Conveniently, it may define an engineered version which is capable of expression in a suitable host organism, such as in bacteria, yeast, insect cells or in mammalian cells. The amino acid sequence defining the parent GPCR may be an amino acid sequence defining a truncated form of the naturally occurring protein (truncated at either or both ends), or an amino acid sequence defining a fusion, either to the naturally occurring protein or to a fragment thereof, or an amino acid sequence that contains mutations compared to the naturally-occurring sequence. Alternatively or additionally, the amino acid sequence defining the parent GPCR, compared to a naturally-occurring GPCR, may be modified in order to improve, for example, solubility or proteolytic stability (eg by truncation, deletion of loops, mutation of glycosylation sites or mutation of reactive amino acid side chains such as cysteine). In any event, it will be appreciated that the amino acid sequence defining the parent GPCR is one that defines a GPCR that is able to bind to a ligand. The ligand may bind to the naturally occurring GPCR, or to a mutant thereof, or to a derivative of the naturally occurring GPCR or mutant thereof. By 'derivative' we include the meaning of a GPCR which compared to the naturally occurring GPCR has been chemically modified, for example by attachment of any chemical moiety to one or more amino acid side chains, or by the insertion of any chemical moiety within the amino acid sequence, but which derivative retains the ability to bind to a ligand.

Conveniently, the amino acid sequence defining a parent GPCR is one that defines a GPCR which, on addition of an appropriate ligand, can affect any one or more of the downstream activities which are commonly known to be affected by activation of G proteins, or other pathways independent of G proteins such as those which include arrestins. For example, where the parent GPCR is a 7-TMR that can signal independently of a G protein (e.g. smoothened or a mutant GPCR which has lost G protein signalling ability but retains signalling to other pathways), the amino acid sequence may be one that defines a parent GPCR which, on addition of an appropriate ligand, activates a G protein independent signalling pathway.

By the "2.46 amino acid residue", we mean the amino acid residue at position 2.46 as defined by the Ballesteros numbering system (Ballesteros JA, Weinstein H. Integrated methods for the construction of three dimensional models and computational probing of structure-function relations in G-protein coupled receptors, *Methods Neurosci* 1995; 25:366-428). This is a general numbering scheme that applies to all rhodopsin-like GPCRs (Class 1 GPCRs). Each residue is identified by the transmembrane helix (TM) number (1 to 7), the most conserved residue within each TM is assigned the number '50', and the positions of all other residues are numbered relative to the most conserved amino acid in each TM segment. Thus, amino acid residue 2.46 corresponds to the residue in TM2 that is 4 residues before the most conserved residue in TM2. The reference residue (i.e. number 50) in each TM has been assigned and they correspond to the following rhodopsin residues: TM1 N55, TM2 D83, TM3 R135, TM4 W161, TM5 P215, TM6 P267 and TM7 P303. The purpose of the Ballesteros numbering system is to facilitate identification of the homologous residues between different GPCRs using rhodopsin alignment as a guide.

Thus, when the parent GPCR is a Class 1 GPCR, i is the position of the 2.46 amino acid residue which can be identified by locating the residue that is the most conserved residue in TM2 (i.e. number 50) and counting four residues before. It is notable that the 2.46 residue is extremely well conserved in all rhodopsin-like GPCRs. Generally, the 2.46 residue is a conserved Leucine residue one helix turn below a conserved Aspartic acid residue, and it is proposed to interact with a conserved sequence domain (NPxxY; SEQ ID NO: 1) within TM7 situated approximately midway within that helix. FIG. 1a provides an alignment of Class 1 GPCRs and shows the position of the 2.46 amino acid residue for each GPCR.

When the parent GPCR is a Class 2 or 3 GPCR, i is the position of an equivalent amino acid residue to the 2.46 amino acid residue. By an 'equivalent amino acid residue to the 2.46 amino acid residue' we mean the amino acid residue in a Class 2 or 3 GPCR that corresponds to the 2.46 amino acid residue in a Class 1 GPCR. It is appreciated that the equivalent amino acid residue in a Class 2 or 3 GPCR may not be one that aligns to the 2.46 amino acid residue in a Class 1 GPCR when the GPCRs are compared, for example by using MacVector and CLUSTALW (Thompson et al (1994) *Nucl. Acids Res.* 22, 4673-4680). Rather, the amino acid residue is equivalent in the sense that it resides in TM2 and interacts with conserved domains within TM7 of Class 2 or 3 GPCRs in the same way that residue 2.46 resides in TM2 and interacts with conserved domains within TM7 of Class 1 GPCRs. Transmembrane helices of GPCRs can be defined using hydrophobicity analysis as is well known in the art.

FIGS. 1b and 14 provide an alignment of Class 2 GPCR amino acid sequences and show the position of the amino acid residue equivalent to the 2.46 amino acid residue for each GPCR. As can be seen, the 2.46 residue in a Class 2 GPCR is typically a highly conserved leucine residue in TM2 adjacent to a highly conserved arginine residue. For example, the 2.46 amino acid residue in the parathyroid hormone receptor (PTHR1) is Leu 232 adjacent to Arg 233. Further, as discussed in Example 3, Leu 164 in human $CRF_1$ is the equivalent to the 2.46 amino acid residue in a Class 1 GPCR. It is appreciated that the equivalent amino acid residue in any other Class 2 GPCR can be identified by locating the amino acid residue that aligns to the 'equivalent amino acid residue' in one of the Class 2 GPCRs listed in FIG. 1b or 14 (e.g. $CRF_1$), when the GPCRs are compared, for example by using MacVector and CLUSTALW (Thompson et al (1994) *Nucl. Acids Res.* 22, 4673-4680).

FIG. 1c provides an alignment of Class 3 GPCR amino acid sequences and shows the position of the amino acid residue equivalent to the 2.46 amino acid residue for each GPCR. As can be seen, the 2.46 residue in a Class 3 GPCR is typically a highly conserved leucine residue in TM2. For example, the 2.46 amino acid residue in the metabotropic glutamate receptor 1 (mGluR1) is Leu 635. It is appreciated that the equivalent amino acid residue in any other Class 3 GPCR can be identified by locating the amino acid residue that aligns to the 'equivalent amino acid residue' in one of the Class 3 GPCRs listed in FIG. 1c, when the GPCRs are compared, for example by using MacVector and CLUSTALW (Thompson et al (1994) *Nucl. Acids Res.* 22, 4673-4680).

Generally, the 2.46 amino acid residue or the equivalent residue is leucine but it is appreciated that it may be another amino acid residue such as isoleucine, methionine, valine, glycine or threonine.

Any suitable method may be used to align two polypeptide sequences, including but not limited to those described in Computational Molecular Biology (A. M. Lesk, ed., Oxford University Press 1988); Biocomputing: Informatics and Genome Projects (D. W. Smith, ed., Academic Press 1993); Computer Analysis of Sequence Data (Part 1, A. M. Griffin and H. G. Griffin, eds., Humana Press 1994); G. von Heinje, Sequence Analysis in Molecular Biology (Academic Press 1987); Sequence Analysis Primer (M. Gribskov and J. Devereux, eds., M. Stockton Press 1991); and Carillo et al., SIAMJ. Applied Math. 48: 1073 (1988). Preferred methods to align polypeptides are designed to give the largest match between the sequences tested. Methods to determine identity and similarity are codified in publicly available computer programs.

Preferred computer program methods to align polypeptide sequences and to determine identity and similarity between two sequences include, but are not limited to, the GCG program package, including GAP (Devereux et al., Nuc. Acids Res. 12: 387 (1984); Genetics Computer Group, University of Wisconsin, Madison, Wis.), BLASTP, BLASTN, and FASTA (Atschul et al., J. Mol. Biol. 215: 403-10 (1990)). The BLAST X program is publicly available from the National Center for Biotechnology Information (NCBI) and other sources (Altschul et al., BLAST Manual (NCB NLM NIH, Bethesda, Md.); Altschul et al., 1990, supra). The well-known Smith Waterman algorithm may also be used to determine identity.

By way of example, using the computer algorithm GAP (Genetics Computer Group), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix (see Dayhoff et al., 5 Atlas of Protein Sequence and Structure (Supp. 3 1978) for the PAM250 comparison matrix; see Henikoff et al., Proc. Natl. Acad. Sci. USA 89: 10915-19 (1992) for the BLOSUM 62 comparison matrix) is also used by the algorithm. Preferred parameters for polypeptide sequence comparison include the following: Algorithm: Needleman and Wunsch, J. Mol. Biol. 48: 443-53 (1970). Comparison matrix: BLOSUM 62 from Henikoff et al., Proc. Natl. Acad.
Sci. U.S.A. 89: 10915-19 (1992) Gap Penalty: 12 Gap Length Penalty: 4 Threshold of Similarity: 0 The GAP program is useful with the above parameters. The aforementioned parameters are the default parameters for polypeptide comparisons (along with no penalty for end gaps) using the GAP algorithm.

By a "window of i plus or minus 5 residues" we include that 2.46 amino acid residue or its equivalent as the case may be, and the five amino acid residues before and the five amino acid residues after, the 2.46 amino acid residue or its equivalent. Thus, within a window of i plus or minus 5 residues, one or more of the i−5, i−4, i−3,i−2, i−1, i, i+1, i+2, i+3, i+4 and i+5 amino acid residues may be mutated, for example any 1, 2, 3, 4, 5, 6, 7, 8, 9, 10 or all 11 of the i−5, i−4, i−3, i−2, i−1, i, i+1, i+2, i+3, i+4 and i+5 amino acid residues may be mutated.

In an embodiment, one or more mutations are made in an amino acid sequence that defines a parent GPCR within a window of i plus or minus 4 residues, where i is the position of amino acid residue 2.46 or its equivalent as the case may be, in the parent GPCR, to provide one or more mutants of the parent GPCR with increased stability. By a "window of i plus or minus 4 residues" we include that 2.46 amino acid residue or its equivalent as the case may be, and the four amino acid residues before and the four amino acid residues after, the 2.46 amino acid residue or its equivalent. Thus, within a window of i plus or minus 4 residues, one or more of the i−4, i−3, i−2, i−1, i, i+1, i+2, i+3 and i+4 amino acid residues may be mutated, for example any 1, 2, 3, 4, 5, 6, 7, 8 or all 9 of the i−4, i−3, i−2, i−1, i, i+1, i+2, i+3 and i+4 amino acid residues may be mutated.

In an embodiment, one or more mutations are made in an amino acid sequence that defines a parent GPCR within a window of i plus or minus 3 residues, where i is the position of amino acid residue 2.46 or its equivalent as the case may be, in the parent GPCR, to provide one or more mutants of the parent GPCR with increased stability. By a "window of i plus or minus 3 residues" we include the 2.46 amino acid residue, or its equivalent, and the three amino acid residues before and the three amino acid residues after, the 2.46 amino acid residue, or its equivalent. Thus, within a window of i plus or minus 3 residues, one or more of the i−3,i−2, i−1, i, i+1, i+2 and i+3 amino acid residues may be mutated, for example any 1, 2, 3, 4, 5, 6 or all 7 of the i−3,i−2, i−1, i, i+1, i+2 and i+3 amino acid residues may be mutated.

In an embodiment, one or more mutations are made in an amino acid sequence that defines a parent GPCR within a window of i plus or minus 2 residues, where i is the position of amino acid residue 2.46 in the parent GPCR or its equivalent as the case may be, to provide one or more mutants of the parent GPCR with increased stability. By a "window of i plus or minus 2 residues" we include the 2.46 amino acid residue, or its equivalent, and the two amino acid residues before and the two amino acid residues after, the 2.46 amino acid residue, or its equivalent. Thus, within a window of i plus or minus 2 residues, one or more of the i−2, i−1, i, i+1 and i+2 amino acid residues may be mutated, for example any 1, 2, 3, 4 or all 5 of the i−2, i−1, i, i+1 and i+2 amino acid residues may be mutated.

In another embodiment, one or more mutations are made in an amino acid sequence that defines a parent GPCR within a window of i plus or minus 1 residue, where i is the position of amino acid residue 2.46 in the parent GPCR or its equivalent as the case may be, to provide one or more mutants of the parent GPCR with increased stability. By a "window of i plus or minus 1 residue" we include the 2.46 amino acid residue, or its equivalent, and the amino acid residue before and the amino acid residue after, the 2.46 amino acid residue, or its equivalent. Thus, within a window of i plus or minus 1 residue, one or more of the i−1, i and i+1 amino acid residues may be mutated, for example any 1, 2 or all 3 of the i−1, i and i+1 amino acid residues may be mutated.

As shown in Example 2, the inventors have demonstrated that making mutations within an amino acid sequence of TM7 of a parent GPCR which amino acid sequence interacts with the window of i plus or minus 5 residues (e.g. with the window of i plus or minus 4 residues) within TM2, can also be used to provide mutant GPCRs with increased stability.

Accordingly, the method of the first aspect of the invention may comprise making one or more mutations in the amino acid sequence that defines a parent GPCR wherein the one or more mutations are located within an amino acid sequence of TM7 of the parent GPCR which amino acid sequence interacts with the window of i plus or minus 5 residues (e.g. with the window of i plus of minus 4 residues) described above, to provide one or more mutants of the parent GPCR with increased stability. It is appreciated that such mutations may be made in addition to or as an alternative to making one or more mutations in the window of i plus or minus 5 residues (e.g. the window of i plus or minus 4 residues).

The amino acid sequence of TM7 within a given GPCR can be identified using any suitable technique in the art, including hydrophobicity analysis as mentioned above.

Figure 10:
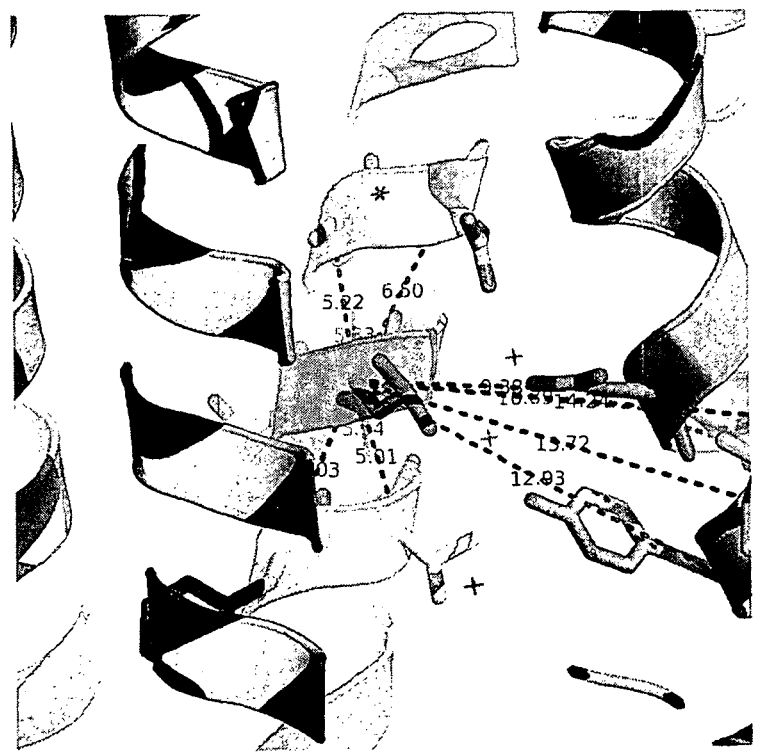
FIG. 10: Representation of adenosine A2A receptor showing distances between L2.46 (Leu 48) and both residues adjacent to L2.46 and residues in the NPxxY (SEQ ID NO: 1) motif.

By 'interacts with the window of i plus of minus 5 residues', we include the meaning that one or more of the amino acids within TM7 are in close proximity in three dimensional space to one or more amino acids within the window of i plus or minus 5 residues described above. By 'interacts with the window of i plus of minus 4 residues', we include the meaning that one or more of the amino acids within TM7 are in close proximity in three dimensional space to one or more amino acids within the window of i plus or minus 4 residues described above. Distances between Cα atoms of Leu 48 (L2.46) in the adenosine $A_{2A}$ receptor and Cα atoms of amino acid residues in the NPxxY (SEQ ID NO: 1) motif in TM7 are provided in Example 2 and FIG. 10. The distances show that the Cα atom of each residue in the NPxxY (SEQ ID NO: 1) motif is within 15 angstroms of the Cα atom of L2.46. Thus in a preferred embodiment, the amino acid sequence that interacts with the window of i plus or minus 5 residues (e.g. the window of i plus or minus 4) residues corresponds to one or more amino acids within TM7 whose Cα atoms are within 15 angstroms of any of the Cα atoms of the amino acids within the window of i plus or minus 5 residues (e.g. the window of i plus or minus 4 residues) such as within 14, 13, 12, 11, 10, 9, 8, 7, 6 or 5 angstroms.

The distances between Cα atoms are those measured based on coordinates in three-dimensions. For example, distances are typically measured by standard geometry from the X, Y and Z coordinates of the two atoms (e.g. SQUAREROOT $((x1-x2)^2+(y1-y2)^2+(z1-z2)^2)$). It is appreciated that where the structure of the parent GPCR is known, the distances are measured when the protein is folded in its native state. Otherwise, the distances may be measured within a structural model of the parent GPCR. Structural models can be generated using any suitable method known in the art. For example, the structural model may be a computer generated model based upon homology or using de novo structure prediction methods (Qian et al *Nature* (2007) 450: 259-64).

In Class 1 GPCRs, the amino acid sequence of TM7 which interacts with the window of i plus or minus 5 residues (e.g. the window of i plus or minus 4 residues) is preferably the NPxxY (SEQ ID NO: 1) motif in TM7, plus or minus 3 residues. Thus, in one embodiment, the method of the first aspect of the invention comprises making one or more mutations in the amino acid sequence that defines a Class 1 parent GPCR, wherein the one or more mutations are located within the NPxxY (SEQ ID NO: 1) amino acid sequence in TM7 plus or minus 3 residues, to provide one or more mutants of the parent GPCR with increased stability. In a further embodiment, the one or more mutations are located within the NPxxY (SEQ ID NO: 1) amino acid sequence in TM7, plus or minus 2 residues, or within the NPxxY (SEQ ID NO: 1) amino acid sequence in TM7 plus or minus 1 residue, or within only the NPxxY (SEQ ID NO: 1) amino acid sequence. By the "NPxxY motif in TM7 plus or minus x (i.e. 1, 2 or 3) residues" we include the NPxxY (SEQ ID NO: 1) motif, and the x (i.e. 1, 2 or 3) amino acids before and the x (i.e. 1, 2 or 3) amino acids after the NPxxY (SEQ ID NO: 1) motif.

In Class 2 GPCRs, the amino acid sequence of TM7 which interacts with the window of i plus or minus 5 residues (e.g. the window of i plus or minus 4 residues) is preferably the SFQ motif in TM7, plus or minus 3 residues. Thus, in one embodiment, the method of the first aspect of the invention comprises making one or more mutations in the amino acid sequence that defines a Class 2 parent GPCR, wherein the one or more mutations are located within the SFQ amino acid sequence in TM7 plus or minus 3 residues, to provide one or more mutants of the parent GPCR with increased stability. In a further embodiment, the one or more mutations are located within the SFQ amino acid sequence in TM7 plus or minus 2 residues, or within the SFQ amino acid sequence in TM7 plus or minus 1 residue, or within only the SFQ amino acid sequence. By the "SFQ motif in TM7 plus or minus x (i.e. 1, 2 or 3) residues" we include the SFQ motif, and the x (i.e. 1, 2 or 3) amino acids before and the x (i.e. 1, 2 or 3) amino acids after the SFQ motif.

In Class 3 GPCRs, the amino acid sequence of TM7 which interacts with the window of i plus or minus 5 residues (e.g. the window of i plus or minus 4 residues) is preferably the xPKxY (SEQ ID NO: 4) motif in TM7 plus or minus 3 residues. Thus, in one embodiment, the method of the first aspect of the invention comprises making one or more mutations in the amino acid sequence that defines a Class 3 parent GPCR, wherein the one or more mutations are located within the xPKxY (SEQ ID NO: 4) amino acid sequence in TM7 plus or minus 3 residues, to provide one or more mutants of the parent GPCR with increased stability. In a further embodiment, the one or more mutations are located within the xPKxY (SEQ ID NO: 4) amino acid sequence in TM7 plus or minus 2 residues, or within the xPKxY (SEQ ID NO: 4) amino acid sequence in TM7 plus or minus 1 residue, or within only the xPKxY (SEQ ID NO: 4) amino acid sequence. By the "xPKxY motif in TM7 plus or minus x (i.e. 1, 2 or 3) residues" we include the xPKxY (SEQ ID NO: 4) motif, and the x (i.e. 1, 2 or 3) amino acids before and the x (i.e. 1, 2 or 3) amino acids after the xPKxY (SEQ ID NO: 4) motif.

As can be seen in Example 1, surprisingly, changes to a single amino acid within the GPCR may increase the stability of the protein compared to the parent protein. Thus, in one embodiment of the method of producing a mutant GPCR with increased stability, a single amino acid residue of the parent protein is changed in the mutant protein. However, it is appreciated that a further increase in stability may be obtained by changing more than one of the amino acids of the parent protein. For example, more than one amino acid within the window of i plus or minus 5 residues (e.g. the window of i plus or minus 4 residues) may be changed in the parent GPCR, and/or more than one amino acid within an amino acid sequence that defines TM7 in the parent GPCR which amino acid sequence interacts with the window of i plus or minus 5 residues (e.g. the window of i plus or minus 4 residues) may be changed.

Typically when producing a mutant GPCR with increased stability, the mutant GPCR contains, compared to the parent protein, from 1 to 11 changed amino acids, preferably from 1 to 8 or from 1 to 6, such as 2 to 6, for example 2, 3, 4, 5 or 6 changed amino acids. However, it is appreciated that the total number of mutations required to confer increased stability may be more than this, and will ultimately vary from receptor to receptor, depending on various factors such as the intrinsic stability of the parent receptor.

Mutations can be made in an amino acid sequence defining a parent GPCR using any suitable technique known in the art. For example, conventional site-directed mutagenesis may be employed, or polymerase chain reaction-based procedures may be used, such that particular amino acid residues are independently replaced with other amino acid residues. Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y.

Typically, making one or more mutations in the amino acid sequence that defines a parent GPCR comprises replacing one or more amino acids by Ala, although it may be replaced by any other amino acid. For example, if a particular amino acid within a window of i plus or minus 5 residues (e.g. a window of i plus or minus 4 residues), where i is the position of amino acid residue 2.46, or its equivalent as the case may be, in the parent GPCR, is Ala, it may conveniently be replaced by Leu (unless it is already that residue as in the case of L2.46). Alternatively, the amino acid may be replaced by Gly for example, which may allow a closer packing of neighbouring helices that may lock the protein in a particular conformation. If the amino acid is Gly, it may conveniently be replaced by Ala for example.

Although the amino acid used to replace a given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic. In some cases the modifications may stabilise the interaction between transmembrane helix 2 and transmembrane helix 7, for example through the introduction of a salt bridge, disulphide link or a metal ion chelation site.

The inventors have shown that mutating residue 2.46, and nearby residues, increases the stability of a particular conformation (eg agonist or antagonist). Thus, the method of the invention may be considered to be a method for producing mutants of a GPCR which have increased stability of a particular conformation, for example they may have increased conformational thermostability. The method of the invention may therefore be used to create stable, conformationally locked GPCRs by mutagenesis. As seen in FIG. 1, the 2.46 residue, or its equivalent as the case may be, is highly conserved in Class 1, Class 2 and Class 3 GPCRs and so the method may be applied to all GPCRs to create stable conformationally locked receptors. The mutant GPCRs are effectively purer forms of the parent molecules in that a much higher proportion of them occupies a particular conformational state. In an embodiment, the one or more mutants of the parent GPCR have increased stability in an agonist or antagonist conformation. It is appreciated that the method of the invention may also be considered to be a method for producing mutant GPCRs which are more tractable to crystallisation.

Conveniently, the method of the first aspect of the invention is performed and the stability of the resulting one or more mutants assessed. Methods for assessing the stability of GPCRs are known in the art and are described, for example, in WO 2008/114020 and in WO 2009/071914. Preferably, it is determined whether the resulting one or more mutants when residing in a particular conformation have increased stability with respect to binding a ligand (the ligand being one which binds to the parent GPCR when the parent GPCR is residing in a particular conformation), compared to the stability of the parent GPCR when residing in the same particular conformation with respect to binding that ligand. It is appreciated that the comparison of stability of the one or more mutants is made by reference to the parent molecule under the same conditions.

Since there are potentially thousands of mutations that can be screened in a GPCR for increased stability, it is advantageous to target particular mutations which are known to be important in conferring stability. Therefore, it will be appreciated that the method of the first aspect of the invention may also be used as a method of selecting mutant GPCRs with increased stability. In particular, carrying out the method of the first aspect of the invention can be used to target mutations to particular amino acid residues (e.g. within a window of i plus or minus 5 residues or within a window of i plus or minus 4 residues, where i is the position of amino acid residue 2.46, or its equivalent as the case may be, in the parent GPCR, although it is appreciated that stabilising mutations may be located outside this window). The resulting one or more mutants can then be tested for increased stability, and those that have increased stability selected.

It is appreciated that the method of the first aspect of the invention may be repeated, for example once the stability of the resulting one or mutants are assessed, with the resulting one or more mutants generated in the first round becoming the parent GPCR in a subsequent round. Thus, the method can be used in an iterative way by, for example, carrying out a method to identify single mutations with increased stability, combining those mutations in a single mutant GPCR, which then becomes the parent GPCR that is mutated in a subsequent round.

For example, in an embodiment of the first aspect of the invention, the one or more mutations in the amino acid sequence that defines a parent GPCR may be made within progressively increasing window sizes. Typically, a small window size is used first, and the stabilising mutations from that sequence subset identified, followed by scanning further residues at increasing window sizes until the desired number of mutations have been found. Thus in a first round, one or more mutations may be made in the amino acid sequence that defines a parent GPCR within a window of i plus or minus 1 residue, wherein i is the position of amino acid residue 2.46, or its equivalent as the case may be, in the parent GPCR. The stability of the resulting mutants may be assessed and those mutants that have an increased stability compared to the parent GPCR selected. The method may then be repeated by making one or more mutations in the amino acid sequence that defines a parent GPCR (corresponding to a mutant selected in the first round) within a window or windows of i plus or minus 2 residues, and so on.

The mutant GPCR may be one which has increased stability to any denaturant or denaturing condition such as to any one or more of heat, a detergent, a chaotropic agent or an extreme of pH.

In relation to an increased stability to heat (ie thermostability), this can readily be determined by measuring ligand binding or by using spectroscopic methods such as fluorescence, CD or light scattering at a particular temperature. Typically, when the GPCR binds to a ligand, the ability of the GPCR to bind that ligand at a particular temperature may be used to determine thermostability of the mutant. It may be convenient to determine a "quasi $T_m$," ie the temperature at which 50% of the receptor is inactivated under stated conditions after incubation for a given period of time (eg 30 minutes). Mutant GPCRs of higher thermostability have an increased quasi Tm compared to their parents. Alternatively, thermostability can be assessed by measuring stability at a given temperature as a function of time. For example, the length of time at a given temperature by which the level of ligand binding falls to 50% of the level of ligand binding at time zero may be determined (Shibata et al, 2009 *J Mol Biol*). In either case however, it is appreciated that temperature is the denaturant.

In relation to an increased stability to a detergent or to a chaotrope, typically the GPCR is incubated for a defined time in the presence of a test detergent or a test chaotropic agent and the stability is determined using, for example, ligand binding or a spectroscopic method as discussed above.

In relation to an extreme of pH, a typical test pH would be chosen (eg in the range 4.5 to 5.5 (low pH) or in the range 8.5 to 9.5 (high pH).

Because relatively harsh detergents are used during crystallisation procedures, it is preferred that the mutant GPCR is stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant GPCR is more stable to any of $C_9$ maltoside or glucoside, $C_8$ maltoside or glucoside, LDAO and SDS, and so it is preferred that these detergents are used for stability testing.

Because of its ease of determination, it is preferred that the mutant GPCR has increased thermostability compared to its parent protein. It will be appreciated that heat is acting as the denaturant, and this can readily be removed by cooling the sample, for example by placing on ice. It is believed that thermostability may also be a guide to the stability to other denaturants or denaturing conditions. Thus, increased thermostability is likely to translate into stability in denaturing detergents, especially those that are more denaturing than DDM, eg those detergents with a smaller head group and a shorter alkyl chain and/or with a charged head group. We have found that a thermostable GPCR is also more stable towards harsh detergents.

When an extreme of pH is used as the denaturing condition, it will be appreciated that this can be removed quickly by adding a neutralising agent. Similarly, when a chaotrope is used as a denaturant, the denaturing effect can be removed by diluting the sample below the concentration in which the chaotrope exerts its chaotropic effect.

In a further embodiment of the method of the first aspect of the invention, it is determined whether the mutant GPCR is able to couple to a G protein or another protein known to interact with a GPCR, for example a signalling protein such as arrestin or a GPCR kinase. Preferably, it is also determined whether the mutant GPCR is able to bind a plurality of ligands of the same class (eg agonist or antagonist), with a comparable spread and/or rank order of affinity as the parent GPCR.

Preferably, the parent GPCR is a Class 1 (i.e. a rhodopsin-like GPCR), such as any of those listed in FIG. 1a including an adenosine receptor, a serotonin receptor, a β-adrenergic receptor, a neurotensin receptor or a muscarinic receptor. More preferably, the parent GPCR is the adenosine $A_{2A}$ receptor or the M4 muscarinic receptor or the $5HT_{2C}$ receptor or the $NTS_1$ neurotensin receptor or the orexin $OX_2$ receptor.

However, the parent GPCR may be any GPCR, including Class 2 and 3 GPCRs as listed in FIGS. 1b, 1c and 14, and in Example 3 (e.g. $CRF_1$), and all those listed by the International Union of Pharmacology as mentioned above.

Mutant Adenosine Receptor

Adenosine receptors are well known in the art. They share sequence homology to each other and bind to adenosine.

In a particularly preferred embodiment, the mutant GPCR with increased stability relative to its parent GPCR is a mutant adenosine receptor which, when compared to the corresponding parent receptor, has a different amino acid at a position which corresponds to one or more of Leu 48 and Asn 284 according to the numbering of the human adenosine $A_{2A}$ receptor as set out in FIG. 2.

The mutant adenosine receptor may be a mutant of any adenosine receptor provided that it is mutated at a position which corresponds to any one or more of Leu 48 and Asn 284 according to the numbering of the human adenosine $A_{2A}$ receptor as set out in FIG. 2.

It is particularly preferred if the mutant GPCR is one that has at least 20% amino acid sequence identity when compared to the given human adenosine $A_{2A}$ receptor whose sequence is set out in FIG. 2, as determined using MacVector and CLUSTALW (Thompson et al (1994) *Nucl. Acids Res.* 22, 4673-4680). More preferably, the mutant GPCR has at least 30% or at least 40% or at least 50%, or at least 60% amino acid sequence identity. There is generally a higher degree of sequence conservation at the adenosine binding site.

As is described in Example 1 below, individual replacement of Leu 48 leads to an increase in thermostability when measured with the agonist 5'-N-ethylcarboxamidoadenosine (NECA). Similarly, as described in Example 2, individual replacement of Asn 284 leads to an increase in thermostability when measured with the agonist NECA.

Thus, the mutant GPCR may be a mutant human adenosine $A_{2A}$ receptor in which, compared to its parent, one or more of Leu 48 and Asn 284 have been replaced by another amino acid residue. The mutant GPCR may also be a mutant adenosine receptor from another source in which one or more corresponding amino acids in the parent receptor are replaced by another amino acid residue. For the avoidance of doubt, the parent may be an adenosine receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another adenosine receptor which aligns to the given amino acid residue in human adenosine $A_{2A}$ receptor when the human adenosine $A_{2A}$ receptor and the other adenosine receptor are compared using MacVector and CLUSTALW.

Other human adenosine receptors include adenosine A2b, A3 and A1 receptors. The amino acid residues corresponding to Leu 48 in the human adenosine $A_{2A}$ receptor in each of the adenosine A2b, A3 and A1 receptors are Leu 49, Leu 54 and Leu 51 respectively. Thus the mutant GPCR may be a mutant adenosine A2b receptor in which Leu 49 has been replaced by another amino acid, or it may be a mutant adenosine A3 receptor in which Leu 54 has been replaced by another amino acid, or it may be a mutant adenosine A1 receptor in which Leu 51 has been replaced by another amino acid.

Mutant Serotonin Receptor

Serotonin receptors are well known in the art. They share sequence homology to each other and bind to serotonin.

In a particularly preferred embodiment, the mutant GPCR with increased stability relative to its parent GPCR is a mutant serotonin receptor which, when compared to the corresponding parent receptor, has a different amino acid at a position which corresponds to any one or more of Met 93, Ser 94, Leu 95, Ile 363 and Leu 366, according to the numbering of the human 5HT$_{2C}$ receptor as set out in FIG. 3.

The mutant serotonin receptor may be a mutant of any serotonin receptor provided that it is mutated at a position which corresponds to any one or more of Leu 95, Ser 94 and Met 93, Ser 94, Leu 95, Ile 363 and Leu 366, according to the numbering of the human 5HT$_{2C}$ receptor as set out in FIG. 3.

It is particularly preferred if the mutant GPCR is one that has at least 20% amino acid sequence identity when compared to the given human 5HT$_{2C}$ receptor whose sequence is set out in FIG. 3, as determined using MacVector and CLUSTALW (Thompson et al (1994) *Nucl. Acids Res.* 22, 4673-4680). More preferably, the mutant GPCR has at least 30% or at least 40% or at least 50%, or at least 60% amino acid sequence identity. There is generally a higher degree of sequence conservation at the serotonin binding site.

As is described in Example 1 below, individual replacement of Leu 95 and Met 93 in the 5HT$_{2C}$ receptor sequence (as shown in FIG. 3) leads to an increase in thermostability when measured with the agonist SCH23390.

Replacement of Ser 94 in the 5HT$_{2C}$ receptor sequence (as shown in FIG. 3) leads to an increase in thermostability when measured with the antagonist mesulergine.

Individual replacement of Ile 363 and Leu 366 in the 5HT$_{2C}$ receptor sequence also leads to an increase in thermostability when measured with the agonist SCH23390, as described in Example 2.

Thus, the mutant GPCR may be a mutant human 5HT$_{2C}$ receptor in which, compared to its parent, one or more of these amino acid residues (i.e. Met 93, Ser 94, Leu 95, Ile 363 and Leu 366), have been replaced by another amino acid residue. The mutant GPCR may also be a mutant serotonin receptor from another source in which one or more corresponding amino acids in the parent receptor are replaced by another amino acid residue. For the avoidance of doubt, the parent may be a serotonin receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another serotonin receptor which aligns to the given amino acid residue in the 5HT$_{2C}$ receptor when the 5HT$_{2C}$ receptor and the other serotonin receptor are compared using MacVector and CLUSTALW.

Other human serotonin receptors include the 5HT$_{1A}$, 5HT$_{1B}$, 5HT$_{1D}$, 5HT$_{1E}$, 5HT$_{1F}$, 5HT$_{3A}$, 5HT$_{2B}$, 5HT$_4$, 5HT$_{5A}$, 5HT$_6$ and 5HT$_7$ receptors.

The amino acid residues corresponding to Leu 95, Ser 94 and Met 93 in the 5HT$_{2C}$ receptor, in the 5HT$_{1A}$ receptor are Leu 78, Ser 77, and Gly 76 respectively and so the mutant GPCR may be a mutant 5HT$_{1A}$ receptor in which one or more of Leu 78, Ser 77 and Gly 76 have been replaced by another amino acid.

The amino acid residues corresponding to Leu 95, Ser 94 and Gly 93 in the 5HT$_{2C}$ receptor, in the 5HT$_{1B}$ receptor, are Leu 91, Ser 90 and Ala 89 respectively, and so the mutant GPCR may be a mutant 5HT$_{1B}$ receptor in which one or more of Leu 91, Ser 90 and Ala 89 have been replaced by another amino acid.

The amino acid residues corresponding to Leu 95, Ser 94 and Gly 93 in the 5HT$_{2C}$ receptor, in the 5HT$_{2A}$ receptor, are Leu 116, Ser 115 and Met 114 respectively, and so the mutant GPCR may be a mutant 5HT$_{2A}$ receptor in which one or more of Leu 116, Ser 115 and Met 114 have been replaced by another amino acid.

The amino acid residues corresponding to Leu 95, Ser 94 and Gly 93 in the 5HT$_{2C}$ receptor, in the 5HT$_6$ receptor, are Leu 68, Ser 67 and Val 66 respectively, and so the mutant GPCR may be a mutant 5HT$_6$ receptor in which one or more of Leu 68, Ser 67 and Val 66 have been replaced by another amino acid.

The amino acid residues corresponding to Leu 95, Ser 94 and Gly 93 in the 5HT$_{2C}$ receptor, in the 5HT$_7$ receptor, are Leu 123, Ser 122 and Val 121 respectively, and so the mutant GPCR may be a mutant 5HT$_7$ receptor in which one or more of Leu 123, Ser 122 and Val 121 have been replaced by another amino acid.

Mutant Muscarinic Receptor

Muscarinic receptors are well known in the art. They share sequence homology to each other and bind to muscarine.

In a particularly preferred embodiment, the mutant GPCR with increased stability relative to its parent GPCR is a mutant muscarinic receptor which, when compared to the corresponding parent receptor, has a different amino acid at a position which corresponds to Leu 71, according to the numbering of the human M4 muscarinic receptor as set out in FIG. 4.

The mutant muscarinic receptor may be a mutant of any muscarinic receptor provided that it is mutated at a position which corresponds to Leu 71, according to the numbering of the human M4 muscarinic receptor as set out in FIG. 4.

It is particularly preferred if the mutant GPCR is one that has at least 20% amino acid sequence identity when compared to the given human M4 muscarinic receptor whose sequence is set out in FIG. 4, as determined using MacVector and CLUSTALW (Thompson et al (1994) *Nucl. Acids Res.* 22, 4673-4680). More preferably, the mutant GPCR has at least 30% or at least 40% or at least 50%, or at least 60% amino acid sequence identity. There is generally a higher degree of sequence conservation at the muscarine binding site.

As is described in Example 1 below, individual replacement of Leu 71 in the M4 muscarinic receptor sequence (as shown in FIG. 4) leads to an increase in thermostability when measured with the antagonist NMS.

Thus, the mutant GPCR may be a human mutant M4 muscarinic receptor in which, compared to its parent, Leu 71 has been replaced by another amino acid residue. The mutant GPCR may also be a mutant muscarinic receptor from another source in which one or more corresponding amino acids in the parent receptor are replaced by another amino acid residue. For the avoidance of doubt, the parent may be a muscarinic receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another muscarinic receptor which aligns to the given amino acid residue in the M4 muscarinic receptor when the M4 muscarinic receptor and the other muscarinic receptor are compared using MacVector and CLUSTALW.

Other human muscarinic receptors include the M1, M2, M3 and M5 muscarinic receptors. The amino acid residues corresponding to Leu 71 in the human M4 muscarinic receptor in each of the M1, M2, M3 and M5 muscarinic receptors are Leu 64, Leu 62, Leu 107 and Leu 69 respectively. Thus the mutant GPCR may be a mutant M1 muscarinic receptor in which Leu 64 has been replaced by another amino acid, or it may be a mutant M2 muscarinic receptor in which Leu 62 has been replaced by another amino acid, or it may be a mutant M3 muscarinic receptor in which Leu 107 has been replaced by another amino acid, or it may be a mutant M5 muscarinic receptor in which Leu 69 has been replaced by another amino acid.

Mutant Neurotensin Receptor

Neurotensin receptors are known in the art. They share sequence homology and bind neurotensin.

In a particularly preferred embodiment, the mutant GPCR with increased stability relative to its parent GPCR is a mutant neurotensin receptor which, when compared to the corresponding parent receptor, has a different amino acid at a position which corresponds to Tyr 369, according to the numbering of the rat neurotensin receptor as set out in FIG. 11.

The mutant neurotensin receptor may be a mutant of any neurotensin receptor provided that it is mutated at a position which corresponds to Tyr 369, according to the numbering of the rat neurotensin receptor as set out in FIG. 11.

It is particularly preferred if the mutant GPCR is one that has at least 20% amino acid sequence identity when compared to the given rat neurotensin receptor whose sequence is set out in FIG. 11, as determined using MacVector and CLUSTALW (Thompson et al (1994) Nucl. Acids Res. 22, 4673-4680). More preferably, the mutant GPCR has at least 30% or at least 40% or at least 50%, or at least 60% amino acid sequence identity. There is generally a higher degree of sequence conservation at the neurotensin binding site.

As is described in Example 2 below, individual replacement of Tyr 369 in the rat neurotensin receptor sequence (as shown in FIG. 11) leads to an increase in thermostability when measured with the agonist neurotensin.

Thus, the mutant GPCR may be a rat neurotensin receptor in which, compared to its parent, Tyr 369 has been replaced by another amino acid residue. The mutant GPCR may also be a mutant neurotensin receptor from another source in which one or more corresponding amino acids in the parent receptor are replaced by another amino acid residue. For the avoidance of doubt, the parent may be a neurotensin receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another neurotensin receptor which aligns to the given amino acid residue in the rat neurotensin receptor when the rat neurotensin receptor and the other neurotensin receptor are compared using MacVector and CLUSTALW.

Mutant Corticotropin Releasing Hormone Receptor

Corticotropin releasing hormone receptors are known in the art. They share sequence homology and bind corticotropin releasing hormone.

In a particularly preferred embodiment, the mutant GPCR with increased stability relative to its parent GPCR is a mutant corticotropin releasing hormone receptor which, when compared to the corresponding parent receptor, has a different amino acid at a position which corresponds to Ile 163 according to the numbering of human corticotropin releasing hormone receptor 1 ($CRF_1$) as set out in FIG. 12.

The mutant corticotropin releasing hormone receptor may be a mutant of any corticotropin releasing hormone receptor provided that it is mutated at a position which corresponds to Ile 163 according to the numbering of human $CRF_1$ as set out in FIG. 12.

It is particularly preferred if the mutant GPCR is one that has at least 20% amino acid sequence identity when compared to the given human $CRF_1$ receptor whose sequence is set out in FIG. 12, as determined using MacVector and CLUSTALW (Thompson et al (1994) Nucl. Acids Res. 22, 4673-4680). More preferably, the mutant GPCR has at least 30% or at least 40% or at least 50%, or at least 60% amino acid sequence identity. There is generally a higher degree of sequence conservation at the corticotropin releasing hormone binding site.

As is described in Example 3 below, replacement of Ile 163 in human $CRF_1$ sequence (as shown in FIG. 12) leads to an increase in thermostability when measured with the antagonist CP-376395.

Thus, the mutant GPCR may be a human $CRF_1$ receptor in which, compared to its parent, Ile 163 has been replaced by another amino acid residue. The mutant GPCR may also be a mutant $CRF_1$ receptor from another source in which the corresponding amino acid in the parent receptor is replaced by another amino acid residue. For the avoidance of doubt, the parent may be a corticotropin releasing hormone receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another corticotropin releasing hormone receptor which aligns to the given amino acid residue in the human $CRF_1$ receptor when the human $CRF_1$ receptor and the other corticotropin releasing hormone receptor are compared using MacVector and CLUSTALW.

Mutant Orexin Receptor

Orexin receptors are known in the art. They share sequence homology and bind orexin.

In a particularly preferred embodiment, the mutant GPCR with increased stability relative to its parent GPCR is a mutant orexin receptor which, when compared to the corresponding parent receptor, has a different amino acid at a position which corresponds to Tyr 91 according to the numbering of human orexin 2 receptor ($OX_2$) as set out in FIG. 13.

The mutant orexin receptor may be a mutant of any orexin receptor provided that it is mutated at a position which corresponds to Tyr 91 according to the numbering of human $OX_2$ as set out in FIG. 13.

It is particularly preferred if the mutant GPCR is one that has at least 20% amino acid sequence identity when compared to the given human $OX_2$ whose sequence is set out in FIG. 13, as determined using MacVector and CLUSTALW (Thompson et al (1994) Nucl. Acids Res. 22, 4673-4680). More preferably, the mutant GPCR has at least 30% or at least 40% or at least 50%, or at least 60% amino acid sequence identity. There is generally a higher degree of sequence conservation at the orexin binding site.

As is described in Example 4 below, individual replacement of Tyr 91 in human $OX_2$ sequence (as shown in FIG. 13) leads to an increase in thermostability when measured with the antagonist EMPA.

Thus, the mutant GPCR may be a human $OX_2$ receptor in which, compared to its parent, Tyr 91 has been replaced by another amino acid residue. The mutant GPCR may also be a mutant orexin receptor from another source in which one or more corresponding amino acids in the parent receptor are replaced by another amino acid residue. For the avoidance of doubt, the parent may be an orexin receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another orexin receptor which aligns to the given amino acid residue in human $OX_2$ when human $OX_2$ and the other orexin receptor are compared using MacVector and CLUSTALW.

A second aspect of the invention provides a mutant GPCR with increased stability relative to its parent GPCR produced by the method of the first aspect of the invention.

The inventors have demonstrated that making mutations in the amino acid sequence that defines a parent GPCR within a window of i plus or minut 5 residues (e.g. a window of i plus or minus 4 residues), where i is the position of residue 2.46 in the parent GPCR, can provide one or more mutants of the parent GPCR that have increased stability. Further, the inventors have demonstrated that making mutations within an amino acid sequence of transmembrane helix 7 within the parent GPCR which amino acid sequence interacts with the window of i plus or minus 5 residues (e.g. the window of i plus or minus 4 residues), can provide one or more mutants of the parent GPCR that have increased stability. Thus, it is appreciated that the mutant GPCRs of the second aspect of the invention will have an extended lifetime, relative to its parent, under destabilising conditions.

Accordingly, a third aspect of the invention provides a mutant GPCR which, when compared to a parent GPCR, has one or more mutations in the amino acid sequence defining the parent GPCR, wherein (i) the one or more mutations are located within a window of i plus or minus 5 residues, where i is the position of amino acid residue 2.46 in the parent GPCR when the patent GPCR is a Class 1 GPCR, or where i is the position of an equivalent amino acid in the parent GPCR when the parent GPCR is a Class 2 or 3 GPCR, and/or (ii) the one or more mutations are located within an amino acid sequence of transmembrane helix 7 in the parent GPCR which amino acid sequence interacts with the window of i plus or minus 5 residues, which mutant GPCR has increased stability compared to a parent GPCR when exposed to a destabilising condition.

Thus, the invention provides a mutant GPCR which, when compared to a parent GPCR, has one or more mutations in the amino acid sequence defining the parent GPCR, wherein (i) the one or more mutations are located within a window of i plus or minus 4 residues, where i is the position of amino acid residue 2.46 in the parent GPCR when the patent GPCR is a Class 1 GPCR, or where i is the position of an equivalent amino acid in the parent GPCR when the parent GPCR is a Class 2 or 3 GPCR, and/or (ii) the one or more mutations are located within an amino acid sequence of transmembrane helix 7 in the parent GPCR which amino acid sequence interacts with the window of i plus or minus 4 residues, which mutant GPCR has increased stability compared to a parent GPCR when exposed to a destabilising condition.

It also appreciated that the invention allows for the production of compositions comprising mutant GPCRs, characterised in that the mutant GPCR is exposed to a destabilising condition. Such compositions have various applications, for example in crystallisation, drug screening, bioassay and biosensor applications.

Thus, a fourth aspect of the invention provides a composition comprising a mutant GPCR which, when compared to a parent GPCR, has one or more mutations in the amino acid sequence defining the parent GPCR, wherein (i) the one or more mutations are located within a window of i plus or minus 5 residues, where i is the position of amino acid residue 2.46 in the parent GPCR when the patent GPCR is a Class 1 GPCR, or where i is the position of an equivalent amino acid in the parent GPCR when the parent GPCR is a Class 2 or 3 GPCR, and/or (ii) the one or more mutations are located within an amino acid sequence of transmembrane helix 7 in the parent GPCR which amino acid sequence interacts with the window of i plus or minus 5 residues, characterised in that the mutant GPCR is exposed to a destabilising condition effective to destabilise a parent GPCR to a greater extent than the mutant GPCR.

Accordingly, the invention provides a composition comprising a mutant GPCR which, when compared to a parent GPCR, has one or more mutations in the amino acid sequence defining the parent GPCR, wherein (i) the one or more mutations are located within a window of i plus or minus 4 residues, where i is the position of amino acid residue 2.46 in the parent GPCR when the patent GPCR is a Class 1 GPCR, or where i is the position of an equivalent amino acid in the parent GPCR when the parent GPCR is a Class 2 or 3 GPCR, and/or (ii) the one or more mutations are located within an amino acid sequence of transmembrane helix 7 in the parent GPCR which amino acid sequence interacts with the window of i plus or minus 4 residues, characterised in that the mutant GPCR is exposed to a destabilising condition effective to destabilise a parent GPCR to a greater extent than the mutant GPCR.

By "destabilising condition" we include any condition which is capable of shifting the equilibrium of a population of GPCR proteins from the folded native state in a membrane to the unfolded state. In this way, the proportion of GPCR proteins existing in the unfolded state is increased and the proportion existing in the folded native state in a membrane is decreased.

By "population" we include a plurality of the same specific type of GPCR, as opposed to a mixture of different GPCRs. For example, the population may comprise at least 2, 5, 10, 50, 100, 200, 500, 1000, 5000, 10000, 100000, $10^6$, $10^7$, $10^8$, $10^9$, $10^{10}$, $10^{11}$, $10^{12}$, $10^{13}$ or $10^{14}$ GPCR molecules. Preferably, the population may comprise GPCR $10^9$ and $10^{12}$ GPCR molecules.

In the folded native state in a membrane, GPCRs exhibit a biological activity, for example a binding activity or a signalling pathway modulation activity. Upon increasing exposure to a destabilising condition as described above, the equilibrium shifts further towards the unfolded state and an increasingly higher proportion of the GPCRs exist in the unfolded state. This change in structure from a folded to an unfolded state leads to a detectable change in the structure of the GPCR population. Moreover, this change in structure may lead to a detectable decrease in a biological activity of the GPCR population.

Accordingly in one embodiment, the destabilising condition is one that is effective to bring about a significant perturbation in the structure of a GPCR population compared to the structure of that population in the absence of the destabilising condition.

By a "significant perturbation in the structure of a GPCR population", we mean a perturbation which, when assessed relative to the statistical variation of the measurements used to detect the perturbation, would arise by chance in less than 1 in 10 measurements, more preferably 1 in 20 measurements and even more preferably 1 in 50 or 1 in 100 measurements.

Various methods to probe protein structure are known in the art and any suitable method may be used. For example, structural perturbations may be assayed by probing conformation directly e.g. with covalently attached fluorescent labels or esr spin labels, or by measuring the accessibility of native or deliberately introduced amino acid side chains within the protein population (Hubbell, W. L. et al., Adv. Protein. Chem. 63, 243-290 (2003); Baneres, J. L. et. al., J. Biol. Chem. 280, 20253-20260 (2005); Kobilka, B. K. and Deupi, X. Trends. Pharmacol. Sci. 28, 397-406 (2007)). For example, changes in fluorescence spectra, can be a sensitive indicator of protein unfolding, either by use of intrinsic tryptophan fluorescence or the use of the thiol specific fluorochrome N-[4-(7-diethylamino-4-methyl-3-coumarinyl)phenyl]maleimide (cpm) that becomes fluorescent upon reacting with cysteine residues exposed upon protein unfolding (Alexandrov et al (2008) Structure 16: 351-359). Proteolytic stability, deuterium/hydrogen exchange measured by mass spectrometry or nuclear magnetic resonance spectroscopy, blue native gels, capillary zone electrophoresis, circular dichroism (CD) or linear dichroism (LD) spectra and light scattering may also be used to measure structural perturbation by loss of signals associated with secondary or tertiary structure.

In another embodiment, the destabilising condition is one that is effective to bring about a significant reduction in a biological activity of a GPCR population (e.g. binding activity or signalling pathway modulation activity), compared to the level of the same activity in the absence of the destabilising condition. For example, the agent may be one that reduces the biological activity of a GPCR population to 90-10%, such as 70-30% or 60-40% of the level of the same activity when measured in the absence of the destabilising condition.

Depending upon the biological activity, it will be appreciated that the activity of the GPCR population may be measured using any suitable method known in the art.

By 'binding activity', we include binding to any binding partner that is known to bind to the GPCR. For example, the binding partner may be a ligand, for example one which causes the GPCR to reside in a particular conformation, or it may be an antibody, for example a conformational-specific antibody. Binding activity can be assessed using routine binding assays known in the art. Conveniently, the binding partner is detectably labelled, eg radiolabelled or fluorescently labelled. Alternatively, binding can be assessed by measuring the amount of unbound binding partner using a secondary detection system, for example an antibody or other high affinity binding partner covalently linked to a detectable moiety, for example an enzyme which may be used in a colorimetric assay (such as alkaline phosphatase or horseradish peroxidase). Biophysical techniques such as patch clamping, fluorescence correlation spectroscopy, fluorescence resonance energy transfer and analytical ultracentrifugation may also be used (as described in New, R. C., *Liposomes: a practical approach.* 1st ed.; Oxford University Press: Oxford, 1990, and Graham, J. M.; Higgins, J. A., *Membrane Analysis.* Springer-Verlag: New York, 1997.)

Where the biological activity is a signalling pathway modulating activity, the activity can be assessed by any suitable assay for the particular signalling pathway. The pathway may be downstream of G protein activation or may be independent of G protein activation. Activation of the G protein can be measured directly by binding of a guanine nucleotide such as radiolabelled GTP to the G protein (Johnson et al, Assay Drug Dev Technol. 2008 June; 6(3):327-37). Alternatively, binding of a signalling protein such as a G protein or an arrestin to the receptor may be measured by fluorescence resonance energy transfer (FRET) (Lohse et al, Adv Protein Chem. 2007; 74:167-88) or related assays such as bioluminescence resonance energy transfer (BRET) (Gales et al, Nat. Methods. 2005 March; 2(3):177-84) or an enzyme complementation assay (Zhao et al, J Biomol Screen. 2008 September; 13(8):737-47. Epub 2008). These assays are commonly available in kits for example from Perkin Elmer or CisBio or DiscoverX. The activity may be measured by using a reporter gene to measure the activity of the particular signalling pathway. By a reporter gene we include genes which encode a reporter protein whose activity may easily be assayed, for example β-galactosidase, chloramphenicol acetyl transferase (CAT) gene, luciferase or Green Fluorescent Protein (see, for example, Tan et al, 1996 *EMBO J.* 15(17): 4629-42). Several techniques are available in the art to detect and measure expression of a reporter gene which would be suitable for use in the present invention. Many of these are available in kits both for determining expression in vitro and in vivo. Alternatively, signalling may be assayed by the analysis of downstream targets. For example, a particular protein whose expression is known to be under the control of a specific signalling pathway may be quantified, or a secondary metabolite may be quantified. Quantification of intracellular cAMP levels as a result of $A_{2A}$ agonist stimulation is described in Example 1. Protein levels in biological samples can be determined using any suitable method known in the art. For example, protein concentration can be studied by a range of antibody based methods including immunoassays, such as ELISAs, western blotting and radioimmunoassay or by the use of biosensors (Ponsioen et al EMBO Rep. 2004 December; 5(12):1176-80).

In an embodiment, the destabilising condition is any of heat, a detergent, a chaotropic agent such as guanidinium thiocyanate, an extreme of pH, an organic solvent, an aqueous solution or a membrane free environment.

For example, the destabilising condition may be a detergent, including for example, detergents that are of interest for subsequent crystallisation studies, for instance short chain-length detergents with a high CMC, such as C8-glucoside, C8-thioglucoside, C9-glucoside, C8-maltoside, C8-thiomaltoside, C9-maltoside, C9-thiomaltoside, Cymal 5, C8E5, or lauryl dimethylamine oxide. Short chain-length detergents are more likely to allow the formation of a 3-dimensional crystal lattice, and are easier to remove from receptor preparations by dialysis or other means than are long chain-length detergents with low CMCs.

It will also be appreciated that the destabilising condition may be any other amphiphilic molecule. For example, the destabilising condition may be any of amphipols, amphiphilic peptides such as mellitin, proteins such as apolipoproteins and their derivatives, organic solvents such as trifluoroethanol, dimethylformide, dimethylsulphoxide and chloroform/methanol mixtures, urea, a cylcodextrin, polyene antibiotics, guanidine hydrogenchloride, local anaesthetics and drugs such as procaine and chlorpromazine, polyols such as butane diol and heptane triol, short chain alcohols such as ethanol, propanol, isopropanol, butane diol and benzyl alcohol.

It will also be appreciated that the destabilising condition may be any aqueous solution.

It will further be appreciated that the destabilising condition may be a membrane free environment, such that the mutant GPCR exists in a form that is membrane free as discussed below.

In any event, the destabilising condition is one which is capable of shifting the equilibrium of a population of GPCR proteins from the folded native state in the membrane, to the unfolded state.

In one embodiment of the third and fourth aspects of the invention, the mutant GPCR is membrane free. By 'membrane free' we include the meaning of the mutant GPCR being substantially free of a membrane such as a lipid bilayer or a lipid monlayer. For example, the mutant GPCR may be in a form where it does not reside within a membrane, unlike when it does reside in a membrane when in the native folded state.

Given the increased stability of a mutant GPCR which, when compared to its parent GPCR has one or more mutations in the amino acid sequence defining the parent GPCR within a window of i plus or minus 5 residues (e.g. a window of i plus or minus 4 residues), where i is the position of amino acid residue 2.46 or its equivalent as the case may be in the parent GPCR, and/or has one or more mutations in an amino acid sequence of transmembrane helix 7 in the parent GPCR which amino acid sequence interacts with the window of i plus or minus 5 residues (e.g. window of i plus or minus 4 residues), it is appreciated that the destabilising condition will destabilise the parent GPCR to a greater extent than the mutant GPCR, i.e. shift the equilibrium of a population of the parent GPCR from the folded native state to the unfolded state, further than it shifts the equilibrium of a population of the mutant GPCR from the folded native state in a membrane to the unfolded state.

Thus, when the parent GPCR manifests, for example, 50% of a biological activity when exposed to a destabilising condition, typically, the mutant GPCR with increased stability relative to the parent protein, will have at least 5%, 10%, 15%, 20%, 25%, 30%, 35%, 40%, 45% or 50% more biological activity than the parent protein when exposed to the destabilising condition, and more preferably at least 60%, 70%, 80%, 90% or 100% more activity, and yet more preferably at least 150% or 200% more activity.

Similarly, a mutant GPCR with increased stability relative to the parent GPCR will have a structure that is more similar to the folded-native state than the structure of the parent protein is to the folded-native state, when exposed to a destabilising condition.

In this way, the invention allows for mutant GPCRs that have increased stability compared to a parent GPCR when exposed to a destabilising condition, and for compositions comprising a mutant GPCR of the invention, characterised in that the mutant GPCR is exposed to a destabilising agent effective to destabilise a parent GPCR to a greater extent than the mutant GPCR. For example, the invention allows for a solubilised form of a mutant GPCR of the invention.

Preferences for the mutant GPCRs are as defined above with respect to the first aspect of the invention. For example, the mutant GPCR of the third aspect of the invention may be, or the composition of the fourth aspect of the invention may comprise, a mutant adenosine receptor which, when compared to the corresponding parent receptor, has a different amino acid at a position which corresponds to one or more of Leu 48 and Asn 284 according to the numbering of the human adenosine $A_{2A}$ receptor as set out in FIG. 2. Preferably, the adenosine receptor has an amino acid sequence which is at least 20% identical to that of the human adenosine receptor whose sequence is set out in FIG. 2.

The mutant GPCR of the third aspect of the invention may be, or the composition of the fourth aspect of the invention may comprise, a mutant serotonin receptor which, when compared to the corresponding parent receptor, has a different amino acid at a position which corresponds to any one or more of Met 93, Ser 94, Leu 95, Ile 363 and Leu 366 according to the numbering of the $5HT_{2C}$ receptor as set out in FIG. 3. Preferably, the serotonin receptor has an amino acid sequence which is at least 20% identical to that of the human $5HT_{2C}$ receptor whose sequence is set out in FIG. 3.

The mutant GPCR of the third aspect of the invention may be, or the composition of the fourth aspect of the invention may comprise, a muscarinic receptor which, when compared to the corresponding parent receptor, has a different amino acid at a position which corresponds to Leu 71, according to the numbering of the M4 muscarinic receptor as set out in FIG. 4. Preferably, the mutant muscarinic receptor has an amino acid sequence which is at least 20% identical to that of the human M4 muscarinic receptor whose sequence is set out in FIG. 4.

The mutant GPCR of the third aspect of the invention may be, or the composition of the fourth aspect of the invention may comprise, a neurotensin receptor which, when compared to the corresponding parent receptor, has a different amino acid at a position which corresponds to Tyr 369, according to the numbering of the rat neurotensin receptor as set out in FIG. 11. Preferably, the mutant neurotensin receptor has an amino acid sequence which is at least 20% identical to that of the rat neurotensin receptor whose sequence is set out in FIG. 11.

The mutant GPCR of the third aspect of the invention may be, or the composition of the fourth aspect of the invention may comprise, a corticotropin releasing hormone receptor which, when compared to the corresponding parent receptor, has a different amino acid at a position which corresponds to Ile 163 according to the numbering of human $CRF_1$ as set out in FIG. 12. Preferably, the mutant corticotropin releasing hormone receptor has an amino acid sequence which is at least 20% identical to that of the human $CRF_1$ receptor whose sequence is set out in FIG. 12.

The mutant GPCR of the third aspect of the invention may be, or the composition of the fourth aspect of the invention may comprise, an orexin receptor which, when compared to the corresponding parent receptor, has a different amino acid at a position which corresponds to Tyr 91 according to the numbering of human $OX_2$ as set out in FIG. 13. Preferably, the mutant orexin receptor has an amino acid sequence which is at least 20% identical to that of the human $OX_2$ receptor whose sequence is set out in FIG. 13.

In an embodiment of the third and fourth aspects of the invention, the mutant GPCR is not a mutant bovine rhodopsin receptor in which the leucine residue at position 79 is changed to an alanine or a serine residue, as described in Madabushi et al, 2004 *J Biol Chem* 279(9): 8126-8132 (incorporated herein by reference, including for the purposes of making any disclaimer).

It is preferred that the mutant GPCR of the second or third aspect of the invention, or the mutant GPCR within the composition of the fourth aspect of the invention, has increased stability to any one of heat, a detergent, a chaotropic agent and an extreme of pH. Preferably, the mutant GPCR has increased stability (e.g. thermostability) compared to its parent when in the presence or absence of a ligand thereto. Typically, the ligand is an antagonist, a full agonist, a partial agonist or an inverse agonist, whether orthosteric or allosteric. The ligand may be a polypeptide, such as an antibody.

It is preferred that the mutant GPCR of the second or third aspect of the invention, or the mutant GPCR within the composition of the fourth aspect of the invention, is at least 1° C. or 2° C. more stable than its parent, preferably at least 5° C. more stable, more preferably at least 8° C. more stable and even more preferably at least 10° C. or 15° C. or 20° C. more stable than its parent. Typically, thermostability of the parent and mutant receptors are measured under the same conditions. Typically, thermostability is assayed under a condition in which the GPCR resides in a particular conformation. Typically, this selected condition is the presence of a ligand which binds the GPCR.

It is preferred that the mutant GPCR of the second or third aspect of the invention, or the mutant GPCR within the composition of the fourth aspect of the invention, when solubilised and purified in a suitable detergent has a similar thermostability to bovine rhodopsin purified in dodecyl maltoside; however it is appreciated that any increase in stability will be useful for applications such as crystallisation studies. It is particularly preferred that the mutant GPCR of the second or third aspect of the invention, or the mutant GPCR within the composition of the fourth aspect of the invention retains at least 50% of its ligand binding activity after heating at 40° C. for 30 minutes. It is further preferred that the mutant GPCR of the second or third aspect of the invention, or the mutant GPCR within the composition of the fourth aspect of the invention retains at least 50% of its ligand binding activity after heating at 55° C. for 30 minutes.

The mutant GPCRs and compositions disclosed herein are useful for crystallisation studies and are useful in drug discovery programmes. They may be used in biophysical measurements of receptor/ligand kinetic and thermodynamic parameters eg by surface plasmon resonance or fluorescence based techniques. They may be used in ligand binding screens, and may be coupled to solid surfaces for use in high throughput screens or as biosensor chips. Biosensor chips containing the mutant GPCRs or compositions may be used to detect molecules, especially biomolecules.

The invention also includes a polynucleotide which encodes a mutant GPCR of the second or third aspect of the invention. In particular, polynucleotides are included which encode the mutant adenosine, mutant serotonin or mutant muscarinic receptors of the invention. The polynucleotide may be DNA or it may be RNA. Typically, it is comprised in a vector, such as a vector which can be used to express the said mutant GPCR. Suitable vectors are ones which propagate in and/or allow the expression in bacterial or mammalian or insect cells.

The invention also includes host cells, such as bacterial or eukaryotic cells, which contain a polynucleotide which encodes the mutant GPCR. Suitable cells include $E.\ coli$ cells, yeast cells, mammalian cells and insect cells.

EXAMPLE 1

The Effect of Mutating Amino Acid Residue 2.46 and Surrounding Residues on Receptor Thermal Stability Introduction In Class 1 GPCRs, 2.46 is one of the most conserved residues in TM2 (approximately L 96%, M 2%, 11.5% and V/T 0.5%). (8, 9). Localised at the bottom of TM2, the side chain of this residue faces the helix bundle and is close to the "micro-switch" constituted by the very well conserved residues N7.49, P7.50 and Y7.53 of the TM7 NPXXY (SEQ ID NO: 1) motif. As described below, our various studies on a number of different receptors have revealed that mutating this residue to alanine increases the thermal stability of the agonist bound receptors. Significantly, mutating some of the nearby residues increase the thermal stability of the antagonist bound receptors. Thus, mutating this residue in particular and its surrounding residues constitutes a general approach to stabilise different GPCRs. Depending on the residue it is possible to increase the thermal stability of the receptor in the agonist or antagonist conformation.

Results

Effect of L2.46a on Agonist Bound $A_{2A}$ Thermal Stability

In order to stabilise an agonist-bound conformation, a systematic Alanine-scan was performed in order to identify mutations that may stabilise the $A_{2A}$ receptor bound to its full agonist NECA. In this $A_{2A}$ agonist-bound study, L2.46 (L48A) is the most stabilising single mutant. When NECA is bound to the solubilised receptor, removing the L48 side chain (in $A_{2A}$-L48A) dramatically increases the thermostability of the ligand-receptor complex resulting in an increase of 14° C. over the wild type receptor in the detergent DDM (FIG. 5a). Interestingly, this mutation abolishes the binding of the antagonist (FIG. 5b), indicating that removing this side-chain induces a conformational change, which may partially or fully lock the receptor in an active conformation. We evaluated the signalling property of the $A_{2A}$ receptor by over-expressing the receptor in CHO cells. $A_{2A}$ agonist stimulation triggers the signal transduction through the Gs-trimeric complex and increases the intracellular cAMP level. The increase in intracellular cAMP can be detected by and quantified by using an anti-cAMP Mab antibody competition assay. The potency of the $A_{2A}$-WT receptor is in good agreement with the published data with a $pEC_{50}$=7.27±0.19. The mutant displays a higher potency ($pEC_{50}$=8.10±0.39). However the signalling efficacy is reduced to 30% (FIG. 6).

Effect of L2.46a on Agonist Bound 5HT2C Thermal Stability

Figure 7:
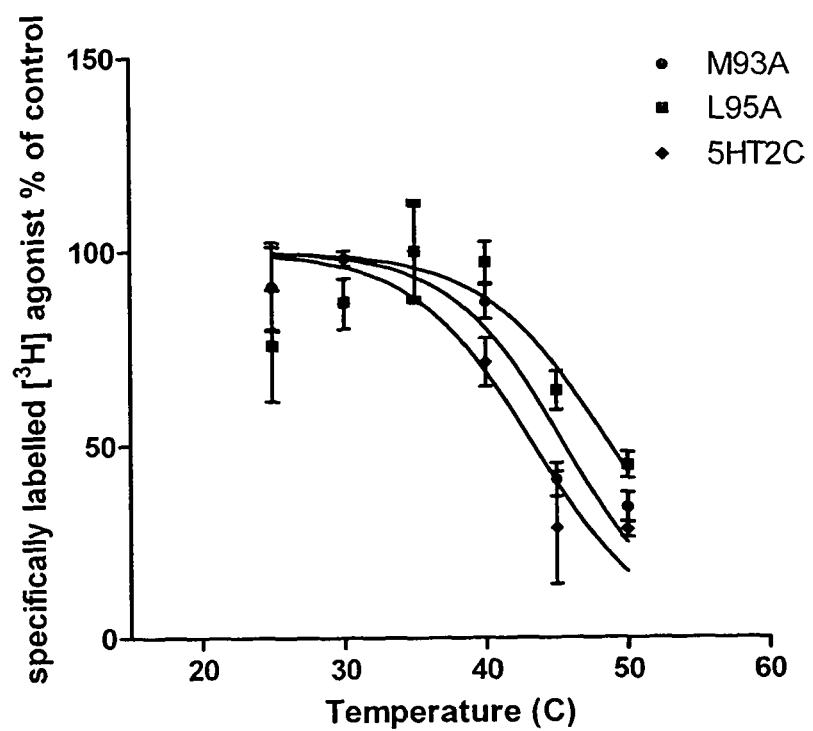
FIG. 7: Thermostability of 5HT2C receptor bound to agonist. $Tm_{5HT2C}=43.35°$ C., $Tm_{M93A}=45.6°$ C. and $TM_{L95A}=48.8°$ C.

An alanine scan has been carried out on the 5HT2C receptor in the presence of the agonist SCH23390 in order to stabilise the agonist conformation. Similar to A2A, it appears that mutating L2.46 (L95 in 5HT2C) to alanine confers significant stability on this receptor increasing the Tm of the receptor by 5.4° C. (FIG. 7). It is notable that in addition to L95, mutating the nearby M93 (two residues away from L2.46) to alanine also confers stability to the agonist bound receptor, resulting in an increase of 2.9° C.

Effect of Mutations in L2.46 Region on Antagonist Bound M4 and 5HT2C Thermal Stability In order to stabilise the M4 muscarinic receptors in antagonist conformation, a systematic alanine-scan was performed to identify mutations that stabilise receptors bound to the muscarinic antagonist, NMS. Mutating M4 L2.46 residue to alanine does not change the thermal stability of this receptor significantly (Data not shown). However, L71A (three residues N-terminal of the L2.46) was identified as a stabilising mutation. This mutation increases the Tm of this receptor by about 2° C. (FIG. 8a).

Similarly, the antagonist alanine scanning of 5HT2C receptor revealed that mutating L2.46 to alanine did not confer any stability on the antagonist bound 5HT2C (Data not shown), however mutating the nearby S94 (one residue away from L2.46) to alanine significantly increased the Tm of the antagonist bound receptor by 11.76° C. (FIG. 8b).

Conclusion

Our collective data from three different receptors clearly demonstrate that L2.46 and its surrounding residues play an important role in stabilising different conformations of receptors. Given the high level of sequence conservation of this region, it seems that the conformation specific stabilising effects of the residues in this region is a general feature of different GPCRs. Although it is not clear how these changes improve the stability of the receptors, mutating these residues may alter the equilibrium between R and R* (active and inactive states). Destabilising the ground state of the receptor might be a good first step in the process of agonist-bound receptor stabilisation. Conversely, preventing the formation of active conformation may in turn further stabilise the ground state by shifting the equilibrium towards the R state.

Materials and Methods

Receptor Expression $A_{2A}R$-(2-316) expression was carried out by using the pRG/III-hs-MBP *E. coli* expression vector and DH5α cells. Cells were grown at 37° C. in 2 L flasks containing 500 mL of 2xTY medium supplemented with Ampicillin (100 μg/mL) and glucose (0.2% w/v). At OD600≈0.7, IPTG and theophylline were added at final concentrations respectively of 0.5 mM and 100 μM, and the temperature was reduced to 20° C. After 22 to 24 hours, cells were harvested in aliquots of 14 mL, centrifuged for 30 min and stored at −20° C. Both 5HT2C and M4 receptors were transiently expressed in HEK293T cells using GeneJuice transfection reagent used according to the manufacturers guidelines.

Receptor Solubilisation and Purification and Thermostability Assay

An aliquot of *E. coli* cells expressing wild type or mutant $A_{2A}R$-(2-316) (14 mL) was thawed on ice and cells were resuspended in 500 μL of buffer A (50 mM Tris HCl mM/pH 7.4; 0.4 M NaCl, 250 μg/mL lysozyme (Sigma), 1 mg/mL DNAse I (Sigma), supplemented with complete EDTA-free Protease inhibitor cocktail (Roche)) and incubated 1 hour at 4° C. Samples were then sonicated 1 min at 4° C. using a cup-horn sonicator. The receptors were solubilised by adding 1% DDM and incubated 1 hour at 4° C. Insoluble material was removed by centrifuging the tube for 5 min at 13000 g at 4° C. The solubilised receptors were partially purified with Ni-NTA agarose (Qiagen). 300 μL of agarose beads pre-equilibrated in buffer A were added to the 700 μL of solubilised receptor. To reduce the detergent concentration, a solution of 50 mM Tris HCl mM/pH 7.4; 0.4 M NaCl was added to a final volume of 2 mL. After 2 hours of incubation at 4° C., samples were centrifuged at 13000 g for 10 seconds at 4° C. and washed 3 times in buffer B (Hepes 25 mM/pH 7.4 KOH, 0.025% DDM) and then eluted in buffer B supplemented with 50 mM histidine, 30 minutes at 4° C. The supernatant was used directly in radioligand-binding assay. Specifically, 108 μL of solubilised receptor was mixed with 12 μL of 4 μM [$^3$H]-NECA (final concentration of 400 nM) or 12 μL of 1 μM [$^3$H]-ZM241385 (final concentration of 100 nM). The sample was incubated for 45 min at 4° C., then 30 min at the specified temperature and then 30 min at 4° C. Receptor bound and free radioligand were separated using a 96-well plate gel filtration assay.

Transiently transfected mammalian cells expressing M4 were harvested about 40 hours post transfection and the receptors were solubilised in 50 mM Tris pH 7.5/250 mM NaCl/1% DDM/EDTA free protease inhibitor mix for 1 hour rotating at 4° C. The solubilised lysate was then cleared by centrifugation at 13000 rpm for 15 minutes at 4° C. The solubilised receptors were then purified on Ni-NTA beads and eluted with 100 mM histidine. The eluted receptor was used in radioligand binding assay. Thermostability of M4 was measured using 25 μL of purified receptor mixed with 95 μL of 12 nM [$^3$H]-NMS (final concentration of 10 nM). The sample was incubated for 60 min at 4° C., then 30 min at the specified temperature and then 30 min at 4° C. Receptor bound and free radioligand were separated using a 96-well plate gel filtration assay.

5HT2C receptor was solubilised from transiently transfected mammalian cells in 50 mM Hepes pH7.4, 100 mM KCl, 0.5% DDM (0.1% CHS/0.6% CHAPS was added to cells for SCH23390 agonist assay). Tm analysis was performed directly on the soluble lysate. The Tm was determined by incubating 108 μl of the lysate with [$N^6$-methyl-$^3$H]Mesulergine radioligand at a final concentration of 17 nM or 9 nM [$^3$H]SCH23390 for one hour at 4° C. The six ligand incubations are then incubated at six different temperatures from 25° C. to 55° C., for thirty minutes. Receptor bound and free radioligand were separated using a 96-well plate gel filtration assay.

cAMP Functional Assay

This assay takes advantage of Homogeneous Time-Resolved Fluorescence (HTRF) using cAMP labeled with the dye d2 in presence of an anti-cAMP Mab labeled with Cryptate. The method is based on a competitive immunoassay between cAMP produced by cells and the cAMP labeled with the dye d2. CHO cells were grown using Glutamax Ham's F12, 10% FBS in 96-well plates, clear bottom and Black wall (Costar). Cells were seeded at a density of 12500 cells per well, grown overnight, washed with PBS and then transfected with 100 ng of pcDNA-3-$A_{2A}$(2-316) pre-incubated with 0.3 μL of GeneJuice (Novagen) per well. After 48 hours of receptor expression, the medium was removed, the cells were washed in PBS then stimulated by using different NECA concentrations, in the presence of Rolipram (50 μM) and Adenosine deaminase in a total volume of 50 μL for 30 minutes. Dilution was realised in Hamf's F12/cAMP-d2 conjugate according to the manufacturer protocol, without serum. After 30 minutes of agonist stimulation, 50 μL of anti-cAMP/Cryptate diluted in conjugate and lysis buffer were added per well. The plate was incubated at room temperature for 1 hour and then read using the Pherastar 96-well time-resolved fluorescence plate reader (Ex 340 nm; Em 665/620 nm).

EXAMPLE 2

The Effect of Mutating Amino Acids within TM7 that Interact with Amino Acid Residue 2.46 on Receptor Stability Results Effect of Mutating Residues in the NpxxY (SEQ ID NO: 1) Motif on Agonist Bound $A_{2A}$ Thermal Stability In the $A_{2A}$ agonist-bound study the effect of mutations from the alanine scan were determined initially by two point thermostability measurements. In these experiments, the wild type receptors and receptors containing single mutants were solubilised in the detergent DDM and the amount of NECA binding retained at 4° C. and at a destabilising temperature such as 30° C. was determined. A>10% increase in agonist binding to the mutant receptor compared to the wild type receptor at the destabilising temperature is considered to be significant and is indicative of an increase in thermostability. In the $A_{2A}$ agonist scan, mutation of residue Asparagine 284 (N284, N7.49) resulted in an increased thermostability as indicated by an increased agonist binding compared to the wild type at the destabilising temperature.

Figure 9:
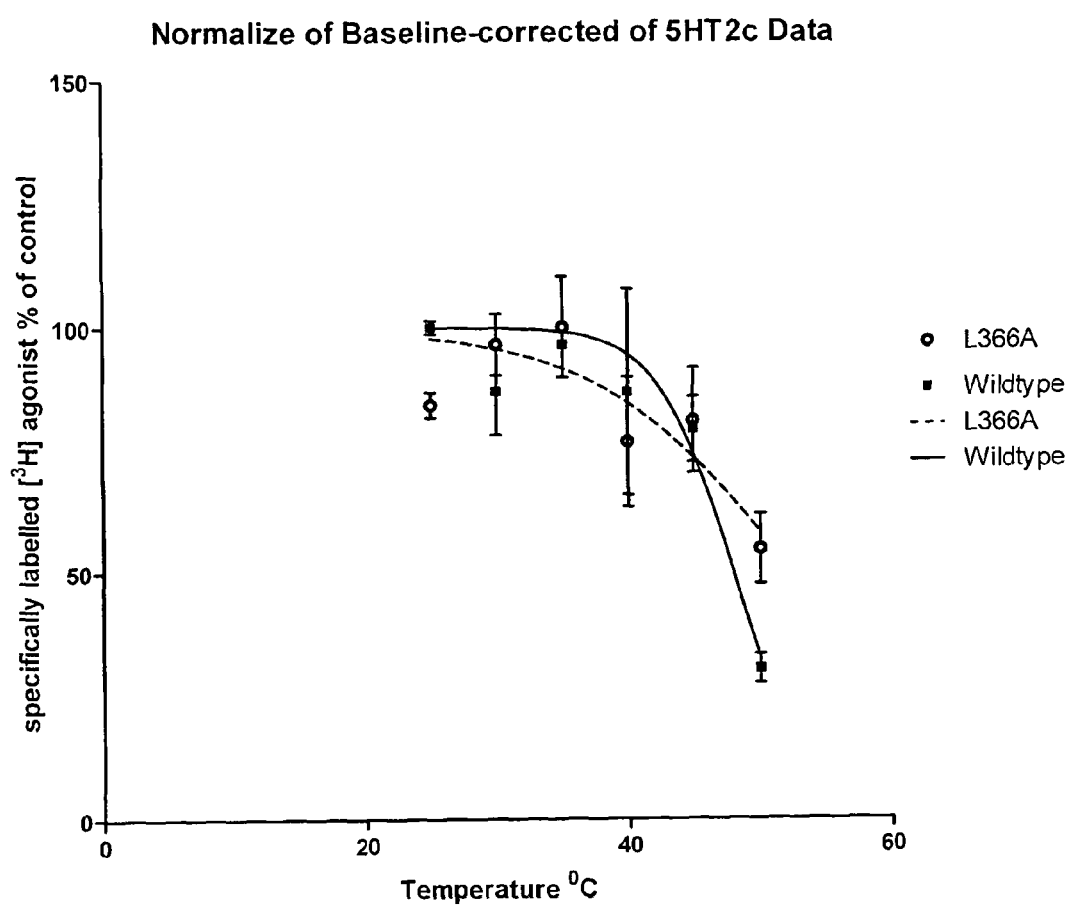
FIG. 9: Thermostability of L366A mutant 5HT2C receptor in 5CH23390 agonist-bound state.

Effect of Mutating Residues in the NpxxY (SEQ ID NO: 1) Motif on Agonist Bound 5HT2C Thermal Stability An alanine scan has been carried out on the 5HT$_{2C}$ receptor in the presence of the agonist SCH23390 in order to stabilise the agonist conformation. Similar to A$_{2A}$, mutating residues within and around the NPxxY (SEQ ID NO: 1) motif resulted in an increase in thermostability. In the two point thermostability assay, mutation of residues 7.48 (I363) and 7.51 (L366) to alanine resulted in an increased agonist binding compared to the wild type receptor at the destabilising temperature, indicating an increase in stability. FIG. 9 shows that mutating L366 (L in the NPLVY (SEQ ID NO: 363) motif) to alanine confers stability, increasing the Tm receptor by 4° C.

Effect of Mutating Residues in the NPxxY (SEQ ID NO: 1) Motif on Agonist Bound Neurotensin Receptor Thermal Stability An alanine scan has been carried out on the rat neurotensin receptor NTS$_1$ in the presence of the agonist neurotensin in order to stabilise the agonist conformation. In the two point thermostability assay mutation of residue 7.53 (Y369) which represents the Y in the NPxxY (SEQ ID NO: 1) to alanine resulted in an increased agonist binding compared to the wild type receptor at the destabilising temperature, indicating an increase in stability.

Effect of Mutations in NPxxY (SEQ ID NO: 1) Region on Antagonist Bound Adenosine A$_{2A}$ and 5HT$_{2C}$ Binding An alanine scan was carried out in a similar fashion on an adenosine A$_{2A}$ receptor along with the 5HT$_{2C}$ receptor in the presence of the antagonist Mesulergine. Both alanine scans were carried out in order to further stabilize the antagonist conformation. It is notable that in both scans antagonist binding appeared to be significantly decreased when the amino acids from the NPxxY (SEQ ID NO: 1) motif were changed to an alanine (Table 1). The motif in Adenosine A$_{2A}$ is NPFIY (SEQ ID NO: 364) and for the 5HT$_{2C}$ is NPLVY (SEQ ID NO: 363). Therefore mutations in this region of the receptor contain stabilising mutations specific to the agonist conformation and detrimentally effect antagonist binding.

Table 1

TABLE 1

| | DPM1 | DPM2 | Average | Average - BG | % of Wildtype binding |
|---|---|---|---|---|---|
| 5HT2c | | | | | |
| Wildtype | 10202 | 9631 | 9916.5 | 9208 | 100 |
| N364A | 3988 | 3569 | 3778.5 | 3347 | 36.35 |
| P365A | 1855 | 1760 | 1807.5 | 1376 | 14.94 |
| 366A | 2515 | 1897 | 2206 | 1774.5 | 19.27 |
| V367A | 2512 | 2449 | 2480.5 | 2049 | 22.25 |
| Y368A | 1328 | 1602 | 1465 | 1033.5 | 11.22 |
| A2a | | | | | |
| Wildtype | 13513 | 12949 | 13231 | 12731 | 100 |
| P285A | 1488 | 1471 | 1479.5 | 979.5 | 7.69 |
| F286A | 519 | 514 | 516.5 | 16.5 | 0.13 |
| 287A | 888 | 820 | 854 | 354 | 2.78 |
| Y288A | 2150 | 2602 | 2376 | 1876 | 14.74 |

The distances between the Cα atom of amino acid residue 2.46 and the Cα atom of each of the 4 residues either side of residue 2.46, and between the Cα atom of amino acid residue 2.46 and the Cα atom of the residues in the NPxxY (SEQ ID NO: 1) motif, are as follows for the adenosine A$_{2A}$ receptor:

| Calpha 1 | Calpha 2 | Distance (A) (Cα1-Cα2) |
|---|---|---|
| L48(L2.46) | F44 | 6.03 |
| | V45 | 5.01 |
| | V46 | 5.24 |
| | S47 | 3.8 |
| | A49 | 3.81 |
| | A50 | 5.33 |
| | A51 | 5.22 |
| | D52 | 6.50 |
| | N284 | 9.38 |
| | P285 | 10.89 |
| | F286 | 14.24 |
| | I287 | 13.72 |
| | Y288 | 12.93 |

Materials and Methods

5HT$_{2C}$ receptor was solubilised from transiently transfected mammalian cells about 40 hours post transfection, in 50 mM Hepes pH7.4/100 mM KCl/0.5% DDM/(0.1% CHS/0.6% CHAPS was added to cells for SCH23390 agonist assay) and protease inhibitor. Cell lysates were left at 4° C. on a rotator and then cleared by centrifugation at 13,200 rpm for 20 minutes at 4° C. Thermostability analysis was performed directly on the soluble lysate. The Tm was determined by incubating 108 μl of the lysate with [N$^6$-methyl-$^3$H]Mesulergine radioligand at a final concentration of 17 nM or 9 nM [$^3$H]SCH23390 for one hour at 4° C. The six ligand incubations are then incubated at six different temperatures from 25° C. to 55° C., for thirty minutes. Receptor bound and free radioligand were separated using G25 Sephadex spin columns.

Adenosine A$_{2A}$ receptor was solubilised from transiently transfected mammalian cells about 36 hours post transfection, in 50 mM Tris pH7.4/400 mM NaCl/0.5% DDM and protease inhibitor. Cell lysates were left at 4° C. on a rotator and then cleared by centrifugation at 13,200 rpm for 20 minutes at 4° C. Solubilised receptors were then purified on Ni-NTA beads and eluted with 50 mM histidine. The eluted receptor was used in radioligand binding assay. The Tm was determined by incubating 108 μl of the eluate with Zm241385 radioligand at a final concentration of 100 nM for one hour at 4° C. The six ligand incubations are then incubated at six different temperatures from 20° C. to 50° C., for thirty minutes. Receptor bound and free radioligand were separated using G25 Sephadex spin columns.

References

1. S. H. White (2004) *Protein Sci* 13, 1948-1949.
2. C. G. Tate (2001) *FEBS Lett* 504, 94-98.
3. R. Grisshammer, C. G. Tate (1995) *Q Rev Biophys* 28, 315-422.
4. J. U. Bowie (2001) *Curr Opin Struct Biol* 11, 397-402.
5. F. W. Lau, S, Nauli, Y. Zhou, J. U. Bowie (1999) *J Mol Biol* 290, 559-564.
6. Y. Zhou, J. U. Bowie (2000) *J Biol Chem* 275, 6975-6979.
7. S. Faham, D. Yang, E. Bare, S. Yohannan, J. P. Whitelegge, J. U. Bowie (2004) *J Mol Biol* 335, 297-305.
8. Madabushi S, Gross A K, Philippi A, Meng E C, Wensel T G, & Lichtarge O (2004) *J Biol Chem* 279, 8126-8132.

9. Urizar E, Claeysen S, Deupi X, Govaerts C, Costagliola S, Vassart G, & Pardo L (2005) *J Biol Chem* 280, 17135-17141.

EXAMPLE 3

The Effect of I2.58A Mutation on Receptor Thermal Stability in Class 2 GPCRs Introduction Class 2 GPCRs have no direct alignment to Class 1, however within the family there are a number of conserved residues that may play key structural roles. Residue L2.59 in Class 2 is located in TM2 in a comparable position to L2.46 in Class 1 (FIG. 14). This residue is one of the most conserved residues.

As described below, our studies on human $CRF_1$ have revealed that mutating the residue in the i-1 position in this receptor (I2.58) to alanine increases the thermal stability of antagonist-bound receptors ($CRF_1$). Thus, it is plausible that, similar to Class 1 GPCRs, mutating residues in this region of the receptor constitutes a general approach for stabilising Class 2 GPCRs.

Results

Effect of I2.58A on Antagonist-Bound $CRF_1$ Thermal Stability

Figure 15:
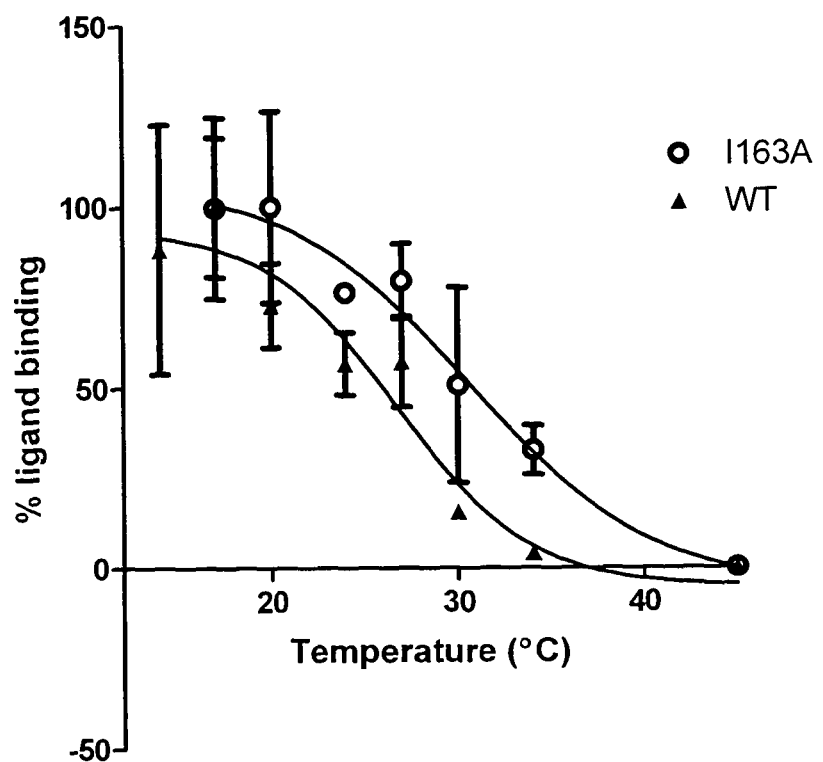
FIG. 15: Thermal stability analysis of $CRF_1$-WT (triangles) and CRF1 I163A mutant (circles) in antagonist-bound state, purified in DDM. $Tm_{WT}=26.8°$ C., $Tm_{I163A}=30.7°$ C.

In order to stabilise $CRF_1$ in the antagonist conformation, a systematic alanine-scan was performed to identify mutations that stabilise receptors bound to the antagonist ligand CP-376395. Mutating I2.58 to alanine (I163A) confers significant stabilisation in $CRF_1$, increasing the thermal stability by 3.9 (±0.5)° C. (FIG. 15).

Materials and Methods

Receptor Expression $CRF_1$ receptors were transiently expressed in HEK293T cells on 10 cm plates using GeneJuice transfection reagent used according to manufacturers guidelines.

Receptor Solubilisation, Purification and Thermostability Assay

Cells expressing $CRF_1$ were harvested in PBS approximately 40 hours post-transfection and re-suspended in 950 µl Re-suspension buffer (50 mM Tris-HCl, 150 mM NaCl, 2× Complete EDTA-free Protease inhibitor cocktail (Roche), pH7.5). Cells were incubated with 120 nM CP-376395 and 30 nM [$^3$H]-CP-376395 at 37° C. for 2 hours before transferring to ice for 5 minutes. The receptors were solubilised by the addition of 1% DDM and incubated at 4° C. for 1 hour with gentle agitation. Insoluble material was removed by centrifugation at 16000×g for 10 minutes at 4° C. The solubilised receptors were partially purified with Ni-NTA agarose (Qiagen). Ni-NTA resin was equilibrated in Equilibration buffer (50 mM Tris-HCl, 150 mM NaCl, 2× Complete EDTA-free Protease inhibitor cocktail (Roche), 0.025% DDM, pH7.5) and 400 µl of a 50:50 resin slurry was added to each sample. Resin slurries were incubated at 4° C. for 1 hour 30 minutes with gentle agitation to bind receptors. Resin slurries were then transferred to a batch column filter plate (Chromabond) and centrifuged at 1000×g for 1 minute, discarding the flow-through. Resin was washed twice with 1 ml of Wash buffer (50 mM Tris-HCl, 150 mM NaCl, 2× Complete EDTA-free Protease inhibitor cocktail (Roche), 0.025% DDM, 20 mM Imidazole, pH7.5) and then eluted in 1 ml of Elution buffer (50 mM Tris-HCl, 150 mM NaCl, 2× Complete EDTA-free Protease inhibitor cocktail (Roche), 0.025% DDM, 100 mM histidine, 30 nM [$^3$H]-CP-376395, 120 nM CP-376395, pH7.5) by resuspension at 4° C. for 30 minutes. Eluted samples were used directly in the thermostability assay. 120 µl of each sample was incubated at specific temperature points for 30 minutes before transferring directly to ice. Receptor bound and free radioligand were then separated using a 96-well plate gel filtration assay.

EXAMPLE 4

The Effect of the L2.46a Mutation on Antagonist Bound $OX_2$ Thermal Stability Orexin 2 ($OX_2$) is a Class 1 GPCR implicated in regulating the sleep-wake cycle and energy homeostasis.

Results

Effect of L2.46A on Antagonist Bound Human $OX_2$ Thermal Stability

Figure 16:
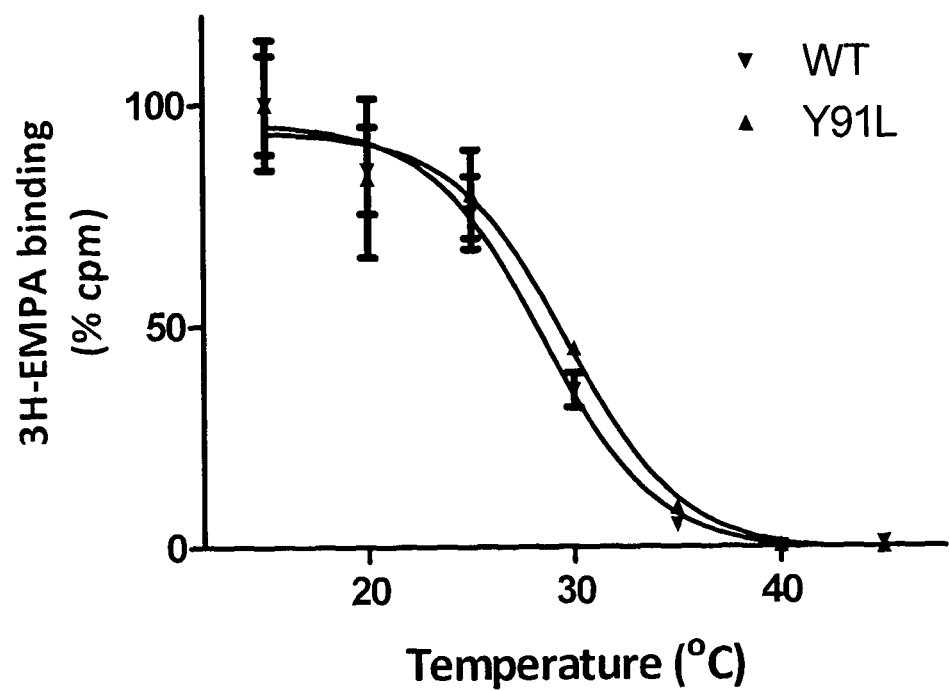
FIG. 16: Thermostability of $OX_2$ receptor bound to antagonist. $Tm_{OX2WT}=28.47°$ C., $Tm_{OX2I91L}=29.69°$ C.

A tandem alanine and leucine scanning mutagenesis strategy was used to identify mutations that enhanced the thermostability of $OX_2$ bound to the small-molecule antagonist EMPA. Substitution of $OX_2$ L2.46 (L96 in $OX_2$) to alanine had little effect on receptor thermostability. However, mutating Tyr91 (five residues N-terminal of L2.46) was found to confer increased stability, raising the Tm by 1° C. compared to WT $OX_2$ (FIG. 16).

Material and Methods

Thermostability assays were preformed on partially purified receptors as described for M4, with the following amendments. Cell lysates were solubilised in 50 mM Tris pH7.4, 150 mM NaCl, 1% DDM supplemented with 1× complete EDTA free protease inhibitor cocktail (Roche). Radioligand binding reactions were set up using 1/10 volume eluted receptor mixed with 20 nM $^3$H-EMPA (final concentration) per temperature point.

The invention claimed is:

1. A method for producing a mutant G-protein coupled receptor (GPCR) with increased stability relative to a parent GPCR, the method comprising changing one or more amino acids in the amino acid sequence that defines a parent GPCR, wherein (i) the one or more changed amino acids are located within a window of i plus or minus 5 residues, where i is the position of amino acid residue 2.46 in the parent GPCR when the parent GPCR is a Class 1 GPCR, or where i is the position of an equivalent amino acid residue in the parent GPCR when the parent GPCR is a Class 2 or 3 GPCR, or (ii) the one or more changed amino acids are located within an amino acid sequence of transmembrane helix 7 in the parent GPCR which amino acid sequence interacts with the window of i plus or minus 5 residues, to provide one or more mutants of the parent GPCR with increased stability.

2. A method according to claim 1 wherein the one or more changed amino acids in step (i) are located within a window of i plus or minus 4 residues, and wherein the one or more changed amino acids in step (ii) are located within an amino acid sequence of transmembrane helix 7 in the parent GPCR which amino acid sequence interacts with the window of i plus or minus 4 residues or wherein the one or more mutants of the parent GPCR have increased stability of a particular conformation.

3. A method according to claim 1, wherein the parent GPCR is a Class 1 GPCR or a Class 2 GPCR.

4. A method according to claim 3, wherein the parent GPCR is any of an adenosine receptor, a serotonin receptor, a β-adrenergic receptor, a neurotensin receptor, a muscarinic receptor, a corticotropin releasing hormone receptor or an orexin receptor.

5. A method according to claim 1, wherein the amino acid sequence of transmembrane helix 7 in the parent GPCR, which amino acid sequence interacts with the window of i plus or minus 5 residues, is the NPxxY (SEQ ID NO: 1) motif plus or minus 3 residues when the parent GPCR is a Class 1 GPCR or is the SFQ motif plus or minus 3 residues when the parent GPCR is a Class 2 GPCR or is the xPKxY (SEQ ID NO: 4) motif plus or minus 3 residues when the parent GPCR is a Class 3 GPCR.

6. A method according to claim 1, wherein the mutant GPCR with increased stability relative to its parent GPCR, is a mutant adenosine receptor which, when compared to the corresponding parent receptor, has a different amino acid at a position which corresponds to any one or more of Leu 48 and Asn 284 according to the numbering of the human adenosine $A_{2A}$ receptor as set out in (SEQ ID NO:315).

7. A method according to claim 1, wherein the mutant GPCR with increased stability relative to its parent GPCR, is a mutant serotonin receptor which, when compared to the corresponding parent receptor, has a different amino acid at a position which corresponds to any one or more of Met 93, Ser 94, Leu 95, Ile 363 and Leu 366 according to the numbering of the human $5HT_{2c}$ receptor as set out in (SEQ ID NO:316).

8. A method according to claim 1, wherein the mutant GPCR with increased stability relative to its parent GPCR, is a mutant muscarinic receptor which, when compared to the corresponding parent receptor, has a different amino acid at a position which corresponds to Leu 71, according to the numbering of the human M4 muscarinic receptor as set out in (SEQ ID NO:317).

9. A method according to claim 1, wherein the mutant GPCR with increased stability relative to its parent GPCR, is a mutant neurotensin receptor which, when compared to the corresponding parent receptor, has a different amino acid at a position which corresponds to Tyr 369, according to the numbering of the rat neurotensin receptor as set out in (SEQ ID NO:318).

10. A method according to claim 1, wherein the mutant GPCR with increased stability relative to its parent GPCR, is a mutant corticotropin releasing hormone receptor which, when compared to the corresponding parent receptor, has a different amino acid at a position which corresponds to Ile 163 according to the numbering of human CRF, as set out in (SEQ ID NO:319).

11. A method according to claim 1, wherein the mutant GPCR with increased stability relative to its parent GPCR, is a mutant orexin receptor which, when compared to the corresponding parent receptor, has a different amino acid at a position which corresponds to Tyr 91 according to the numbering of human $OX_2$ as set out in (SEQ ID NO:320).

12. A mutant GPCR with increased stability relative to its parent GPCR produced by the method of claim 1.

13. A method according to claim 1 wherein the method comprises changing one or more amino acids in the amino acid sequence that defines a parent GPCR, wherein (i) the one or more changed amino acids are located within a window of i plus or minus 5 residues, where i is the position of amino acid residue 2.46 in the parent GPCR when the parent GPCR is a Class 1 GPCR, or where i is the position of an equivalent amino acid residue in the parent GPCR when the parent GPCR is a Class 2 or 3 GPCR, and (ii) the one or more changed amino acids are located within an amino acid sequence of transmembrane helix 7 in the parent GPCR which amino acid sequence interacts with the window of i plus or minus 5 residues, to provide one or more mutants of the parent GPCR with increased stability.

14. A mutant GPCR which, when compared to a parent GPCR, has one or more changed amino acids in the amino acid sequence defining the parent GPCR, wherein (i) the one or more changed amino acids are located within a window of i plus or minus 5 residues, where i is the position of amino acid residue 2.46 in the parent GPCR when the parent GPCR is a Class 1 GPCR, or where i is the position of an equivalent amino acid in the parent GPCR when the parent GPCR is a Class 2 or 3 GPCR or (ii) the one or more changed amino acids are located within an amino acid sequence of transmembrane helix 7 in the parent GPCR which amino acid sequence interacts with the window of i plus or minus 5 residues, which mutant GPCR has increased stability compared to a parent GPCR when exposed to a destabilising condition.

15. A mutant GPCR according to claim 14, wherein the mutant GPCR is a mutant adenosine receptor which, when compared to the corresponding parent receptor, has a different amino acid at a position which corresponds to any one or more of Leu 48 and Asn 284 according to the numbering of the human adenosine $A_{2A}$ receptor as set out in (SEQ ID NO:315).

16. A mutant GPCR according to claim 14, wherein the mutant GPCR is a mutant serotonin receptor which, when compared to the corresponding parent receptor, has a different amino acid at a position which corresponds to any one or more of Met 93, Ser 94, Leu 95, Ile 363 and Leu 366 according to the numbering of the human $5HT_{2C}$ receptor as set out in (SEQ ID NO:316).

17. A mutant GPCR according to claim 14, wherein the mutant GPCR is a muscarinic receptor which, when compared to the corresponding parent receptor, has a different amino acid at a position which corresponds to Leu 71 according to the numbering of the human M4 muscarinic receptor as set out in (SEQ ID NO:317).

18. A mutant GPCR according to claim 14, wherein the mutant GPCR is a neurotensin receptor which, when compared to the corresponding parent receptor, has a different amino acid at a position which corresponds to Tyr 369 according to the numbering of the rat neurotensin receptor as set out in (SEQ ID NO:318).

19. A mutant GPCR according to claim 14, wherein the mutant GPCR is a corticotropin releasing hormone receptor which, when compared to the corresponding parent receptor, has a different amino acid at a position which corresponds to Ile 163 according to the numbering of human CRF, as set out in (SEQ ID NO:319).

20. A mutant GPCR according to claim 14, wherein the mutant GPCR is an orexin receptor which, when compared to the corresponding parent receptor, has a different amino acid at a position which corresponds to Tyr 91 according to the numbering of human $OX_2$ as set out in (SEQ ID NO:320).

21. A mutant GPCR according to claim 14, which when compared to a parent GPCR, has one or more changed amino acids in the amino acid sequence defining the parent GPCR, wherein (i) the one or more changed amino acids are located within a window of i plus or minus 5 residues, where i is the position of amino acid residue 2.46 in the parent GPCR when the parent GPCR is a Class 1 GPCR, or where i is the position of an equivalent amino acid in the parent GPCR when the parent GPCR is a Class 2 or 3 GPCR and (ii) the one or more changed amino acids are located within an amino acid sequence of transmembrane helix 7 in the parent GPCR which amino acid sequence interacts with the window of i plus or minus 5 residues, which mutant GPCR has increased stability compared to a parent GPCR when exposed to a destabilising condition.

22. A composition comprising a mutant GPCR which, when compared to a parent GPCR, has one or more changed amino acids in the amino acid sequence defining the parent GPCR, wherein (i) the one or more changed amino acids are located within a window of i plus or minus 5 residues, where i is the position of amino acid residue 2.46 in the parent GPCR when the parent GPCR is a Class 1 GPCR, or where i is the position of the equivalent amino acid residue in the parent GPCR when the parent GPCR is a Class 2 or 3 GPCR or (ii) the one or more changed amino acids are located within an amino acid sequence of transmembrane helix 7 in the parent GPCR which amino acid sequence interacts with the window of i plus or minus 5 residues, characterised in that the mutant GPCR is exposed to a destabilising condition effective to destabilise a parent GPCR to a greater extent than the mutant GPCR.

23. A composition according to claim 22, comprising a mutant GPCR which, when compared to a parent GPCR, has one or more changed amino acids in the amino acid sequence defining the parent GPCR, wherein (i) the one or more changed amino acids are located within a window of i plus or minus 5 residues, where i is the position of amino acid residue 2.46 in the parent GPCR when the parent GPCR is a Class 1 GPCR, or where i is the position of the equivalent amino acid residue in the parent GPCR when the parent GPCR is a Class 2 or 3 GPCR and (ii) the one or more changed amino acids are located within an amino acid sequence of transmembrane helix 7 in the parent GPCR which amino acid sequence interacts with the window of i plus or minus 5 residues, characterised in that the mutant GPCR is exposed to a destabilising condition effective to destabilise a parent GPCR to a greater extent than the mutant GPCR.

* * * * *

UNITED STATES PATENT AND TRADEMARK OFFICE
CERTIFICATE OF CORRECTION

PATENT NO.        : 8,703,915 B2
APPLICATION NO.   : 13/379872
DATED             : April 22, 2014
INVENTOR(S)       : Jazayeri-Dezfuly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 19 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 364

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (3)..(4)

-continued

<223> OTHER INFORMATION: Xaa is any amino acid

<400> SEQUENCE: 1

Asn Pro Xaa Xaa Tyr
1               5

<210> SEQ ID NO 2
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Asn or Ser
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Ala or Ser

<400> SEQUENCE: 2

Xaa Leu Ala Xaa Xaa Asp
1               5

<210> SEQ ID NO 3
<211> LENGTH: 6
<212> TYPE: PRT
<213> ORGANISM: Homo sapiens

<400> SEQUENCE: 3

Ser Leu Ala Cys Ala Asp
1               5

<210> SEQ ID NO 4
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid

<400> SEQUENCE: 4

Xaa Pro Lys Xaa Tyr
1               5

<210> SEQ ID NO 5
<211> LENGTH: 46
<212> TYPE: PRT
<213> ORGANISM: Homo sapiens

<400> SEQUENCE: 5

Ala Asn Ala Trp Ile Ile Leu Ser Ile Ser Ala Lys Gln Gln Lys His
1               5                   10                  15

Lys Pro Leu Glu Leu Leu Leu Cys Phe Leu Ala Gly Thr His Ile Leu
            20                  25                  30

Met Ala Ala Val Pro Leu Thr Thr Phe Ala Val Val Gln Leu
                35                  40                  45

<210> SEQ ID NO 6
<211> LENGTH: 46

<212> TYPE: PRT
<213> ORGANISM: Homo sapiens

<400> SEQUENCE: 6

Ala Asn Ala Trp Gly Ile Leu Ser Val Gly Ala Lys Gln Lys Lys Trp
1               5                   10                  15

Lys Pro Leu Glu Phe Leu Leu Cys Thr Leu Ala Ala Thr His Met Leu
            20                  25                  30

Asn Val Ala Val Pro Ile Ala Thr Tyr Ser Val Val Gln Leu
        35                  40                  45

<210> SEQ ID NO 7
<211> LENGTH: 45
<212> TYPE: PRT
<213> ORGANISM: Homo sapiens

<400> SEQUENCE: 7

Gly Asn Ala Val Val Leu Trp Leu Leu Gly Cys Arg Met Arg Arg Asn
1               5                   10                  15

Ala Val Ser Ile Tyr Ile Leu Asn Leu Val Ala Ala Asp Phe Leu Phe
            20                  25                  30

Leu Ser Gly His Ile Ile Cys Ser Pro Leu Arg Leu Ile
        35                  40                  45

<210> SEQ ID NO 8
<211> LENGTH: 45
<212> TYPE: PRT
<213> ORGANISM: Homo sapiens

<400> SEQUENCE: 8

Gly Asn Ala Val Val Leu Trp Leu Leu Gly Tyr Arg Met Arg Arg Ser
1               5                   10                  15

Ala Val Ser Ile Tyr Ile Leu Asn Leu Ala Ala Ala Asp Phe Leu Phe
            20                  25                  30

Leu Ser Phe Gln Ile Ile Arg Ser Pro Leu Arg Leu Ile
        35                  40                  45

<210> SEQ ID NO 9
<211> LENGTH: 45
<212> TYPE: PRT
<213> ORGANISM: Homo sapiens

<400> SEQUENCE: 9

Gly Asn Ala Val Val Leu Trp Leu Leu Gly Cys Arg Met Arg Arg Asn
1               5                   10                  15

Ala Phe Ser Ile Tyr Ile Leu Asn Leu Ala Ala Ala Asp Phe Leu Phe
            20                  25                  30

Leu Ser Gly Arg Leu Ile Tyr Ser Leu Leu Ser Phe Ile
        35                  40                  45

<210> SEQ ID NO 10
<211> LENGTH: 45
<212> TYPE: PRT
<213> ORGANISM: Homo sapiens

<400> SEQUENCE: 10

Gly Asn Gly Phe Val Leu Trp Leu Leu Gly Phe Arg Met Arg Arg Asn
1               5                   10                  15

Ala Phe Ser Val Tyr Val Leu Ser Leu Ala Gly Ala Asp Phe Leu Phe
            20                  25                  30

Leu Cys Phe Gln Ile Ile Asn Cys Leu Val Tyr Leu Ser

```
                35                  40                  45

<210> SEQ ID NO 11
<211> LENGTH: 45
<212> TYPE: PRT
<213> ORGANISM: Homo sapiens

<400> SEQUENCE: 11

Gly Asn Ser Met Val Ile Trp Leu Leu Gly Phe Arg Met His Arg Asn
1               5                   10                  15

Pro Phe Cys Ile Tyr Ile Leu Asn Leu Ala Ala Ala Asp Leu Leu Phe
            20                  25                  30

Leu Phe Ser Met Ala Ser Thr Leu Ser Leu Glu Thr Gln
        35                  40                  45

<210> SEQ ID NO 12
<211> LENGTH: 45
<212> TYPE: PRT
<213> ORGANISM: Homo sapiens

<400> SEQUENCE: 12

Gly Asn Gly Ala Val Leu Trp Leu Leu Ser Ser Asn Val Tyr Arg Asn
1               5                   10                  15

Pro Phe Ala Ile Tyr Leu Leu Asp Val Ala Cys Ala Asp Leu Ile Phe
            20                  25                  30

Leu Gly Cys His Met Val Ala Ile Val Pro Asp Leu Leu
        35                  40                  45

<210> SEQ ID NO 13
<211> LENGTH: 45
<212> TYPE: PRT
<213> ORGANISM: Homo sapiens

<400> SEQUENCE: 13

Gly Asn Gly Leu Val Leu Trp Asn Leu Gly Phe Arg Ile Lys Lys Gly
1               5                   10                  15

Pro Phe Ser Ile Tyr Leu Leu His Leu Ala Ala Ala Asp Phe Leu Phe
            20                  25                  30

Leu Ser Cys Arg Val Gly Phe Ser Val Ala Gln Ala Ala
        35                  40                  45

<210> SEQ ID NO 14
<211> LENGTH: 45
<212> TYPE: PRT
<213> ORGANISM: Homo sapiens

<400> SEQUENCE: 14

Gly Asn Gly Leu Val Leu Trp Phe Phe Gly Phe Ser Ile Lys Arg Asn
1               5                   10                  15

Pro Phe Ser Ile Tyr Phe Leu His Leu Ala Ser Ala Asp Val Gly Tyr
            20                  25                  30

Leu Phe Ser Lys Ala Val Phe Ser Ile Leu Asn Thr Gly
        35                  40                  45

<210> SEQ ID NO 15
<211> LENGTH: 44
<212> TYPE: PRT
<213> ORGANISM: Homo sapiens

<400> SEQUENCE: 15

Leu Asn Gly Thr Val Phe Trp Leu Leu Cys Cys Gly Ala Thr Asn Pro
1               5                   10                  15
```

```
Tyr Met Val Tyr Ile Leu His Leu Val Ala Ala Asp Val Ile Tyr Leu
            20                  25                  30

Cys Cys Ser Ala Val Gly Phe Leu Gln Val Thr Leu
            35                  40
```

<210> SEQ ID NO 16
<211> LENGTH: 45
<212> TYPE: PRT
<213> ORGANISM: Homo sapiens

<400> SEQUENCE: 16

```
Glu Asn Gly Ile Leu Leu Trp Phe Leu Cys Phe Arg Met Arg Arg Asn
1               5                   10                  15

Pro Phe Thr Val Tyr Ile Thr His Leu Ser Ile Ala Asp Ile Ser Leu
            20                  25                  30

Leu Phe Cys Ile Phe Ile Leu Ser Ile Asp Tyr Ala Leu
            35                  40                  45
```

<210> SEQ ID NO 17
<211> LENGTH: 50
<212> TYPE: PRT
<213> ORGANISM: Homo sapiens

<400> SEQUENCE: 17

```
Gly Leu Pro Ala Asn Ile Leu Thr Val Ile Ile Leu Ser Gln Leu Val
1               5                   10                  15

Ala Arg Arg Gln Lys Ser Ser Tyr Asn Tyr Leu Leu Ala Leu Ala Ala
            20                  25                  30

Ala Asp Ile Leu Val Leu Phe Phe Ile Val Phe Val Asp Phe Leu Leu
            35                  40                  45

Glu Asp
    50
```

<210> SEQ ID NO 18
<211> LENGTH: 50
<212> TYPE: PRT
<213> ORGANISM: Homo sapiens

<400> SEQUENCE: 18

```
Gly Leu Pro Val Ser Leu Leu Thr Ala Val Ala Leu Ala Arg Leu Ala
1               5                   10                  15

Thr Arg Thr Arg Arg Pro Ser Tyr Tyr Tyr Leu Leu Ala Leu Thr Ala
            20                  25                  30

Ser Asp Ile Ile Ile Gln Val Val Ile Val Phe Ala Gly Phe Leu Leu
            35                  40                  45

Gln Gly
    50
```

<210> SEQ ID NO 19
<211> LENGTH: 47
<212> TYPE: PRT
<213> ORGANISM: Homo sapiens

<400> SEQUENCE: 19

```
Ser Asn Ala Leu Val Leu Leu Cys Leu Leu His Ser Ala Asp Ile Arg
1               5                   10                  15

Arg Gln Ala Pro Ala Leu Phe Thr Leu Asn Leu Thr Cys Gly Asn Leu
            20                  25                  30

Leu Cys Thr Val Val Asn Met Pro Leu Thr Leu Ala Gly Val Val
            35                  40                  45
```

<210> SEQ ID NO 20
<211> LENGTH: 47
<212> TYPE: PRT
<213> ORGANISM: Homo sapiens

<400> SEQUENCE: 20

Ser Asn Ala Leu Val Leu Leu Cys Leu Leu His Ser Ala Asp Ile Arg
1               5                   10                  15

Arg Gln Ala Pro Ala Leu Phe Thr Leu Asn Leu Thr Cys Gly Asn Leu
            20                  25                  30

Leu Cys Thr Val Val Asn Met Pro Leu Thr Leu Ala Gly Val Val
        35                  40                  45

<210> SEQ ID NO 21
<211> LENGTH: 47
<212> TYPE: PRT
<213> ORGANISM: Homo sapiens

<400> SEQUENCE: 21

Ser Asn Ala Leu Val Leu Leu Cys Cys Ala Tyr Ser Ala Glu Leu Arg
1               5                   10                  15

Thr Arg Ala Ser Gly Val Leu Leu Val Asn Leu Ser Leu Gly His Leu
            20                  25                  30

Leu Leu Ala Ala Leu Asp Met Pro Phe Thr Leu Leu Gly Val Met
        35                  40                  45

<210> SEQ ID NO 22
<211> LENGTH: 52
<212> TYPE: PRT
<213> ORGANISM: Homo sapiens

<400> SEQUENCE: 22

Ser Asn Leu Leu Ala Leu Ala Leu Leu Ala Gln Ala Ala Gly Arg Leu
1               5                   10                  15

Arg Arg Arg Arg Ser Ala Thr Thr Phe Leu Leu Phe Val Ala Ser Leu
            20                  25                  30

Leu Ala Thr Asp Leu Ala Gly His Val Ile Pro Gly Ala Leu Val Leu
        35                  40                  45

Arg Leu Tyr Thr
    50

<210> SEQ ID NO 23
<211> LENGTH: 51
<212> TYPE: PRT
<213> ORGANISM: Homo sapiens

<400> SEQUENCE: 23

Ser Asn Ser Leu Ala Ile Ala Ile Leu Met Lys Ala Tyr Gln Arg Phe
1               5                   10                  15

Arg Gln Lys Ser Lys Ala Ser Phe Leu Leu Leu Ala Ser Gly Leu Val
            20                  25                  30

Ile Thr Asp Phe Phe Gly His Leu Ile Asn Gly Ala Ile Ala Val Phe
        35                  40                  45

Val Tyr Ala
    50

<210> SEQ ID NO 24
<211> LENGTH: 50
<212> TYPE: PRT
<213> ORGANISM: Homo sapiens

```
<400> SEQUENCE: 24

Ser Asn Leu Leu Ala Leu Ser Val Leu Ala Gly Ala Arg Gln Gly Gly
1               5                   10                  15

Ser His Thr Arg Ser Ser Phe Leu Thr Phe Leu Cys Gly Leu Val Leu
                20                  25                  30

Thr Asp Phe Leu Gly Leu Leu Val Thr Gly Thr Ile Val Val Ser Gln
            35                  40                  45

His Ala
    50

<210> SEQ ID NO 25
<211> LENGTH: 51
<212> TYPE: PRT
<213> ORGANISM: Homo sapiens

<400> SEQUENCE: 25

Gly Asn Ala Leu Ala Met Leu Leu Val Ser Arg Ser Tyr Arg Arg Arg
1               5                   10                  15

Glu Ser Lys Arg Lys Lys Ser Phe Leu Leu Cys Ile Gly Trp Leu Ala
                20                  25                  30

Leu Thr Asp Leu Val Gly Gln Leu Leu Thr Thr Pro Val Val Ile Val
            35                  40                  45

Val Tyr Leu
    50

<210> SEQ ID NO 26
<211> LENGTH: 47
<212> TYPE: PRT
<213> ORGANISM: Homo sapiens

<400> SEQUENCE: 26

Gly Asn Gly Leu Ala Leu Gly Ile Leu Ser Ala Arg Arg Pro Ala Arg
1               5                   10                  15

Pro Ser Ala Phe Ala Val Leu Val Thr Gly Leu Ala Ala Thr Asp Leu
                20                  25                  30

Leu Gly Thr Ser Phe Leu Ser Pro Ala Val Phe Val Ala Tyr Ala
            35                  40                  45

<210> SEQ ID NO 27
<211> LENGTH: 56
<212> TYPE: PRT
<213> ORGANISM: Homo sapiens

<400> SEQUENCE: 27

Gly Asn Leu Leu Ala Leu Gly Leu Leu Ala Arg Ser Gly Leu Gly Trp
1               5                   10                  15

Cys Ser Arg Arg Pro Leu Arg Pro Leu Pro Ser Val Phe Tyr Met Leu
                20                  25                  30

Val Cys Gly Leu Thr Val Thr Asp Leu Leu Gly Lys Cys Leu Leu Ser
            35                  40                  45

Pro Val Val Leu Ala Ala Tyr Ala
    50                  55

<210> SEQ ID NO 28
<211> LENGTH: 57
<212> TYPE: PRT
<213> ORGANISM: Homo sapiens

<400> SEQUENCE: 28
```

```
Gly Asn Leu Ile Ala Leu Ala Leu Leu Ala Arg Arg Trp Arg Gly Asp
1               5                   10                  15

Val Gly Cys Ser Ala Gly Arg Arg Ser Ser Leu Ser Leu Phe His Val
                20                  25                  30

Leu Val Thr Glu Leu Val Phe Thr Asp Leu Leu Gly Thr Cys Leu Ile
            35                  40                  45

Ser Pro Val Val Leu Ala Ser Tyr Ala
            50                  55
```

<210> SEQ ID NO 29
<211> LENGTH: 48
<212> TYPE: PRT
<213> ORGANISM: Homo sapiens

<400> SEQUENCE: 29

```
Gly Asn Leu Val Ala Ile Val Val Leu Cys Lys Ser Arg Lys Glu Gln
1               5                   10                  15

Lys Glu Thr Thr Phe Tyr Thr Leu Val Cys Gly Leu Ala Val Thr Asp
                20                  25                  30

Leu Leu Gly Thr Leu Leu Val Ser Pro Val Thr Ile Ala Thr Tyr Met
            35                  40                  45
```

<210> SEQ ID NO 30
<211> LENGTH: 46
<212> TYPE: PRT
<213> ORGANISM: Homo sapiens

<400> SEQUENCE: 30

```
Gly Asn Ala Ile Leu Pro Leu Leu Val Leu Lys Glu Arg Ala Leu His
1               5                   10                  15

Lys Ala Pro Tyr Tyr Phe Leu Leu Asp Leu Cys Leu Ala Asp Gly Ile
                20                  25                  30

Arg Ser Ala Val Cys Phe Pro Phe Val Leu Ala Ser Val Arg
            35                  40                  45
```

<210> SEQ ID NO 31
<211> LENGTH: 46
<212> TYPE: PRT
<213> ORGANISM: Homo sapiens

<400> SEQUENCE: 31

```
Gly Asn Leu Leu Ile Ser Ile Leu Leu Val Lys Asp Lys Thr Leu His
1               5                   10                  15

Arg Ala Pro Tyr Tyr Phe Leu Leu Asp Leu Cys Cys Ser Asp Ile Leu
                20                  25                  30

Arg Ser Ala Ile Cys Phe Pro Phe Val Phe Asn Ser Val Lys
            35                  40                  45
```

<210> SEQ ID NO 32
<211> LENGTH: 46
<212> TYPE: PRT
<213> ORGANISM: Homo sapiens

<400> SEQUENCE: 32

```
Gly Asn Val Leu Phe Ala Leu Leu Ile Val Arg Glu Arg Ser Leu His
1               5                   10                  15

Arg Ala Pro Tyr Tyr Leu Leu Leu Asp Leu Cys Leu Ala Asp Gly Leu
                20                  25                  30

Arg Ala Leu Ala Cys Leu Pro Ala Val Met Leu Ala Ala Arg
            35                  40                  45
```

```
<210> SEQ ID NO 33
<211> LENGTH: 43
<212> TYPE: PRT
<213> ORGANISM: Homo sapiens

<400> SEQUENCE: 33

Gly Asn Val Leu Val Cys Trp Ala Val Trp Leu Asn Ser Asn Leu Gln
1               5                   10                  15

Asn Val Thr Asn Tyr Phe Val Val Ser Leu Ala Ala Ala Asp Ile Ala
            20                  25                  30

Val Gly Val Leu Ala Ile Pro Phe Ala Ile Thr
        35                  40

<210> SEQ ID NO 34
<211> LENGTH: 43
<212> TYPE: PRT
<213> ORGANISM: Homo sapiens

<400> SEQUENCE: 34

Gly Asn Val Leu Val Cys Ala Ala Val Gly Thr Ala Asn Thr Leu Gln
1               5                   10                  15

Thr Pro Thr Asn Tyr Phe Leu Val Ser Leu Ala Ala Ala Asp Val Ala
            20                  25                  30

Val Gly Leu Phe Ala Ile Pro Phe Ala Ile Thr
        35                  40

<210> SEQ ID NO 35
<211> LENGTH: 43
<212> TYPE: PRT
<213> ORGANISM: Homo sapiens

<400> SEQUENCE: 35

Gly Asn Val Leu Val Ile Trp Ala Val Lys Val Asn Gln Ala Leu Arg
1               5                   10                  15

Asp Ala Thr Phe Cys Phe Ile Val Ser Leu Ala Val Ala Asp Val Ala
            20                  25                  30

Val Gly Ala Leu Val Ile Pro Leu Ala Ile Leu
        35                  40

<210> SEQ ID NO 36
<211> LENGTH: 43
<212> TYPE: PRT
<213> ORGANISM: Homo sapiens

<400> SEQUENCE: 36

Gly Asn Val Leu Val Ile Cys Val Val Lys Leu Asn Pro Ser Leu Gln
1               5                   10                  15

Thr Thr Thr Phe Tyr Phe Ile Val Ser Leu Ala Leu Ala Asp Ile Ala
            20                  25                  30

Val Gly Val Leu Val Met Pro Leu Ala Ile Val
        35                  40

<210> SEQ ID NO 37
<211> LENGTH: 46
<212> TYPE: PRT
<213> ORGANISM: Homo sapiens

<400> SEQUENCE: 37

Glu Asn Ile Leu Val Ile Val Ala Ile Ala Lys Asn Lys Asn Leu His
1               5                   10                  15

Ser Pro Met Tyr Phe Phe Ile Cys Ser Leu Ala Val Ala Asp Met Leu
```

```
              20                  25                  30

Val Ser Val Ser Asn Gly Ser Glu Thr Ile Ile Ile Thr Leu
        35                  40                  45

<210> SEQ ID NO 38
<211> LENGTH: 46
<212> TYPE: PRT
<213> ORGANISM: Homo sapiens

<400> SEQUENCE: 38

Glu Asn Ile Leu Val Ile Gly Ala Ile Val Lys Asn Lys Asn Leu His
1               5                   10                  15

Ser Pro Met Tyr Phe Phe Val Cys Ser Leu Ala Val Ala Asp Met Leu
                20                  25                  30

Val Ser Met Ser Ser Ala Trp Glu Thr Ile Thr Ile Tyr Leu
        35                  40                  45

<210> SEQ ID NO 39
<211> LENGTH: 46
<212> TYPE: PRT
<213> ORGANISM: Homo sapiens

<400> SEQUENCE: 39

Glu Asn Ile Leu Val Ile Leu Ala Val Val Arg Asn Gly Asn Leu His
1               5                   10                  15

Ser Pro Met Tyr Phe Phe Leu Cys Ser Leu Ala Val Ala Asp Met Leu
                20                  25                  30

Val Ser Val Ser Asn Ala Leu Glu Thr Ile Met Ile Ala Ile
        35                  40                  45

<210> SEQ ID NO 40
<211> LENGTH: 46
<212> TYPE: PRT
<213> ORGANISM: Homo sapiens

<400> SEQUENCE: 40

Glu Asn Ala Leu Val Val Ala Thr Ile Ala Lys Asn Arg Asn Leu His
1               5                   10                  15

Ser Pro Met Tyr Cys Phe Ile Cys Cys Leu Ala Leu Ser Asp Leu Leu
                20                  25                  30

Val Ser Gly Thr Asn Val Leu Glu Thr Ala Val Ile Leu Leu
        35                  40                  45

<210> SEQ ID NO 41
<211> LENGTH: 46
<212> TYPE: PRT
<213> ORGANISM: Homo sapiens

<400> SEQUENCE: 41

Glu Asn Leu Ile Val Leu Leu Ala Val Phe Lys Asn Lys Asn Leu Gln
1               5                   10                  15

Ala Pro Met Tyr Phe Phe Ile Cys Ser Leu Ala Ile Ser Asp Met Leu
                20                  25                  30

Gly Ser Leu Tyr Lys Ile Leu Glu Asn Ile Leu Ile Ile Leu
        35                  40                  45

<210> SEQ ID NO 42
<211> LENGTH: 44
<212> TYPE: PRT
<213> ORGANISM: Homo sapiens

<400> SEQUENCE: 42
```

```
Glu Asn Ile Phe Val Leu Leu Thr Ile Trp Lys Thr Lys Lys Phe His
1               5                   10                  15

Arg Pro Met Tyr Tyr Phe Ile Gly Asn Leu Ala Leu Ser Asp Leu Leu
            20                  25                  30

Ala Gly Val Ala Tyr Thr Ala Asn Leu Leu Leu Ser
        35                  40
```

<210> SEQ ID NO 43
<211> LENGTH: 44
<212> TYPE: PRT
<213> ORGANISM: Homo sapiens

<400> SEQUENCE: 43

```
Glu Asn Leu Met Val Leu Ile Ala Ile Trp Lys Asn Asn Lys Phe His
1               5                   10                  15

Asn Arg Met Tyr Phe Phe Ile Gly Asn Leu Ala Leu Cys Asp Leu Leu
            20                  25                  30

Ala Gly Ile Ala Tyr Lys Val Asn Ile Leu Met Ser
        35                  40
```

<210> SEQ ID NO 44
<211> LENGTH: 44
<212> TYPE: PRT
<213> ORGANISM: Homo sapiens

<400> SEQUENCE: 44

```
Glu Asn Leu Leu Val Leu Ile Ala Val Ala Arg Asn Ser Lys Phe His
1               5                   10                  15

Ser Ala Met Tyr Leu Phe Leu Gly Asn Leu Ala Ala Ser Asp Leu Leu
            20                  25                  30

Ala Gly Val Ala Phe Val Ala Asn Thr Leu Leu Ser
        35                  40
```

<210> SEQ ID NO 45
<211> LENGTH: 44
<212> TYPE: PRT
<213> ORGANISM: Homo sapiens

<400> SEQUENCE: 45

```
Glu Asn Leu Ala Val Leu Leu Val Leu Gly Arg His Pro Arg Phe His
1               5                   10                  15

Ala Pro Met Phe Leu Leu Leu Gly Ser Leu Thr Leu Ser Asp Leu Leu
            20                  25                  30

Ala Gly Ala Ala Tyr Ala Ala Asn Ile Leu Leu Ser
        35                  40
```

<210> SEQ ID NO 46
<211> LENGTH: 44
<212> TYPE: PRT
<213> ORGANISM: Homo sapiens

<400> SEQUENCE: 46

```
Glu Asn Leu Leu Val Leu Ala Ala Ile Thr Ser His Met Arg Ser Arg
1               5                   10                  15

Arg Trp Val Tyr Tyr Cys Leu Val Asn Ile Thr Leu Ser Asp Leu Leu
            20                  25                  30

Thr Gly Ala Ala Tyr Leu Ala Asn Val Leu Leu Ser
        35                  40
```

<210> SEQ ID NO 47

```
<211> LENGTH: 44
<212> TYPE: PRT
<213> ORGANISM: Homo sapiens

<400> SEQUENCE: 47

Ala Asn Leu Leu Val Met Val Ala Ile Tyr Val Asn Arg Arg Phe His
1               5                   10                  15

Phe Pro Ile Tyr Tyr Leu Met Ala Asn Leu Ala Ala Ala Asp Phe Phe
            20                  25                  30

Ala Gly Leu Ala Tyr Phe Tyr Leu Met Phe Asn Thr
            35                  40

<210> SEQ ID NO 48
<211> LENGTH: 44
<212> TYPE: PRT
<213> ORGANISM: Homo sapiens

<400> SEQUENCE: 48

Thr Asn Leu Leu Val Ile Ala Ala Ile Ala Ser Asn Arg Arg Phe His
1               5                   10                  15

Gln Pro Ile Tyr Tyr Leu Leu Gly Asn Leu Ala Ala Ala Asp Leu Phe
            20                  25                  30

Ala Gly Val Ala Tyr Leu Phe Leu Met Phe His Thr
            35                  40

<210> SEQ ID NO 49
<211> LENGTH: 44
<212> TYPE: PRT
<213> ORGANISM: Homo sapiens

<400> SEQUENCE: 49

Ser Asn Ser Leu Val Ile Ala Ala Val Ile Lys Asn Arg Lys Phe His
1               5                   10                  15

Phe Pro Phe Tyr Tyr Leu Leu Ala Asn Leu Ala Ala Ala Asp Phe Phe
            20                  25                  30

Ala Gly Ile Ala Tyr Val Phe Leu Met Phe Asn Thr
            35                  40

<210> SEQ ID NO 50
<211> LENGTH: 45
<212> TYPE: PRT
<213> ORGANISM: Homo sapiens

<400> SEQUENCE: 50

Glu Asn Leu Leu Val Leu Cys Val Ile Leu His Ser Arg Ser Leu Arg
1               5                   10                  15

Cys Arg Pro Ser Tyr His Phe Ile Gly Ser Leu Ala Val Ala Asp Leu
            20                  25                  30

Leu Gly Ser Val Ile Phe Val Tyr Ser Phe Ile Asp Phe
            35                  40                  45

<210> SEQ ID NO 51
<211> LENGTH: 45
<212> TYPE: PRT
<213> ORGANISM: Homo sapiens

<400> SEQUENCE: 51

Glu Asn Val Ala Val Leu Tyr Leu Ile Leu Ser Ser His Gln Leu Arg
1               5                   10                  15

Arg Lys Pro Ser Tyr Leu Phe Ile Gly Ser Leu Ala Gly Ala Asp Phe
            20                  25                  30
```

```
Leu Ala Ser Val Val Phe Ala Cys Ser Phe Val Asn Phe
        35                  40                  45

<210> SEQ ID NO 52
<211> LENGTH: 44
<212> TYPE: PRT
<213> ORGANISM: Homo sapiens

<400> SEQUENCE: 52

Glu Asn Ala Leu Val Val Ala Leu Ile Ala Ser Thr Pro Ala Leu Arg
1               5                   10                  15

Thr Pro Met Phe Val Leu Val Gly Ser Leu Ala Thr Ala Asp Leu Leu
            20                  25                  30

Ala Gly Cys Gly Leu Ile Leu His Phe Val Phe Gln
        35                  40

<210> SEQ ID NO 53
<211> LENGTH: 44
<212> TYPE: PRT
<213> ORGANISM: Homo sapiens

<400> SEQUENCE: 53

Glu Asn Ala Ile Val Val Leu Ile Ile Phe His Asn Pro Ser Leu Arg
1               5                   10                  15

Ala Pro Met Phe Leu Leu Ile Gly Ser Leu Ala Leu Ala Asp Leu Leu
            20                  25                  30

Ala Gly Ile Gly Leu Ile Thr Asn Phe Val Phe Ala
        35                  40

<210> SEQ ID NO 54
<211> LENGTH: 44
<212> TYPE: PRT
<213> ORGANISM: Homo sapiens

<400> SEQUENCE: 54

Glu Asn Ala Leu Val Val Ala Ile Ile Val Gly Thr Pro Ala Phe Arg
1               5                   10                  15

Ala Pro Met Phe Leu Leu Val Gly Ser Leu Ala Val Ala Asp Leu Leu
            20                  25                  30

Ala Gly Leu Gly Leu Val Leu His Phe Ala Ala Val
        35                  40

<210> SEQ ID NO 55
<211> LENGTH: 45
<212> TYPE: PRT
<213> ORGANISM: Homo sapiens

<400> SEQUENCE: 55

Gly Asn Leu Leu Val Ile Leu Ser Val Tyr Arg Asn Lys Lys Leu Arg
1               5                   10                  15

Asn Ala Gly Asn Ile Phe Val Val Ser Leu Ala Val Ala Asp Leu Val
            20                  25                  30

Val Ala Ile Tyr Pro Tyr Pro Leu Val Leu Met Ser Ile
        35                  40                  45

<210> SEQ ID NO 56
<211> LENGTH: 45
<212> TYPE: PRT
<213> ORGANISM: Homo sapiens

<400> SEQUENCE: 56

Gly Asn Leu Leu Val Ile Leu Ser Val Leu Arg Asn Arg Lys Leu Arg
```

```
                1               5                  10                  15
Asn Ala Gly Asn Leu Phe Leu Val Ser Leu Ala Leu Ala Asp Leu Val
                        20                  25                  30

Val Ala Phe Tyr Pro Tyr Pro Leu Ile Leu Val Ala Ile
                35                  40                  45

<210> SEQ ID NO 57
<211> LENGTH: 45
<212> TYPE: PRT
<213> ORGANISM: Homo sapiens

<400> SEQUENCE: 57

Gly Asn Ser Met Val Ile Leu Ala Val Thr Lys Asn Lys Lys Leu Arg
1               5                  10                  15

Asn Ser Gly Asn Ile Phe Val Val Ser Leu Ser Val Ala Asp Met Leu
                        20                  25                  30

Val Ala Ile Tyr Pro Tyr Pro Leu Met Leu His Ala Met
                35                  40                  45

<210> SEQ ID NO 58
<211> LENGTH: 46
<212> TYPE: PRT
<213> ORGANISM: Homo sapiens

<400> SEQUENCE: 58

Ser Asn Ala Phe Val Ile Ala Thr Val Tyr Arg Thr Arg Lys Leu His
1               5                  10                  15

Thr Pro Ala Asn Tyr Leu Ile Ala Ser Leu Ala Val Thr Asp Leu Leu
                        20                  25                  30

Val Ser Ile Leu Val Met Pro Ile Ser Thr Met Tyr Thr Val
                35                  40                  45

<210> SEQ ID NO 59
<211> LENGTH: 46
<212> TYPE: PRT
<213> ORGANISM: Homo sapiens

<400> SEQUENCE: 59

Ser Asn Ala Phe Val Leu Thr Thr Ile Leu Leu Thr Arg Lys Leu His
1               5                  10                  15

Thr Pro Ala Asn Tyr Leu Ile Gly Ser Leu Ala Thr Thr Asp Leu Leu
                        20                  25                  30

Val Ser Ile Leu Val Met Pro Ile Ser Ile Ala Tyr Thr Ile
                35                  40                  45

<210> SEQ ID NO 60
<211> LENGTH: 45
<212> TYPE: PRT
<213> ORGANISM: Homo sapiens

<400> SEQUENCE: 60

Asn Leu Ala Val Ile Met Ala Ile Gly Thr Thr Lys Lys Leu His Gln
1               5                  10                  15

Pro Ala Asn Tyr Leu Ile Cys Ser Leu Ala Val Thr Asp Leu Leu Val
                        20                  25                  30

Ala Val Leu Val Met Pro Leu Ser Ile Ile Tyr Ile Val
                35                  40                  45

<210> SEQ ID NO 61
<211> LENGTH: 46
<212> TYPE: PRT
```

<213> ORGANISM: Homo sapiens

<400> SEQUENCE: 61

Ile Asn Ser Leu Val Ile Ala Ala Ile Ile Val Thr Arg Lys Leu His
1               5                   10                  15

His Pro Ala Asn Tyr Leu Ile Cys Ser Leu Ala Val Thr Asp Phe Leu
            20                  25                  30

Val Ala Val Leu Val Met Pro Phe Ser Ile Val Tyr Ile Val
        35                  40                  45

<210> SEQ ID NO 62
<211> LENGTH: 46
<212> TYPE: PRT
<213> ORGANISM: Homo sapiens

<400> SEQUENCE: 62

Gly Asn Ala Cys Val Ala Ala Ile Ala Leu Glu Arg Ser Leu Gln
1               5                   10                  15

Asn Val Ala Asn Tyr Leu Ile Gly Ser Leu Ala Val Thr Asp Leu Met
            20                  25                  30

Val Ser Val Leu Val Leu Pro Met Ala Ala Leu Tyr Gln Val
        35                  40                  45

<210> SEQ ID NO 63
<211> LENGTH: 46
<212> TYPE: PRT
<213> ORGANISM: Homo sapiens

<400> SEQUENCE: 63

Trp Asn Leu Leu Val Leu Ala Thr Ile Leu Arg Val Arg Thr Phe His
1               5                   10                  15

Arg Val Pro His Asn Leu Val Ala Ser Met Ala Val Ser Asp Val Leu
            20                  25                  30

Val Ala Ala Leu Val Met Pro Leu Ser Leu Val His Glu Leu
        35                  40                  45

<210> SEQ ID NO 64
<211> LENGTH: 46
<212> TYPE: PRT
<213> ORGANISM: Homo sapiens

<400> SEQUENCE: 64

Trp Asn Leu Leu Val Pro Val Thr Ile Pro Arg Val Arg Ala Phe His
1               5                   10                  15

Arg Val Pro His Asn Leu Val Ala Ser Thr Ala Val Ser Asp Glu Leu
            20                  25                  30

Val Ala Ala Leu Ala Met Pro Pro Ser Leu Ala Ser Glu Leu
        35                  40                  45

<210> SEQ ID NO 65
<211> LENGTH: 46
<212> TYPE: PRT
<213> ORGANISM: Homo sapiens

<400> SEQUENCE: 65

Gly Asn Ile Leu Val Ile Met Ala Val Ser Met Glu Lys Lys Leu His
1               5                   10                  15

Asn Ala Thr Asn Tyr Phe Leu Met Ser Leu Ala Ile Ala Asp Met Leu
            20                  25                  30

Val Gly Leu Leu Val Met Pro Leu Ser Leu Leu Ala Ile Leu
        35                  40                  45

```
<210> SEQ ID NO 66
<211> LENGTH: 46
<212> TYPE: PRT
<213> ORGANISM: Homo sapiens

<400> SEQUENCE: 66

Gly Asn Ile Leu Val Ile Met Ala Val Ser Leu Glu Lys Lys Leu Gln
1               5                   10                  15

Asn Ala Thr Asn Tyr Phe Leu Met Ser Leu Ala Ile Ala Asp Met Leu
            20                  25                  30

Leu Gly Phe Leu Val Met Pro Val Ser Met Leu Thr Ile Leu
        35                  40                  45

<210> SEQ ID NO 67
<211> LENGTH: 46
<212> TYPE: PRT
<213> ORGANISM: Homo sapiens

<400> SEQUENCE: 67

Gly Asn Thr Leu Val Ile Leu Ala Val Ser Leu Glu Lys Lys Leu Gln
1               5                   10                  15

Tyr Ala Thr Asn Tyr Phe Leu Met Ser Leu Ala Val Ala Asp Leu Leu
            20                  25                  30

Val Gly Leu Phe Val Met Pro Ile Ala Leu Leu Thr Ile Met
        35                  40                  45

<210> SEQ ID NO 68
<211> LENGTH: 46
<212> TYPE: PRT
<213> ORGANISM: Homo sapiens

<400> SEQUENCE: 68

Gly Asn Val Leu Val Ile Ile Ala Val Phe Thr Ser Arg Ala Leu Lys
1               5                   10                  15

Ala Pro Gln Asn Leu Phe Leu Val Ser Leu Ala Ser Ala Asp Ile Leu
            20                  25                  30

Val Ala Thr Leu Val Ile Pro Phe Ser Leu Ala Asn Glu Val
        35                  40                  45

<210> SEQ ID NO 69
<211> LENGTH: 46
<212> TYPE: PRT
<213> ORGANISM: Homo sapiens

<400> SEQUENCE: 69

Gly Asn Val Leu Val Val Ile Ala Val Leu Thr Ser Arg Ala Leu Arg
1               5                   10                  15

Ala Pro Gln Asn Leu Phe Leu Val Ser Leu Ala Ser Ala Asp Ile Leu
            20                  25                  30

Val Ala Thr Leu Val Met Pro Phe Ser Leu Ala Asn Glu Leu
        35                  40                  45

<210> SEQ ID NO 70
<211> LENGTH: 46
<212> TYPE: PRT
<213> ORGANISM: Homo sapiens

<400> SEQUENCE: 70

Gly Asn Ala Leu Val Ile Leu Ala Val Leu Thr Ser Arg Ser Leu Arg
1               5                   10                  15
```

Ala Pro Gln Asn Leu Phe Leu Val Ser Leu Ala Ala Ala Asp Ile Leu
            20                  25                  30

Val Ala Thr Leu Ile Ile Pro Phe Ser Leu Ala Asn Glu Leu
        35                  40                  45

<210> SEQ ID NO 71
<211> LENGTH: 46
<212> TYPE: PRT
<213> ORGANISM: Homo sapiens

<400> SEQUENCE: 71

Gly Asn Leu Leu Val Ile Leu Ser Val Ala Cys Asn Arg His Leu Gln
1               5                   10                  15

Thr Val Thr Asn Tyr Phe Ile Val Asn Leu Ala Val Ala Asp Leu Leu
            20                  25                  30

Leu Ser Ala Thr Val Leu Pro Phe Ser Ala Thr Met Glu Val
        35                  40                  45

<210> SEQ ID NO 72
<211> LENGTH: 46
<212> TYPE: PRT
<213> ORGANISM: Homo sapiens

<400> SEQUENCE: 72

Gly Asn Ile Leu Val Ile Leu Ser Val Ala Cys Asn Arg His Leu Arg
1               5                   10                  15

Thr Pro Thr Asn Tyr Phe Ile Val Asn Leu Ala Met Ala Asp Leu Leu
            20                  25                  30

Leu Ser Phe Thr Val Leu Pro Phe Ser Ala Ala Leu Glu Val
        35                  40                  45

<210> SEQ ID NO 73
<211> LENGTH: 46
<212> TYPE: PRT
<213> ORGANISM: Homo sapiens

<400> SEQUENCE: 73

Gly Asn Ile Leu Val Ile Leu Ser Val Ala Cys His Arg His Leu His
1               5                   10                  15

Ser Val Thr His Tyr Tyr Ile Val Asn Leu Ala Val Ala Asp Leu Leu
            20                  25                  30

Leu Thr Ser Thr Val Leu Pro Phe Ser Ala Ile Phe Glu Val
        35                  40                  45

<210> SEQ ID NO 74
<211> LENGTH: 47
<212> TYPE: PRT
<213> ORGANISM: Homo sapiens

<400> SEQUENCE: 74

Gly Asn Thr Leu Val Cys Ala Ala Val Ile Arg Phe Arg His Leu Arg
1               5                   10                  15

Ser Lys Val Thr Asn Phe Phe Val Ile Ser Leu Ala Val Ser Asp Leu
            20                  25                  30

Leu Val Ala Val Leu Val Met Pro Trp Lys Ala Val Ala Glu Ile
        35                  40                  45

<210> SEQ ID NO 75
<211> LENGTH: 47
<212> TYPE: PRT
<213> ORGANISM: Homo sapiens -continued

<400> SEQUENCE: 75

Gly Asn Val Leu Val Cys Ala Ala Ile Val Arg Ser Arg His Leu Arg
1               5                   10                  15

Ala Asn Met Thr Asn Val Phe Ile Val Ser Leu Ala Val Ser Asp Leu
            20                  25                  30

Phe Val Ala Leu Leu Val Met Pro Trp Lys Ala Val Ala Glu Val
        35                  40                  45

<210> SEQ ID NO 76
<211> LENGTH: 46
<212> TYPE: PRT
<213> ORGANISM: Homo sapiens

<400> SEQUENCE: 76

Gly Asn Val Leu Val Cys Met Ala Val Ser Arg Glu Lys Ala Leu Gln
1               5                   10                  15

Thr Thr Thr Asn Tyr Leu Ile Val Ser Leu Ala Val Ala Asp Leu Leu
            20                  25                  30

Val Ala Thr Leu Val Met Pro Trp Val Val Tyr Leu Glu Val
        35                  40                  45

<210> SEQ ID NO 77
<211> LENGTH: 46
<212> TYPE: PRT
<213> ORGANISM: Homo sapiens

<400> SEQUENCE: 77

Gly Asn Gly Leu Val Cys Met Ala Val Leu Lys Glu Arg Ala Leu Gln
1               5                   10                  15

Thr Thr Thr Asn Tyr Leu Val Val Ser Leu Ala Val Ala Asp Leu Leu
            20                  25                  30

Val Ala Thr Leu Val Met Pro Trp Val Val Tyr Leu Glu Val
        35                  40                  45

<210> SEQ ID NO 78
<211> LENGTH: 46
<212> TYPE: PRT
<213> ORGANISM: Homo sapiens

<400> SEQUENCE: 78

Gly Asn Ser Leu Val Cys Val Ser Val Ala Thr Glu Arg Ala Leu Gln
1               5                   10                  15

Thr Pro Thr Asn Ser Phe Ile Val Ser Leu Ala Ala Ala Asp Leu Leu
            20                  25                  30

Leu Ala Leu Leu Val Leu Pro Leu Phe Val Tyr Ser Glu Val
        35                  40                  45

<210> SEQ ID NO 79
<211> LENGTH: 47
<212> TYPE: PRT
<213> ORGANISM: Homo sapiens

<400> SEQUENCE: 79

Gly Asn Leu Leu Val Met Val Ala Val Cys Trp Asp Arg Gln Leu Arg
1               5                   10                  15

Lys Ile Lys Thr Asn Tyr Phe Ile Val Ser Leu Ala Phe Ala Asp Leu
            20                  25                  30

Leu Val Ser Val Leu Val Met Pro Phe Gly Ala Ile Glu Leu Val
        35                  40                  45

```
<210> SEQ ID NO 80
<211> LENGTH: 46
<212> TYPE: PRT
<213> ORGANISM: Homo sapiens

<400> SEQUENCE: 80

Gly Asn Val Val Cys Leu Ala Val Gly Leu Asn Arg Arg Leu Arg
1               5                   10                  15

Asn Leu Thr Asn Cys Phe Ile Val Ser Leu Ala Ile Thr Asp Leu Leu
            20                  25                  30

Leu Gly Leu Leu Val Leu Pro Phe Ser Ala Ile Tyr Gln Leu
        35                  40                  45

<210> SEQ ID NO 81
<211> LENGTH: 46
<212> TYPE: PRT
<213> ORGANISM: Homo sapiens

<400> SEQUENCE: 81

Gly Asn Cys Leu Val Ile Ser Val Cys Phe Val Lys Lys Leu Arg
1               5                   10                  15

Gln Pro Ser Asn Tyr Leu Ile Val Ser Leu Ala Leu Ala Asp Leu Ser
            20                  25                  30

Val Ala Val Ala Val Met Pro Phe Val Ser Val Thr Asp Leu
        35                  40                  45

<210> SEQ ID NO 82
<211> LENGTH: 46
<212> TYPE: PRT
<213> ORGANISM: Homo sapiens

<400> SEQUENCE: 82

Gly Asn Val Leu Val Ile Val Ala Ile Ala Lys Thr Pro Arg Leu Gln
1               5                   10                  15

Thr Leu Thr Asn Leu Phe Ile Met Ser Leu Ala Ser Ala Asp Leu Val
            20                  25                  30

Met Gly Leu Leu Val Val Pro Phe Gly Ala Thr Ile Val Val
        35                  40                  45

<210> SEQ ID NO 83
<211> LENGTH: 46
<212> TYPE: PRT
<213> ORGANISM: Homo sapiens

<400> SEQUENCE: 83

Gly Asn Val Leu Val Ile Thr Ala Ile Ala Lys Phe Glu Arg Leu Gln
1               5                   10                  15

Thr Val Thr Asn Tyr Phe Ile Thr Ser Leu Ala Cys Ala Asp Leu Val
            20                  25                  30

Met Gly Leu Ala Val Val Pro Phe Gly Ala Ala His Ile Leu
        35                  40                  45

<210> SEQ ID NO 84
<211> LENGTH: 46
<212> TYPE: PRT
<213> ORGANISM: Homo sapiens

<400> SEQUENCE: 84

Gly Asn Leu Leu Val Ile Val Ala Ile Ala Trp Thr Pro Arg Leu Gln
1               5                   10                  15

Thr Met Thr Asn Val Phe Val Thr Ser Leu Ala Ala Ala Asp Leu Val
            20                  25                  30
```

```
Met Gly Leu Leu Val Pro Pro Ala Ala Thr Leu Ala Leu
        35                  40                  45
```

<210> SEQ ID NO 85
<211> LENGTH: 46
<212> TYPE: PRT
<213> ORGANISM: Homo sapiens

<400> SEQUENCE: 85

```
Ala Asn Ser Leu Leu Ile Ala Leu Ile Cys Thr Gln Pro Ala Leu Arg
1               5                   10                  15

Asn Thr Ser Asn Phe Phe Leu Val Ser Leu Phe Thr Ser Asp Leu Met
            20                  25                  30

Val Gly Leu Val Val Met Pro Pro Ala Met Leu Asn Ala Leu
        35                  40                  45
```

<210> SEQ ID NO 86
<211> LENGTH: 46
<212> TYPE: PRT
<213> ORGANISM: Homo sapiens

<400> SEQUENCE: 86

```
Ala Asn Gly Met Val Ile Tyr Leu Val Ser Ser Phe Arg Lys Leu Gln
1               5                   10                  15

Thr Thr Ser Asn Ala Phe Ile Val Asn Gly Cys Ala Ala Asp Leu Ser
            20                  25                  30

Val Cys Ala Leu Trp Met Pro Gln Glu Ala Val Leu Gly Leu
        35                  40                  45
```

<210> SEQ ID NO 87
<211> LENGTH: 46
<212> TYPE: PRT
<213> ORGANISM: Homo sapiens

<400> SEQUENCE: 87

```
Leu Asn Leu Leu Val Leu Tyr Ala Val Arg Ser Glu Arg Lys Leu His
1               5                   10                  15

Thr Val Gly Asn Leu Tyr Ile Val Ser Leu Ser Val Ala Asp Leu Ile
            20                  25                  30

Val Gly Ala Val Val Met Pro Met Asn Ile Leu Tyr Leu Leu
        35                  40                  45
```

<210> SEQ ID NO 88
<211> LENGTH: 48
<212> TYPE: PRT
<213> ORGANISM: Homo sapiens

<400> SEQUENCE: 88

```
Gly Ser Asn Leu Thr Val Leu Val Leu Tyr Cys Met Lys Ser Asn Leu
1               5                   10                  15

Ile Asn Ser Val Ser Asn Ile Ile Thr Met Asn Leu His Val Leu Asp
            20                  25                  30

Val Ile Ile Cys Val Gly Cys Ile Pro Leu Thr Ile Val Ile Leu Leu
        35                  40                  45
```

<210> SEQ ID NO 89
<211> LENGTH: 46
<212> TYPE: PRT
<213> ORGANISM: Homo sapiens

<400> SEQUENCE: 89

Gly Asn Leu Leu Val Leu Ile Ser Phe Lys Val Asn Thr Glu Leu Lys
1               5                   10                  15

Thr Val Asn Asn Tyr Phe Leu Ser Leu Ala Cys Ala Asp Leu Ile
            20                  25                  30

Ile Gly Thr Phe Ser Met Asn Leu Tyr Thr Thr Tyr Leu Leu
            35                  40                  45

<210> SEQ ID NO 90
<211> LENGTH: 46
<212> TYPE: PRT
<213> ORGANISM: Homo sapiens

<400> SEQUENCE: 90

Gly Asn Val Leu Val Met Ile Ser Phe Lys Val Asn Ser Gln Leu Lys
1               5                   10                  15

Thr Val Asn Asn Tyr Tyr Leu Leu Ser Leu Ala Cys Ala Asp Leu Ile
            20                  25                  30

Ile Gly Ile Phe Ser Met Asn Leu Tyr Thr Thr Tyr Ile Leu
            35                  40                  45

<210> SEQ ID NO 91
<211> LENGTH: 46
<212> TYPE: PRT
<213> ORGANISM: Homo sapiens

<400> SEQUENCE: 91

Gly Asn Ile Leu Val Ile Val Ser Phe Lys Val Asn Lys Gln Leu Lys
1               5                   10                  15

Thr Val Asn Asn Tyr Phe Leu Leu Ser Leu Ala Cys Ala Asp Leu Ile
            20                  25                  30

Ile Gly Val Ile Ser Met Asn Leu Phe Thr Thr Tyr Ile Ile
            35                  40                  45

<210> SEQ ID NO 92
<211> LENGTH: 46
<212> TYPE: PRT
<213> ORGANISM: Homo sapiens

<400> SEQUENCE: 92

Gly Asn Ile Leu Val Met Val Ser Ile Lys Val Asn Arg His Leu Gln
1               5                   10                  15

Thr Val Asn Asn Tyr Phe Leu Phe Ser Leu Ala Cys Ala Asp Leu Ile
            20                  25                  30

Ile Gly Val Phe Ser Met Asn Leu Tyr Thr Leu Tyr Thr Val
            35                  40                  45

<210> SEQ ID NO 93
<211> LENGTH: 46
<212> TYPE: PRT
<213> ORGANISM: Homo sapiens

<400> SEQUENCE: 93

Gly Asn Ile Leu Val Met Leu Ser Ile Lys Val Asn Arg Gln Leu Gln
1               5                   10                  15

Thr Val Asn Asn Tyr Phe Leu Phe Ser Leu Ala Cys Ala Asp Leu Ile
            20                  25                  30

Ile Gly Ala Phe Ser Met Asn Leu Tyr Thr Val Tyr Ile Ile
            35                  40                  45

<210> SEQ ID NO 94
<211> LENGTH: 46

```
<212> TYPE: PRT
<213> ORGANISM: Homo sapiens

<400> SEQUENCE: 94

Gly Asn Ala Leu Val Met Leu Ala Phe Val Ala Asp Ser Ser Leu Arg
1               5                   10                  15

Thr Gln Asn Asn Phe Phe Leu Leu Asn Leu Ala Ile Ser Asp Phe Leu
            20                  25                  30

Val Gly Ala Phe Cys Ile Pro Leu Tyr Val Pro Tyr Val Leu
        35                  40                  45

<210> SEQ ID NO 95
<211> LENGTH: 46
<212> TYPE: PRT
<213> ORGANISM: Homo sapiens

<400> SEQUENCE: 95

Gly Asn Ala Leu Val Ile Leu Ala Phe Val Val Asp Lys Asn Leu Arg
1               5                   10                  15

His Arg Ser Ser Tyr Phe Phe Leu Asn Leu Ala Ile Ser Asp Phe Phe
            20                  25                  30

Val Gly Val Ile Ser Ile Pro Leu Tyr Ile Pro His Thr Leu
        35                  40                  45

<210> SEQ ID NO 96
<211> LENGTH: 46
<212> TYPE: PRT
<213> ORGANISM: Homo sapiens

<400> SEQUENCE: 96

Gly Asn Leu Ala Met Ile Ile Ser Ile Ser Tyr Phe Lys Gln Leu His
1               5                   10                  15

Thr Pro Thr Asn Phe Leu Ile Leu Ser Met Ala Ile Thr Asp Phe Leu
            20                  25                  30

Leu Gly Phe Thr Ile Met Pro Tyr Ser Met Ile Arg Ser Val
        35                  40                  45

<210> SEQ ID NO 97
<211> LENGTH: 46
<212> TYPE: PRT
<213> ORGANISM: Homo sapiens

<400> SEQUENCE: 97

Gly Asn Leu Val Ile Met Val Ser Ile Ser His Phe Lys Gln Leu His
1               5                   10                  15

Ser Pro Thr Asn Phe Leu Ile Leu Ser Met Ala Thr Thr Asp Phe Leu
            20                  25                  30

Leu Gly Phe Val Ile Met Pro Tyr Ser Ile Met Arg Ser Val
        35                  40                  45

<210> SEQ ID NO 98
<211> LENGTH: 46
<212> TYPE: PRT
<213> ORGANISM: Homo sapiens

<400> SEQUENCE: 98

Gly Asn Leu Ile Val Ile Val Ser Ile Ser His Phe Lys Gln Leu His
1               5                   10                  15

Thr Pro Thr Asn Trp Leu Ile His Ser Met Ala Thr Val Asp Phe Leu
            20                  25                  30

Leu Gly Cys Leu Val Met Pro Tyr Ser Met Val Arg Ser Ala
```

35                  40                  45

<210> SEQ ID NO 99
<211> LENGTH: 46
<212> TYPE: PRT
<213> ORGANISM: Homo sapiens

<400> SEQUENCE: 99

Gly Asn Leu Leu Val Met Ile Ser Ile Leu His Phe Lys Gln Leu His
1               5                   10                  15

Ser Pro Thr Asn Phe Leu Val Ala Ser Leu Ala Cys Ala Asp Phe Leu
            20                  25                  30

Val Gly Val Thr Val Met Pro Phe Ser Met Val Arg Thr Val
            35                  40                  45

<210> SEQ ID NO 100
<211> LENGTH: 46
<212> TYPE: PRT
<213> ORGANISM: Homo sapiens

<400> SEQUENCE: 100

Gly Asn Leu Leu Val Met Thr Ser Val Leu His Phe Lys Gln Leu His
1               5                   10                  15

Ser Pro Thr Asn Phe Leu Ile Ala Ser Leu Ala Cys Ala Asp Phe Leu
            20                  25                  30

Val Gly Val Thr Val Met Leu Phe Ser Met Val Arg Thr Val
            35                  40                  45

<210> SEQ ID NO 101
<211> LENGTH: 46
<212> TYPE: PRT
<213> ORGANISM: Homo sapiens

<400> SEQUENCE: 101

Gly Asn Leu Leu Val Met Ile Ala Ile Leu His Phe Lys Gln Leu His
1               5                   10                  15

Thr Pro Thr Asn Phe Leu Ile Ala Ser Leu Ala Cys Ala Asp Phe Leu
            20                  25                  30

Val Gly Val Thr Val Met Pro Phe Ser Thr Val Arg Ser Val
            35                  40                  45

<210> SEQ ID NO 102
<211> LENGTH: 46
<212> TYPE: PRT
<213> ORGANISM: Homo sapiens

<400> SEQUENCE: 102

Gly Asn Val Phe Val Ala Phe Ala Val Ser Tyr Phe Lys Ala Leu His
1               5                   10                  15

Thr Pro Thr Asn Phe Leu Leu Leu Ser Leu Ala Leu Ala Asp Met Phe
            20                  25                  30

Leu Gly Leu Leu Val Leu Pro Leu Ser Thr Ile Arg Ser Val
            35                  40                  45

<210> SEQ ID NO 103
<211> LENGTH: 46
<212> TYPE: PRT
<213> ORGANISM: Homo sapiens

<400> SEQUENCE: 103

Gly Asn Phe Val Phe Ile Ala Ala Leu Thr Arg Tyr Lys Lys Leu Arg
1               5                   10                  15

```
Asn Leu Thr Asn Leu Leu Ile Ala Asn Leu Ala Ile Ser Asp Phe Leu
            20                  25                  30

Val Ala Ile Ile Cys Cys Pro Phe Glu Met Asp Tyr Tyr Val
        35                  40                  45
```

<210> SEQ ID NO 104
<211> LENGTH: 46
<212> TYPE: PRT
<213> ORGANISM: Homo sapiens

<400> SEQUENCE: 104

```
Gly Asn Phe Ile Phe Ile Ala Ala Leu Val Arg Tyr Lys Lys Leu Arg
1               5                   10                  15

Asn Leu Thr Asn Leu Leu Ile Ala Asn Leu Ala Ile Ser Asp Phe Leu
            20                  25                  30

Val Ala Ile Val Cys Cys Pro Phe Glu Met Asp Tyr Tyr Val
        35                  40                  45
```

<210> SEQ ID NO 105
<211> LENGTH: 46
<212> TYPE: PRT
<213> ORGANISM: Homo sapiens

<400> SEQUENCE: 105

```
Gly Asn Val Leu Thr Leu Leu Ala Leu Ala Ile Gln Pro Lys Leu Arg
1               5                   10                  15

Thr Arg Phe Asn Leu Leu Ile Ala Asn Leu Thr Leu Ala Asp Leu Leu
            20                  25                  30

Tyr Cys Thr Leu Leu Gln Pro Phe Ser Val Asp Thr Tyr Leu
        35                  40                  45
```

<210> SEQ ID NO 106
<211> LENGTH: 46
<212> TYPE: PRT
<213> ORGANISM: Homo sapiens

<400> SEQUENCE: 106

```
Gly Asn Thr Leu Val Cys Leu Ala Val Trp Arg Asn His His Met Arg
1               5                   10                  15

Thr Val Thr Asn Tyr Phe Ile Val Asn Leu Ser Leu Ala Asp Val Leu
            20                  25                  30

Val Thr Ala Ile Cys Leu Pro Ala Ser Leu Leu Val Asp Ile
        35                  40                  45
```

<210> SEQ ID NO 107
<211> LENGTH: 46
<212> TYPE: PRT
<213> ORGANISM: Homo sapiens

<400> SEQUENCE: 107

```
Gly Asn Val Leu Val Cys Val Ala Val Trp Lys Asn His His Met Arg
1               5                   10                  15

Thr Val Thr Asn Tyr Phe Ile Val Asn Leu Ser Leu Ala Asp Val Leu
            20                  25                  30

Val Thr Ile Thr Cys Leu Pro Ala Thr Leu Val Val Asp Ile
        35                  40                  45
```

<210> SEQ ID NO 108
<211> LENGTH: 46
<212> TYPE: PRT
<213> ORGANISM: Homo sapiens

<400> SEQUENCE: 108

Gly Asn Thr Val Val Cys Phe Ile Val Met Arg Asn Lys His Met His
1               5                   10                  15

Thr Val Thr Asn Leu Phe Ile Leu Asn Leu Ala Ile Ser Asp Leu Leu
            20                  25                  30

Val Gly Ile Phe Cys Met Pro Ile Thr Leu Leu Asp Asn Ile
        35                  40                  45

<210> SEQ ID NO 109
<211> LENGTH: 46
<212> TYPE: PRT
<213> ORGANISM: Homo sapiens

<400> SEQUENCE: 109

Gly Asn Thr Leu Val Cys Phe Ile Val Leu Lys Asn Arg His Met His
1               5                   10                  15

Thr Val Thr Asn Met Phe Ile Leu Asn Leu Ala Val Ser Asp Leu Leu
            20                  25                  30

Val Gly Ile Phe Cys Met Pro Thr Thr Leu Val Asp Asn Leu
        35                  40                  45

<210> SEQ ID NO 110
<211> LENGTH: 46
<212> TYPE: PRT
<213> ORGANISM: Homo sapiens

<400> SEQUENCE: 110

Gly Asn Ala Leu Val Phe Tyr Val Val Thr Arg Ser Lys Ala Met Arg
1               5                   10                  15

Thr Val Thr Asn Ile Phe Ile Cys Ser Leu Ala Leu Ser Asp Leu Leu
            20                  25                  30

Ile Thr Phe Phe Cys Ile Pro Val Thr Met Leu Gln Asn Ile
        35                  40                  45

<210> SEQ ID NO 111
<211> LENGTH: 46
<212> TYPE: PRT
<213> ORGANISM: Homo sapiens

<400> SEQUENCE: 111

Gly Asn Ser Leu Val Ile His Val Val Ile Lys Phe Lys Ser Met Arg
1               5                   10                  15

Thr Val Thr Asn Phe Phe Ile Ala Asn Leu Ala Val Ala Asp Leu Leu
            20                  25                  30

Val Asn Thr Leu Cys Leu Pro Phe Thr Leu Thr Tyr Thr Leu
        35                  40                  45

<210> SEQ ID NO 112
<211> LENGTH: 46
<212> TYPE: PRT
<213> ORGANISM: Homo sapiens

<400> SEQUENCE: 112

Gly Asn Thr Leu Val Ile Thr Val Leu Ile Arg Asn Lys Arg Met Arg
1               5                   10                  15

Thr Val Thr Asn Ile Phe Leu Leu Ser Leu Ala Val Ser Asp Leu Met
            20                  25                  30

Leu Cys Leu Phe Cys Met Pro Phe Asn Leu Ile Pro Asn Leu
        35                  40                  45

```
<210> SEQ ID NO 113
<211> LENGTH: 46
<212> TYPE: PRT
<213> ORGANISM: Homo sapiens

<400> SEQUENCE: 113

Gly Asn Met Leu Ile Val Val Leu Gly Leu Ser Arg Arg Leu Arg
1               5                   10                  15

Thr Val Thr Asn Ala Phe Leu Leu Ser Leu Ala Val Ser Asp Leu Leu
            20                  25                  30

Leu Ala Val Ala Cys Met Pro Phe Thr Leu Leu Pro Asn Leu
        35                  40                  45

<210> SEQ ID NO 114
<211> LENGTH: 46
<212> TYPE: PRT
<213> ORGANISM: Homo sapiens

<400> SEQUENCE: 114

Gly Asn Leu Ala Leu Ile Ile Ile Leu Lys Gln Lys Glu Met Arg
1               5                   10                  15

Asn Val Thr Asn Ile Leu Ile Val Asn Leu Ser Phe Ser Asp Leu Leu
            20                  25                  30

Val Ala Ile Met Cys Leu Pro Phe Thr Phe Val Tyr Thr Leu
        35                  40                  45

<210> SEQ ID NO 115
<211> LENGTH: 47
<212> TYPE: PRT
<213> ORGANISM: Homo sapiens

<400> SEQUENCE: 115

Gly Asn Leu Ser Leu Ile Ile Ile Phe Lys Lys Gln Arg Lys Ala
1               5                   10                  15

Gln Asn Phe Thr Ser Ile Leu Ile Ala Asn Leu Ser Leu Ser Asp Thr
            20                  25                  30

Leu Val Cys Val Met Cys Ile His Phe Thr Ile Ile Tyr Thr Leu
        35                  40                  45

<210> SEQ ID NO 116
<211> LENGTH: 46
<212> TYPE: PRT
<213> ORGANISM: Homo sapiens

<400> SEQUENCE: 116

Gly Asn Leu Cys Leu Met Cys Val Thr Val Arg Gln Lys Glu Lys Ala
1               5                   10                  15

Asn Val Thr Asn Leu Leu Ile Ala Asn Leu Ala Phe Ser Asp Phe Leu
            20                  25                  30

Met Cys Leu Leu Cys Gln Pro Leu Thr Ala Val Tyr Thr Ile
        35                  40                  45

<210> SEQ ID NO 117
<211> LENGTH: 46
<212> TYPE: PRT
<213> ORGANISM: Homo sapiens

<400> SEQUENCE: 117

Gly Asn Leu Leu Ile Leu Met Ala Leu Met Lys Lys Arg Asn Gln Lys
1               5                   10                  15

Thr Thr Val Asn Phe Leu Ile Gly Asn Leu Ala Phe Ser Asp Ile Leu
```

```
                20                  25                  30
Val Val Leu Phe Cys Ser Pro Phe Thr Leu Thr Ser Val Leu
        35                  40                  45

<210> SEQ ID NO 118
<211> LENGTH: 46
<212> TYPE: PRT
<213> ORGANISM: Homo sapiens

<400> SEQUENCE: 118

Gly Asn Cys Leu Leu Val Leu Ile Ala Arg Val Arg Arg Leu His
1               5                   10                  15

Asn Val Thr Asn Phe Leu Ile Gly Asn Leu Ala Leu Ser Asp Val Leu
                20                  25                  30

Met Cys Thr Ala Cys Val Pro Leu Thr Leu Ala Tyr Ala Phe
        35                  40                  45

<210> SEQ ID NO 119
<211> LENGTH: 46
<212> TYPE: PRT
<213> ORGANISM: Homo sapiens

<400> SEQUENCE: 119

Gly Asn Ile Thr Leu Ile Lys Ile Phe Cys Thr Val Lys Ser Met Arg
1               5                   10                  15

Asn Val Pro Asn Leu Phe Ile Ser Ser Leu Ala Leu Gly Asp Leu Leu
                20                  25                  30

Leu Leu Ile Thr Cys Ala Pro Val Asp Ala Ser Arg Tyr Leu
        35                  40                  45

<210> SEQ ID NO 120
<211> LENGTH: 46
<212> TYPE: PRT
<213> ORGANISM: Homo sapiens

<400> SEQUENCE: 120

Gly Asn Ile Met Leu Val Lys Ile Phe Ile Thr Asn Ser Ala Met Arg
1               5                   10                  15

Ser Val Pro Asn Ile Phe Ile Ser Asn Leu Ala Ala Gly Asp Leu Leu
                20                  25                  30

Leu Leu Leu Thr Cys Val Pro Val Asp Ala Ser Arg Tyr Phe
        35                  40                  45

<210> SEQ ID NO 121
<211> LENGTH: 46
<212> TYPE: PRT
<213> ORGANISM: Homo sapiens

<400> SEQUENCE: 121

Gly Asn Ala Ile Leu Ile Lys Val Phe Phe Lys Thr Lys Ser Met Gln
1               5                   10                  15

Thr Val Pro Asn Ile Phe Ile Thr Ser Leu Ala Phe Gly Asp Leu Leu
                20                  25                  30

Leu Leu Leu Thr Cys Val Pro Val Asp Ala Thr His Tyr Leu
        35                  40                  45

<210> SEQ ID NO 122
<211> LENGTH: 46
<212> TYPE: PRT
<213> ORGANISM: Homo sapiens

<400> SEQUENCE: 122
```

```
Gly Asn Ala Thr Leu Leu Arg Ile Ile Tyr Gln Asn Lys Cys Met Arg
1               5                   10                  15

Asn Gly Pro Asn Ala Leu Ile Ala Ser Leu Ala Leu Gly Asp Leu Ile
                20                  25                  30

Tyr Val Val Ile Asp Leu Pro Ile Asn Val Phe Lys Leu Leu
                35                  40                  45
```

<210> SEQ ID NO 123
<211> LENGTH: 46
<212> TYPE: PRT
<213> ORGANISM: Homo sapiens

<400> SEQUENCE: 123

```
Gly Asn Ser Thr Leu Leu Arg Ile Ile Tyr Lys Asn Lys Cys Met Arg
1               5                   10                  15

Asn Gly Pro Asn Ile Leu Ile Ala Ser Leu Ala Leu Gly Asp Leu Leu
                20                  25                  30

His Ile Val Ile Asp Ile Pro Ile Asn Val Tyr Lys Leu Leu
                35                  40                  45
```

<210> SEQ ID NO 124
<211> LENGTH: 46
<212> TYPE: PRT
<213> ORGANISM: Homo sapiens

<400> SEQUENCE: 124

```
Gly Asn Leu Ser Val Met Cys Ile Val Trp His Ser Tyr Tyr Leu Lys
1               5                   10                  15

Ser Ala Trp Asn Ser Ile Leu Ala Ser Leu Ala Leu Trp Asp Phe Leu
                20                  25                  30

Val Leu Phe Phe Cys Leu Pro Ile Val Ile Phe Asn Glu Ile
                35                  40                  45
```

<210> SEQ ID NO 125
<211> LENGTH: 46
<212> TYPE: PRT
<213> ORGANISM: Homo sapiens

<400> SEQUENCE: 125

```
Gly Asn Val Val Val Cys His Val Ile Phe Lys Asn Gln Arg Met His
1               5                   10                  15

Ser Ala Thr Ser Leu Phe Ile Val Asn Leu Thr Val Ala Asp Ile Met
                20                  25                  30

Ile Thr Leu Leu Asn Thr Pro Phe Thr Leu Val Arg Phe Val
                35                  40                  45
```

<210> SEQ ID NO 126
<211> LENGTH: 46
<212> TYPE: PRT
<213> ORGANISM: Homo sapiens

<400> SEQUENCE: 126

```
Gly Asn Ser Leu Val Cys Leu Val Ile His Arg Ser Arg Arg Thr Gln
1               5                   10                  15

Ser Thr Thr Asn Tyr Phe Val Val Ser Met Ala Cys Ala Asp Leu Leu
                20                  25                  30

Ile Ser Val Ala Ser Thr Pro Phe Val Leu Leu Gln Phe Thr
                35                  40                  45
```

<210> SEQ ID NO 127

```
<211> LENGTH: 46
<212> TYPE: PRT
<213> ORGANISM: Homo sapiens

<400> SEQUENCE: 127

Gly Asn Thr Val Val Cys Ile Ile Val Tyr Gln Arg Pro Ala Met Arg
1               5                   10                  15

Ser Ala Ile Asn Leu Leu Leu Ala Thr Leu Ala Phe Ser Asp Ile Met
            20                  25                  30

Leu Ser Leu Cys Cys Met Pro Phe Thr Ala Val Thr Leu Ile
        35                  40                  45

<210> SEQ ID NO 128
<211> LENGTH: 46
<212> TYPE: PRT
<213> ORGANISM: Homo sapiens

<400> SEQUENCE: 128

Gly Asn Leu Val Val Cys Leu Met Val Tyr Gln Lys Ala Ala Met Arg
1               5                   10                  15

Ser Ala Ile Asn Ile Leu Leu Ala Ser Leu Ala Phe Ala Asp Met Leu
            20                  25                  30

Leu Ala Val Leu Asn Met Pro Phe Ala Leu Val Thr Ile Leu
        35                  40                  45

<210> SEQ ID NO 129
<211> LENGTH: 46
<212> TYPE: PRT
<213> ORGANISM: Homo sapiens

<400> SEQUENCE: 129

Gly Asn Leu Val Ile Val Val Thr Leu Tyr Lys Lys Ser Tyr Leu Leu
1               5                   10                  15

Thr Leu Ser Asn Lys Phe Val Phe Ser Leu Thr Leu Ser Asn Phe Leu
            20                  25                  30

Leu Ser Val Leu Val Leu Pro Phe Val Val Thr Ser Ser Ile
        35                  40                  45

<210> SEQ ID NO 130
<211> LENGTH: 46
<212> TYPE: PRT
<213> ORGANISM: Homo sapiens

<400> SEQUENCE: 130

Gly Asn Ile Val Leu Ala Leu Val Leu Gln Arg Lys Pro Gln Leu Leu
1               5                   10                  15

Gln Val Thr Asn Arg Phe Ile Phe Asn Leu Leu Val Thr Asp Leu Leu
            20                  25                  30

Gln Ile Ser Leu Val Ala Pro Trp Val Val Ala Thr Ser Val
        35                  40                  45

<210> SEQ ID NO 131
<211> LENGTH: 46
<212> TYPE: PRT
<213> ORGANISM: Homo sapiens

<400> SEQUENCE: 131

Gly Asn Gly Tyr Val Leu Tyr Met Ser Ser Arg Arg Lys Lys Lys Leu
1               5                   10                  15

Arg Pro Ala Glu Ile Met Thr Ile Asn Leu Ala Val Cys Asp Leu Gly
            20                  25                  30
```

Ile Ser Val Val Gly Lys Pro Phe Thr Ile Ile Ser Cys Phe
            35                  40                  45

<210> SEQ ID NO 132
<211> LENGTH: 46
<212> TYPE: PRT
<213> ORGANISM: Homo sapiens

<400> SEQUENCE: 132

Gly Asn Leu Thr Val Ile Tyr Thr Phe Cys Arg Ser Arg Ser Leu Arg
1               5                   10                  15

Thr Pro Ala Asn Met Phe Ile Ile Asn Leu Ala Val Ser Asp Phe Leu
            20                  25                  30

Met Ser Phe Thr Gln Ala Pro Val Phe Phe Thr Ser Ser Leu
            35                  40                  45

<210> SEQ ID NO 133
<211> LENGTH: 46
<212> TYPE: PRT
<213> ORGANISM: Homo sapiens

<400> SEQUENCE: 133

Asn Asn Leu Leu Val Leu Val Leu Tyr Tyr Lys Phe Gln Arg Leu Arg
1               5                   10                  15

Thr Pro Thr His Leu Leu Leu Val Asn Ile Ser Leu Ser Asp Leu Leu
            20                  25                  30

Val Ser Leu Phe Gly Val Thr Phe Thr Phe Val Ser Cys Leu
            35                  40                  45

<210> SEQ ID NO 134
<211> LENGTH: 46
<212> TYPE: PRT
<213> ORGANISM: Homo sapiens

<400> SEQUENCE: 134

Leu Asn Thr Leu Thr Ile Phe Ser Phe Cys Lys Thr Pro Glu Leu Arg
1               5                   10                  15

Thr Pro Cys His Leu Leu Val Leu Ser Leu Ala Leu Ala Asp Ser Gly
            20                  25                  30

Ile Ser Leu Asn Ala Leu Val Ala Ala Thr Ser Ser Leu Leu
            35                  40                  45

<210> SEQ ID NO 135
<211> LENGTH: 46
<212> TYPE: PRT
<213> ORGANISM: Homo sapiens

<400> SEQUENCE: 135

Thr Asn Gly Leu Val Leu Ala Ala Thr Met Lys Phe Lys Lys Leu Arg
1               5                   10                  15

His Pro Leu Asn Trp Ile Leu Val Asn Leu Ala Val Ala Asp Leu Ala
            20                  25                  30

Glu Thr Val Ile Ala Ser Thr Ile Ser Ile Val Asn Gln Val
            35                  40                  45

<210> SEQ ID NO 136
<211> LENGTH: 46
<212> TYPE: PRT
<213> ORGANISM: Homo sapiens

<400> SEQUENCE: 136

Thr Asn Gly Leu Val Leu Ala Ala Thr Met Lys Phe Lys Lys Leu Arg

-continued

```
              1               5                  10                 15
         His Pro Leu Asn Trp Ile Leu Val Asn Leu Ala Val Ala Asp Leu Ala
                         20                 25                 30
         Glu Thr Val Ile Ala Ser Thr Ile Ser Val Val Asn Gln Val
                         35                 40                 45

<210> SEQ ID NO 137
<211> LENGTH: 46
<212> TYPE: PRT
<213> ORGANISM: Homo sapiens

<400> SEQUENCE: 137

Leu Asn Ala Met Val Leu Val Ala Thr Leu Arg Tyr Lys Lys Leu Arg
1               5                  10                 15
Gln Pro Leu Asn Tyr Ile Leu Val Asn Val Ser Phe Gly Gly Phe Leu
                20                 25                 30
Leu Cys Ile Phe Ser Val Phe Pro Val Phe Val Ala Ser Cys
            35                 40                 45

<210> SEQ ID NO 138
<211> LENGTH: 46
<212> TYPE: PRT
<213> ORGANISM: Homo sapiens

<400> SEQUENCE: 138

Ile Asn Phe Leu Thr Leu Tyr Val Thr Val Gln His Lys Lys Leu Arg
1               5                  10                 15
Thr Pro Leu Asn Tyr Ile Leu Leu Asn Leu Ala Val Ala Asp Leu Phe
                20                 25                 30
Met Val Leu Gly Gly Phe Thr Ser Thr Leu Tyr Thr Ser Leu
            35                 40                 45

<210> SEQ ID NO 139
<211> LENGTH: 46
<212> TYPE: PRT
<213> ORGANISM: Homo sapiens

<400> SEQUENCE: 139

Gly Asn Ile Met Val Val Leu Val Met Arg Thr Lys His Met Arg
1               5                  10                 15
Thr Pro Thr Asn Cys Tyr Leu Val Ser Leu Ala Val Ala Asp Leu Met
                20                 25                 30
Val Leu Val Ala Ala Gly Leu Pro Asn Ile Thr Asp Ser Ile
            35                 40                 45

<210> SEQ ID NO 140
<211> LENGTH: 44
<212> TYPE: PRT
<213> ORGANISM: Homo sapiens

<400> SEQUENCE: 140

Gly Asn Leu Leu Thr Met Leu Val Val Ser Arg Phe Arg Glu Leu Arg
1               5                  10                 15
Thr Thr Thr Asn Leu Tyr Leu Ser Ser Met Ala Phe Ser Asp Leu Leu
                20                 25                 30
Ile Phe Leu Cys Met Pro Leu Asp Leu Val Arg Leu
            35                 40

<210> SEQ ID NO 141
<211> LENGTH: 44
<212> TYPE: PRT
```

<213> ORGANISM: Homo sapiens

<400> SEQUENCE: 141

Gly Asn Val Val Thr Val Met Leu Ile Gly Arg Tyr Arg Asp Met Arg
1               5                   10                  15

Thr Thr Thr Asn Leu Tyr Leu Gly Ser Met Ala Val Ser Asp Leu Leu
            20                  25                  30

Ile Leu Leu Gly Leu Pro Phe Asp Leu Tyr Arg Leu
        35                  40

<210> SEQ ID NO 142
<211> LENGTH: 45
<212> TYPE: PRT
<213> ORGANISM: Homo sapiens

<400> SEQUENCE: 142

Gly Asn Gly Leu Thr Cys Leu Val Ile Leu Arg His Lys Ala Met Arg
1               5                   10                  15

Thr Pro Thr Asn Tyr Tyr Leu Phe Ser Leu Ala Val Ser Asp Leu Leu
            20                  25                  30

Val Leu Leu Val Gly Leu Pro Leu Glu Leu Tyr Glu Met
        35                  40                  45

<210> SEQ ID NO 143
<211> LENGTH: 45
<212> TYPE: PRT
<213> ORGANISM: Homo sapiens

<400> SEQUENCE: 143

Gly Asn Val Leu Val Cys Leu Val Ile Leu Gln His Gln Ala Met Lys
1               5                   10                  15

Thr Pro Thr Asn Tyr Tyr Leu Phe Ser Leu Ala Val Ser Asp Leu Leu
            20                  25                  30

Val Leu Leu Leu Gly Met Pro Leu Glu Val Tyr Glu Met
        35                  40                  45

<210> SEQ ID NO 144
<211> LENGTH: 49
<212> TYPE: PRT
<213> ORGANISM: Homo sapiens

<400> SEQUENCE: 144

Gly Asn Thr Val Thr Ala Phe Thr Leu Ala Arg Lys Lys Ser Leu Gln
1               5                   10                  15

Ser Leu Gln Ser Thr Val His Tyr His Leu Gly Ser Leu Ala Leu Ser
            20                  25                  30

Asp Leu Leu Thr Leu Leu Leu Ala Met Pro Val Glu Leu Tyr Asn Phe
        35                  40                  45

Ile

<210> SEQ ID NO 145
<211> LENGTH: 47
<212> TYPE: PRT
<213> ORGANISM: Homo sapiens

<400> SEQUENCE: 145

Gly Asn Ala Leu Ser Val His Val Leu Lys Ala Arg Ala Gly Arg
1               5                   10                  15

Ala Gly Arg Leu Arg His His Val Leu Ser Leu Ala Leu Ala Gly Leu
            20                  25                  30

Leu Leu Leu Leu Val Gly Val Pro Val Glu Leu Tyr Ser Phe Val
            35                  40                  45

<210> SEQ ID NO 146
<211> LENGTH: 49
<212> TYPE: PRT
<213> ORGANISM: Homo sapiens

<400> SEQUENCE: 146

Gly Asn Ser Ala Thr Ile Arg Val Thr Gln Val Leu Gln Lys Lys Gly
1               5                   10                  15

Tyr Leu Gln Lys Glu Val Thr Asp His Met Val Ser Leu Ala Cys Ser
                20                  25                  30

Asp Ile Leu Val Phe Leu Ile Gly Met Pro Met Glu Phe Tyr Ser Ile
            35                  40                  45

Ile

<210> SEQ ID NO 147
<211> LENGTH: 47
<212> TYPE: PRT
<213> ORGANISM: Homo sapiens

<400> SEQUENCE: 147

Gly Asn Leu Thr Val Ile Phe Val Phe His Cys Ala Pro Leu Leu His
1               5                   10                  15

His Tyr Thr Thr Ser Tyr Phe Ile Gln Thr Met Ala Tyr Ala Asp Leu
                20                  25                  30

Phe Val Gly Val Ser Cys Leu Val Pro Thr Leu Ser Leu Leu His
            35                  40                  45

<210> SEQ ID NO 148
<211> LENGTH: 47
<212> TYPE: PRT
<213> ORGANISM: Homo sapiens

<400> SEQUENCE: 148

Gly Asn Ile Ile Val Ile Phe Val Phe His Cys Ala Pro Leu Leu Asn
1               5                   10                  15

His His Thr Thr Ser Tyr Phe Ile Gln Thr Met Ala Tyr Ala Asp Leu
                20                  25                  30

Phe Val Gly Val Ser Cys Val Val Pro Ser Leu Ser Leu Leu His
            35                  40                  45

<210> SEQ ID NO 149
<211> LENGTH: 46
<212> TYPE: PRT
<213> ORGANISM: Homo sapiens

<400> SEQUENCE: 149

Gly Asn Cys Ala Val Met Gly Val Ile Val Lys His Arg Gln Leu Arg
1               5                   10                  15

Thr Val Thr Asn Ala Phe Ile Leu Ser Leu Ser Leu Ser Asp Leu Leu
                20                  25                  30

Thr Ala Leu Leu Cys Leu Pro Ala Ala Phe Leu Asp Leu Phe
            35                  40                  45

<210> SEQ ID NO 150
<211> LENGTH: 48
<212> TYPE: PRT
<213> ORGANISM: Homo sapiens

<400> SEQUENCE: 150

-continued

```
Gly Asn Phe Ile Val Phe Leu Ser Phe Phe Asp Pro Ala Phe Arg Lys
1               5                   10                  15

Phe Arg Thr Asn Phe Asp Phe Met Ile Leu Asn Leu Ser Phe Cys Asp
                20                  25                  30

Leu Phe Ile Cys Gly Val Thr Ala Pro Met Phe Thr Phe Val Leu Phe
            35                  40                  45
```

<210> SEQ ID NO 151
<211> LENGTH: 46
<212> TYPE: PRT
<213> ORGANISM: Homo sapiens

<400> SEQUENCE: 151

```
Gly Asn Val Val Val Met Trp Ile Ile Leu Ala His Lys Arg Met Arg
1               5                   10                  15

Thr Val Thr Asn Tyr Phe Leu Val Asn Leu Ala Phe Ala Glu Ala Ser
                20                  25                  30

Met Ala Ala Phe Asn Thr Val Val Asn Phe Thr Tyr Ala Val
            35                  40                  45
```

<210> SEQ ID NO 152
<211> LENGTH: 46
<212> TYPE: PRT
<213> ORGANISM: Homo sapiens

<400> SEQUENCE: 152

```
Gly Asn Leu Ile Val Ile Trp Ile Ile Leu Ala His Lys Arg Met Arg
1               5                   10                  15

Thr Val Thr Asn Tyr Phe Leu Val Asn Leu Ala Phe Ser Asp Ala Ser
                20                  25                  30

Met Ala Ala Phe Asn Thr Leu Val Asn Phe Ile Tyr Ala Leu
            35                  40                  45
```

<210> SEQ ID NO 153
<211> LENGTH: 46
<212> TYPE: PRT
<213> ORGANISM: Homo sapiens

<400> SEQUENCE: 153

```
Gly Asn Ala Ile Val Ile Trp Ile Ile Leu Ala His Arg Gly Met Arg
1               5                   10                  15

Thr Val Thr Asn Tyr Phe Ile Val Asn Leu Ala Leu Ala Asp Leu Cys
                20                  25                  30

Met Ala Ala Leu Asn Ala Ala Phe Asn Phe Val Tyr Ala Ser
            35                  40                  45
```

<210> SEQ ID NO 154
<211> LENGTH: 46
<212> TYPE: PRT
<213> ORGANISM: Homo sapiens

<400> SEQUENCE: 154

```
Gly Asn Thr Leu Val Leu Ala Val Leu Leu Arg Gly Gly Gln Ala Val
1               5                   10                  15

Ser Thr Thr Asn Leu Phe Ile Leu Asn Leu Gly Val Ala Asp Leu Cys
                20                  25                  30

Phe Ile Leu Cys Cys Val Pro Phe Gln Ala Thr Ile Tyr Thr
            35                  40                  45
```

<210> SEQ ID NO 155

```
<211> LENGTH: 51
<212> TYPE: PRT
<213> ORGANISM: Homo sapiens

<400> SEQUENCE: 155

Gly Asn Gly Leu Val Leu Ala Val Leu Leu Gln Pro Gly Pro Ser Ala
1               5                   10                  15

Trp Gln Glu Pro Gly Ser Thr Thr Asp Leu Phe Ile Leu Asn Leu Ala
            20                  25                  30

Val Ala Asp Leu Cys Phe Ile Leu Cys Cys Val Pro Phe Gln Ala Thr
        35                  40                  45

Ile Tyr Thr
    50

<210> SEQ ID NO 156
<211> LENGTH: 48
<212> TYPE: PRT
<213> ORGANISM: Homo sapiens

<400> SEQUENCE: 156

Gly Asn Ser Leu Val Ile Thr Val Leu Ala Arg Ser Lys Pro Gly Lys
1               5                   10                  15

Pro Arg Ser Thr Thr Asn Leu Phe Ile Leu Asn Leu Ser Ile Ala Asp
            20                  25                  30

Leu Ala Tyr Leu Leu Phe Cys Ile Pro Phe Gln Ala Thr Val Tyr Ala
        35                  40                  45

<210> SEQ ID NO 157
<211> LENGTH: 46
<212> TYPE: PRT
<213> ORGANISM: Homo sapiens

<400> SEQUENCE: 157

Gly Asn Ser Leu Val Ile Tyr Val Ile Cys Arg His Lys Pro Met Arg
1               5                   10                  15

Thr Val Thr Asn Phe Tyr Ile Ala Asn Leu Ala Ala Thr Asp Val Thr
            20                  25                  30

Phe Leu Leu Cys Cys Val Pro Phe Thr Ala Leu Leu Tyr Pro
        35                  40                  45

<210> SEQ ID NO 158
<211> LENGTH: 46
<212> TYPE: PRT
<213> ORGANISM: Homo sapiens

<400> SEQUENCE: 158

Gly Asn Gly Leu Val Leu Trp Thr Val Phe Arg Ser Ser Arg Glu Lys
1               5                   10                  15

Arg Arg Ser Ala Asp Ile Phe Ile Ala Ser Leu Ala Val Ala Asp Leu
            20                  25                  30

Thr Phe Val Val Thr Leu Pro Leu Trp Ala Thr Tyr Thr Tyr
        35                  40                  45

<210> SEQ ID NO 159
<211> LENGTH: 45
<212> TYPE: PRT
<213> ORGANISM: Homo sapiens

<400> SEQUENCE: 159

Gly Asn Leu Val Leu Met Gly Ala Leu His Phe Lys Pro Gly Ser Arg
1               5                   10                  15
```

-continued

Arg Leu Ile Asp Ile Phe Ile Ile Asn Leu Ala Ala Ser Asp Phe Ile
            20                  25                  30

Phe Leu Val Thr Leu Pro Leu Trp Val Asp Lys Glu Ala
            35                  40                  45

<210> SEQ ID NO 160
<211> LENGTH: 46
<212> TYPE: PRT
<213> ORGANISM: Homo sapiens

<400> SEQUENCE: 160

Gly Asn Leu Leu Val Leu Tyr Leu Met Lys Ser Met Gln Gly Trp Arg
1               5                   10                  15

Lys Ser Ser Ile Asn Leu Phe Val Thr Asn Leu Ala Leu Thr Asp Phe
            20                  25                  30

Gln Phe Val Leu Thr Leu Pro Phe Trp Ala Val Glu Asn Ala
            35                  40                  45

<210> SEQ ID NO 161
<211> LENGTH: 47
<212> TYPE: PRT
<213> ORGANISM: Homo sapiens

<400> SEQUENCE: 161

Gly Asn Leu Ala Val Leu Trp Val Leu Ser Asn Cys Ala Arg Arg Ala
1               5                   10                  15

Pro Gly Pro Pro Ser Asp Thr Phe Val Phe Asn Leu Ala Leu Ala Asp
            20                  25                  30

Leu Gly Leu Ala Leu Thr Leu Pro Phe Trp Ala Ala Glu Ser Ala
            35                  40                  45

<210> SEQ ID NO 162
<211> LENGTH: 45
<212> TYPE: PRT
<213> ORGANISM: Homo sapiens

<400> SEQUENCE: 162

Gly Asn Leu Phe Val Leu Leu Val Phe Leu Leu Pro Arg Arg Gln Leu
1               5                   10                  15

Asn Val Ala Glu Ile Tyr Leu Ala Asn Leu Ala Ala Ser Asp Leu Val
            20                  25                  30

Phe Val Leu Gly Leu Pro Phe Trp Ala Glu Asn Ile Trp
            35                  40                  45

<210> SEQ ID NO 163
<211> LENGTH: 45
<212> TYPE: PRT
<213> ORGANISM: Homo sapiens

<400> SEQUENCE: 163

Glu Asn Ile Phe Val Leu Ser Val Phe Cys Leu His Lys Ser Ser Cys
1               5                   10                  15

Thr Val Ala Glu Ile Tyr Leu Gly Asn Leu Ala Ala Ala Asp Leu Ile
            20                  25                  30

Leu Ala Cys Gly Leu Pro Phe Trp Ala Ile Thr Ile Ser
            35                  40                  45

<210> SEQ ID NO 164
<211> LENGTH: 45
<212> TYPE: PRT
<213> ORGANISM: Homo sapiens -continued

```
<400> SEQUENCE: 164

Val Asn Ile Val Val Thr Leu Phe Cys Cys Gln Lys Gly Pro Lys
1               5                   10                  15

Lys Val Ser Ser Ile Tyr Ile Phe Asn Leu Ala Val Ala Asp Leu Leu
                20                  25                  30

Leu Leu Ala Thr Leu Pro Leu Trp Ala Thr Tyr Tyr Ser
            35                  40                  45

<210> SEQ ID NO 165
<211> LENGTH: 44
<212> TYPE: PRT
<213> ORGANISM: Homo sapiens

<400> SEQUENCE: 165

Gly Asn Ser Leu Val Met Leu Val Ile Leu Tyr Ser Arg Val Gly Arg
1               5                   10                  15

Ser Val Thr Asp Val Tyr Leu Leu Asn Leu Ala Leu Ala Asp Leu Leu
                20                  25                  30

Phe Ala Leu Thr Leu Pro Ile Trp Ala Ala Ser Lys
            35                  40

<210> SEQ ID NO 166
<211> LENGTH: 44
<212> TYPE: PRT
<213> ORGANISM: Homo sapiens

<400> SEQUENCE: 166

Gly Asn Ser Leu Val Met Leu Val Ile Leu Tyr Ser Arg Val Gly Arg
1               5                   10                  15

Ser Val Thr Asp Val Tyr Leu Leu Asn Leu Ala Leu Ala Asp Leu Leu
                20                  25                  30

Phe Ala Leu Thr Leu Pro Ile Trp Ala Ala Ser Lys
            35                  40

<210> SEQ ID NO 167
<211> LENGTH: 44
<212> TYPE: PRT
<213> ORGANISM: Homo sapiens

<400> SEQUENCE: 167

Gly Asn Ser Leu Val Ile Leu Val Tyr Trp Tyr Cys Thr Arg Val Lys
1               5                   10                  15

Thr Met Thr Asp Met Phe Leu Leu Asn Leu Ala Ile Ala Asp Leu Leu
                20                  25                  30

Phe Leu Val Thr Leu Pro Phe Trp Ala Ile Ala Ala
            35                  40

<210> SEQ ID NO 168
<211> LENGTH: 44
<212> TYPE: PRT
<213> ORGANISM: Homo sapiens

<400> SEQUENCE: 168

Gly Asn Gly Leu Val Ile Leu Val Met Gly Tyr Gln Lys Lys Leu Arg
1               5                   10                  15

Ser Met Thr Asp Lys Tyr Arg Leu His Leu Ser Val Ala Asp Leu Leu
                20                  25                  30

Phe Val Ile Thr Leu Pro Phe Trp Ala Val Asp Ala
            35                  40
```

```
<210> SEQ ID NO 169
<211> LENGTH: 44
<212> TYPE: PRT
<213> ORGANISM: Homo sapiens

<400> SEQUENCE: 169

Gly Asn Ile Leu Val Val Ile Thr Phe Ala Phe Tyr Lys Lys Ala Arg
1               5                   10                  15

Ser Met Thr Asp Val Tyr Leu Leu Asn Met Ala Ile Ala Asp Ile Leu
            20                  25                  30

Phe Val Leu Thr Leu Pro Phe Trp Ala Val Ser His
        35                  40

<210> SEQ ID NO 170
<211> LENGTH: 44
<212> TYPE: PRT
<213> ORGANISM: Homo sapiens

<400> SEQUENCE: 170

Gly Asn Gly Leu Val Val Leu Thr Tyr Ile Tyr Phe Lys Arg Leu Lys
1               5                   10                  15

Thr Met Thr Asp Thr Tyr Leu Leu Asn Leu Ala Val Ala Asp Ile Leu
            20                  25                  30

Phe Leu Leu Thr Leu Pro Phe Trp Ala Tyr Ser Ala
        35                  40

<210> SEQ ID NO 171
<211> LENGTH: 44
<212> TYPE: PRT
<213> ORGANISM: Homo sapiens

<400> SEQUENCE: 171

Gly Asn Ser Met Val Val Ala Ile Tyr Ala Tyr Tyr Lys Lys Gln Arg
1               5                   10                  15

Thr Lys Thr Asp Val Tyr Ile Leu Asn Leu Ala Val Ala Asp Leu Leu
            20                  25                  30

Leu Leu Phe Thr Leu Pro Phe Trp Ala Val Asn Ala
        35                  40

<210> SEQ ID NO 172
<211> LENGTH: 44
<212> TYPE: PRT
<213> ORGANISM: Homo sapiens

<400> SEQUENCE: 172

Gly Asn Ser Leu Val Leu Val Ile Ser Ile Phe Tyr His Lys Leu Gln
1               5                   10                  15

Ser Leu Thr Asp Val Phe Leu Val Asn Leu Pro Leu Ala Asp Leu Val
            20                  25                  30

Phe Val Cys Thr Leu Pro Phe Trp Ala Tyr Ala Gly
        35                  40

<210> SEQ ID NO 173
<211> LENGTH: 45
<212> TYPE: PRT
<213> ORGANISM: Homo sapiens

<400> SEQUENCE: 173

Gly Asn Ser Leu Val Val Ile Val Ile Tyr Phe Tyr Met Lys Leu Lys
1               5                   10                  15

Thr Val Ala Ser Val Phe Leu Leu Asn Leu Ala Leu Ala Asp Leu Cys
            20                  25                  30
```

```
Phe Leu Leu Thr Leu Pro Leu Trp Ala Val Tyr Thr Ala
         35                  40                  45
```

<210> SEQ ID NO 174
<211> LENGTH: 45
<212> TYPE: PRT
<213> ORGANISM: Homo sapiens

<400> SEQUENCE: 174

```
Gly Asn Ser Val Val Leu Val Leu Phe Lys Tyr Lys Arg Leu Arg
1               5                   10                  15

Ser Met Thr Asp Val Tyr Leu Leu Asn Leu Ala Ile Ser Asp Leu Leu
                20                  25                  30

Phe Val Phe Ser Leu Pro Phe Trp Gly Tyr Tyr Ala Ala
         35                  40                  45
```

<210> SEQ ID NO 175
<211> LENGTH: 45
<212> TYPE: PRT
<213> ORGANISM: Homo sapiens

<400> SEQUENCE: 175

```
Gly Asn Ser Leu Val Ile Leu Val Leu Glu Val Cys Lys Lys Leu Arg
1               5                   10                  15

Ser Ile Thr Asp Val Tyr Leu Leu Asn Leu Ala Leu Ser Asp Leu Leu
                20                  25                  30

Phe Val Phe Ser Phe Pro Phe Gln Thr Tyr Tyr Leu Leu
         35                  40                  45
```

<210> SEQ ID NO 176
<211> LENGTH: 45
<212> TYPE: PRT
<213> ORGANISM: Homo sapiens

<400> SEQUENCE: 176

```
Gly Asn Leu Leu Leu Leu Met Val Leu Leu Arg Tyr Val Pro Arg Arg
1               5                   10                  15

Arg Met Val Glu Ile Tyr Leu Leu Asn Leu Ala Ile Ser Asn Leu Leu
                20                  25                  30

Phe Leu Val Thr Leu Pro Phe Trp Gly Ile Ser Val Ala
         35                  40                  45
```

<210> SEQ ID NO 177
<211> LENGTH: 45
<212> TYPE: PRT
<213> ORGANISM: Homo sapiens

<400> SEQUENCE: 177

```
Gly Asn Val Val Val Val Met Ile Leu Ile Lys Tyr Arg Arg Leu Arg
1               5                   10                  15

Ile Met Thr Asn Ile Tyr Leu Leu Asn Leu Ala Ile Ser Asp Leu Leu
                20                  25                  30

Phe Leu Val Thr Leu Pro Phe Trp Ile His Tyr Ala Arg
         35                  40                  45
```

<210> SEQ ID NO 178
<211> LENGTH: 45
<212> TYPE: PRT
<213> ORGANISM: Homo sapiens

<400> SEQUENCE: 178

```
Gly Asn Ile Leu Val Leu Val Leu Val Gln Tyr Lys Arg Leu Lys
1               5                   10                  15

Asn Met Thr Ser Ile Tyr Leu Leu Asn Leu Ala Ile Ser Asp Leu Leu
            20                  25                  30

Phe Leu Phe Thr Leu Pro Phe Trp Ile Asp Tyr Lys Leu
        35                  40                  45
```

<210> SEQ ID NO 179
<211> LENGTH: 44
<212> TYPE: PRT
<213> ORGANISM: Homo sapiens

<400> SEQUENCE: 179

```
Asp Asn Leu Leu Val Leu Ile Leu Val Lys Tyr Lys Gly Leu Lys
1               5                   10                  15

Arg Val Glu Asn Ile Tyr Leu Leu Asn Leu Ala Val Ser Asn Leu Cys
            20                  25                  30

Phe Leu Leu Thr Leu Pro Phe Trp Ala His Ala Gly
        35                  40
```

<210> SEQ ID NO 180
<211> LENGTH: 45
<212> TYPE: PRT
<213> ORGANISM: Homo sapiens

<400> SEQUENCE: 180

```
Gly Asn Met Leu Val Val Leu Ile Leu Ile Asn Cys Lys Lys Leu Lys
1               5                   10                  15

Cys Leu Thr Asp Ile Tyr Leu Leu Asn Leu Ala Ile Ser Asp Leu Leu
            20                  25                  30

Phe Leu Ile Thr Leu Pro Leu Trp Ala His Ser Ala Ala
        35                  40                  45
```

<210> SEQ ID NO 181
<211> LENGTH: 45
<212> TYPE: PRT
<213> ORGANISM: Homo sapiens

<400> SEQUENCE: 181

```
Gly Asn Met Leu Val Ile Leu Ile Leu Ile Asn Cys Lys Arg Leu Lys
1               5                   10                  15

Ser Met Thr Asp Ile Tyr Leu Leu Asn Leu Ala Ile Ser Asp Leu Phe
            20                  25                  30

Phe Leu Leu Thr Val Pro Phe Trp Ala His Tyr Ala Ala
        35                  40                  45
```

<210> SEQ ID NO 182
<211> LENGTH: 45
<212> TYPE: PRT
<213> ORGANISM: Homo sapiens

<400> SEQUENCE: 182

```
Gly Asn Leu Leu Val Val Phe Ala Leu Thr Asn Ser Lys Lys Pro Lys
1               5                   10                  15

Ser Val Thr Asp Ile Tyr Leu Leu Asn Leu Ala Leu Ser Asp Leu Leu
            20                  25                  30

Phe Val Ala Thr Leu Pro Phe Trp Thr His Tyr Leu Ile
        35                  40                  45
```

<210> SEQ ID NO 183
<211> LENGTH: 45

```
<212> TYPE: PRT
<213> ORGANISM: Homo sapiens

<400> SEQUENCE: 183

Glu Asn Leu Leu Val Ile Cys Val Asn Trp Arg Gly Ser Gly Arg Ala
 1               5                  10                  15

Gly Leu Met Asn Leu Tyr Ile Leu Asn Met Ala Ile Ala Asp Leu Gly
             20                  25                  30

Ile Val Leu Ser Leu Pro Val Trp Met Leu Glu Val Thr
             35                  40                  45

<210> SEQ ID NO 184
<211> LENGTH: 45
<212> TYPE: PRT
<213> ORGANISM: Homo sapiens

<400> SEQUENCE: 184

Ala Asn Ser Val Val Trp Val Asn Ile Gln Ala Lys Thr Thr Gly
 1               5                  10                  15

Tyr Asp Thr His Cys Tyr Ile Leu Asn Leu Ala Ile Ala Asp Leu Trp
             20                  25                  30

Val Val Leu Thr Ile Pro Val Trp Val Val Ser Leu Val
             35                  40                  45

<210> SEQ ID NO 185
<211> LENGTH: 43
<212> TYPE: PRT
<213> ORGANISM: Homo sapiens

<400> SEQUENCE: 185

Gly Asn Ile Leu Ile Leu Val Val Asn Ile Ser Phe Arg Glu Lys Met
 1               5                  10                  15

Thr Ile Pro Asp Leu Tyr Phe Ile Asn Leu Ala Val Ala Asp Leu Ile
             20                  25                  30

Leu Val Ala Asp Ser Leu Ile Glu Val Phe Asn
             35                  40

<210> SEQ ID NO 186
<211> LENGTH: 45
<212> TYPE: PRT
<213> ORGANISM: Homo sapiens

<400> SEQUENCE: 186

Gly Asn Val Leu Val Met Phe Gly Ile Val Arg Tyr Thr Lys Met Lys
 1               5                  10                  15

Thr Ala Thr Asn Ile Tyr Ile Phe Asn Leu Ala Leu Ala Asp Ala Leu
             20                  25                  30

Ala Thr Ser Thr Leu Pro Phe Gln Ser Ala Lys Tyr Leu
             35                  40                  45

<210> SEQ ID NO 187
<211> LENGTH: 45
<212> TYPE: PRT
<213> ORGANISM: Homo sapiens

<400> SEQUENCE: 187

Gly Asn Phe Leu Val Met Tyr Val Ile Val Arg Tyr Thr Lys Met Lys
 1               5                  10                  15

Thr Ala Thr Asn Ile Tyr Ile Phe Asn Leu Ala Leu Ala Asp Ala Leu
             20                  25                  30

Ala Thr Ser Thr Leu Pro Phe Gln Ser Val Asn Tyr Leu
```

35                  40                  45

<210> SEQ ID NO 188
<211> LENGTH: 45
<212> TYPE: PRT
<213> ORGANISM: Homo sapiens

<400> SEQUENCE: 188

Gly Asn Ser Leu Val Met Phe Val Ile Ile Arg Tyr Thr Lys Met Lys
1               5                   10                  15

Thr Ala Thr Asn Ile Tyr Ile Phe Asn Leu Ala Leu Ala Asp Ala Leu
            20                  25                  30

Val Thr Thr Thr Met Pro Phe Gln Ser Thr Val Tyr Leu
        35                  40                  45

<210> SEQ ID NO 189
<211> LENGTH: 45
<212> TYPE: PRT
<213> ORGANISM: Homo sapiens

<400> SEQUENCE: 189

Gly Asn Cys Leu Val Met Tyr Val Ile Leu Arg His Thr Lys Met Lys
1               5                   10                  15

Thr Ala Thr Asn Ile Tyr Ile Phe Asn Leu Ala Leu Ala Asp Thr Leu
            20                  25                  30

Val Leu Leu Thr Leu Pro Phe Gln Gly Thr Asp Ile Leu
        35                  40                  45

<210> SEQ ID NO 190
<211> LENGTH: 45
<212> TYPE: PRT
<213> ORGANISM: Homo sapiens

<400> SEQUENCE: 190

Gly Asn Ser Met Val Ile Tyr Val Ile Leu Arg Tyr Ala Lys Met Lys
1               5                   10                  15

Thr Ala Thr Asn Ile Tyr Ile Leu Asn Leu Ala Ile Ala Asp Glu Leu
            20                  25                  30

Leu Met Leu Ser Val Pro Phe Leu Val Thr Ser Thr Leu
        35                  40                  45

<210> SEQ ID NO 191
<211> LENGTH: 45
<212> TYPE: PRT
<213> ORGANISM: Homo sapiens

<400> SEQUENCE: 191

Gly Asn Ala Leu Val Ile Phe Val Ile Leu Arg Tyr Ala Lys Met Lys
1               5                   10                  15

Thr Ala Thr Asn Ile Tyr Leu Leu Asn Leu Ala Val Ala Asp Glu Leu
            20                  25                  30

Phe Met Leu Ser Val Pro Phe Val Ala Ser Ser Ala Ala
        35                  40                  45

<210> SEQ ID NO 192
<211> LENGTH: 45
<212> TYPE: PRT
<213> ORGANISM: Homo sapiens

<400> SEQUENCE: 192

Gly Asn Thr Leu Val Ile Tyr Val Ile Leu Arg Tyr Ala Lys Met Lys
1               5                   10                  15

Thr Ile Thr Asn Ile Tyr Ile Leu Asn Leu Ala Ile Ala Asp Glu Leu
            20                  25                  30

Phe Met Leu Gly Leu Pro Phe Leu Ala Met Gln Val Ala
        35                  40                  45

<210> SEQ ID NO 193
<211> LENGTH: 45
<212> TYPE: PRT
<213> ORGANISM: Homo sapiens

<400> SEQUENCE: 193

Gly Asn Thr Leu Val Ile Tyr Val Val Leu Arg Phe Ala Lys Met Lys
1               5                   10                  15

Thr Val Thr Asn Ile Tyr Ile Leu Asn Leu Ala Val Ala Asp Val Leu
            20                  25                  30

Tyr Met Leu Gly Leu Pro Phe Leu Ala Thr Gln Asn Ala
        35                  40                  45

<210> SEQ ID NO 194
<211> LENGTH: 45
<212> TYPE: PRT
<213> ORGANISM: Homo sapiens

<400> SEQUENCE: 194

Gly Asn Ser Leu Val Ile Tyr Val Val Leu Arg His Thr Ala Ser Pro
1               5                   10                  15

Ser Val Thr Asn Val Tyr Ile Leu Asn Leu Ala Leu Ala Asp Glu Leu
            20                  25                  30

Phe Met Leu Gly Leu Pro Phe Leu Ala Ala Gln Asn Ala
        35                  40                  45

<210> SEQ ID NO 195
<211> LENGTH: 45
<212> TYPE: PRT
<213> ORGANISM: Homo sapiens

<400> SEQUENCE: 195

Gly Asn Ser Ala Val Leu Tyr Val Leu Leu Arg Ala Pro Arg Met Lys
1               5                   10                  15

Thr Val Thr Asn Leu Phe Ile Leu Asn Leu Ala Ile Ala Asp Glu Leu
            20                  25                  30

Phe Thr Leu Val Leu Pro Ile Asn Ile Ala Asp Phe Leu
        35                  40                  45

<210> SEQ ID NO 196
<211> LENGTH: 45
<212> TYPE: PRT
<213> ORGANISM: Homo sapiens

<400> SEQUENCE: 196

Gly Asn Thr Ala Val Ile Leu Val Ile Leu Arg Ala Pro Lys Met Lys
1               5                   10                  15

Thr Val Thr Asn Val Phe Ile Leu Asn Leu Ala Val Ala Asp Gly Leu
            20                  25                  30

Phe Thr Leu Val Leu Pro Val Asn Ile Ala Glu His Leu
        35                  40                  45

<210> SEQ ID NO 197
<211> LENGTH: 48
<212> TYPE: PRT
<213> ORGANISM: Homo sapiens

<400> SEQUENCE: 197

Gly Asn Ser Thr Val Ile Phe Ala Val Val Lys Ser Lys Leu His
1               5                   10                  15

Trp Cys Asn Asn Val Pro Asp Ile Phe Ile Asn Leu Ser Val Val
                20                  25                  30

Asp Leu Leu Phe Leu Leu Gly Met Pro Phe Met Ile His Gln Leu Met
            35                  40                  45

<210> SEQ ID NO 198
<211> LENGTH: 44
<212> TYPE: PRT
<213> ORGANISM: Homo sapiens

<400> SEQUENCE: 198

Gly Asn Ile Leu Ile Val Phe Thr Ile Ile Arg Ser Arg Lys Lys Thr
1               5                   10                  15

Val Pro Asp Ile Tyr Ile Cys Asn Leu Ala Val Ala Asp Leu Val His
                20                  25                  30

Ile Val Gly Met Pro Phe Leu Ile His Gln Trp Ala
            35                  40

<210> SEQ ID NO 199
<211> LENGTH: 44
<212> TYPE: PRT
<213> ORGANISM: Homo sapiens

<400> SEQUENCE: 199

Gly Asn Val Cys Ala Leu Val Leu Val Ala Arg Arg Arg Arg Gly
1               5                   10                  15

Ala Thr Ala Cys Leu Val Leu Asn Leu Phe Cys Ala Asp Leu Leu Phe
                20                  25                  30

Ile Ser Ala Ile Pro Leu Val Leu Ala Val Arg Trp
            35                  40

<210> SEQ ID NO 200
<211> LENGTH: 45
<212> TYPE: PRT
<213> ORGANISM: Homo sapiens

<400> SEQUENCE: 200

Gly Asn Ala Val Ala Leu Trp Thr Phe Leu Phe Arg Val Arg Val Trp
1               5                   10                  15

Lys Pro Tyr Ala Val Tyr Leu Leu Asn Leu Ala Leu Ala Asp Leu Leu
                20                  25                  30

Leu Ala Ala Cys Leu Pro Phe Leu Ala Ala Phe Tyr Leu
            35                  40                  45

<210> SEQ ID NO 201
<211> LENGTH: 45
<212> TYPE: PRT
<213> ORGANISM: Homo sapiens

<400> SEQUENCE: 201

Gly Asn Ala Tyr Thr Leu Val Val Thr Cys Arg Ser Leu Arg Ala Val
1               5                   10                  15

Ala Ser Met Tyr Val Tyr Val Asn Leu Ala Leu Ala Asp Leu Leu
                20                  25                  30

Tyr Leu Leu Ser Ile Pro Phe Ile Val Ala Thr Tyr Val
            35                  40                  45

<210> SEQ ID NO 202
<211> LENGTH: 45
<212> TYPE: PRT
<213> ORGANISM: Homo sapiens

<400> SEQUENCE: 202

Gly Asn Ala Phe Val Val Trp Leu Leu Ala Gly Arg Gly Pro Arg
1               5                   10                  15

Arg Leu Val Asp Thr Phe Val Leu His Leu Ala Ala Ala Asp Leu Gly
            20                  25                  30

Phe Val Leu Thr Leu Pro Leu Trp Ala Ala Ala Ala
        35                  40                  45

<210> SEQ ID NO 203
<211> LENGTH: 45
<212> TYPE: PRT
<213> ORGANISM: Homo sapiens

<400> SEQUENCE: 203

Gly Asn Gly Ala Val Ala Ala Val Leu Leu Ser Arg Arg Thr Ala Leu
1               5                   10                  15

Ser Ser Thr Asp Thr Phe Leu Leu His Leu Ala Val Ala Asp Thr Leu
            20                  25                  30

Leu Val Leu Thr Leu Pro Leu Trp Ala Val Asp Ala Ala
        35                  40                  45

<210> SEQ ID NO 204
<211> LENGTH: 45
<212> TYPE: PRT
<213> ORGANISM: Homo sapiens

<400> SEQUENCE: 204

Gly Asn Val Leu Val Leu Val Ile Leu Glu Arg His Arg Gln Thr Arg
1               5                   10                  15

Ser Ser Thr Glu Thr Phe Leu Phe His Leu Ala Val Ala Asp Leu Leu
            20                  25                  30

Leu Val Phe Ile Leu Pro Phe Ala Val Ala Glu Gly Ser
        35                  40                  45

<210> SEQ ID NO 205
<211> LENGTH: 46
<212> TYPE: PRT
<213> ORGANISM: Homo sapiens

<400> SEQUENCE: 205

Gly Asn Gly Leu Val Leu Ala Thr His Leu Ala Ala Arg Arg Ala Ala
1               5                   10                  15

Arg Ser Pro Thr Ser Ala His Leu Leu Gln Leu Ala Leu Ala Asp Leu
            20                  25                  30

Leu Leu Ala Leu Thr Leu Pro Phe Ala Ala Ala Gly Ala Leu
        35                  40                  45

<210> SEQ ID NO 206
<211> LENGTH: 44
<212> TYPE: PRT
<213> ORGANISM: Homo sapiens

<400> SEQUENCE: 206

Gly Asn Ala Ile Val Ile Trp Phe Thr Gly Leu Lys Trp Lys Lys Thr
1               5                   10                  15

Val Thr Thr Leu Trp Phe Leu Asn Leu Ala Ile Ala Asp Phe Ile Phe

```
                        20                  25                  30

Leu Leu Phe Leu Pro Leu Tyr Ile Ser Tyr Val Ala
        35                  40

<210> SEQ ID NO 207
<211> LENGTH: 44
<212> TYPE: PRT
<213> ORGANISM: Homo sapiens

<400> SEQUENCE: 207

Gly Asn Gly Leu Val Ile Ile Ile Ala Thr Phe Lys Met Lys Lys Thr
1               5                   10                  15

Val Asn Met Val Trp Phe Leu Asn Leu Ala Val Ala Asp Phe Leu Phe
                20                  25                  30

Asn Val Phe Leu Pro Ile His Ile Thr Tyr Ala Ala
        35                  40

<210> SEQ ID NO 208
<211> LENGTH: 44
<212> TYPE: PRT
<213> ORGANISM: Homo sapiens

<400> SEQUENCE: 208

Gly Asn Gly Leu Val Ile Trp Val Ala Gly Phe Arg Met Thr Arg Thr
1               5                   10                  15

Val Thr Thr Ile Cys Tyr Leu Asn Leu Ala Leu Ala Asp Phe Ser Phe
                20                  25                  30

Thr Ala Thr Leu Pro Phe Leu Ile Val Ser Met Ala
        35                  40

<210> SEQ ID NO 209
<211> LENGTH: 44
<212> TYPE: PRT
<213> ORGANISM: Homo sapiens

<400> SEQUENCE: 209

Gly Asn Gly Leu Val Ile Trp Val Ala Gly Phe Arg Met Thr Arg Thr
1               5                   10                  15

Val Asn Thr Ile Cys Tyr Leu Asn Leu Ala Leu Ala Asp Phe Ser Phe
                20                  25                  30

Ser Ala Ile Leu Pro Phe Arg Met Val Ser Val Ala
        35                  40

<210> SEQ ID NO 210
<211> LENGTH: 44
<212> TYPE: PRT
<213> ORGANISM: Homo sapiens

<400> SEQUENCE: 210

Gly Asn Gly Leu Val Ile Trp Val Ala Gly Phe Arg Met Thr His Thr
1               5                   10                  15

Val Thr Thr Ile Ser Tyr Leu Asn Leu Ala Val Ala Asp Phe Cys Phe
                20                  25                  30

Thr Ser Thr Leu Pro Phe Phe Met Val Arg Lys Ala
        35                  40

<210> SEQ ID NO 211
<211> LENGTH: 44
<212> TYPE: PRT
<213> ORGANISM: Homo sapiens

<400> SEQUENCE: 211
```

Thr Asn Gly Leu Tyr Leu Trp Val Leu Arg Phe Lys Met Lys Gln Thr
1               5                   10                  15

Val Asn Thr Leu Leu Phe Phe His Leu Ile Leu Ser Tyr Phe Ile Ser
                20                  25                  30

Thr Met Ile Leu Pro Phe Met Ala Thr Ser Gln Leu
                35                  40

<210> SEQ ID NO 212
<211> LENGTH: 43
<212> TYPE: PRT
<213> ORGANISM: Homo sapiens

<400> SEQUENCE: 212

Asn Gly Val Ile Leu Phe Val Val Gly Cys Arg Met Arg Gln Thr Val
1               5                   10                  15

Val Thr Thr Trp Val Leu His Leu Ala Leu Ser Asp Leu Leu Ala Ser
                20                  25                  30

Ala Ser Leu Pro Phe Phe Thr Tyr Phe Leu Ala
                35                  40

<210> SEQ ID NO 213
<211> LENGTH: 44
<212> TYPE: PRT
<213> ORGANISM: Homo sapiens

<400> SEQUENCE: 213

Gly Asn Gly Leu Val Leu Trp Val Ala Gly Leu Lys Met Gln Arg Thr
1               5                   10                  15

Val Asn Thr Ile Trp Phe Leu His Leu Thr Leu Ala Asp Leu Leu Cys
                20                  25                  30

Cys Leu Ser Leu Pro Phe Ser Leu Ala His Leu Ala
                35                  40

<210> SEQ ID NO 214
<211> LENGTH: 44
<212> TYPE: PRT
<213> ORGANISM: Homo sapiens

<400> SEQUENCE: 214

Gly Asn Gly Leu Val Leu Trp Met Thr Val Phe Arg Met Ala Arg Thr
1               5                   10                  15

Val Ser Thr Val Cys Phe Phe His Leu Ala Leu Ala Asp Phe Met Leu
                20                  25                  30

Ser Leu Ser Leu Pro Ile Ala Met Tyr Tyr Ile Val
                35                  40

<210> SEQ ID NO 215
<211> LENGTH: 44
<212> TYPE: PRT
<213> ORGANISM: Homo sapiens

<400> SEQUENCE: 215

Gly Asn Ala Met Val Ala Trp Val Ala Gly Lys Val Ala Arg Arg Arg
1               5                   10                  15

Val Gly Ala Thr Trp Leu Leu His Leu Ala Val Ala Asp Leu Leu Cys
                20                  25                  30

Cys Leu Ser Leu Pro Ile Leu Ala Val Pro Ile Ala
                35                  40

<210> SEQ ID NO 216

```
<211> LENGTH: 44
<212> TYPE: PRT
<213> ORGANISM: Homo sapiens

<400> SEQUENCE: 216

Gly Asn Ala Leu Val Val Trp Val Thr Ala Phe Glu Ala Lys Arg Thr
1               5                   10                  15

Ile Asn Ala Ile Trp Phe Leu Asn Leu Ala Val Ala Asp Phe Leu Ser
            20                  25                  30

Cys Leu Ala Leu Pro Ile Leu Phe Thr Ser Ile Val
        35                  40

<210> SEQ ID NO 217
<211> LENGTH: 47
<212> TYPE: PRT
<213> ORGANISM: Homo sapiens

<400> SEQUENCE: 217

Ala Asn Gly Leu Met Ala Trp Leu Ala Gly Ser Gln Ala Arg His Gly
1               5                   10                  15

Ala Gly Thr Arg Leu Ala Leu Leu Leu Ser Leu Ala Leu Ser Asp
            20                  25                  30

Phe Leu Phe Leu Ala Ala Ala Ala Phe Gln Ile Leu Glu Ile Arg
        35                  40                  45

<210> SEQ ID NO 218
<211> LENGTH: 45
<212> TYPE: PRT
<213> ORGANISM: Homo sapiens

<400> SEQUENCE: 218

Gly Asn Ser Phe Val Val Trp Ser Ile Leu Lys Arg Met Gln Lys Arg
1               5                   10                  15

Ser Val Thr Ala Leu Met Val Leu Asn Leu Ala Leu Ala Asp Leu Ala
            20                  25                  30

Val Leu Leu Thr Ala Pro Phe Phe Leu His Phe Leu Ala
        35                  40                  45

<210> SEQ ID NO 219
<211> LENGTH: 47
<212> TYPE: PRT
<213> ORGANISM: Homo sapiens

<400> SEQUENCE: 219

Gly Asn Gly Phe Val Val Trp Ser Leu Ala Gly Trp Arg Pro Ala Arg
1               5                   10                  15

Gly Arg Pro Leu Ala Ala Thr Leu Val Leu His Leu Ala Leu Ala Asp
            20                  25                  30

Gly Ala Val Leu Leu Leu Thr Pro Leu Phe Val Ala Phe Leu Thr
        35                  40                  45

<210> SEQ ID NO 220
<211> LENGTH: 46
<212> TYPE: PRT
<213> ORGANISM: Homo sapiens

<400> SEQUENCE: 220

Leu Asn Val Leu Ala Ile Arg Gly Ala Thr Ala His Ala Arg Leu Arg
1               5                   10                  15

Leu Thr Pro Ser Leu Val Tyr Ala Leu Asn Leu Gly Cys Ser Asp Leu
            20                  25                  30
```

Leu Leu Thr Val Ser Leu Pro Leu Lys Ala Val Glu Ala Leu
            35                  40                  45

<210> SEQ ID NO 221
<211> LENGTH: 49
<212> TYPE: PRT
<213> ORGANISM: Homo sapiens

<400> SEQUENCE: 221

Leu Asn Leu Leu Ala Ile His Gly Phe Ser Thr Phe Leu Lys Asn Arg
1               5                   10                  15

Trp Pro Asp Tyr Ala Ala Thr Ser Ile Tyr Met Ile Asn Leu Ala Val
            20                  25                  30

Phe Asp Leu Leu Leu Val Leu Ser Leu Pro Phe Lys Met Val Leu Ser
            35                  40                  45

Gln

<210> SEQ ID NO 222
<211> LENGTH: 46
<212> TYPE: PRT
<213> ORGANISM: Homo sapiens

<400> SEQUENCE: 222

Leu Asn Leu Leu Ala Leu Val Val Phe Val Gly Lys Leu Gln Arg Arg
1               5                   10                  15

Pro Val Ala Val Asp Val Leu Leu Asn Leu Thr Ala Ser Asp Leu
            20                  25                  30

Leu Leu Leu Leu Phe Leu Pro Phe Arg Met Val Glu Ala Ala
            35                  40                  45

<210> SEQ ID NO 223
<211> LENGTH: 48
<212> TYPE: PRT
<213> ORGANISM: Homo sapiens

<400> SEQUENCE: 223

Pro Ala Asn Leu Leu Ala Leu Arg Ala Phe Val Gly Arg Ile Arg Gln
1               5                   10                  15

Pro Gln Pro Ala Pro Val His Ile Leu Leu Leu Ser Leu Thr Leu Ala
            20                  25                  30

Asp Leu Leu Leu Leu Leu Leu Pro Phe Lys Ile Ile Glu Ala Ala
            35                  40                  45

<210> SEQ ID NO 224
<211> LENGTH: 45
<212> TYPE: PRT
<213> ORGANISM: Homo sapiens

<400> SEQUENCE: 224

Leu Asn Ile Met Ala Ile Val Val Phe Ile Leu Lys Met Lys Val Lys
1               5                   10                  15

Lys Pro Ala Val Val Tyr Met Leu His Leu Ala Thr Ala Asp Val Leu
            20                  25                  30

Phe Val Ser Val Leu Pro Phe Lys Ile Ser Tyr Tyr Phe
            35                  40                  45

<210> SEQ ID NO 225
<211> LENGTH: 45
<212> TYPE: PRT
<213> ORGANISM: Homo sapiens

<400> SEQUENCE: 225

```
Gly Asn Thr Leu Ala Leu Trp Leu Phe Ile Arg Asp His Lys Ser Gly
1               5                   10                  15

Thr Pro Ala Asn Val Phe Leu Met His Leu Ala Val Ala Asp Leu Ser
                20                  25                  30

Cys Val Leu Val Leu Pro Thr Arg Leu Val Tyr His Phe
                35                  40                  45
```

<210> SEQ ID NO 226
<211> LENGTH: 45
<212> TYPE: PRT
<213> ORGANISM: Homo sapiens

<400> SEQUENCE: 226

```
Ser Asn Cys Val Ala Ile Tyr Ile Phe Ile Cys Val Leu Lys Val Arg
1               5                   10                  15

Asn Glu Thr Thr Thr Tyr Met Ile Asn Leu Ala Met Ser Asp Leu Leu
                20                  25                  30

Phe Val Phe Thr Leu Pro Phe Arg Ile Phe Tyr Phe Thr
                35                  40                  45
```

<210> SEQ ID NO 227
<211> LENGTH: 45
<212> TYPE: PRT
<213> ORGANISM: Homo sapiens

<400> SEQUENCE: 227

```
Thr Asn Ser Val Ser Leu Phe Val Phe Cys Phe Arg Met Lys Met Arg
1               5                   10                  15

Ser Glu Thr Ala Ile Phe Ile Thr Asn Leu Ala Val Ser Asp Leu Leu
                20                  25                  30

Phe Val Cys Thr Leu Pro Phe Lys Ile Phe Tyr Asn Phe
                35                  40                  45
```

<210> SEQ ID NO 228
<211> LENGTH: 45
<212> TYPE: PRT
<213> ORGANISM: Homo sapiens

<400> SEQUENCE: 228

```
Gly Asn Leu Phe Ser Leu Trp Val Leu Cys Arg Arg Met Gly Pro Arg
1               5                   10                  15

Ser Pro Ser Val Ile Phe Met Ile Asn Leu Ser Val Thr Asp Leu Met
                20                  25                  30

Leu Ala Ser Val Leu Pro Phe Gln Ile Tyr Tyr His Cys
                35                  40                  45
```

<210> SEQ ID NO 229
<211> LENGTH: 45
<212> TYPE: PRT
<213> ORGANISM: Homo sapiens

<400> SEQUENCE: 229

```
Ala Asn Ser Ala Ala Leu Trp Val Leu Cys Arg Phe Ile Ser Lys Lys
1               5                   10                  15

Asn Lys Ala Ile Ile Phe Met Ile Asn Leu Ser Val Ala Asp Leu Ala
                20                  25                  30

His Val Leu Ser Leu Pro Leu Arg Ile Tyr Tyr Tyr Ile
                35                  40                  45
```

<210> SEQ ID NO 230

```
<211> LENGTH: 45
<212> TYPE: PRT
<213> ORGANISM: Homo sapiens

<400> SEQUENCE: 230

Gly Asn Ile Leu Ala Leu Trp Val Phe Tyr Gly Tyr Met Lys Glu Thr
1               5                   10                  15

Lys Arg Ala Val Ile Phe Met Ile Asn Leu Ala Ile Ala Asp Leu Leu
                20                  25                  30

Gln Val Leu Ser Leu Pro Leu Arg Ile Phe Tyr Tyr Leu
            35                  40                  45

<210> SEQ ID NO 231
<211> LENGTH: 45
<212> TYPE: PRT
<213> ORGANISM: Homo sapiens

<400> SEQUENCE: 231

Ser Asn Gly Met Ala Leu Trp Val Phe Leu Phe Arg Thr Lys Lys Lys
1               5                   10                  15

His Pro Ala Val Ile Tyr Met Ala Asn Leu Ala Leu Ala Asp Leu Leu
                20                  25                  30

Ser Val Ile Trp Phe Pro Leu Lys Ile Ala Tyr His Ile
            35                  40                  45

<210> SEQ ID NO 232
<211> LENGTH: 44
<212> TYPE: PRT
<213> ORGANISM: Homo sapiens

<400> SEQUENCE: 232

Ala Asn Ala Val Thr Leu Trp Met Leu Phe Phe Arg Thr Arg Ser Ile
1               5                   10                  15

Cys Thr Thr Val Phe Tyr Thr Asn Leu Ala Ile Ala Asp Phe Leu Phe
                20                  25                  30

Cys Val Thr Leu Pro Phe Lys Ile Ala Tyr His Leu
            35                  40

<210> SEQ ID NO 233
<211> LENGTH: 44
<212> TYPE: PRT
<213> ORGANISM: Homo sapiens

<400> SEQUENCE: 233

Ala Asn Gly Leu Ala Leu Trp Val Leu Ala Thr Gln Ala Pro Arg Leu
1               5                   10                  15

Pro Ser Thr Met Leu Leu Met Asn Leu Ala Thr Ala Asp Leu Leu Leu
                20                  25                  30

Ala Leu Ala Leu Pro Pro Arg Ile Ala Tyr His Leu
            35                  40

<210> SEQ ID NO 234
<211> LENGTH: 45
<212> TYPE: PRT
<213> ORGANISM: Homo sapiens

<400> SEQUENCE: 234

Gly Asn Gly Leu Ser Ile Tyr Val Phe Leu Gln Pro Tyr Lys Lys Ser
1               5                   10                  15

Thr Ser Val Asn Val Phe Met Leu Asn Leu Ala Ile Ser Asp Leu Leu
                20                  25                  30
```

```
Phe Ile Ser Thr Leu Pro Phe Arg Ala Asp Tyr Tyr Leu
            35                  40                  45

<210> SEQ ID NO 235
<211> LENGTH: 45
<212> TYPE: PRT
<213> ORGANISM: Homo sapiens

<400> SEQUENCE: 235

Gly Asn Gly Phe Val Leu Tyr Val Leu Ile Lys Thr Tyr His Lys Lys
1               5                   10                  15

Ser Ala Phe Gln Val Tyr Met Ile Asn Leu Ala Val Ala Asp Leu Leu
            20                  25                  30

Cys Val Cys Thr Leu Pro Leu Arg Val Val Tyr Tyr Val
            35                  40                  45

<210> SEQ ID NO 236
<211> LENGTH: 47
<212> TYPE: PRT
<213> ORGANISM: Homo sapiens

<400> SEQUENCE: 236

Ala Asn Gly Tyr Val Leu Trp Val Phe Ala Arg Leu Tyr Pro Cys Lys
1               5                   10                  15

Lys Phe Asn Glu Ile Lys Ile Phe Met Val Asn Leu Thr Met Ala Asp
            20                  25                  30

Met Leu Phe Leu Ile Thr Leu Pro Leu Trp Ile Val Tyr Tyr Gln
            35                  40                  45

<210> SEQ ID NO 237
<211> LENGTH: 45
<212> TYPE: PRT
<213> ORGANISM: Homo sapiens

<400> SEQUENCE: 237

Gly Asn Leu Leu Ala Leu Val Val Ile Val Gln Asn Arg Lys Lys Ile
1               5                   10                  15

Asn Ser Thr Thr Leu Tyr Ser Thr Asn Leu Val Ile Ser Asp Ile Leu
            20                  25                  30

Phe Thr Thr Ala Leu Pro Thr Arg Ile Ala Tyr Tyr Ala
            35                  40                  45

<210> SEQ ID NO 238
<211> LENGTH: 45
<212> TYPE: PRT
<213> ORGANISM: Homo sapiens

<400> SEQUENCE: 238

Ala Asn Cys Leu Ser Leu Tyr Phe Gly Tyr Leu Gln Ile Lys Ala Arg
1               5                   10                  15

Asn Glu Leu Gly Val Tyr Leu Cys Asn Leu Thr Val Ala Asp Leu Phe
            20                  25                  30

Tyr Ile Cys Ser Leu Pro Phe Trp Leu Gln Tyr Val Leu
            35                  40                  45

<210> SEQ ID NO 239
<211> LENGTH: 45
<212> TYPE: PRT
<213> ORGANISM: Homo sapiens

<400> SEQUENCE: 239

Thr Asn Cys Leu Ala Leu Trp Ala Ala Tyr Arg Gln Val Gln Gln Arg
```

-continued

```
                1               5                  10                 15

Asn Glu Leu Gly Val Tyr Leu Met Asn Leu Ser Ile Ala Asp Leu Leu
                                20                 25                 30

Tyr Ile Cys Thr Leu Pro Leu Trp Val Asp Tyr Phe Leu
                35                 40                 45

<210> SEQ ID NO 240
<211> LENGTH: 45
<212> TYPE: PRT
<213> ORGANISM: Homo sapiens

<400> SEQUENCE: 240

Ala Asn Cys Leu Thr Ala Trp Leu Ala Leu Leu Gln Val Leu Gln Gly
1               5                  10                 15

Asn Val Leu Ala Val Tyr Leu Leu Cys Leu Ala Leu Cys Glu Leu Leu
                20                 25                 30

Tyr Thr Gly Thr Leu Pro Leu Trp Val Ile Tyr Ile Arg
                35                 40                 45

<210> SEQ ID NO 241
<211> LENGTH: 45
<212> TYPE: PRT
<213> ORGANISM: Homo sapiens

<400> SEQUENCE: 241

Ala Asn Ile Gly Ser Leu Cys Val Ser Phe Leu Gln Ala Lys Lys Glu
1               5                  10                 15

Ser Glu Leu Gly Ile Tyr Leu Phe Ser Leu Ser Leu Ser Asp Leu Leu
                20                 25                 30

Tyr Ala Leu Thr Leu Pro Leu Trp Ile Asp Tyr Thr Trp
                35                 40                 45

<210> SEQ ID NO 242
<211> LENGTH: 45
<212> TYPE: PRT
<213> ORGANISM: Homo sapiens

<400> SEQUENCE: 242

Leu Asn Ala Val Ala Leu Tyr Ile Phe Leu Cys Arg Leu Lys Thr Trp
1               5                  10                 15

Asn Ala Ser Thr Thr Tyr Met Phe His Leu Ala Val Ser Asp Ala Leu
                20                 25                 30

Tyr Ala Ala Ser Leu Pro Leu Leu Val Tyr Tyr Tyr Ala
                35                 40                 45

<210> SEQ ID NO 243
<211> LENGTH: 45
<212> TYPE: PRT
<213> ORGANISM: Homo sapiens

<400> SEQUENCE: 243

Leu Asn Ala Pro Thr Leu Trp Leu Phe Ile Phe Arg Leu Arg Pro Trp
1               5                  10                 15

Asp Ala Thr Ala Thr Tyr Met Phe His Leu Ala Leu Ser Asp Thr Leu
                20                 25                 30

Tyr Val Leu Ser Leu Pro Thr Leu Ile Tyr Tyr Tyr Ala
                35                 40                 45

<210> SEQ ID NO 244
<211> LENGTH: 44
<212> TYPE: PRT
```

<213> ORGANISM: Homo sapiens

<400> SEQUENCE: 244

Leu Asn Gly Thr Val Leu Trp His Ser Trp Gly Gln Thr Lys Arg Trp
1               5                   10                  15

Ser Cys Ala Thr Thr Tyr Leu Val Asn Leu Met Val Ala Asp Leu Leu
            20                  25                  30

Tyr Val Leu Leu Pro Phe Leu Ile Ile Thr Tyr Ser
        35                  40

<210> SEQ ID NO 245
<211> LENGTH: 45
<212> TYPE: PRT
<213> ORGANISM: Homo sapiens

<400> SEQUENCE: 245

Leu Asn Ile Cys Val Ile Thr Gln Ile Cys Thr Ser Arg Arg Ala Leu
1               5                   10                  15

Thr Arg Thr Ala Val Tyr Thr Leu Asn Leu Ala Leu Ala Asp Leu Leu
            20                  25                  30

Tyr Ala Cys Ser Leu Pro Leu Leu Ile Tyr Asn Tyr Ala
        35                  40                  45

<210> SEQ ID NO 246
<211> LENGTH: 45
<212> TYPE: PRT
<213> ORGANISM: Homo sapiens

<400> SEQUENCE: 246

Gly Asn Ser Val Ala Ile Trp Met Phe Val Phe His Met Lys Pro Trp
1               5                   10                  15

Ser Gly Ile Ser Val Tyr Met Phe Asn Leu Ala Leu Ala Asp Phe Leu
            20                  25                  30

Tyr Val Leu Thr Leu Pro Ala Leu Ile Phe Tyr Tyr Phe
        35                  40                  45

<210> SEQ ID NO 247
<211> LENGTH: 45
<212> TYPE: PRT
<213> ORGANISM: Homo sapiens

<400> SEQUENCE: 247

Gly Asn Ala Val Val Ile Ser Thr Tyr Ile Phe Lys Met Arg Pro Trp
1               5                   10                  15

Lys Ser Ser Thr Ile Ile Met Leu Asn Leu Ala Cys Thr Asp Leu Leu
            20                  25                  30

Tyr Leu Thr Ser Leu Pro Phe Leu Ile His Tyr Tyr Ala
        35                  40                  45

<210> SEQ ID NO 248
<211> LENGTH: 45
<212> TYPE: PRT
<213> ORGANISM: Homo sapiens

<400> SEQUENCE: 248

Gly Asn Thr Ile Val Val Tyr Gly Tyr Ile Phe Ser Leu Lys Asn Trp
1               5                   10                  15

Asn Ser Ser Asn Ile Tyr Leu Phe Asn Leu Ser Val Ser Asp Leu Ala
            20                  25                  30

Phe Leu Cys Thr Leu Pro Met Leu Ile Arg Ser Tyr Ala
        35                  40                  45

<210> SEQ ID NO 249
<211> LENGTH: 45
<212> TYPE: PRT
<213> ORGANISM: Homo sapiens

<400> SEQUENCE: 249

Gly Asn Ile Ile Ala Leu Tyr Val Phe Leu Gly Ile His Arg Lys Arg
1               5                   10                  15

Asn Ser Ile Gln Ile Tyr Leu Leu Asn Val Ala Ile Ala Asp Leu Leu
            20                  25                  30

Leu Ile Phe Cys Leu Pro Phe Arg Ile Met Tyr His Ile
        35                  40                  45

<210> SEQ ID NO 250
<211> LENGTH: 45
<212> TYPE: PRT
<213> ORGANISM: Homo sapiens

<400> SEQUENCE: 250

Val Asn Ile Thr Ala Leu Trp Val Phe Ser Cys Thr Thr Lys Lys Arg
1               5                   10                  15

Thr Thr Val Thr Ile Tyr Met Met Asn Val Ala Leu Val Asp Leu Ile
            20                  25                  30

Phe Ile Met Thr Leu Pro Phe Arg Met Phe Tyr Tyr Ala
        35                  40                  45

<210> SEQ ID NO 251
<211> LENGTH: 44
<212> TYPE: PRT
<213> ORGANISM: Homo sapiens

<400> SEQUENCE: 251

Leu Asn Ser Leu Ala Leu Trp Val Phe Cys Cys Arg Met Gln Gln Trp
1               5                   10                  15

Thr Glu Thr Arg Ile Tyr Met Thr Asn Leu Ala Val Ala Asp Leu Cys
            20                  25                  30

Leu Leu Cys Thr Leu Pro Phe Val Leu His Ser Leu
        35                  40

<210> SEQ ID NO 252
<211> LENGTH: 44
<212> TYPE: PRT
<213> ORGANISM: Homo sapiens

<400> SEQUENCE: 252

Leu Asn Gly Leu Ala Leu Tyr Val Phe Cys Cys Arg Thr Arg Ala Lys
1               5                   10                  15

Thr Pro Ser Val Ile Tyr Thr Ile Asn Leu Val Val Thr Asp Leu Leu
            20                  25                  30

Val Gly Leu Ser Leu Pro Thr Arg Phe Ala Val Tyr
        35                  40

<210> SEQ ID NO 253
<211> LENGTH: 44
<212> TYPE: PRT
<213> ORGANISM: Homo sapiens

<400> SEQUENCE: 253

Leu Asn Ala Leu Ala Leu Trp Val Phe Leu Arg Ala Leu Arg Val His
1               5                   10                  15

-continued

```
Ser Val Val Ser Val Tyr Met Cys Asn Leu Ala Ala Ser Asp Leu Leu
                20                  25                  30

Phe Thr Leu Ser Leu Pro Val Arg Leu Ser Tyr Tyr
                35                  40

<210> SEQ ID NO 254
<211> LENGTH: 44
<212> TYPE: PRT
<213> ORGANISM: Homo sapiens

<400> SEQUENCE: 254

Leu Asn Gly Val Ser Gly Trp Ile Phe Phe Tyr Val Pro Ser Ser Lys
1               5                   10                  15

Ser Phe Ile Ile Tyr Leu Lys Asn Ile Val Ile Ala Asp Phe Val Met
                20                  25                  30

Ser Leu Thr Phe Pro Phe Lys Ile Leu Gly Asp Ser
                35                  40

<210> SEQ ID NO 255
<211> LENGTH: 44
<212> TYPE: PRT
<213> ORGANISM: Homo sapiens

<400> SEQUENCE: 255

Leu Asn Thr Leu Ala Leu Trp Val Phe Val His Ile Pro Ser Ser Ser
1               5                   10                  15

Thr Phe Ile Ile Tyr Leu Lys Asn Thr Leu Val Ala Asp Leu Ile Met
                20                  25                  30

Thr Leu Met Leu Pro Phe Lys Ile Leu Ser Asp Ser
                35                  40

<210> SEQ ID NO 256
<211> LENGTH: 44
<212> TYPE: PRT
<213> ORGANISM: Homo sapiens

<400> SEQUENCE: 256

Thr Asn Gly Leu Ala Met Arg Ile Phe Phe Gln Ile Arg Ser Lys Ser
1               5                   10                  15

Asn Phe Ile Ile Phe Leu Lys Asn Thr Val Ile Ser Asp Leu Leu Met
                20                  25                  30

Ile Leu Thr Phe Pro Phe Lys Ile Leu Ser Asp Ala
                35                  40

<210> SEQ ID NO 257
<211> LENGTH: 44
<212> TYPE: PRT
<213> ORGANISM: Homo sapiens

<400> SEQUENCE: 257

Leu Asn Gly Leu Ala Val Trp Ile Phe Phe His Ile Arg Asn Lys Thr
1               5                   10                  15

Ser Phe Ile Phe Tyr Leu Lys Asn Ile Val Val Ala Asp Leu Ile Met
                20                  25                  30

Thr Leu Thr Phe Pro Phe Arg Ile Val His Asp Ala
                35                  40

<210> SEQ ID NO 258
<211> LENGTH: 45
<212> TYPE: PRT
<213> ORGANISM: Homo sapiens
```

```
<400> SEQUENCE: 258

Gly Ser Cys Phe Ala Thr Trp Ala Phe Ile Gln Lys Asn Thr Asn His
 1               5                  10                  15

Arg Cys Val Ser Ile Tyr Leu Ile Asn Leu Leu Thr Ala Asp Phe Leu
             20                  25                  30

Leu Thr Leu Ala Leu Pro Val Lys Ile Val Val Asp Leu
         35                  40                  45

<210> SEQ ID NO 259
<211> LENGTH: 45
<212> TYPE: PRT
<213> ORGANISM: Homo sapiens

<400> SEQUENCE: 259

Gly Ser Cys Phe Ala Thr Trp Ala Phe Ile Gln Lys Asn Thr Asn His
 1               5                  10                  15

Arg Cys Val Ser Ile Tyr Leu Ile Asn Leu Leu Thr Ala Asp Phe Leu
             20                  25                  30

Leu Thr Leu Ala Leu Pro Val Lys Ile Val Val Asp Leu
         35                  40                  45

<210> SEQ ID NO 260
<211> LENGTH: 45
<212> TYPE: PRT
<213> ORGANISM: Homo sapiens

<400> SEQUENCE: 260

Gly Asn Gly Leu Ala Leu Trp Ile Phe Cys Phe His Leu Lys Ser Trp
 1               5                  10                  15

Lys Ser Ser Arg Ile Phe Leu Phe Asn Leu Ala Val Ala Asp Phe Leu
             20                  25                  30

Leu Ile Ile Cys Leu Pro Phe Leu Met Asp Asn Tyr Val
         35                  40                  45

<210> SEQ ID NO 261
<211> LENGTH: 45
<212> TYPE: PRT
<213> ORGANISM: Homo sapiens

<400> SEQUENCE: 261

Gly Asn Gly Leu Ala Leu Trp Ile Phe Cys Phe His Leu Lys Ser Trp
 1               5                  10                  15

Lys Ser Ser Arg Ile Phe Leu Phe Asn Leu Ala Val Ala Asp Phe Leu
             20                  25                  30

Leu Ile Ile Cys Leu Pro Phe Val Met Asp Tyr Tyr Val
         35                  40                  45

<210> SEQ ID NO 262
<211> LENGTH: 45
<212> TYPE: PRT
<213> ORGANISM: Homo sapiens

<400> SEQUENCE: 262

Gly Asn Gly Val Ala Leu Cys Gly Phe Cys Phe His Met Lys Thr Trp
 1               5                  10                  15

Lys Pro Ser Thr Val Tyr Leu Phe Asn Leu Ala Val Ala Asp Phe Leu
             20                  25                  30

Leu Met Ile Cys Leu Pro Phe Arg Thr Asp Tyr Tyr Leu
         35                  40                  45
```

```
<210> SEQ ID NO 263
<211> LENGTH: 45
<212> TYPE: PRT
<213> ORGANISM: Homo sapiens

<400> SEQUENCE: 263

Gly Asn Ser Leu Ala Leu Phe Ile Phe Cys Ile His Thr Arg Pro Trp
1               5                   10                  15

Thr Ser Asn Thr Val Phe Leu Val Ser Leu Val Ala Ala Asp Phe Leu
                20                  25                  30

Leu Ile Ser Asn Leu Pro Leu Arg Val Asp Tyr Tyr Leu
            35                  40                  45

<210> SEQ ID NO 264
<211> LENGTH: 46
<212> TYPE: PRT
<213> ORGANISM: Homo sapiens

<400> SEQUENCE: 264

Ser Asn Gly Leu Ala Leu Tyr Arg Phe Ser Ile Arg Lys Gln Arg Pro
1               5                   10                  15

Trp His Pro Ala Val Val Phe Ser Val Gln Leu Ala Val Ser Asp Leu
                20                  25                  30

Leu Cys Ala Leu Thr Leu Pro Pro Leu Ala Ala Tyr Leu Tyr
            35                  40                  45

<210> SEQ ID NO 265
<211> LENGTH: 46
<212> TYPE: PRT
<213> ORGANISM: Homo sapiens

<400> SEQUENCE: 265

Gly Asn Ser Ser Val Leu Leu Ala Leu His Arg Thr Pro Arg Lys Thr
1               5                   10                  15

Ser Arg Met His Leu Phe Ile Arg His Leu Ser Leu Ala Asp Leu Ala
                20                  25                  30

Val Ala Phe Phe Gln Val Leu Pro Gln Met Cys Trp Asp Ile
            35                  40                  45

<210> SEQ ID NO 266
<211> LENGTH: 46
<212> TYPE: PRT
<213> ORGANISM: Homo sapiens

<400> SEQUENCE: 266

Gly Asn Leu Ala Val Leu Leu Thr Leu Gly Gln Leu Gly Arg Lys Arg
1               5                   10                  15

Ser Arg Met His Leu Phe Val Leu His Leu Ala Leu Thr Asp Leu Ala
                20                  25                  30

Val Ala Leu Phe Gln Val Leu Pro Gln Leu Leu Trp Asp Ile
            35                  40                  45

<210> SEQ ID NO 267
<211> LENGTH: 46
<212> TYPE: PRT
<213> ORGANISM: Homo sapiens

<400> SEQUENCE: 267

Gly Asn Ala Cys Val Leu Leu Ala Leu Arg Thr Thr Arg Gln Lys His
1               5                   10                  15

Ser Arg Leu Phe Phe Phe Met Lys His Leu Ser Ile Ala Asp Leu Val
                20                  25                  30
```

```
Val Ala Val Phe Gln Val Leu Pro Gln Leu Leu Trp Asp Ile
        35                  40                  45

<210> SEQ ID NO 268
<211> LENGTH: 48
<212> TYPE: PRT
<213> ORGANISM: Homo sapiens

<400> SEQUENCE: 268

Ser Asn Gly Leu Val Leu Ala Ala Leu Ala Arg Arg Gly Arg Arg Gly
1               5                   10                  15

His Trp Ala Pro Ile His Val Phe Ile Gly His Leu Cys Leu Ala Asp
            20                  25                  30

Leu Ala Val Ala Leu Phe Gln Val Leu Pro Gln Leu Ala Trp Lys Ala
        35                  40                  45

<210> SEQ ID NO 269
<211> LENGTH: 45
<212> TYPE: PRT
<213> ORGANISM: Homo sapiens

<400> SEQUENCE: 269

Gly Asn Ser Val Val Leu Phe Ser Thr Trp Arg Arg Lys Lys Lys Ser
1               5                   10                  15

Arg Met Thr Phe Phe Val Thr Gln Leu Ala Ile Thr Asp Ser Phe Thr
            20                  25                  30

Gly Leu Val Asn Ile Leu Thr Asp Ile Ile Trp Arg Phe
        35                  40                  45

<210> SEQ ID NO 270
<211> LENGTH: 46
<212> TYPE: PRT
<213> ORGANISM: Homo sapiens

<400> SEQUENCE: 270

Gly Asn Met Thr Val Leu Phe Val Leu Leu Thr Ser Arg Tyr Lys Leu
1               5                   10                  15

Thr Val Pro Arg Phe Leu Met Cys Asn Leu Ser Phe Ala Asp Phe Cys
            20                  25                  30

Met Gly Leu Tyr Leu Leu Leu Ile Ala Ser Val Asp Ser Gln
        35                  40                  45

<210> SEQ ID NO 271
<211> LENGTH: 46
<212> TYPE: PRT
<213> ORGANISM: Homo sapiens

<400> SEQUENCE: 271

Gly Asn Val Phe Val Leu Leu Ile Leu Leu Thr Ser His Tyr Lys Leu
1               5                   10                  15

Asn Val Pro Arg Phe Leu Met Cys Asn Leu Ala Phe Ala Asp Phe Cys
            20                  25                  30

Met Gly Met Tyr Leu Leu Leu Ile Ala Ser Val Asp Leu Tyr
        35                  40                  45

<210> SEQ ID NO 272
<211> LENGTH: 46
<212> TYPE: PRT
<213> ORGANISM: Homo sapiens

<400> SEQUENCE: 272
```

Gly Asn Ile Ile Val Leu Val Ile Leu Thr Thr Ser Gln Tyr Lys Leu
1               5                   10                  15

Thr Val Pro Arg Phe Leu Met Cys Asn Leu Ala Phe Ala Asp Leu Cys
                20                  25                  30

Ile Gly Ile Tyr Leu Leu Leu Ile Ala Ser Val Asp Ile His
            35                  40                  45

<210> SEQ ID NO 273
<211> LENGTH: 46
<212> TYPE: PRT
<213> ORGANISM: Homo sapiens

<400> SEQUENCE: 273

Cys Asn Ala Leu Val Thr Ser Thr Val Phe Arg Ser Pro Leu Tyr Ile
1               5                   10                  15

Ser Pro Ile Lys Leu Leu Ile Gly Val Ile Ala Ala Val Asn Met Leu
                20                  25                  30

Thr Gly Val Ser Ser Ala Val Leu Ala Gly Val Asp Ala Phe
            35                  40                  45

<210> SEQ ID NO 274
<211> LENGTH: 47
<212> TYPE: PRT
<213> ORGANISM: Homo sapiens

<400> SEQUENCE: 274

Cys Asn Gly Leu Val Leu Leu Thr Val Phe Ala Gly Gly Pro Val Pro
1               5                   10                  15

Leu Pro Pro Val Lys Phe Val Val Gly Ala Ile Ala Gly Ala Asn Thr
                20                  25                  30

Leu Thr Gly Ile Ser Cys Gly Leu Leu Ala Ser Val Asp Ala Leu
            35                  40                  45

<210> SEQ ID NO 275
<211> LENGTH: 46
<212> TYPE: PRT
<213> ORGANISM: Homo sapiens

<400> SEQUENCE: 275

Phe Asn Leu Leu Val Ile Leu Thr Thr Phe Ala Ser Cys Thr Ser Leu
1               5                   10                  15

Pro Ser Ser Lys Leu Phe Ile Gly Leu Ile Ser Val Ser Asn Leu Phe
                20                  25                  30

Met Gly Ile Tyr Thr Gly Ile Leu Thr Phe Leu Asp Ala Val
            35                  40                  45

<210> SEQ ID NO 276
<211> LENGTH: 46
<212> TYPE: PRT
<213> ORGANISM: Homo sapiens

<400> SEQUENCE: 276

Gly Asn Phe Met Val Leu Trp Ser Thr Cys Arg Thr Thr Val Phe Lys
1               5                   10                  15

Ser Val Thr Asn Arg Phe Ile Lys Asn Leu Ala Cys Ser Gly Ile Cys
                20                  25                  30

Ala Ser Leu Val Cys Val Pro Phe Asp Ile Ile Leu Ser Thr
            35                  40                  45

<210> SEQ ID NO 277
<211> LENGTH: 52

```
<212> TYPE: PRT
<213> ORGANISM: Homo sapiens

<400> SEQUENCE: 277

Phe Asn Ala Ser Phe Leu Leu Lys Leu Gln Lys Trp Thr Gln Lys Lys
1               5                   10                  15

Glu Lys Gly Lys Lys Leu Ser Arg Met Lys Leu Leu Leu Lys His Leu
            20                  25                  30

Thr Leu Ala Asn Leu Leu Glu Thr Leu Ile Val Met Pro Leu Asp Gly
        35                  40                  45

Met Trp Asn Ile
    50

<210> SEQ ID NO 278
<211> LENGTH: 48
<212> TYPE: PRT
<213> ORGANISM: Homo sapiens

<400> SEQUENCE: 278

Gly Asn Leu Cys Val Ile Gly Ile Leu Leu His Asn Ala Trp Lys Gly
1               5                   10                  15

Lys Pro Ser Met Ile His Ser Leu Ile Leu Asn Leu Ser Leu Ala Asp
            20                  25                  30

Leu Ser Leu Leu Leu Phe Ser Ala Pro Ile Arg Ala Thr Ala Tyr Ser
        35                  40                  45

<210> SEQ ID NO 279
<211> LENGTH: 46
<212> TYPE: PRT
<213> ORGANISM: Homo sapiens

<400> SEQUENCE: 279

Gly Asn Ile Phe Val Ile Cys Met Arg Pro Tyr Ile Arg Ser Glu Asn
1               5                   10                  15

Lys Leu Tyr Ala Met Ser Ile Ile Ser Leu Cys Cys Ala Asp Cys Leu
            20                  25                  30

Met Gly Ile Tyr Leu Phe Val Ile Gly Gly Phe Asp Leu Lys
        35                  40                  45

<210> SEQ ID NO 280
<211> LENGTH: 45
<212> TYPE: PRT
<213> ORGANISM: Homo sapiens

<400> SEQUENCE: 280

Gly Asn Thr Leu Ser Gln Trp Ile Phe Leu Thr Lys Ile Gly Lys Lys
1               5                   10                  15

Thr Ser Thr His Ile Tyr Leu Ser His Leu Val Thr Ala Asn Leu Leu
            20                  25                  30

Val Cys Ser Ala Met Pro Phe Met Ser Ile Tyr Phe Leu
        35                  40                  45

<210> SEQ ID NO 281
<211> LENGTH: 47
<212> TYPE: PRT
<213> ORGANISM: Homo sapiens

<400> SEQUENCE: 281

Thr Asn Thr Leu Val Ala Val Ala Val Leu Leu Leu Ile His Lys Asn
1               5                   10                  15

Asp Gly Val Ser Leu Cys Phe Thr Leu Asn Leu Ala Val Ala Asp Thr
```

```
                20                  25                  30
Leu Ile Gly Val Ala Ile Ser Gly Leu Leu Thr Asp Gln Leu Ser
            35                  40                  45

<210> SEQ ID NO 282
<211> LENGTH: 45
<212> TYPE: PRT
<213> ORGANISM: Homo sapiens

<400> SEQUENCE: 282

Val Ser Pro Leu Leu Val Thr Ile Leu Arg Asn Gln Arg Leu Arg
1               5                   10                  15

Gln Glu Pro His Tyr Leu Leu Pro Ala Asn Ile Leu Leu Ser Asp Leu
                20                  25                  30

Ala Tyr Ile Leu Leu His Met Leu Ile Ser Ser Ser Ser
            35                  40                  45

<210> SEQ ID NO 283
<211> LENGTH: 47
<212> TYPE: PRT
<213> ORGANISM: Homo sapiens

<400> SEQUENCE: 283

Ala Asn Leu Leu Ala Leu Gly Ile Ala Trp Asp Arg Arg Leu Arg
1               5                   10                  15

Ser Pro Pro Ala Gly Cys Phe Phe Leu Ser Leu Leu Leu Ala Gly Leu
                20                  25                  30

Leu Thr Gly Leu Ala Leu Pro Thr Leu Pro Gly Leu Trp Asn Gln
            35                  40                  45

<210> SEQ ID NO 284
<211> LENGTH: 47
<212> TYPE: PRT
<213> ORGANISM: Homo sapiens

<400> SEQUENCE: 284

Ala Ser Ser Thr Val Leu Phe Met Leu Phe Arg Pro Leu Phe Arg Trp
1               5                   10                  15

Gln Leu Cys Pro Gly Trp Pro Val Leu Ala Gln Leu Ala Val Gly Ser
                20                  25                  30

Ala Leu Phe Ser Ile Val Val Pro Val Leu Ala Pro Gly Leu Gly
            35                  40                  45

<210> SEQ ID NO 285
<211> LENGTH: 44
<212> TYPE: PRT
<213> ORGANISM: Homo sapiens

<400> SEQUENCE: 285

Ser Leu Gly Cys Gln Arg Val Thr Leu His Lys Asn Met Phe Leu Thr
1               5                   10                  15

Tyr Ile Leu Asn Ser Met Ile Ile Ile His Leu Val Glu Val Val
                20                  25                  30

Pro Asn Gly Glu Leu Val Arg Arg Asp Pro Val Ser
            35                  40

<210> SEQ ID NO 286
<211> LENGTH: 44
<212> TYPE: PRT
<213> ORGANISM: Homo sapiens

<400> SEQUENCE: 286
```

```
Ser Leu Ser Cys Gln Arg Ile Thr Leu His Lys Asn Leu Phe Phe Ser
1               5                   10                  15

Phe Val Cys Asn Ser Val Val Thr Ile Ile His Leu Thr Ala Val Ala
                20                  25                  30

Asn Asn Gln Ala Leu Val Ala Thr Asn Pro Val Ser
            35                  40
```

<210> SEQ ID NO 287
<211> LENGTH: 50
<212> TYPE: PRT
<213> ORGANISM: Homo sapiens

<400> SEQUENCE: 287

```
His Leu His Cys Thr Arg Asn Tyr Ile His Leu Asn Leu Phe Ala Ser
1               5                   10                  15

Phe Ile Leu Arg Ala Leu Ser Val Phe Ile Lys Asp Ala Ala Leu Lys
                20                  25                  30

Trp Met Tyr Ser Thr Ala Ala Gln Gln His Gln Trp Asp Gly Leu Leu
            35                  40                  45

Ser Tyr
    50
```

<210> SEQ ID NO 288
<211> LENGTH: 48
<212> TYPE: PRT
<213> ORGANISM: Homo sapiens

<400> SEQUENCE: 288

```
Lys Leu His Cys Thr Arg Asn Tyr Ile His Met Asn Leu Phe Ala Ser
            1                   5                   10                              15

Phe Ile Leu Arg Thr Leu Ala Val Leu Val Lys Asp Val Val Phe Tyr
                20                  25                  30

Asn Ser Tyr Ser Lys Arg Pro Asp Asn Glu Asn Gly Trp Met Ser Tyr
            35                  40                  45
```

<210> SEQ ID NO 289
<211> LENGTH: 49
<212> TYPE: PRT
<213> ORGANISM: Homo sapiens

<400> SEQUENCE: 289

```
Lys Leu His Cys Thr Arg Asn Tyr Ile His Leu Asn Leu Phe Leu Ser
1               5                   10                  15

Phe Ile Leu Arg Ala Ile Ser Val Leu Val Lys Asp Asp Val Leu Tyr
                20                  25                  30

Ser Ser Ser Gly Thr Leu His Cys Pro Asp Gln Pro Ser Ser Trp Val
            35                  40                  45

Gly
```

<210> SEQ ID NO 290
<211> LENGTH: 46
<212> TYPE: PRT
<213> ORGANISM: Homo sapiens

<400> SEQUENCE: 290

```
Lys Leu His Cys Thr Arg Asn Tyr Ile His Met His Leu Phe Ile Ser
1               5                   10                  15

Phe Ile Leu Arg Ala Ala Ala Val Phe Ile Lys Asp Leu Ala Leu Phe
                20                  25                  30
```

Asp Ser Gly Glu Ser Asp Gln Cys Ser Glu Gly Ser Val Gly
            35                  40                  45

<210> SEQ ID NO 291
<211> LENGTH: 46
<212> TYPE: PRT
<213> ORGANISM: Homo sapiens

<400> SEQUENCE: 291

Arg Leu His Cys Thr Arg Asn Tyr Ile His Met His Leu Phe Val Ser
1               5                   10                  15

Phe Ile Leu Arg Ala Leu Ser Asn Phe Ile Lys Asp Ala Val Leu Phe
            20                  25                  30

Ser Ser Asp Asp Val Thr Tyr Cys Asp Pro His Arg Ala Gly
            35                  40                  45

<210> SEQ ID NO 292
<211> LENGTH: 46
<212> TYPE: PRT
<213> ORGANISM: Homo sapiens

<400> SEQUENCE: 292

Lys Leu His Cys Thr Arg Asn Phe Ile His Met Asn Leu Phe Val Ser
1               5                   10                  15

Phe Met Leu Arg Ala Ile Ser Val Phe Ile Lys Asp Trp Ile Leu Tyr
            20                  25                  30

Ala Glu Gln Asp Ser Asn His Cys Phe Ile Ser Thr Val Glu
            35                  40                  45

<210> SEQ ID NO 293
<211> LENGTH: 46
<212> TYPE: PRT
<213> ORGANISM: Homo sapiens

<400> SEQUENCE: 293

Arg Leu His Cys Pro Arg Asn Tyr Val His Thr Gln Leu Phe Thr Thr
1               5                   10                  15

Phe Ile Leu Lys Ala Gly Arg Val Phe Leu Lys Asp Ala Ala Leu Phe
            20                  25                  30

His Ser Asp Asp Thr Asp His Cys Ser Phe Ser Thr Val Leu
            35                  40                  45

<210> SEQ ID NO 294
<211> LENGTH: 47
<212> TYPE: PRT
<213> ORGANISM: Homo sapiens

<400> SEQUENCE: 294

Arg Leu His Cys Thr Arg Asn Tyr Ile His Ile Asn Leu Phe Thr Ser
1               5                   10                  15

Phe Met Leu Arg Ala Ala Ala Ile Leu Ser Arg Asp Arg Leu Leu Pro
            20                  25                  30

Arg Pro Gly Pro Tyr Leu Gly Asp Gln Ala Leu Ala Leu Trp Asn
            35                  40                  45

<210> SEQ ID NO 295
<211> LENGTH: 50
<212> TYPE: PRT
<213> ORGANISM: Homo sapiens

<400> SEQUENCE: 295

Lys Leu His Cys Thr Arg Asn Ala Ile His Ala Asn Leu Phe Ala Ser

```
                1               5                  10                 15
Phe Val Leu Lys Ala Ser Ser Val Leu Val Ile Asp Gly Leu Leu Arg
                20                 25                 30

Thr Arg Tyr Ser Gln Lys Ile Gly Asp Asp Leu Ser Val Ser Thr Trp
        35                 40                 45

Leu Ser
    50

<210> SEQ ID NO 296
<211> LENGTH: 60
<212> TYPE: PRT
<213> ORGANISM: Homo sapiens

<400> SEQUENCE: 296

Arg Leu His Cys Thr Arg Asn Tyr Ile His Met His Leu Phe Leu Ser
1               5                  10                 15

Phe Met Leu Arg Ala Val Ser Ile Phe Val Lys Asp Ala Val Leu Tyr
                20                 25                 30

Ser Gly Ala Thr Leu Asp Glu Ala Glu Arg Leu Thr Glu Glu Glu Leu
        35                 40                 45

Arg Ala Ile Ala Gln Ala Pro Pro Pro Ala Thr
    50                 55                 60

<210> SEQ ID NO 297
<211> LENGTH: 58
<212> TYPE: PRT
<213> ORGANISM: Homo sapiens

<400> SEQUENCE: 297

Arg Leu His Cys Thr Arg Asn Tyr Ile His Met His Leu Phe Val Ser
1               5                  10                 15

Phe Met Leu Arg Ala Thr Ser Ile Phe Val Lys Asp Arg Val Val His
                20                 25                 30

Ala His Ile Gly Val Lys Glu Leu Glu Ser Leu Ile Met Gln Asp Asp
        35                 40                 45

Pro Gln Asn Ser Ile Glu Ala Thr Ser Val
    50                 55

<210> SEQ ID NO 298
<211> LENGTH: 41
<212> TYPE: PRT
<213> ORGANISM: Homo sapiens

<400> SEQUENCE: 298

Ser Ile Arg Cys Leu Arg Asn Ile Ile His Trp Asn Leu Ile Ser Ala
1               5                  10                 15

Phe Ile Leu Arg Asn Ala Thr Trp Phe Val Val Gln Leu Thr Met Ser
                20                 25                 30

Pro Glu Val His Gln Ser Asn Val Gly
        35                 40

<210> SEQ ID NO 299
<211> LENGTH: 40
<212> TYPE: PRT
<213> ORGANISM: Homo sapiens

<400> SEQUENCE: 299

Ser Ile Arg Cys Leu Arg Asn Val Ile His Trp Asn Leu Ile Thr Thr
1               5                  10                 15

Phe Ile Leu Arg Asn Val Met Trp Phe Leu Leu Gln Leu Val Asp His
```

```
                20                  25                  30
Glu Val His Glu Ser Asn Glu Val
         35                  40

<210> SEQ ID NO 300
<211> LENGTH: 56
<212> TYPE: PRT
<213> ORGANISM: Homo sapiens

<400> SEQUENCE: 300

Leu Gly Ile Leu Val Thr Leu Phe Val Thr Leu Ile Phe Val Leu Tyr
1               5                   10                  15

Arg Asp Thr Pro Val Val Lys Ser Ser Ser Arg Glu Leu Cys Tyr Ile
                20                  25                  30

Ile Leu Ala Gly Ile Phe Leu Gly Tyr Val Cys Pro Phe Thr Leu Ile
            35                  40                  45

Ala Lys Pro Thr Thr Thr Ser Cys
        50                  55

<210> SEQ ID NO 301
<211> LENGTH: 56
<212> TYPE: PRT
<213> ORGANISM: Homo sapiens

<400> SEQUENCE: 301

Leu Gly Leu Leu Ala Thr Leu Phe Val Thr Val Val Phe Ile Ile Tyr
1               5                   10                  15

Arg Asp Thr Pro Val Val Lys Ser Ser Ser Arg Glu Leu Cys Tyr Ile
                20                  25                  30

Ile Leu Ala Gly Ile Cys Leu Gly Tyr Leu Cys Thr Phe Cys Leu Ile
            35                  40                  45

Ala Lys Pro Lys Gln Ile Tyr Cys
        50                  55

<210> SEQ ID NO 302
<211> LENGTH: 56
<212> TYPE: PRT
<213> ORGANISM: Homo sapiens

<400> SEQUENCE: 302

Leu Gly Ala Leu Ala Thr Leu Phe Val Leu Gly Val Phe Val Arg His
1               5                   10                  15

Asn Ala Thr Pro Val Val Lys Ala Ser Gly Arg Glu Leu Cys Tyr Ile
                20                  25                  30

Leu Leu Gly Gly Val Phe Leu Cys Tyr Cys Met Thr Phe Ile Phe Ile
            35                  40                  45

Ala Lys Pro Ser Thr Ala Val Cys
        50                  55

<210> SEQ ID NO 303
<211> LENGTH: 56
<212> TYPE: PRT
<213> ORGANISM: Homo sapiens

<400> SEQUENCE: 303

Leu Gly Phe Met Cys Thr Cys Met Val Val Thr Val Phe Ile Lys His
1               5                   10                  15

Asn Asn Thr Pro Leu Val Lys Ala Ser Gly Arg Glu Leu Cys Tyr Ile
                20                  25                  30

Leu Leu Phe Gly Val Gly Leu Ser Tyr Cys Met Thr Phe Phe Phe Ile
```

```
                35                  40                  45
Ala Lys Pro Ser Pro Val Ile Cys
    50                  55

<210> SEQ ID NO 304
<211> LENGTH: 56
<212> TYPE: PRT
<213> ORGANISM: Homo sapiens

<400> SEQUENCE: 304

Leu Gly Ile Ile Ala Thr Thr Phe Val Ile Val Thr Phe Val Arg Tyr
1               5                   10                  15

Asn Asp Thr Pro Ile Val Arg Ala Ser Gly Arg Glu Leu Ser Tyr Val
                20                  25                  30

Leu Leu Thr Gly Ile Phe Leu Cys Tyr Ser Ile Thr Phe Leu Met Ile
            35                  40                  45

Ala Ala Pro Asp Thr Ile Ile Cys
    50                  55

<210> SEQ ID NO 305
<211> LENGTH: 56
<212> TYPE: PRT
<213> ORGANISM: Homo sapiens

<400> SEQUENCE: 305

Leu Gly Ile Ile Ala Thr Ile Phe Val Met Ala Thr Phe Ile Arg Tyr
1               5                   10                  15

Asn Asp Thr Pro Ile Val Arg Ala Ser Gly Arg Glu Leu Ser Tyr Val
                20                  25                  30

Leu Leu Thr Gly Ile Phe Leu Cys Tyr Ile Ile Thr Phe Leu Met Ile
            35                  40                  45

Ala Lys Pro Asp Val Ala Val Cys
    50                  55

<210> SEQ ID NO 306
<211> LENGTH: 56
<212> TYPE: PRT
<213> ORGANISM: Homo sapiens

<400> SEQUENCE: 306

Val Gly Ile Ala Ala Thr Leu Phe Val Ile Thr Phe Val Arg Tyr
1               5                   10                  15

Asn Asp Thr Pro Ile Val Lys Ala Ser Gly Arg Glu Leu Ser Tyr Val
                20                  25                  30

Leu Leu Ala Gly Ile Phe Leu Cys Tyr Ala Thr Thr Phe Leu Met Ile
            35                  40                  45

Ala Glu Pro Asp Leu Gly Thr Cys
    50                  55

<210> SEQ ID NO 307
<211> LENGTH: 56
<212> TYPE: PRT
<213> ORGANISM: Homo sapiens

<400> SEQUENCE: 307

Leu Gly Ile Val Ala Thr Thr Val Val Ala Thr Phe Val Arg Tyr
1               5                   10                  15

Asn Asn Thr Pro Ile Val Arg Ala Ser Gly Arg Glu Leu Ser Tyr Val
                20                  25                  30

Leu Leu Thr Gly Ile Phe Leu Ile Tyr Ala Ile Thr Phe Leu Met Val
```

```
                35                  40                  45

Ala Glu Pro Gly Ala Ala Val Cys
    50                  55

<210> SEQ ID NO 308
<211> LENGTH: 56
<212> TYPE: PRT
<213> ORGANISM: Homo sapiens

<400> SEQUENCE: 308

Leu Gly Ile Phe Leu Thr Ala Phe Val Leu Gly Val Phe Ile Lys Phe
1               5                   10                  15

Arg Asn Thr Pro Ile Val Lys Ala Thr Asn Arg Glu Leu Ser Tyr Leu
            20                  25                  30

Leu Leu Phe Ser Leu Leu Cys Cys Phe Ser Ser Ser Leu Phe Phe Ile
        35                  40                  45

Gly Glu Pro Gln Asp Trp Thr Cys
    50                  55

<210> SEQ ID NO 309
<211> LENGTH: 56
<212> TYPE: PRT
<213> ORGANISM: Homo sapiens

<400> SEQUENCE: 309

Leu Gly Ile Val Leu Ala Val Val Cys Leu Ser Phe Asn Ile Tyr Asn
1               5                   10                  15

Ser His Val Arg Tyr Ile Gln Asn Ser Gln Pro Asn Leu Asn Asn Leu
            20                  25                  30

Thr Ala Val Gly Cys Ser Leu Ala Leu Ala Ala Val Phe Pro Leu Gly
        35                  40                  45

Leu Asp Gly Tyr His Ile Gly Arg
    50                  55

<210> SEQ ID NO 310
<211> LENGTH: 56
<212> TYPE: PRT
<213> ORGANISM: Homo sapiens

<400> SEQUENCE: 310

Leu Gly Met Ile Met Ala Ser Ala Phe Leu Phe Phe Asn Ile Lys Asn
1               5                   10                  15

Arg Asn Gln Lys Leu Ile Lys Met Ser Ser Pro Tyr Met Asn Asn Leu
            20                  25                  30

Ile Ile Leu Gly Gly Met Leu Ser Tyr Ala Ser Ile Phe Leu Phe Gly
        35                  40                  45

Leu Asp Gly Ser Phe Val Ser Glu
    50                  55

<210> SEQ ID NO 311
<211> LENGTH: 56
<212> TYPE: PRT
<213> ORGANISM: Homo sapiens

<400> SEQUENCE: 311

Ile Val Thr Thr Phe Val Leu Thr Ile Ile Leu Val Ala Ser Leu Pro
1               5                   10                  15

Phe Val Gln Asp Thr Lys Lys Arg Ser Leu Leu Gly Thr Gln Val Phe
            20                  25                  30

Phe Leu Leu Gly Thr Leu Gly Leu Phe Cys Leu Val Phe Ala Cys Val
```

```
                35                  40                  45
Val Lys Pro Asp Phe Ser Thr Cys
    50                  55

<210> SEQ ID NO 312
<211> LENGTH: 56
<212> TYPE: PRT
<213> ORGANISM: Homo sapiens

<400> SEQUENCE: 312

Val Val Thr Ser Val Ala Phe Met Leu Thr Leu Pro Ile Leu Val Cys
1               5                   10                  15

Lys Val Gln Asp Ser Asn Arg Arg Lys Met Leu Pro Thr Gln Phe Leu
            20                  25                  30

Phe Leu Leu Gly Val Leu Gly Ile Phe Gly Leu Thr Phe Ala Phe Ile
        35                  40                  45

Ile Gly Leu Asp Gly Ser Thr Gly
    50                  55

<210> SEQ ID NO 313
<211> LENGTH: 56
<212> TYPE: PRT
<213> ORGANISM: Homo sapiens

<400> SEQUENCE: 313

Ile Val Val Thr Ile Leu Leu Leu Ala Phe Leu Phe Leu Met Arg
1               5                   10                  15

Lys Ile Gln Asp Cys Ser Gln Trp Asn Val Leu Pro Thr Gln Leu Leu
            20                  25                  30

Phe Leu Leu Ser Val Leu Gly Leu Phe Gly Leu Ala Phe Ala Phe Ile
        35                  40                  45

Ile Glu Leu Asn Gln Gln Thr Ala
    50                  55

<210> SEQ ID NO 314
<211> LENGTH: 56
<212> TYPE: PRT
<213> ORGANISM: Homo sapiens

<400> SEQUENCE: 314

Ala Leu Ile Thr Leu Leu Leu Met Leu Ile Leu Val Arg Leu Pro
1               5                   10                  15

Phe Ile Lys Glu Lys Glu Lys Ser Pro Val Gly Leu His Phe Leu
            20                  25                  30

Phe Leu Leu Gly Thr Leu Gly Leu Phe Gly Leu Thr Phe Ala Phe Ile
        35                  40                  45

Ile Gln Glu Asp Glu Thr Ile Cys
    50                  55

<210> SEQ ID NO 315
<211> LENGTH: 412
<212> TYPE: PRT
<213> ORGANISM: Homo sapiens

<400> SEQUENCE: 315

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
```

```
                  35                  40                  45
Ala Ala Ala Asp Ile Ala Val Gly Val Leu Ala Ile Pro Phe Ala Ile
 50                  55                  60
Thr Ile Ser Thr Gly Phe Cys Ala Ala Cys His Gly Cys Leu Phe Ile
 65                  70                  75                  80
Ala Cys Phe Val Leu Val Leu Thr Gln Ser Ile Phe Ser Leu Leu
                     85                  90                  95
Ala Ile Ala Ile Asp Arg Tyr Ile Ala Ile Arg Ile Pro Leu Arg Tyr
                100                 105                 110
Asn Gly Leu Val Thr Gly Thr Arg Ala Lys Gly Ile Ile Ala Ile Cys
                115                 120                 125
Trp Val Leu Ser Phe Ala Ile Gly Leu Thr Pro Met Leu Gly Trp Asn
130                 135                 140
Asn Cys Gly Gln Pro Lys Glu Gly Lys Asn His Ser Gln Gly Cys Gly
145                 150                 155                 160
Glu Gly Gln Val Ala Cys Leu Phe Glu Asp Val Val Pro Met Asn Tyr
                165                 170                 175
Met Val Tyr Phe Asn Phe Phe Ala Cys Val Leu Val Pro Leu Leu Leu
                180                 185                 190
Met Leu Gly Val Tyr Leu Arg Ile Phe Leu Ala Ala Arg Arg Gln Leu
                195                 200                 205
Lys Gln Met Glu Ser Gln Pro Leu Pro Gly Glu Arg Ala Arg Ser Thr
210                 215                 220
Leu Gln Lys Glu Val His Ala Ala Lys Ser Leu Ala Ile Ile Val Gly
225                 230                 235                 240
Leu Phe Ala Leu Cys Trp Leu Pro Leu His Ile Ile Asn Cys Phe Thr
                245                 250                 255
Phe Phe Cys Pro Asp Cys Ser His Ala Pro Leu Trp Leu Met Tyr Leu
                260                 265                 270
Ala Ile Val Leu Ser His Thr Asn Ser Val Val Asn Pro Phe Ile Tyr
                275                 280                 285
Ala Tyr Arg Ile Arg Glu Phe Arg Gln Thr Phe Arg Lys Ile Ile Arg
290                 295                 300
Ser His Val Leu Arg Gln Gln Glu Pro Phe Lys Ala Ala Gly Thr Ser
305                 310                 315                 320
Ala Arg Val Leu Ala Ala His Gly Ser Asp Gly Glu Gln Val Ser Leu
                325                 330                 335
Arg Leu Asn Gly His Pro Pro Gly Val Trp Ala Asn Gly Ser Ala Pro
                340                 345                 350
His Pro Glu Arg Arg Pro Asn Gly Tyr Ala Leu Gly Leu Val Ser Gly
                355                 360                 365
Gly Ser Ala Gln Glu Ser Gln Gly Asn Thr Gly Leu Pro Asp Val Glu
370                 375                 380
Leu Leu Ser His Glu Leu Lys Gly Val Cys Pro Glu Pro Gly Leu
385                 390                 395                 400
Asp Asp Pro Leu Ala Gln Asp Gly Ala Gly Val Ser
                405                 410

<210> SEQ ID NO 316
<211> LENGTH: 458
<212> TYPE: PRT
<213> ORGANISM: Homo sapiens

<400> SEQUENCE: 316

Met Val Asn Leu Arg Asn Ala Val His Ser Phe Leu Val His Leu Ile
```

-continued

```
1               5                   10                  15
Gly Leu Leu Val Trp Gln Cys Asp Ile Ser Val Ser Pro Val Ala Ala
                20                  25                  30

Ile Val Thr Asp Ile Phe Asn Thr Ser Asp Gly Gly Arg Phe Lys Phe
                35                  40                  45

Pro Asp Gly Val Gln Asn Trp Pro Ala Leu Ser Ile Val Ile Ile Ile
50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
                100                 105                 110

Ala Ile Leu Tyr Asp Tyr Val Trp Pro Leu Pro Arg Tyr Leu Cys Pro
                115                 120                 125

Val Trp Ile Ser Leu Asp Val Leu Phe Ser Thr Ala Ser Ile Met His
                130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
                180                 185                 190

Gly Leu Arg Asp Glu Glu Lys Val Phe Val Asn Asn Thr Thr Cys Val
                195                 200                 205

Leu Asn Asp Pro Asn Phe Val Leu Ile Gly Ser Phe Val Ala Phe Phe
210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
                260                 265                 270

Glu Glu Glu Asn Ser Ala Asn Pro Asn Gln Asp Gln Asn Ala Arg Arg
                275                 280                 285

Arg Lys Lys Lys Glu Arg Arg Pro Arg Gly Thr Met Gln Ala Ile Asn
290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
                340                 345                 350

Phe Val Trp Ile Gly Tyr Val Cys Ser Gly Ile Asn Pro Leu Val Tyr
                355                 360                 365

Thr Leu Phe Asn Lys Ile Tyr Arg Arg Ala Phe Ser Asn Tyr Leu Arg
                370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
                420                 425                 430
```

```
Gly Ile Glu Met Gln Val Glu Asn Leu Glu Leu Pro Val Asn Pro Ser
        435                 440                 445

Ser Val Ser Glu Arg Ile Ser Ser Val
    450                 455

<210> SEQ ID NO 317
<211> LENGTH: 479
<212> TYPE: PRT
<213> ORGANISM: Homo sapiens

<400> SEQUENCE: 317

Met Ala Asn Phe Thr Pro Val Asn Gly Ser Ser Gly Asn Gln Ser Val
1               5                   10                  15

Arg Leu Val Thr Ser Ser His Asn Arg Tyr Glu Thr Val Glu Met
                20                  25                  30

Val Phe Ile Ala Thr Val Thr Gly Ser Leu Ser Leu Val Thr Val Val
                35                  40                  45

Gly Asn Ile Leu Val Met Leu Ser Ile Lys Val Asn Arg Gln Leu Gln
    50                  55                  60

Thr Val Asn Asn Tyr Phe Leu Phe Ser Leu Ala Cys Ala Asp Leu Ile
65                  70                  75                  80

Ile Gly Ala Phe Ser Met Asn Leu Tyr Thr Val Tyr Ile Ile Lys Gly
                85                  90                  95

Tyr Trp Pro Leu Gly Ala Val Val Cys Asp Leu Trp Leu Ala Leu Asp
                100                 105                 110

Tyr Val Val Ser Asn Ala Ser Val Met Asn Leu Leu Ile Ile Ser Phe
                115                 120                 125

Asp Arg Tyr Phe Cys Val Thr Lys Pro Leu Thr Tyr Pro Ala Arg Arg
    130                 135                 140

Thr Thr Lys Met Ala Gly Leu Met Ile Ala Ala Ala Trp Val Leu Ser
145                 150                 155                 160

Phe Val Leu Trp Ala Pro Ala Ile Leu Phe Trp Gln Phe Val Val Gly
                165                 170                 175

Lys Arg Thr Val Pro Asp Asn Gln Cys Phe Ile Gln Phe Leu Ser Asn
                180                 185                 190

Pro Ala Val Thr Phe Gly Thr Ala Ile Ala Ala Phe Tyr Leu Pro Val
                195                 200                 205

Val Ile Met Thr Val Leu Tyr Ile His Ile Ser Leu Ala Ser Arg Ser
    210                 215                 220

Arg Val His Lys His Arg Pro Glu Gly Pro Lys Glu Lys Lys Ala Lys
225                 230                 235                 240

Thr Leu Ala Phe Leu Lys Ser Pro Leu Met Lys Gln Ser Val Lys Lys
                245                 250                 255

Pro Pro Pro Gly Glu Ala Ala Arg Glu Glu Leu Arg Asn Gly Lys Leu
                260                 265                 270

Glu Glu Ala Pro Pro Pro Ala Leu Pro Pro Pro Arg Pro Val Ala
    275                 280                 285

Asp Lys Asp Thr Ser Asn Glu Ser Ser Ser Gly Ser Ala Thr Gln Asn
    290                 295                 300

Thr Lys Glu Arg Pro Ala Thr Glu Leu Ser Thr Thr Glu Ala Thr Thr
305                 310                 315                 320

Pro Ala Met Pro Ala Pro Pro Leu Gln Pro Arg Ala Leu Asn Pro Ala
                325                 330                 335

Ser Arg Trp Ser Lys Ile Gln Ile Val Thr Lys Gln Thr Gly Asn Glu
                340                 345                 350
```

-continued

```
Cys Val Thr Ala Ile Glu Ile Val Pro Ala Thr Pro Ala Gly Met Arg
            355                 360                 365

Pro Ala Ala Asn Val Ala Arg Lys Phe Ala Ser Ile Ala Arg Asn Gln
370                 375                 380

Val Arg Lys Lys Arg Gln Met Ala Ala Arg Glu Arg Lys Val Thr Arg
385                 390                 395                 400

Thr Ile Phe Ala Ile Leu Leu Ala Phe Ile Leu Thr Trp Thr Pro Tyr
                405                 410                 415

Asn Val Met Val Leu Val Asn Thr Phe Cys Gln Ser Cys Ile Pro Asp
                420                 425                 430

Thr Val Trp Ser Ile Gly Tyr Trp Leu Cys Tyr Val Asn Ser Thr Ile
                435                 440                 445

Asn Pro Ala Cys Tyr Ala Leu Cys Asn Ala Thr Phe Lys Lys Thr Phe
            450                 455                 460

Arg His Leu Leu Leu Cys Gln Tyr Arg Asn Ile Gly Thr Ala Arg
465                 470                 475

<210> SEQ ID NO 318
<211> LENGTH: 424
<212> TYPE: PRT
<213> ORGANISM: Rattus norvegicus

<400> SEQUENCE: 318

Met His Leu Asn Ser Ser Val Pro Gln Gly Thr Pro Gly Glu Pro Asp
1               5                   10                  15

Ala Gln Pro Phe Ser Gly Pro Gln Ser Glu Met Glu Ala Thr Phe Leu
                20                  25                  30

Ala Leu Ser Leu Ser Asn Gly Ser Gly Asn Thr Ser Glu Ser Asp Thr
            35                  40                  45

Ala Gly Pro Asn Ser Asp Leu Asp Val Asn Thr Asp Ile Tyr Ser Lys
        50                  55                  60

Val Leu Val Thr Ala Ile Tyr Leu Ala Leu Phe Val Val Gly Thr Val
65                  70                  75                  80

Gly Asn Ser Val Thr Ala Phe Thr Leu Ala Arg Lys Lys Ser Leu Gln
                85                  90                  95

Ser Leu Gln Ser Thr Val His Tyr His Leu Gly Ser Leu Ala Leu Ser
                100                 105                 110

Asp Leu Leu Ile Leu Leu Leu Ala Met Pro Val Glu Leu Tyr Asn Phe
            115                 120                 125

Ile Trp Val His His Pro Trp Ala Phe Gly Asp Ala Gly Cys Arg Gly
        130                 135                 140

Tyr Tyr Phe Leu Arg Asp Ala Cys Thr Tyr Ala Thr Ala Leu Asn Val
145                 150                 155                 160

Ala Ser Leu Ser Val Glu Arg Tyr Leu Ala Ile Cys His Pro Phe Lys
                165                 170                 175

Ala Lys Thr Leu Met Ser Arg Ser Arg Thr Lys Lys Phe Ile Ser Ala
                180                 185                 190

Ile Trp Leu Ala Ser Ala Leu Leu Ala Ile Pro Met Leu Phe Thr Met
        195                 200                 205

Gly Leu Gln Asn Arg Ser Gly Asp Gly Thr His Pro Gly Gly Leu Val
    210                 215                 220

Cys Thr Pro Ile Val Asp Thr Ala Thr Val Lys Val Val Ile Gln Val
225                 230                 235                 240

Asn Thr Phe Met Ser Phe Leu Phe Pro Met Leu Val Ile Ser Ile Leu
                245                 250                 255
```

```
Asn Thr Val Ile Ala Asn Lys Leu Thr Val Met Val His Gln Ala Ala
            260                 265                 270

Glu Gln Gly Arg Val Cys Thr Val Gly Thr His Asn Gly Leu Glu His
        275                 280                 285

Ser Thr Phe Asn Met Thr Ile Glu Pro Gly Arg Val Gln Ala Leu Arg
    290                 295                 300

His Gly Val Leu Val Leu Arg Ala Val Val Ile Ala Phe Val Val Cys
305                 310                 315                 320

Trp Leu Pro Tyr His Val Arg Arg Leu Met Phe Cys Tyr Ile Ser Asp
                325                 330                 335

Glu Gln Trp Thr Thr Phe Leu Phe Asp Phe Tyr His Tyr Phe Tyr Met
            340                 345                 350

Leu Thr Asn Ala Leu Phe Tyr Val Ser Ser Ala Ile Asn Pro Ile Leu
        355                 360                 365

Tyr Asn Leu Val Ser Ala Asn Phe Arg Gln Val Phe Leu Ser Thr Leu
    370                 375                 380

Ala Cys Leu Cys Pro Gly Trp Arg His Arg Arg Lys Lys Arg Pro Thr
385                 390                 395                 400

Phe Ser Arg Lys Pro Asn Ser Met Ser Ser Asn His Ala Phe Ser Thr
                405                 410                 415

Ser Ala Thr Arg Glu Thr Leu Tyr
            420

<210> SEQ ID NO 319
<211> LENGTH: 414
<212> TYPE: PRT
<213> ORGANISM: Homo sapiens

<400> SEQUENCE: 319

Met Gly Gly His Pro Gln Leu Arg Leu Val Lys Ala Leu Leu Leu Leu
1               5                   10                  15

Gly Leu Asn Pro Val Ser Ala Ser Leu Gln Asp Gln His Cys Glu Ser
            20                  25                  30

Leu Ser Leu Ala Ser Asn Ile Ser Gly Leu Gln Cys Asn Ala Ser Val
        35                  40                  45

Asp Leu Ile Gly Thr Cys Trp Pro Arg Ser Pro Gly Gln Leu Val Val
    50                  55                  60

Arg Pro Cys Pro Ala Phe Phe Tyr Gly Val Arg Tyr Asn Thr Thr Asn
65                  70                  75                  80

Asn Gly Tyr Arg Glu Cys Leu Ala Asn Gly Ser Trp Ala Ala Arg Val
                85                  90                  95

Asn Tyr Ser Glu Cys Gln Glu Ile Leu Asn Glu Glu Lys Lys Ser Lys
            100                 105                 110

Val His Tyr His Val Ala Val Ile Ile Asn Tyr Leu Gly His Cys Ile
        115                 120                 125

Ser Leu Val Ala Leu Leu Val Ala Phe Val Leu Phe Leu Arg Leu Arg
    130                 135                 140

Ser Ile Arg Cys Leu Arg Asn Ile Ile His Trp Asn Leu Ile Ser Ala
145                 150                 155                 160

Phe Ile Leu Arg Asn Ala Thr Trp Phe Val Val Gln Leu Thr Met Ser
                165                 170                 175

Pro Glu Val His Gln Ser Asn Val Gly Trp Cys Arg Leu Val Thr Ala
            180                 185                 190

Ala Tyr Asn Tyr Phe His Val Thr Asn Phe Phe Trp Met Phe Gly Glu
        195                 200                 205
```

```
Gly Cys Tyr Leu His Thr Ala Ile Val Leu Thr Tyr Ser Thr Asp Arg
    210                 215                 220

Leu Arg Lys Trp Met Phe Ile Cys Ile Gly Trp Gly Val Pro Phe Pro
225                 230                 235                 240

Ile Ile Val Ala Trp Ala Ile Gly Lys Leu Tyr Tyr Asp Asn Glu Lys
                245                 250                 255

Cys Trp Phe Gly Lys Arg Pro Gly Val Tyr Thr Asp Tyr Ile Tyr Gln
                260                 265                 270

Gly Pro Met Ile Leu Val Leu Leu Ile Asn Phe Ile Phe Leu Phe Asn
            275                 280                 285

Ile Val Arg Ile Leu Met Thr Lys Leu Arg Ala Ser Thr Thr Ser Glu
        290                 295                 300

Thr Ile Gln Tyr Arg Lys Ala Val Lys Ala Thr Leu Val Leu Leu Pro
305                 310                 315                 320

Leu Leu Gly Ile Thr Tyr Met Leu Phe Phe Val Asn Pro Gly Glu Asp
                325                 330                 335

Glu Val Ser Arg Val Val Phe Ile Tyr Phe Asn Ser Phe Leu Glu Ser
                340                 345                 350

Phe Gln Gly Phe Phe Val Ser Val Phe Tyr Cys Phe Leu Asn Ser Glu
            355                 360                 365

Val Arg Ser Ala Ile Arg Lys Arg Trp His Arg Trp Gln Asp Lys His
        370                 375                 380

Ser Ile Arg Ala Arg Val Ala Arg Ala Met Ser Ile Pro Thr Ser Pro
385                 390                 395                 400

Thr Arg Val Ser Phe His Ser Ile Lys Gln Ser Thr Ala Val
                405                 410

<210> SEQ ID NO 320
<211> LENGTH: 444
<212> TYPE: PRT
<213> ORGANISM: Homo sapiens

<400> SEQUENCE: 320

Met Ser Gly Thr Lys Leu Glu Asp Ser Pro Pro Cys Arg Asn Trp Ser
1               5                   10                  15

Ser Ala Ser Glu Leu Asn Glu Thr Gln Glu Pro Leu Leu Asn Pro Thr
            20                  25                  30

Asp Tyr Asp Asp Glu Glu Phe Leu Arg Tyr Leu Trp Arg Glu Tyr Leu
        35                  40                  45

His Pro Lys Glu Tyr Glu Trp Val Leu Ile Ala Gly Tyr Ile Ile Val
    50                  55                  60

Phe Val Val Ala Leu Ile Gly Asn Val Leu Val Cys Val Ala Val Trp
65                  70                  75                  80

Lys Asn His His Met Arg Thr Val Thr Asn Tyr Phe Ile Val Asn Leu
                85                  90                  95

Ser Leu Ala Asp Val Leu Val Thr Ile Thr Cys Leu Pro Ala Thr Leu
            100                 105                 110

Val Val Asp Ile Thr Glu Thr Trp Phe Phe Gly Gln Ser Leu Cys Lys
        115                 120                 125

Val Ile Pro Tyr Leu Gln Thr Val Ser Val Ser Val Ser Val Leu Thr
130                 135                 140

Leu Ser Cys Ile Ala Leu Asp Arg Trp Tyr Ala Ile Cys His Pro Leu
145                 150                 155                 160

Met Phe Lys Ser Thr Ala Lys Arg Ala Arg Asn Ser Ile Val Ile Ile
                165                 170                 175
```

```
Trp Ile Val Ser Cys Ile Ile Met Ile Pro Gln Ala Ile Val Met Glu
            180                 185                 190
Cys Ser Thr Val Phe Pro Gly Leu Ala Asn Lys Thr Thr Leu Phe Thr
        195                 200                 205
Val Cys Asp Glu Arg Trp Gly Gly Ile Tyr Pro Lys Met Tyr His
    210                 215                 220
Ile Cys Phe Phe Leu Val Thr Tyr Met Ala Pro Leu Cys Leu Met Val
225                 230                 235                 240
Leu Ala Tyr Leu Gln Ile Phe Arg Lys Leu Trp Cys Arg Gln Ile Pro
                245                 250                 255
Gly Thr Ser Ser Val Val Gln Arg Lys Trp Lys Pro Leu Gln Pro Val
            260                 265                 270
Ser Gln Pro Arg Gly Pro Gly Gln Pro Thr Lys Ser Arg Met Ser Ala
        275                 280                 285
Val Ala Ala Glu Ile Lys Gln Ile Arg Ala Arg Arg Lys Thr Ala Arg
    290                 295                 300
Met Leu Met Val Val Leu Leu Val Phe Ala Ile Cys Tyr Leu Pro Ile
305                 310                 315                 320
Ser Ile Leu Asn Val Leu Lys Arg Val Phe Gly Met Phe Ala His Thr
                325                 330                 335
Glu Asp Arg Glu Thr Val Tyr Ala Trp Phe Thr Phe Ser His Trp Leu
            340                 345                 350
Val Tyr Ala Asn Ser Ala Ala Asn Pro Ile Ile Tyr Asn Phe Leu Ser
        355                 360                 365
Gly Lys Phe Arg Glu Glu Phe Lys Ala Ala Phe Ser Cys Cys Cys Leu
    370                 375                 380
Gly Val His His Arg Gln Glu Asp Arg Leu Thr Arg Gly Arg Thr Ser
385                 390                 395                 400
Thr Glu Ser Arg Lys Ser Leu Thr Thr Gln Ile Ser Asn Phe Asp Asn
                405                 410                 415
Ile Ser Lys Leu Ser Glu Gln Val Val Leu Thr Ser Ile Ser Thr Leu
            420                 425                 430
Pro Ala Ala Asn Gly Ala Gly Pro Leu Gln Asn Trp
        435                 440

<210> SEQ ID NO 321
<211> LENGTH: 31
<212> TYPE: PRT
<213> ORGANISM: Rattus norvegicus

<400> SEQUENCE: 321

Arg Asn Ile Ile His Trp Asn Leu Ile Ser Ala Phe Ile Leu Arg Asn
1               5                   10                  15
Ala Thr Trp Phe Val Val Gln Leu Thr Val Ser Pro Glu Val His
            20                  25                  30

<210> SEQ ID NO 322
<211> LENGTH: 31
<212> TYPE: PRT
<213> ORGANISM: Mus musculus

<400> SEQUENCE: 322

Arg Asn Ile Ile His Trp Asn Leu Ile Ser Ala Phe Ile Leu Arg Asn
1               5                   10                  15
Ala Thr Trp Phe Val Val Gln Leu Thr Val Ser Pro Glu Val His
            20                  25                  30
```

```
<210> SEQ ID NO 323
<211> LENGTH: 31
<212> TYPE: PRT
<213> ORGANISM: Homo sapiens

<400> SEQUENCE: 323

Arg Asn Ile Ile His Trp Asn Leu Ile Ser Ala Phe Ile Leu Arg Asn
1               5                   10                  15

Ala Thr Trp Phe Val Val Gln Leu Thr Met Ser Pro Glu Val His
            20                  25                  30

<210> SEQ ID NO 324
<211> LENGTH: 31
<212> TYPE: PRT
<213> ORGANISM: Mus musculus

<400> SEQUENCE: 324

Arg Asn Val Ile His Trp Asn Leu Ile Thr Thr Phe Ile Leu Arg Asn
1               5                   10                  15

Ile Ala Trp Phe Leu Leu Gln Leu Ile Asp His Glu Val His Glu
            20                  25                  30

<210> SEQ ID NO 325
<211> LENGTH: 31
<212> TYPE: PRT
<213> ORGANISM: Rattus norvegicus

<400> SEQUENCE: 325

Arg Asn Val Ile His Trp Asn Leu Ile Thr Thr Phe Ile Leu Arg Asn
1               5                   10                  15

Ile Thr Trp Phe Leu Leu Gln Leu Ile Asp His Glu Val His Glu
            20                  25                  30

<210> SEQ ID NO 326
<211> LENGTH: 31
<212> TYPE: PRT
<213> ORGANISM: Homo sapiens

<400> SEQUENCE: 326

Arg Asn Val Ile His Trp Asn Leu Ile Thr Thr Phe Ile Leu Arg Asn
1               5                   10                  15

Val Met Trp Phe Leu Leu Gln Leu Val Asp His Glu Val His Glu
            20                  25                  30

<210> SEQ ID NO 327
<211> LENGTH: 31
<212> TYPE: PRT
<213> ORGANISM: Rattus norvegicus

<400> SEQUENCE: 327

Arg Asn Tyr Ile His Met His Met Phe Leu Ser Phe Met Leu Arg Ala
1               5                   10                  15

Ala Ser Ile Phe Val Lys Asp Ala Val Leu Tyr Ser Gly Phe Thr
            20                  25                  30

<210> SEQ ID NO 328
<211> LENGTH: 31
<212> TYPE: PRT
<213> ORGANISM: Mus musculus

<400> SEQUENCE: 328

Arg Asn Tyr Ile His Met His Met Phe Leu Ser Phe Met Leu Arg Ala
1               5                   10                  15
```

Ala Ser Ile Phe Val Lys Asp Ala Val Leu Tyr Ser Gly Phe Thr
            20                  25                  30

<210> SEQ ID NO 329
<211> LENGTH: 31
<212> TYPE: PRT
<213> ORGANISM: Homo sapiens

<400> SEQUENCE: 329

Arg Asn Tyr Ile His Met His Leu Phe Leu Ser Phe Met Leu Arg Ala
1               5                   10                  15

Val Ser Ile Phe Val Lys Asp Ala Val Leu Tyr Ser Gly Ala Thr
            20                  25                  30

<210> SEQ ID NO 330
<211> LENGTH: 31
<212> TYPE: PRT
<213> ORGANISM: Mus musculus

<400> SEQUENCE: 330

Arg Asn Tyr Ile His Leu His Leu Phe Val Ser Phe Met Leu Arg Ala
1               5                   10                  15

Met Ser Ile Phe Val Lys Asp Arg Val Ala Gln Ala His Leu Gly
            20                  25                  30

<210> SEQ ID NO 331
<211> LENGTH: 30
<212> TYPE: PRT
<213> ORGANISM: Rattus norvegicus

<400> SEQUENCE: 331

Arg Asn Tyr Ile His Leu His Leu Phe Val Ser Phe Met Leu Arg Ala
1               5                   10                  15

Ser Ile Phe Val Lys Asp Arg Val Ala Gln Ala His Leu Gly
            20                  25                  30

<210> SEQ ID NO 332
<211> LENGTH: 31
<212> TYPE: PRT
<213> ORGANISM: Homo sapiens

<400> SEQUENCE: 332

Arg Asn Tyr Ile His Met His Leu Phe Val Ser Phe Met Leu Arg Ala
1               5                   10                  15

Thr Ser Ile Phe Val Lys Asp Arg Val Val His Ala His Ile Gly
            20                  25                  30

<210> SEQ ID NO 333
<211> LENGTH: 31
<212> TYPE: PRT
<213> ORGANISM: Mus musculus

<400> SEQUENCE: 333

Arg Asn Tyr Ile His Met His Leu Phe Met Ser Phe Ile Leu Arg Ala
1               5                   10                  15

Thr Ala Val Phe Ile Lys Asp Met Ala Leu Phe Asn Asn Gly Glu
            20                  25                  30

<210> SEQ ID NO 334
<211> LENGTH: 31
<212> TYPE: PRT
<213> ORGANISM: Rattus norvegicus

<400> SEQUENCE: 334

Arg Asn Tyr Ile His Met His Leu Phe Met Ser Phe Ile Leu Arg Ala
1               5                   10                  15

Thr Ala Val Phe Ile Lys Asp Met Ala Leu Phe Asn Ser Gly Glu
            20                  25                  30

<210> SEQ ID NO 335
<211> LENGTH: 31
<212> TYPE: PRT
<213> ORGANISM: Homo sapiens

<400> SEQUENCE: 335

Arg Asn Tyr Ile His Met His Leu Phe Ile Ser Phe Ile Leu Arg Ala
1               5                   10                  15

Ala Ala Val Phe Ile Lys Asp Leu Ala Leu Phe Asp Ser Gly Glu
            20                  25                  30

<210> SEQ ID NO 336
<211> LENGTH: 31
<212> TYPE: PRT
<213> ORGANISM: Mus musculus

<400> SEQUENCE: 336

Arg Asn Tyr Ile His Leu Asn Leu Phe Leu Ser Phe Met Leu Arg Ala
1               5                   10                  15

Ile Ser Val Leu Val Lys Asp Ser Val Leu Tyr Ser Ser Ser Gly
            20                  25                  30

<210> SEQ ID NO 337
<211> LENGTH: 31
<212> TYPE: PRT
<213> ORGANISM: Rattus norvegicus

<400> SEQUENCE: 337

Arg Asn Tyr Ile His Leu Asn Leu Phe Leu Ser Phe Met Leu Arg Ala
1               5                   10                  15

Ile Ser Val Leu Val Lys Asp Ser Val Leu Tyr Ser Ser Ser Gly
            20                  25                  30

<210> SEQ ID NO 338
<211> LENGTH: 31
<212> TYPE: PRT
<213> ORGANISM: Homo sapiens

<400> SEQUENCE: 338

Arg Asn Tyr Ile His Leu Asn Leu Phe Leu Ser Phe Ile Leu Arg Ala
1               5                   10                  15

Ile Ser Val Leu Val Lys Asp Asp Val Leu Tyr Ser Ser Ser Gly
            20                  25                  30

<210> SEQ ID NO 339
<211> LENGTH: 31
<212> TYPE: PRT
<213> ORGANISM: Mus musculus

<400> SEQUENCE: 339

Arg Asn Phe Ile His Met Asn Leu Phe Val Ser Phe Met Leu Arg Ala
1               5                   10                  15

Ile Ser Val Phe Ile Lys Asp Trp Ile Leu Tyr Ala Glu Gln Asp
            20                  25                  30

<210> SEQ ID NO 340
<211> LENGTH: 31

```
<212> TYPE: PRT
<213> ORGANISM: Rattus norvegicus

<400> SEQUENCE: 340

Arg Asn Phe Ile His Met Asn Leu Phe Val Ser Phe Met Leu Arg Ala
1               5                   10                  15

Ile Ser Val Phe Ile Lys Asp Trp Ile Leu Tyr Ala Glu Gln Asp
                20                  25                  30

<210> SEQ ID NO 341
<211> LENGTH: 31
<212> TYPE: PRT
<213> ORGANISM: Homo sapiens

<400> SEQUENCE: 341

Arg Asn Phe Ile His Met Asn Leu Phe Val Ser Phe Met Leu Arg Ala
1               5                   10                  15

Ile Ser Val Phe Ile Lys Asp Trp Ile Leu Tyr Ala Glu Gln Asp
                20                  25                  30

<210> SEQ ID NO 342
<211> LENGTH: 31
<212> TYPE: PRT
<213> ORGANISM: Homo sapiens

<400> SEQUENCE: 342

Arg Asn Tyr Ile His Met His Leu Phe Val Ser Phe Ile Leu Arg Ala
1               5                   10                  15

Leu Ser Asn Phe Ile Lys Asp Ala Val Leu Phe Ser Ser Asp Asp
                20                  25                  30

<210> SEQ ID NO 343
<211> LENGTH: 31
<212> TYPE: PRT
<213> ORGANISM: Rattus norvegicus

<400> SEQUENCE: 343

Arg Asn Tyr Ile His Met His Leu Phe Val Ser Phe Ile Leu Arg Ala
1               5                   10                  15

Leu Ser Asn Phe Ile Lys Asp Ala Val Leu Phe Ser Ser Asp Asp
                20                  25                  30

<210> SEQ ID NO 344
<211> LENGTH: 31
<212> TYPE: PRT
<213> ORGANISM: Mus musculus

<400> SEQUENCE: 344

Arg Asn Tyr Ile His Thr Gln Leu Phe Ala Thr Phe Ile Leu Lys Ala
1               5                   10                  15

Ser Ala Val Phe Leu Lys Asp Ala Ala Ile Phe Gln Gly Asp Ser
                20                  25                  30

<210> SEQ ID NO 345
<211> LENGTH: 31
<212> TYPE: PRT
<213> ORGANISM: Rattus norvegicus

<400> SEQUENCE: 345

Arg Asn Tyr Ile His Thr Gln Leu Phe Ala Thr Phe Ile Leu Lys Ala
1               5                   10                  15

Ser Ala Val Phe Leu Lys Asp Ala Ala Val Phe Gln Gly Asp Ser
                20                  25                  30
```

<210> SEQ ID NO 346
<211> LENGTH: 31
<212> TYPE: PRT
<213> ORGANISM: Homo sapiens

<400> SEQUENCE: 346

Arg Asn Tyr Val His Thr Gln Leu Phe Thr Thr Phe Ile Leu Lys Ala
1               5                   10                  15

Gly Ala Val Phe Leu Lys Asp Ala Ala Leu Phe His Ser Asp Asp
            20                  25                  30

<210> SEQ ID NO 347
<211> LENGTH: 31
<212> TYPE: PRT
<213> ORGANISM: Homo sapiens

<400> SEQUENCE: 347

Arg Asn Tyr Ile His Ile Asn Leu Phe Thr Ser Phe Met Leu Arg Ala
1               5                   10                  15

Ala Ala Ile Leu Ser Arg Asp Arg Leu Leu Pro Arg Pro Gly Pro
            20                  25                  30

<210> SEQ ID NO 348
<211> LENGTH: 31
<212> TYPE: PRT
<213> ORGANISM: Rattus norvegicus

<400> SEQUENCE: 348

Arg Asn Tyr Ile His Met Asn Leu Phe Thr Ser Phe Met Leu Arg Ala
1               5                   10                  15

Gly Ala Ile Leu Thr Arg Asp Gln Leu Leu Pro Pro Leu Gly Pro
            20                  25                  30

<210> SEQ ID NO 349
<211> LENGTH: 31
<212> TYPE: PRT
<213> ORGANISM: Mus musculus

<400> SEQUENCE: 349

Arg Asn Tyr Ile His Leu Asn Leu Phe Ala Ser Phe Ile Leu Arg Ala
1               5                   10                  15

Leu Ser Val Phe Ile Lys Asp Ala Ala Leu Lys Trp Met Tyr Ser
            20                  25                  30

<210> SEQ ID NO 350
<211> LENGTH: 31
<212> TYPE: PRT
<213> ORGANISM: Rattus norvegicus

<400> SEQUENCE: 350

Arg Asn Tyr Ile His Leu Asn Leu Phe Ala Ser Phe Ile Leu Arg Ala
1               5                   10                  15

Leu Ser Val Phe Ile Lys Asp Ala Ala Leu Lys Trp Met Tyr Ser
            20                  25                  30

<210> SEQ ID NO 351
<211> LENGTH: 31
<212> TYPE: PRT
<213> ORGANISM: Homo sapiens

<400> SEQUENCE: 351

Arg Asn Tyr Ile His Leu Asn Leu Phe Ala Ser Phe Ile Leu Arg Ala

```
                1               5              10              15
Leu Ser Val Phe Ile Lys Asp Ala Ala Leu Lys Trp Met Tyr Ser
                20              25              30

<210> SEQ ID NO 352
<211> LENGTH: 31
<212> TYPE: PRT
<213> ORGANISM: Homo sapiens

<400> SEQUENCE: 352

Arg Asn Tyr Ile His Met Asn Leu Phe Ala Ser Phe Ile Leu Arg Thr
1               5                  10                  15

Leu Ala Val Leu Val Lys Asp Val Val Phe Tyr Asn Ser Tyr Ser
                20              25              30

<210> SEQ ID NO 353
<211> LENGTH: 31
<212> TYPE: PRT
<213> ORGANISM: Rattus norvegicus

<400> SEQUENCE: 353

Arg Asn Tyr Ile His Met Asn Leu Phe Ala Ser Phe Ile Leu Lys Val
1               5                  10                  15

Leu Ala Val Leu Val Lys Asp Met Val Ser His Asn Ser Tyr Ser
                20              25              30

<210> SEQ ID NO 354
<211> LENGTH: 31
<212> TYPE: PRT
<213> ORGANISM: Mus musculus

<400> SEQUENCE: 354

Arg Asn Tyr Ile His Gly Asn Leu Phe Ala Ser Phe Val Leu Lys Ala
1               5                  10                  15

Gly Ser Val Leu Val Ile Asp Trp Leu Leu Lys Thr Arg Tyr Ser
                20              25              30

<210> SEQ ID NO 355
<211> LENGTH: 31
<212> TYPE: PRT
<213> ORGANISM: Rattus norvegicus

<400> SEQUENCE: 355

Arg Asn Tyr Ile His Gly Asn Leu Phe Ala Ser Phe Val Leu Lys Ala
1               5                  10                  15

Gly Ser Val Leu Val Ile Asp Trp Leu Leu Lys Thr Arg Tyr Ser
                20              25              30

<210> SEQ ID NO 356
<211> LENGTH: 31
<212> TYPE: PRT
<213> ORGANISM: Homo sapiens

<400> SEQUENCE: 356

Arg Asn Ala Ile His Ala Asn Leu Phe Ala Ser Phe Val Leu Lys Ala
1               5                  10                  15

Ser Ser Val Leu Val Ile Asp Gly Leu Leu Arg Thr Arg Tyr Ser
                20              25              30

<210> SEQ ID NO 357
<211> LENGTH: 31
<212> TYPE: PRT
<213> ORGANISM: Mus musculus
```

```
<400> SEQUENCE: 357

Arg Val Thr Leu His Lys His Met Phe Leu Thr Tyr Ile Leu Asn Ser
1               5                   10                  15

Ile Ile Ile Ile Ile His Leu Val Glu Val Val Pro Asn Gly Asp
            20                  25                  30

<210> SEQ ID NO 358
<211> LENGTH: 31
<212> TYPE: PRT
<213> ORGANISM: Rattus norvegicus

<400> SEQUENCE: 358

Arg Val Thr Leu His Lys Asn Met Phe Leu Thr Tyr Ile Leu Asn Ser
1               5                   10                  15

Ile Ile Ile Ile Ile His Leu Val Glu Val Val Pro Asn Gly Asp
            20                  25                  30

<210> SEQ ID NO 359
<211> LENGTH: 31
<212> TYPE: PRT
<213> ORGANISM: Homo sapiens

<400> SEQUENCE: 359

Arg Val Thr Leu His Lys Asn Met Phe Leu Thr Tyr Ile Leu Asn Ser
1               5                   10                  15

Met Ile Ile Ile Ile His Leu Val Glu Val Val Pro Asn Gly Glu
            20                  25                  30

<210> SEQ ID NO 360
<211> LENGTH: 31
<212> TYPE: PRT
<213> ORGANISM: Rattus norvegicus

<400> SEQUENCE: 360

Arg Ile Thr Leu His Lys Asn Leu Phe Phe Ser Phe Val Cys Asn Ser
1               5                   10                  15

Ile Val Thr Ile Ile His Leu Thr Ala Val Ala Asn Asn Gln Ala
            20                  25                  30

<210> SEQ ID NO 361
<211> LENGTH: 31
<212> TYPE: PRT
<213> ORGANISM: Homo sapiens

<400> SEQUENCE: 361

Arg Ile Thr Leu His Lys Asn Leu Phe Phe Ser Phe Val Cys Asn Ser
1               5                   10                  15

Val Val Thr Ile Ile His Leu Thr Ala Val Ala Asn Asn Gln Ala
            20                  25                  30

<210> SEQ ID NO 362
<211> LENGTH: 31
<212> TYPE: PRT
<213> ORGANISM: Mus musculus

<400> SEQUENCE: 362

Arg Ile Thr Leu His Lys Asn Leu Phe Phe Ser Phe Ile Cys Asn Ser
1               5                   10                  15

Ile Val Thr Ile Ile His Leu Thr Ala Val Ala Asn Asn Gln Ala
            20                  25                  30
```

```
<210> SEQ ID NO 363
<211> LENGTH: 5
<212> TYPE: PRT
<213> ORGANISM: Artificial Sequence
<220> FEATURE:
<223> OTHER INFORMATION: Structural motif found in Class 1 GPCRs

<400> SEQUENCE: 363

Asn Pro Leu Val Tyr
1               5

<210> SEQ ID NO 364
<211> LENGTH: 5
<212> TYPE: PRT
<213> ORGANISM: Artificial Sequence
<220> FEATURE:
<223> OTHER INFORMATION: Structural motif found in Class 1 GPCRs

<400> SEQUENCE: 364

Asn Pro Phe Ile Tyr
1               5
```